(12) United States Patent
Priepke et al.

(10) Patent No.: US 8,586,604 B2
(45) Date of Patent: Nov. 19, 2013

(54) INHIBITORS OF THE MICROSOMAL PROSTAGLANDIN E2 SYNTHASE-1

(75) Inventors: Henning Priepke, Warthausen (DE); Henri Doods, Warthausen (DE); Raimund Kuelzer, Mittelbiberach (DE); Roland Pfau, Biberach (DE); Dirk Stenkamp, Biberach (DE); Benjamin Pelcman, Stockholm (SE); Robert Roenn, Uppsala (SE); Dimitrijs Lubriks, Riga (LV); Edgars Suna, Riga (LV)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/211,471

(22) Filed: Aug. 17, 2011

(65) Prior Publication Data

US 2012/0208839 A1    Aug. 16, 2012

(30) Foreign Application Priority Data

Aug. 20, 2010 (EP) .................................... 10173502

(51) Int. Cl.
  A61K 31/437  (2006.01)
  A61P 29/00   (2006.01)
  C07D 471/04  (2006.01)

(52) U.S. Cl.
  USPC ........................................... 514/303; 546/118

(58) Field of Classification Search
  None
  See application file for complete search history.

(56) References Cited

U.S. PATENT DOCUMENTS

| 6,608,084 B1 | 8/2003 | Bourzat et al. |
| 2004/0198768 A1 | 10/2004 | Park Choo et al. |
| 2006/0287344 A1 | 12/2006 | Albers et al. |
| 2007/0060598 A1 | 3/2007 | Albers et al. |
| 2010/0004301 A1 | 1/2010 | Pelcman et al. |
| 2010/0256188 A1 | 10/2010 | Pfau et al. |
| 2011/0275656 A1 | 11/2011 | Pfau et al. |
| 2011/0312935 A1 | 12/2011 | Pfau et al. |
| 2012/0115902 A1 | 5/2012 | Pfau et al. |
| 2012/0122930 A1 | 5/2012 | Pfau et al. |
| 2012/0149676 A1 | 6/2012 | Priepke et al. |
| 2012/0196897 A1 | 8/2012 | Pfau et al. |
| 2012/0208839 A1 | 8/2012 | Priepke et al. |
| 2012/0214786 A1 | 8/2012 | Priepke et al. |
| 2012/0309738 A1 | 12/2012 | Priepke et al. |
| 2012/0309755 A1 | 12/2012 | Priepke et al. |

FOREIGN PATENT DOCUMENTS

| EP | 0034743 A1 | 9/1981 |
| EP | 0295656 A1 | 12/1988 |
| EP | 0419210 A1 | 3/1991 |
| EP | 1069124 A1 | 1/2001 |
| FR | 2851563 A1 | 8/2004 |
| FR | 2852957 A1 | 10/2004 |
| WO | 0015612 A1 | 3/2000 |
| WO | 0049005 A1 | 8/2000 |
| WO | 0061580 A1 | 10/2000 |
| WO | 0068213 A1 | 11/2000 |
| WO | 0125238 A2 | 4/2001 |
| WO | 03053939 A1 | 7/2003 |
| WO | 03074515 A1 | 9/2003 |
| WO | 03082272 A1 | 10/2003 |
| WO | 2004005323 A2 | 1/2004 |
| WO | 2004035740 A1 | 4/2004 |
| WO | 2004072068 A1 | 8/2004 |
| WO | 2004085425 A1 | 10/2004 |
| WO | 2004089951 A1 | 10/2004 |
| WO | 2005044793 A2 | 5/2005 |
| WO | 2005070906 A1 | 8/2005 |
| WO | 2005070920 A1 | 8/2005 |
| WO | 2005123674 A1 | 12/2005 |
| WO | 2006077366 A1 | 7/2006 |
| WO | 2006090167 A2 | 8/2006 |
| WO | 2007095124 A2 | 8/2007 |
| WO | 2007127382 A1 | 11/2007 |
| WO | 2008009924 A2 | 1/2008 |
| WO | 2008035956 A1 | 3/2008 |

(Continued)

OTHER PUBLICATIONS

Richard B. Silverman, The Organic Chemistry of Drug Design and Drug Action, Chapter 2: Drug Discovery, Design, and Development, Academic Press, p. 5-51 (1992).*

(Continued)

Primary Examiner — Janet Andres
Assistant Examiner — Timothy R Rozof
(74) Attorney, Agent, or Firm — Michael P. Morris; Philip I. Datlow

(57) ABSTRACT

This invention relates to compounds of formula I

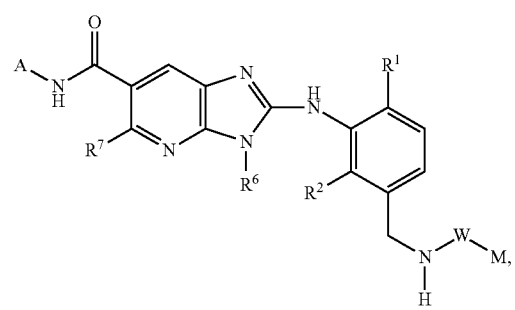

their use as inhibitors of the microsomal prostaglandin $E_2$ synthase-1 (mPGES-1), pharmaceutical compositions containing them, and their use as medicaments for the treatment and/or prevention of inflammatory diseases and associated conditions. A, M, W, $R^1$, $R^2$, $R^6$, $R^7$ have meanings given in the description.

15 Claims, No Drawings

(56) References Cited

FOREIGN PATENT DOCUMENTS

| WO | 2008071944 A1 | 6/2008 |
|---|---|---|
| WO | 2008129276 A1 | 10/2008 |
| WO | 2010034796 A1 | 4/2010 |
| WO | 2010034797 A1 | 4/2010 |
| WO | 2010034798 A1 | 4/2010 |
| WO | 2010034799 A1 | 4/2010 |
| WO | 2010100249 A1 | 9/2010 |

OTHER PUBLICATIONS

R.D. Carpenter et al., Carbodiimide-based benzinidazole library method, Journal of Combinatorial Chemistry, Oct. 27, 2006, pp. 907-914, vol. 8, No. 6.

D.J. Gale et al., The Amidomethylation of Some N,N-Dialkylanilines; Aust.J. Chem.; pp. 2447-2458; vol. 28; 1975.

International Search Report Form PCT/ISA/210 and Written Opinion Form PCT/ISA/237 for corresponding PCT/EP2011/064257; date of mailing: Nov. 16, 2011.

Cancer and Metastasis reviews (1998), 17 (1), 91-106.

Science (1999), vol. 286, 531-537.

Cancer [online], [retrieved on Jul. 6, 2007]. Retrieved from the internet, URL http://www.nlm.nih.gov/medlineplus/cancer.html>.

Cancer [online], [retrieved on Jul. 6, 2007]. Retrieved from the internet, URL http://en.wikipedia.org|wiki|Cancer.

Samuelsson et al., Pharmacology Review, vol. 59, No. 3, pp. 207-224, 2007.

\* cited by examiner

INHIBITORS OF THE MICROSOMAL PROSTAGLANDIN E2 SYNTHASE-1

FIELD OF THE INVENTION

This invention relates to novel compounds, which are inhibitors of the microsomal prostaglandin $E_2$ synthase-1 (mPGES-1), pharmaceutical compositions containing them, and their use as medicaments for the treatment and/or prevention of inflammatory diseases and associated conditions such as inflammatory/nociceptive pain.

BACKGROUND OF THE INVENTION

There are many acute and chronic diseases/disorders that are inflammatory in their nature including but not limited to rheumatoid diseases e.g. rheumatoid arthritis, osteoarthritis, diseases of the visceral system e.g. inflammatory bowel syndrome, autoimmune diseases, e.g. lupus erythematodes, lung diseases like asthma and COPD. Current treatment with non-steroidal anti-inflammatory drugs (NSAIDs) and cyclooxygenase (COX)-2 inhibitors are efficacious, but show a prevalence for gastrointestinal and cardiovascular side effects. There is a high need for new treatment options showing equivalent efficacy with an improved side effect profile.

mPGES inhibitors may show such an improved side effect profile because they block the generation of $PGE_2$ in a more specific manner as described below.

NSAIDs and COX-2 inhibitors reduce inflammation and pain through inhibition of one or both isoformes of COX enzymes. The cyclooxygenase (COX) enzyme exists in two forms, one that is constitutively expressed in many cells and tissues (COX-1), and one that in most cells and tissues is induced by pro-inflammatory stimuli, such as cytokines, during an inflammatory response (COX-2). COXs metabolise arachidonic acid to the unstable intermediate prostaglandin $H_2$ ($PGH_2$). $PGH_2$ is further metabolized to other prostaglandins including $PGE_2$, $PGF_{2\alpha}$, $PGD_2$, prostacyclin and thromboxane $A_2$. These arachidonic acid metabolites are known to have pronounced physiological and pathophysiological activity including pro-inflammatory effects. $PGE_2$ in particular is known to be a strong pro-inflammatory mediator, and is also known to induce fever, inflammation and pain. Consequently, numerous drugs were developed with a view to inhibiting the formation of $PGE_2$, including "NSAIDs" (non-steroidal antiinflammatory drugs) and "coxibs" (selective COX-2 inhibitors). These drugs act predominantly by inhibition of COX-1 and/or COX-2, thereby reducing the formation of $PGE_2$.

However, the inhibition of COXs has the disadvantage that it results in the reduction of the formation of all metabolites downstream of $PGH_2$, some of which are known to have beneficial properties. In view of this, drugs which act by inhibition of COXs are therefore known/suspected to cause adverse biological effects.

For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

An alternative treatment of inflammatory diseases that does not give rise to the above-mentioned side effects would thus be of real benefit in the clinic. In particular, a drug that preferably inhibits the transformation of $PGH_2$ to the pro-inflammatory mediator $PGE_2$ selectively might be expected to reduce the inflammatory response in the absence of a corresponding reduction of the formation of other, beneficial arachidonic acid metabolites. Such inhibition would accordingly be expected to alleviate the undesirable side-effects mentioned above.

$PGH_2$ may be transformed to $PGE_2$ by prostaglandin E synthases (PGES). Two microsomal prostaglandin E synthases (mPGES-1 and mPGES-2), and one cytosolic prostaglandin E synthase (cPGES) have been described. mPGES-1 is proposed to be closely linked to COX-2 and both enzymes are upregulated during e.g. inflammation. Thus agents that are capable of inhibiting the action of mPGES-1 and thereby reducing the formation of $PGE_2$ are likely to be of benefit for the treatment of inflammation and more general acute and chronic pain conditions Benzimidazole and imidazopyridine derivatives with mPGES-1 inhibitory activity are disclosed in WO 2010/034796, WO 2010/034797, WO 2010/034798, WO 2010/034799. PCT/EP2010/052799 describes a broad class of different 2-arylamino benzimidazoles in which the aryl group bears a particular side chain.

DETAILED DESCRIPTION OF THE INVENTION

The present invention is a selection from the general formula of PCT/EP2010/052799 providing compounds of the imidazopyridine class.

The present invention provides a compound of formula I,

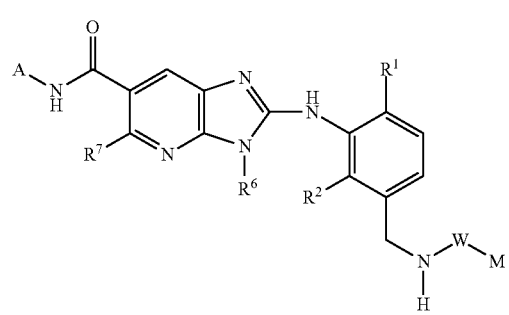

in which $R^1$ represents halo, —$C_{1-3}$alkyl, which latter alkyl group is optionally substituted by one or more fluorine atoms;

$R^2$ represent hydrogen, halo, —$C_{1-3}$alkyl, which latter alkyl group is optionally substituted by one or more fluorine atoms;

W represents —C(O)—, —C(O)O—, which groups are bound to the nitrogen of the —NH— moiety via the carbon atom;

M represents
—$C_{1-6}$alkyl, —$C_{3-7}$cycloalkyl, both of which groups are optionally substituted by one or more groups selected from —F, —OH, —CN, —$NH_2$, —NH($C_{1-2}$alkyl), —N($C_{1-2}$alkyl)$_2$, —$OC_{1-3}$alkyl, —$C_{1-5}$alkyl, —$C_{3-4}$cycloalkyl, in which latter three groups the alkyl or cycloalkyl groups are optionally substituted by one or more fluorine atoms;
or
oxetanyl-, tetrahydrofuranyl-, tetrahydropyranyl-, azetidinyl-, pyrrolidinyl-, piperidinyl-, all of which groups are optionally substituted by one or more substituents selected from fluoro, —CN, —$C_{1-3}$alkyl, which latter alkyl group is optionally substituted by one or more fluorine atoms;
or
phenyl-, pyridyl-, thienyl-, pyrrolyl-, pyrazolyl-, thiazolyl-, oxazolyl-, or isoxazolyl-, all of which groups are optionally substituted by one or more substituents selected from halo, —CN or —C$_{1-3}$alkyl, which latter alkyl group is optionally further substituted by one or more fluorine atoms;

R$^6$ represents —H, —C$_{1-5}$alkyl, —C$_{0-2}$alkyl-C$_{3-5}$cycloalkyl, in which latter two groups the alkyl or cycloalkyl fragments are optionally substituted by one or more fluorine atoms;

R$^7$ represents C$_{1-5}$alkyl-O—, C$_{3-7}$cycloalkyl-C$_{0-2}$alkyl-O—, 4-7-membered heterocycloalkyl-C$_{0-2}$alkyl-O—, in which latter three groups the alkyl, cycloalkyl or heterocycloalkyl fragments are optionally substituted by one or more substituents selected from —F and —OC$_{1-3}$alkyl which latter alkyl group is optionally further substituted by one or more fluorine atoms;

A represents C$_{1-8}$ alkyl-, phenyl-, pyridyl-, pyrrolyl-, pyrazolyl-, thiazolyl-, oxazolyl-, isoxazolyl-, phenyl-C$_{1-3}$ alkyl-, pyridyl-C$_{1-3}$alkyl-, C$_{3-7}$cycloalkyl-C$_{0-3}$alkyl-, oxetanyl-C$_{0-3}$alkyl-, tetra-hydrofuranyl-C$_{0-3}$alkyl, tetrahydropyranyl-C$_{0-3}$alkyl, in which groups the alkyl-, cycloalkyl- and heterocycloalkyl fragments are optionally substituted by one or more substituents selected from R$^{9a}$ and the aryl and heteroaryl fragments are optionally substituted by one or more substituents selected from R$^{9b}$;

each R$^{9a}$ independently represents —F, —Cl, —C$_{1-3}$alkyl which is optionally substituted by one or more substituents selected from —F, —OC$_{1-3}$ alkyl;

each R$^{9b}$ represents independently -halo, —CN; —C$_{1-3}$ alkyl which is optionally substituted by one or more fluorine atoms;

or a salt thereof, particularly a physiologically acceptable salt thereof.

In second embodiment, in the general formula I, A, M, W, R$^1$, R$^2$, R$^7$ have the same meaning as defined in any of the preceding embodiments
and
R$^6$ represents —H, —CH$_3$, or —CH$_2$CHF$_2$.

In another embodiment, in the general formula I, A, M, W, R$^2$, R$^6$, R$^7$ have the same meaning as defined in any of the preceding embodiments
and
R$^1$ represents chloro, fluoro or —CH$_3$, —CH$_2$F, —CHF$_2$, —CF$_3$.

In another embodiment, in the general formula I, A, M, W, R$^1$, R$^6$, R$^7$ have the same meaning as defined in any of the preceding embodiments, and
R$^2$ represents —H, chloro, -fluoro, —CH$_3$, —CH$_2$F, —CHF$_2$, —CF$_3$.

In another embodiment, in the general formula I, A, M, W, R$^1$, R$^2$, R$^6$ have the same meaning as defined in any of the preceding embodiments, and
R$^7$ represents fluoro, —OCHF$_2$, —OCF$_3$, —OCH$_2$CHF$_2$, —OCH$_2$CF$_3$, —OCH$_2$CH$_2$OCH$_3$, —OCH$_2$CH$_2$OCHF$_2$.

In another embodiment, in the general formula I, M, W, R$^1$, R$^2$, R$^6$, R$^7$ have the same meaning as defined in any of the preceding embodiments, and
A represents C$_{1-4}$ alkyl-, C$_{3-6}$cycloalkyl-C$_{0-2}$alkyl-, phenyl-, in which groups the alkyl- and cycloalkyl-fragments are optionally substituted by one or more substituents selected from —F, —CH$_3$, —CH$_2$F, —CHF$_2$, —CF$_3$, and the phenyl fragment is optionally substituted by —F, —Cl, —Br.

In another embodiment, in the general formula I, A, W, R$^1$, R$^2$, R$^6$, R$^7$ have the same meaning as defined in any of the preceding embodiments, and M represents
—C$_{1-4}$ alkyl, —C$_{3-5}$ cycloalkyl, both of which groups are optionally substituted by one or more groups selected from —F, —OH, —CN, —NH$_2$, —OCH$_3$, —CH$_3$, —CH$_2$F, —CHF$_2$, —CF$_3$, cyclopropyl;
or
oxetanyl-, tetrahydrofuranyl- or pyrrolidinyl-, all of which groups are optionally substituted by one or more substituents selected from —F, —CH$_3$, —CH$_2$F, —CHF$_2$, —CF$_3$;
or
phenyl-, thienyl-, pyrrolyl-, pyrazolyl-, imidazolyl-, thiazolyl-, or isoxazolyl-, all of which groups are optionally substituted by one or more substituents selected from —F, —Cl, —CH$_3$, —CH$_2$F, —CHF$_2$, —CF$_3$.

A further embodiment of the present invention comprises compounds of formula Ia

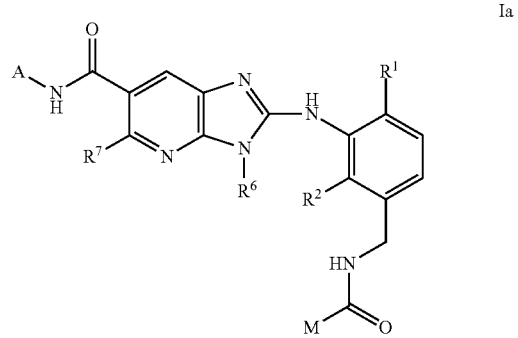

Ia in which
A, M, R$^1$, R$^2$, R$^6$, R$^7$ have the same meaning as defined in any of the preceding embodiments.

A further embodiment of the present invention comprises compounds of formula Ia

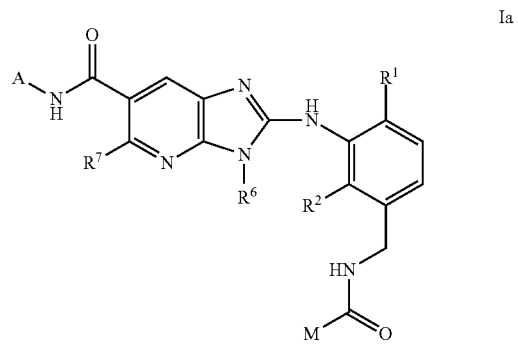

Ia in which
M represents
methyl, ethyl, propyl, i-propyl, n-butyl, s-butyl, t-butyl, cyclopropyl, —CH$_2$— cyclopropyl, cyclobutyl, cyclopentyl, all of which groups are optionally substituted by one or more groups selected from —F, —OH, —CN, —NH$_2$, —OCH$_3$, —CH$_3$, —CF$_3$;
or is selected from the following groups

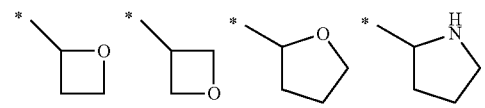

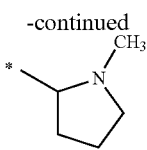

which latter five groups are optionally substituted by one or more substituents selected from —F, —CH$_3$, —CF$_3$;
or is selected from the following groups

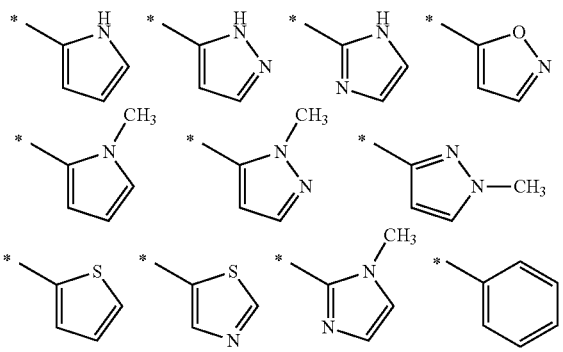

which latter eleven groups are optionally substituted by one or more substituents selected from —F, —Cl, —CH$_3$, —CF$_3$;
and
A, R$^1$, R$^2$, R$^6$, R$^7$ have the same meaning as defined in any of the preceding embodiments.

A further embodiment of the present invention comprises compounds of formula Ia in which A represents methyl, ethyl, propyl, butyl, which latter four groups are optionally substituted by one or more fluorine atoms,
or cyclopropyl, cyclobutyl, cyclopentyl, cyclohexyl, which latter four groups are optionally substituted by one or more substituents selected from —F,
—CH$_3$, —CHF$_2$, —CF$_3$;
or the group

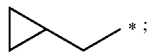

or phenyl which is optionally substituted by one or more substituents selected from —F, —Cl, —Br;
and
M, R$^1$, R$^2$, R$^6$, R$^7$ have the same meaning as defined in any of the preceding embodiments.

A further embodiment of the present invention comprises compounds of formula Ib

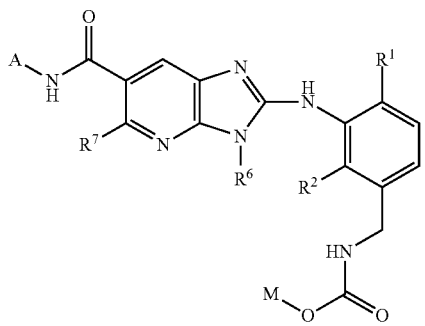

in which
M is tert-butyl;
and
A, R$^1$, R$^2$, R$^6$, R$^7$ have the same meaning as defined in any of the preceding embodiments.

A further embodiment of the present invention comprises compounds of formula Ia or Ib

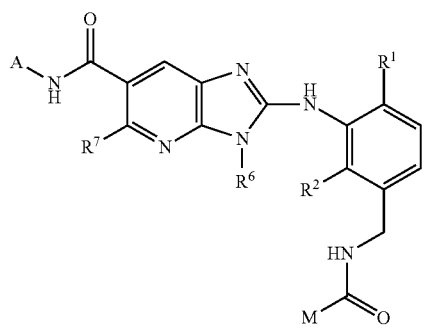

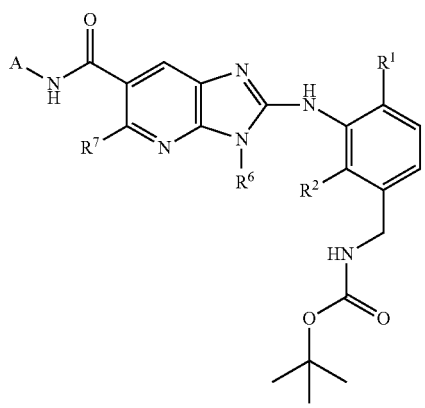

in which
R$^1$ represents chloro, fluoro or —CH$_3$, —CH$_2$F, —CHF$_2$, —CF$_3$;
R$^2$ represents —H, chloro, fluoro, —CH$_3$, —CH$_2$F, —CHF$_2$, —CF$_3$;
R$^6$ represents —H; —CH$_3$, —CH$_2$CHF$_2$;
R$^7$ represents fluoro, —OCHF$_2$, —OCF$_3$, —OCH$_2$CHF$_2$, —OCH$_2$CF$_3$, —OCH$_2$CH$_2$OCH$_3$, —OCH$_2$CH$_2$OCHF$_2$;
A represents methyl, ethyl, propyl, butyl, which latter four groups are optionally substituted by one or more fluorine atoms,
or cyclopropyl, cyclobutyl, cyclopentyl, cyclohexyl, which latter four groups are optionally substituted by one or more substituents selected from —F,
—CH$_3$, —CHF$_2$, —CF$_3$;
or the group

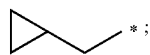

or phenyl which is optionally substituted by one or more substituents selected from —F, —Cl, —Br;
M represents
methyl, ethyl, propyl, i-propyl, n-butyl, s-butyl, t-butyl, cyclopropyl, —CH$_2$— cyclopropyl, cyclobutyl, cyclopentyl, all of which groups are optionally substituted by one or more groups selected from —F, —OH, —CN, —NH₂, —OCH₃, —CH₃, —CF₃;
or is selected from the following groups

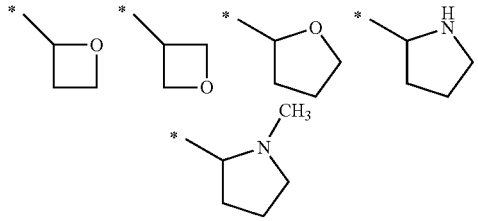

which latter five groups are optionally substituted by one or more substituents selected from —F, —CH₃, —CF₃;
or is selected from the following groups

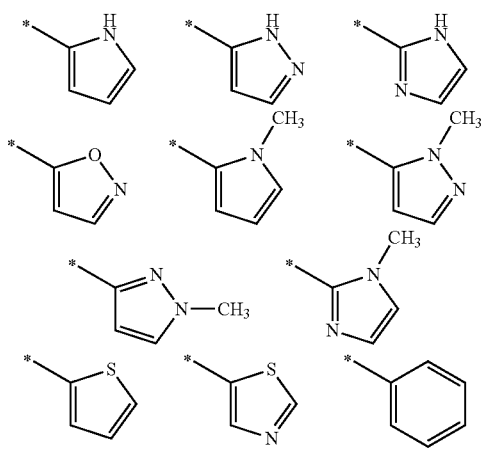

which latter eleven groups are optionally substituted by one or more substituents selected from —F, —Cl, —CH₃, —CF₃.

A further embodiment of the present invention comprises compounds of formula I, Ia or Ib in which
R¹ and R² independently represent chloro, fluoro, —CH₃, —CH₂F, —CHF₂, —CF₃; and
A, M, R⁶, R⁷ have the same meaning as defined in any of the preceding embodiments.

Terms and Definitions Used

General Definitions:

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined, for example a cyclopropylmethyl-group would be represented by the following drawing:

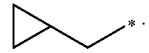

Stereochemistry/Solvates/Hydrates:

Unless specifically indicated, throughout the specification and the appended claims, a given chemical formula or name shall encompass tautomers (e.g. 1H-benzimidazole may be considered to be identical to a corresponding compound containing a 3H-benzimidazole) and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycerophosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Halogen:

The term halogen generally denotes fluorine, chlorine, bromine and iodine.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Cycloalkyl:

The term "$C_{3-n}$-cycloalkyl", wherein n is an integer >3, either alone or in combination with another radical denotes a cyclic, saturated, hydrocarbon radical with 3 to n C atoms. For example the term $C_{3-7}$-cycloalkyl includes cyclopropyl, cyclobutyl, cyclopentyl, cyclohexyl and cycloheptyl.

The term "cycloalkyl" also includes bi-, tri- or tetra-cyclic ring structures consisting only of carbon and containing between one and four rings wherein such rings may be attached together in a pendent manner or may be fused. The term "cycloalkyl" additionally encompasses spiro systems, and bridged systems. The cyclic hydrocarbon radical may also be fused to an phenyl ring.

Thus, the term "cycloalkyl" includes the following exemplary structures which are not depicted as radicals as each form may be attached through a covalent bond to any atom of the cyclalkyl ring fragment as long as appropriate valencies are maintained:

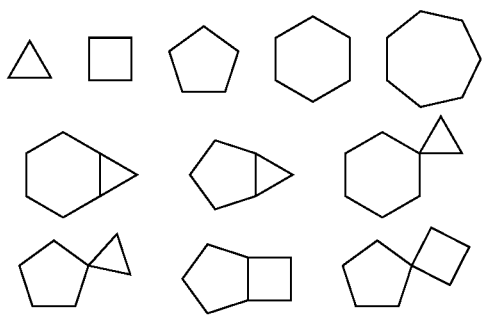

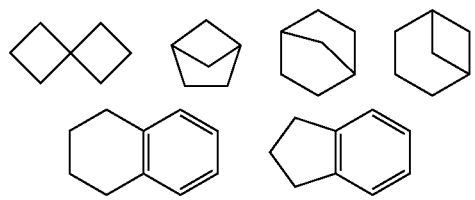

Heterocycloalkyl:

The term "$C_{3-n}$-heterocycloalkyl", wherein n is an integer >3, either alone or in combination with another radical denotes a cyclic non-aromatic mono-, bi-, tri- or spirocyclic radical with 3 to n ring atoms wherein at least one ring atom is selected from N, O or S and wherein n is the upper limit of ring atoms. The cyclic hydrocarbon radical may also be fused to an phenyl ring.

Substituents on heterocycloalkyl groups may, where appropriate, be located on any atom in the ring system including a heteroatom.

The point of attachment of heterocycloalkyl radicals may be via any atom in the non-aromatic ring system including (where appropriate) a heteroatom (such as a nitrogen atom) and also including an atom on any fused non-aromatic carbocyclic ring fragment that may be present as part of the ring system.

Thus, the term "heterocycloalkyl" includes the following exemplary structures which are not depicted as radicals as each form may be attached through a covalent bond to any atom as long as appropriate valencies are maintained:

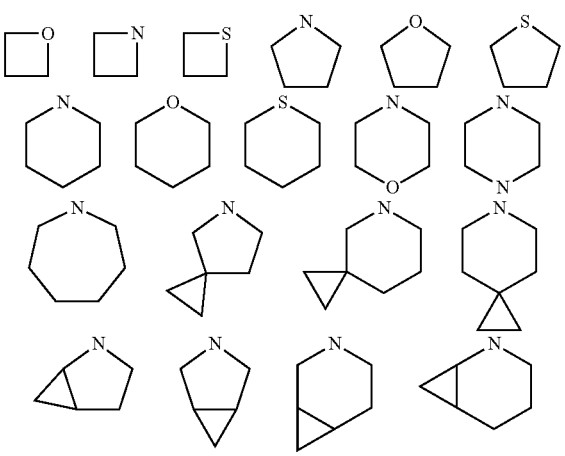

Methods of Preparation

Compounds of the present invention can be prepared in accordance with techniques that are well known to those skilled in the art, for example as described hereinafter and in the experimental section or in analogy to methods described in WO2010/034796, WO2010/034797 and WO2010/034799. According to a further aspect of the invention there is provided a process for the preparation of a compound of formula I, which process can be performed for example according to the following schemes A-C.

Scheme A (all variable groups are as defined in claim 1):

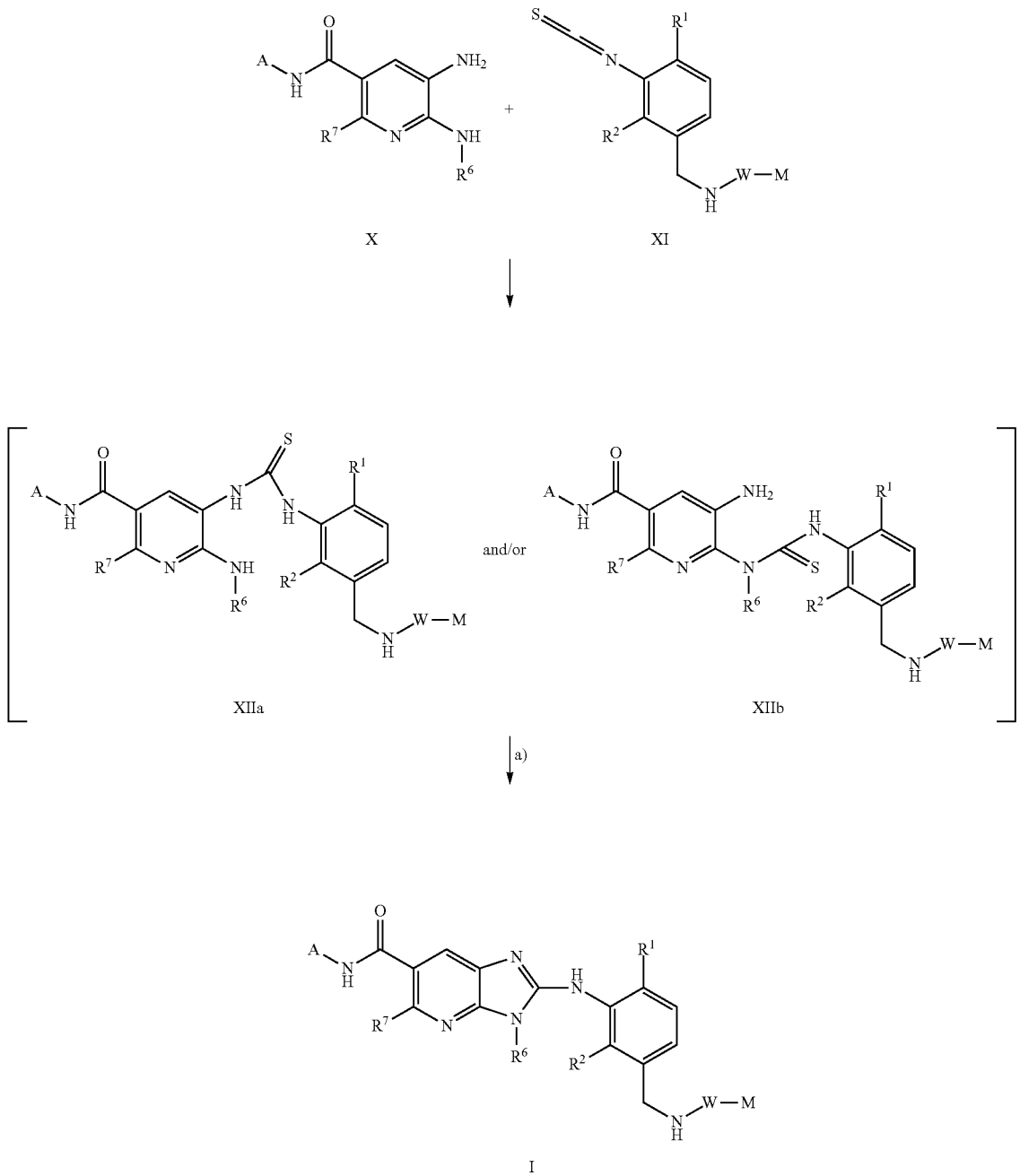

The reaction between phenylenediamine X and the thio-isocyanate XI (Step a) can be performed under standard conditions known to those skilled in the art—for example in analogy to R. Pfau et al. WO2010/034799—in presence of a suitable solvent such as diethyl ether (Et$_2$O), dimethylformamide (DMF), dichloromethane (DCM), acetonitrile (MeCN) and/or tetrahydrofuran (THF). The reaction is preferably performed in the presence of a suitable reagent which enhances the cyclisation step as for instance CH$_3$—I or a carbodiimide based compound such as N,N'-dicyclohexylcarbodiimide (DCC), 1-ethyl-3-(3-dimethylaminopropyl) carbodiimide (EDCI, or its salt, e.g. hydrochloride EDC) or N,N'-diisopropylcarbodiimide (DIC). The reaction may proceed at any suitable temperature between 0° C. to 200° C., preferably between room temperature and 100° C. Step a can be performed in a step-wise reaction under isolation of the thiourea intermediates XIIa and/or XIIb or in a one-pot procedure.

Alternatively the compounds of formula I can be synthesized according to scheme B.

Scheme B (all variable groups are as defined in claim 1 and PG$^{acid}$ is a protecting group of a carboxylic acid function):

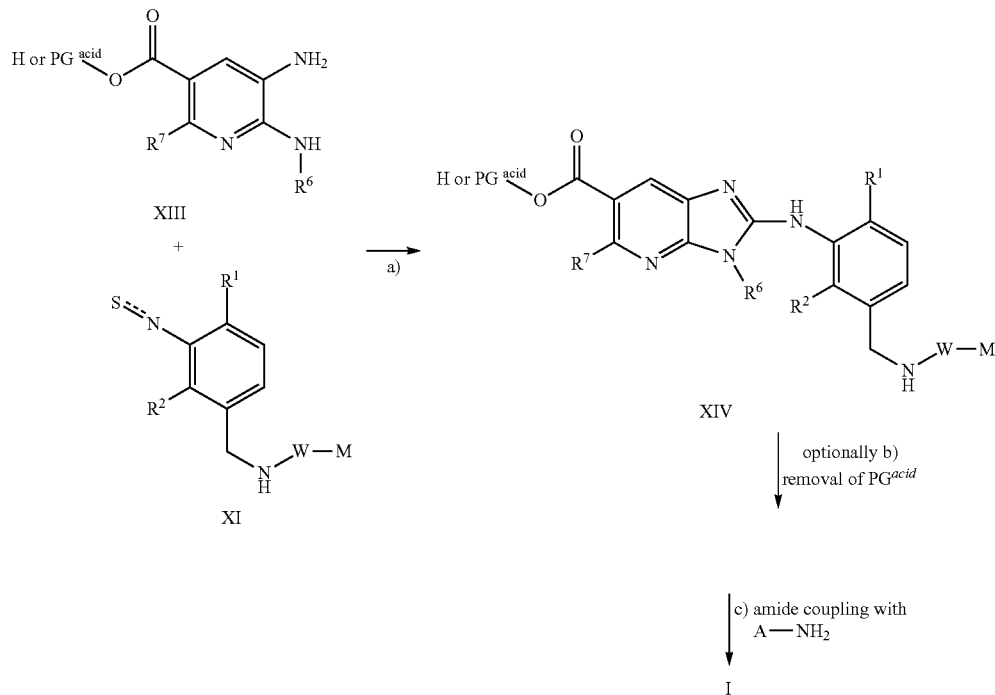

The protecting group PG$^{acid}$ is a literature known protecting group of a carboxylic acid, well known to those skilled in the art as for example described in "*Protective Groups in Organic Synthesis*", 3$^{rd}$ edition, T. W. Greene & P. G. M. Wutz, Wiley-Interscience (1999), for example a C$_{1-5}$-alkyl-, allyl- or a benzyl-group.

Step a) can be performed as described in scheme A, but may also be performed in the presence of an additive (such as 2,2,2-trifluoro-N,O-bis-(trimethylsilyl)-acetamide) when an unprotected carboxylic acid moiety is present in XIII.

Step b) can be performed under known saponification conditions, for example with aqueous LiOH, NaOH or KOH in ethanol (EtOH), methanol (MeOH), DMF, MeCN, THF or dioxane or with Pd/C in MeOH.

The amide formation in step c) can be performed with an additional in-situ activating agent like 1-propylphosphonic acid cyclic anhydride (PPA), O-(benzotriazol-1-yl)-N,N,N',N'-tetramethyl-uronium tetrafluoroborate (TBTU), O-(benzotriazol-1-yl)-N,N,N',N'-tetramethyl-uronium hexafluorophosphate (HBTU), O-(7-azabenzotriazol-1-yl)-N,N,N',N'-tetramethyluronium-hexafluorophosphate (HATU), DCC, EDCI, carbonyldiimidazole (CDI), carbonyldiitriazole (CDT), 1-chloro-2-methyl-propenyl-dimethylamine, oxalyl chloride or other activating agents of the state of the art.

The coupling reaction is preferably performed in the presence of a base such as NaOH, KOH, NaHCO$_3$, triethylamine (TEA), N-ethyldiisopropylamine (DIPEA), pyridine, N,N,-di-methylaminopyridine (DMAP) or other appropriate bases of the state of the art and for example described in Houben-Weyl, "Methods in Organic Synthesis", Vol. E22a, p 425ff.

The coupling reactions are performed in an appropriate solvent for example DCM, dioxane, THF, MeCN, DMF, dimethylacetamide (DMA), N-methylpyrrolidone (NMP) or in mixtures of the above mentioned solvents, preferably between 0° C. and 100° C.

When PG$^{acid}$ is a methyl or ethyl group the conversion of XIV to I can also be carried out in a one-pot procedure for example with trimethylaluminium or triethylaluminium in hexane, dioxane, THF at 20-80° C.

Alternatively the compounds of formula I can be synthesized according to scheme C.

Scheme C (all variable groups are as defined in claim 1 an PG$^{amino}$ is a protecting group of the benzylic amino group):

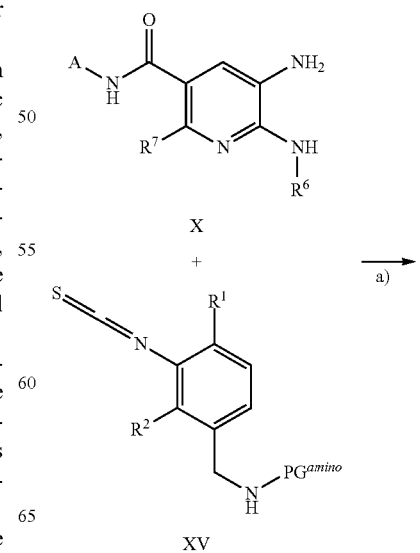

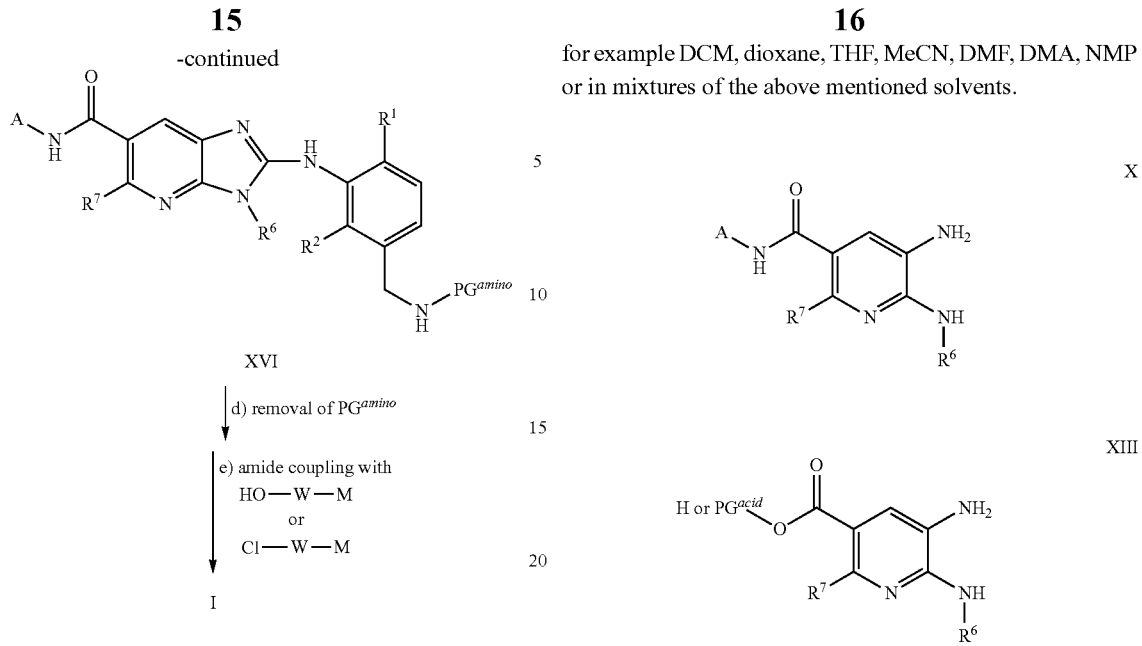

XVI d) removal of PG$^{amino}$ e) amide coupling with
HO—W—M
or
Cl—W—M

I

The protecting group PG$^{amino}$ in XV is a literature known protecting group of an amino group well known to those skilled in the art as for example described in "*Protective Groups in Organic Synthesis*", 3$^{rd}$ edition, T. W. Greene & P. G. M. Wutz, Wiley-Interscience (1999), for example a tert-butoxycarbonyl-, benzyloxycarbonyl-, ethoxycarbonyl-, methoxycarbonyl-, allyloxycarbonyl- or trifluormethylcarbonyl group.

Step a) can be performed as described in scheme A.

Step d) PG$^{amino}$ in XVI can be removed in accordance with techniques that are well known to those skilled in the art and which are exemplified hereinafter. For example XVI can be deprotected using an appropriate agent depending on the protecting group used such as for example trifluoro acetic acid, HCl or H$_2$SO$_4$ solutions, KOH; Ba(OH)$_2$, Pd on carbon (Pd/C), trimethylsilyl iodide or other conditions as described in "*Protective Groups in Organic Synthesis*", 3$^{rd}$ edition, T. W. Greene & P. G. M. Wutz, Wiley-Interscience (1999). Appropriate co-solvent for this step is for example DCM, THF, MeCN, DMF, DMA, NMP or mixtures of the above mentioned solvents, preferably between 0° C. and 100° C.

The amide formation in step e) can be performed with the acids HO-W-M and an additional in-situ activating agent like PPA, TBTU, HBTU, HATU, DCC, EDCI, CDI, CTI, 1-chloro-2-methyl-propenyl-dimethylamine, oxalyl chloride in analogy to scheme B step c) or directly with the corresponding acid chlorides Cl-W-M under analogous conditions without an additional in-situ activating agent.

The coupling reaction is preferably performed in the presence of a base such as NaOH, KOH, NaHCO$_3$, TEA, DIPEA, pyridine, DMAP or other appropriate bases of the state of the art and for example described in described in Houben-Weyl, "Methods in Organic Synthesis", Vol. E22a, p 425ff. The coupling reactions are performed in an appropriate solvent for example DCM, dioxane, THF, MeCN, DMF, DMA, NMP or in mixtures of the above mentioned solvents.

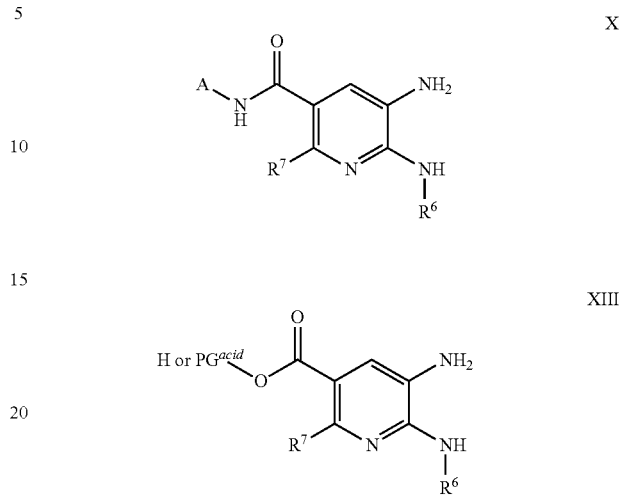

The synthesis of building blocks X and XIII wherein A, R$^6$-R$^8$ have the meaning as defined in claim 1 and PG$^{acid}$ is a literature known carboxylic acid protecting group as described above, can be performed in analogy to literature procedures which are well known to those skilled in the art, as for example in analogy to methods described in WO2010/034799.

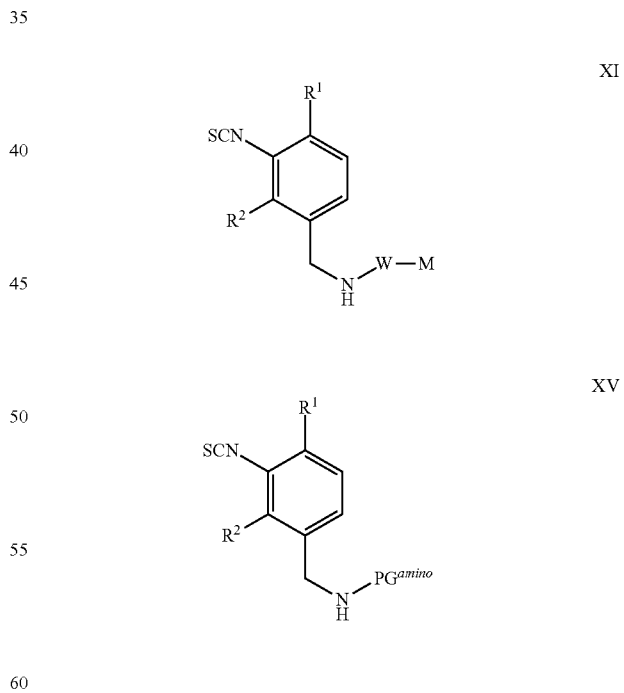

The synthesis of the building blocks XI and XV—wherein all variable groups are as defined in claim 1 and PG$^{amino}$ is a protecting group of the benzylic amino group—is employing standard reaction conditions according to scheme D known to those skilled in the art which are exemplified in the experimental part in detail.

Scheme D (all variable groups are as defined in claim 1 and PG$^{amino}$ is a protecting group of the benzylic amino group):

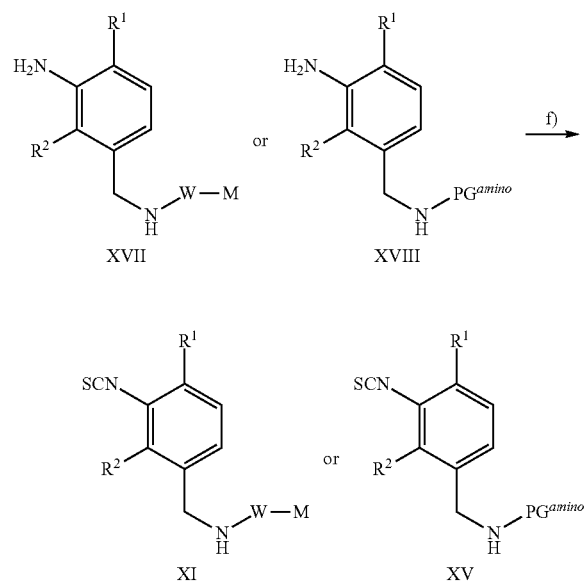

Step f) can be performed according to standard literature procedures for example with reagents such as 1,1'-thiocarbonyldi-2-pyridone, O,O'-di-2-pyridylthiocarbonate, 1,1'-thiocarbonyldiimidazole or with thiophosgene in a solvent as for example DCM, dioxane or DMF at temperatures between 0-150° C. and optionally under addition of a base like DMAP or TEA.

The building blocks XVII and XVIII can be prepared according to scheme E:

The amide formation in step g) can be performed in analogy to step c) or e) to synthesize compound XVII or by using common reagents for amino group protection for example di-tert-butyl-dicarbonate, methyl-, ethyl-, benzyl or allyl-chloroformate under standard reaction conditions as described in "Protective Groups in Organic Synthesis", 3$^{rd}$ edition, T. W. Greene & P. G. M. Wutz, Wiley-Interscience (1999) to synthesize compounds XVIII.

The nitro group in precursor XVIIa or XVIIIa can be reduced to the amino group in step h) under literature known reduction conditions for example via hydrogenation preferably at 1-5 bar in presence of Pd/C or RaNi in MeOH, EtOH or THF optionally under acidic conditions in presence of HCl, or by using SnCl$_2$/HCl, Na$_2$S$_2$O$_4$, Zn/HCl, Fe/HCl, Fe-powder/aqueous NH$_4$Cl solution or according to procedures described in the literature for example R. Larock, Comprehensive Organic Transformations, VCH Verlagsgemeinschaft, Weinheim (1989). Appropriate solvent for this step is for example DCM, THF, MeCN, DMF, DMA, NMP, EtOH, MeOH or mixtures of the above mentioned solvents at temperatures between 0-100° C.

The building blocks XIX and XX can be prepared according to scheme F-G:

Scheme E (all variable groups are as defined in claim 1 and PG$^{amino}$ is a protecting group of the benzylic amino group):

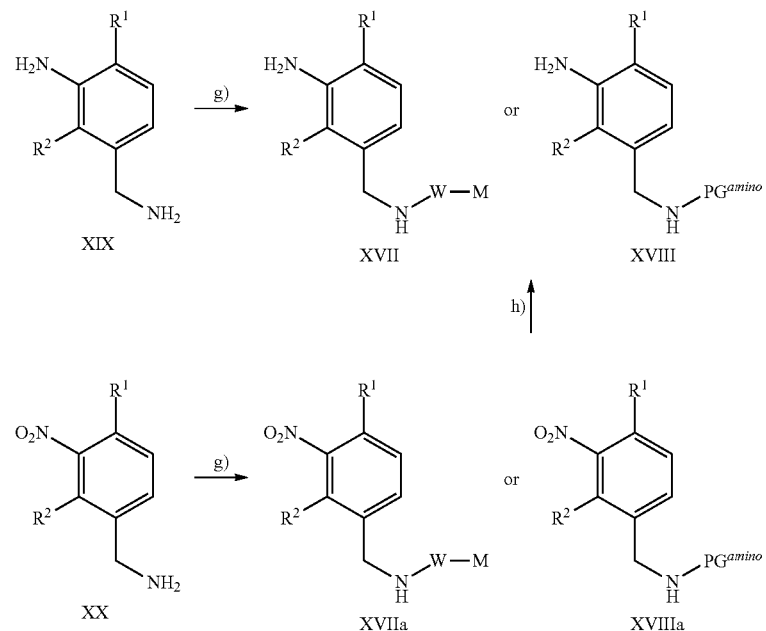

Scheme F (all variable groups are defined in claim 1):

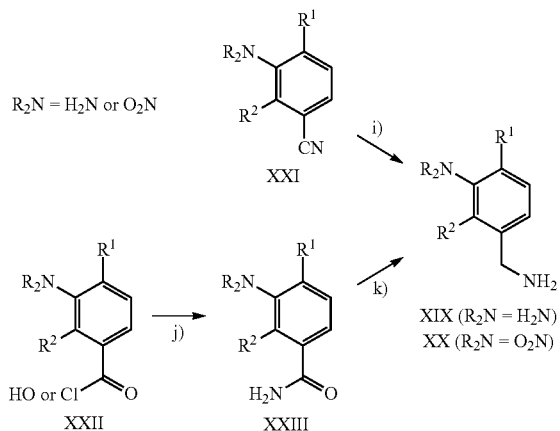

Step i) can be performed via hydrogenation (1-5 bar) with a catalyst like Pd/C, PtO$_2$ or RaNi in a suitable solvent like MeOH or EtOH optionally using HCl or NH$_3$ as additive at temperatures between 0-60° C. or via reduction with LiAlH$_4$ or BH$_3$-containing reagents under literature-known conditions.

Step j) can be performed under the amide coupling conditions described for step e) and using NH$_3$ as coupling partner, for example 1-chloro-2-methyl-propenyl-dimethylamine in THF can be used as activating agent.

Step k) can be performed using LiAlH$_4$ or BH$_3$-containing reagents under literature known conditions as for example compiled in R. C. Larock, Comprehensive Organic Transformations, VCH, 1989, p. 432-433, preferably with LiAlH$_4$ in THF at 0-80° C.

Alternatively compounds XIX and XX can be prepared according to scheme G

Scheme G (all variable groups are as defined in claim 1):

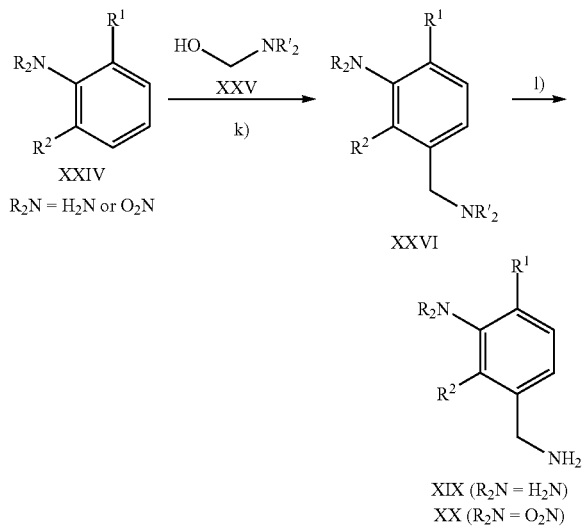

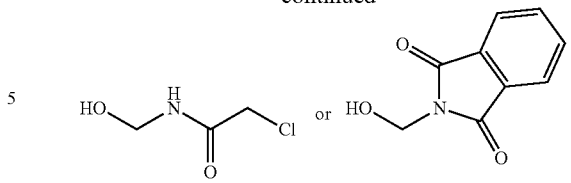

Step k) can be performed mixing XXIV with reagent XXV in concentrated H$_2$SO$_4$ or F$_3$C—SO$_3$H at temperatures between 0-150° C., preferably between 20-80° C.

Step l) can be performed using literature known deprotection procedures for the corresponding nitrogen protecting groups for example treatment of the phthalimide with hydrazine or cleavage of the amide bond using bases like NaOH in MeOH or EtOH at temperatures between 20-80° C. or under acidic conditions using aqeous HCl solution or HCl in dioxane at temperatures between 20-80° C.

Alternatively compounds XIX and XX can be prepared according to scheme H

Scheme H (all variable groups are as defined in claim 1):

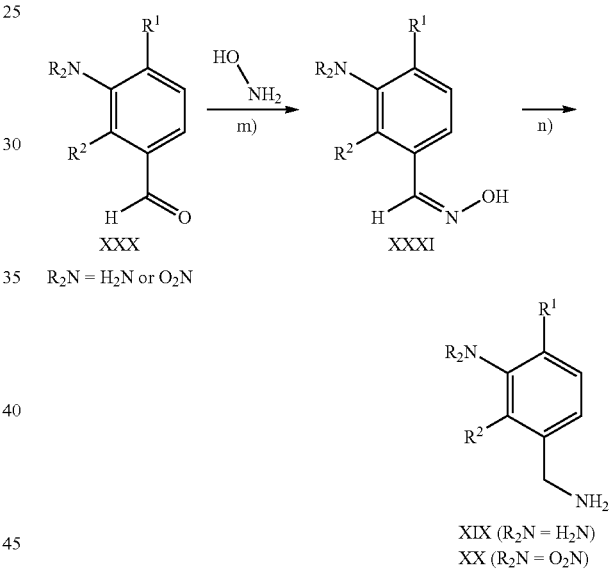

Step m) can be performed mixing XXX with HO—NH$_2$ in an appropriate solvent for example MeCN, DCM, THF, optionally using HCl as additive at temperatures between 0-60° C.

Step n) can be performed applying literature known reduction conditions for example via hydrogenation preferably at 1-5 bar H$_2$ pressure in presence of Pd/C or Ra—Ni in MeOH, EtOH or THF optionally using HCl or HOAc as catalyst, or by using SnCl$_2$/HCl, Zn/HCl, Fe/HCl, Fe-powder/aqueous NH$_4$Cl solution or according to procedures described in the literature for example R. Larock, *Comprehensive Organic Transformations*, VCH Verlagsgemeinschaft, Weinheim (1989).

Biological Assays mPGES Protein Production

Microsomes from Rosetta *E. coli* bacteria expressing recombinant human mPGES-1 can be derived as described below:

Inoculate 5 ml LB with Ampicilin (50 µg/ml) and Chloramphenicol (34 µg/ml) with bacteria from freeze culture. Incubate 8 h at 37° C. with 200 rpm. Thereafter, inoculate 500-1000 ml LB containing Amp and Chloro with the 5 ml on culture and grow to OD640 of 0.8-1.0.

Chill the culture to +4° C. before induction. Induce the culture with IPTG at a final concentration of 400 µM. Express the protein at room temp 18-23° C. with 200 rpm shaking over night.

The following steps can be performed on the following day:
1. Spin down the cells in 250 ml centrifuge flasks for 15 min at 7000 rpm (Beckmann Coulte Avanti J-E centrifuge)
2. Dissolve the pellet from 250 ml culture in 12.5 ml homogenization buffer
3. (15 mM Tris-HCL pH8, 1 mM EDTA pH8, 0.25 mM Sucrose, 2.5 mM GSH, 1 Tablet Protease inhibitor per 50 ml buffer)
4. Disintegrate the cells by sonication, 5×10 seconds at 48% amplitude of a 750 W sonifier
5. Add 2.5 ml $MgCl_2$ (100 mM) and DNase 12.5 µl (0.8 mg/ml) and incubate on ice for 30 min
6. Spin down the bacteria debris and save the supernatant, 7000 rpm for 15 min
7. Isolate the protein containing membranes in the supernatant by ultracentrifugation 120000×g for 2 hour at 4° C. (Sorvall T880 rotor).
8. Discard the supernatant and dissolve the pellet in 20 mM Potassium phosphate buffer pH7.4 ($KH_2PO_4$ and $K_2HPO_4$) buffer by sonication (5×10 s, 30% of a 50 W sonifier) and aliquot the enzyme and store aliquots at −80° C.

Before each experiment is performed an aliquot of the enzyme is thawed and it can then be dissolved in 0.1 M Potassium phosphate buffer pH7.4 ($KH_2PO_4$ and $K_2HPO_4$) buffer containing 2.5 mM GSH.

mPGES-1 Enzyme Assay

The aim of this assay is to determine the affinity of a test compound for the mPGES-1 enzyme.

47 µl of recombinant human mPGES-1 (~0.5 µg protein/well) containing microsomal suspension in a buffer containing GSH, (2.5 mmol/L L-Glutathione reduced, dissolved in 0.1 mol/L Phosphat Buffer pH 7.4) is dispensed in a 384-well plate and thereafter 1 µl of the test compound(s) is/are added and incubated for 25 minutes at room temperature. The enzyme reaction is started by the addition of 2 ul PGH2 (final conc. 2 µM) dissolved in water-free Diglyme. After 60 seconds the reaction is terminated by addition of a stop solution containing $FeCl_2$ (10 µL 0.074 mol/l $FeCl_2$). The samples are diluted between 1:25 in PBS (Phosphate Buffered Saline). 10 µl of the diluted samples are transferred to 384-well low volume plate. In order to quantify the amount of $PGE_2$ that has been formed, a homogenous time resolved fluorescent (HTRF) detecting of $PGE_2$ has been performed using a commercially available kit from Cisbio according to the manufactures recommendation. This HTRF-based assay has been described in detail (see: Goedken et al., J Biomol Screen, 2008, 13(7), 619-625). Briefly, the diluted samples are mixed with 5 µl $PGE_2$-d2 conjungate and 5 µl anti-$PGE_2$ cryptate conjungate. After an incubation period of the plates over night, the fluorescence is measured by the use of an appropriate microplate reader.

The fluorescence of Europium cryptate (maxex=307 nm, maxem=620 nm) and d2-$PGE_2$ (maxex=620 nm, maxem=665 nm) are measured.

The extent of the specific HTRF is measured as a ratio of the emission intensity at 665 nm vs. that at 620 nm at an excitation pulse of 320 nm. The quantification plate contains also wells with different concentrations of $PGE_2$ as calibration curve for the calculation of the $PGE_2$ concentrations from the HTRF ratio values.

From all mPGES enzyme assay the background is subtracted and the $IC_{50}$ is calculated over a nonlinear regression with conventional software.

TABLE A mPGES-1 inhibitory effect ($IC_{50}$ values in nM) of compounds in the enzyme assay

| example | IC50 [nM] |
|---------|-----------|
| 1       | 9         |
| 2       | 3         |
| 3       | 21        |
| 4       | 8         |
| 5       | 4         |
| 6       | 4         |
| 7       | 8         |
| 8       | 3         |
| 9       | 6         |
| 10      | 5         |
| 11      | 4         |
| 12      | 1         |
| 14      | 1         |
| 15      | 4         |
| 156     | 1         |
| 157     | 2         |

A549 Cell-based Assay

Although the enzymatic assay is a high throughput assay the disadvantage is that it uses a recombinant protein which is not in its natural environment. Accordingly a cellular assay was established in which a cell line of human origin (A549) expressing the mPGES-1 protein was used. In addition in order to mimic the situation in humans in which compounds can be bound to plasma proteins 50% human serum is addicted in the assay. By having the combination of testing mPGES-1 in a cellular environment and the presence of 50% human serum this assay has a higher relevance to judge the therapeutic potential of a mPGES-inhibitor than the pure enzyme assay.

A549 cells (ATCC: CCL-185) are grown to about 90% confluence in F-12K Nutrient Mixture (Kaighn's Mod. Gibco) containing 10% FBS in a humidified incubator at 37° C. and 5% $CO_2$. Cells were detached using Trypsin-EDTA. A549 cells were seeded in a 384-well collagene plate at a density of 7000 cells/well (50 µl) in F-12 medium containing 1% Penicillin-Streptomycin and 50% human serum. The cells were allowed to attach for 3-4 h. After that the cells were incubated for 20-24 h in F-12k medium supplemented with 50 human serum, 1% Penicillin-Streptomycin and containing IL-1ß at a final concentration of 5 ng/ml as well as 10 nM arachidonic acid in the presence of a vehicle or a test compound. The total volume is 100 µl.

Concentrations of $PGE_2$ in the cell free medium (10 µl) were measured using a commercially available HTRF kit from Cisbio (as described above). The $PGE_2$ formation in the absence of test compound was taken as 100%.

$IC_{50}$ values were derived from at 6-8 point titrations using conventional software. In general, compounds according to this invention show an mPGES-1 inhibitory effect in the cell based assay at a concentration $IC_{50}$<1000 nM.

Method of Treatment

The present invention relates to compounds of formula I which are useful in the prevention and/or treatment of a disease and/or condition in which the inhibition of prostaglandin E synthases, in particular that of the microsomal prostaglandin $E_2$ synthase-1 (mPGES-1) is of therapeutic benefit, including but not limited to the treatment and/or prevention of inflammatory diseases and/or associated conditions.

The term "inflammation" will be understood to include any inflammatory disease, disorder or condition per se, any condition that has an inflammatory component associated with it, and/or any condition characterised by inflammation as a symptom, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Where a condition has an inflammatory component associated with it, or a condition characterised by inflammation as a symptom, the skilled person will appreciate that compounds of the invention may be useful in the treatment of the inflammatory symptoms and/or the inflammation associated with the condition.

Compounds of the invention may also have effects that are not linked to inflammatory mechanisms, such as in the reduction of bone loss in a subject. Such conditions include osteoporosis, osteoarthritis, Paget's disease and/or periodontal diseases.

A further aspect of the present invention relates to a compound of formula I as a medicament.

Another aspect of the present invention is the use of compounds of formula I for the treatment and/or prevention of a disease and/or condition in which the inhibition of the mPGES-1 is of therapeutic benefit. A further aspect of the present invention is the use of a compound of formula I for the treatment and/or prevention of inflammatory diseases and/or associated conditions.

The present invention also relates to the use of compounds of formula I for the treatment and/or prevention of the following diseases and conditions:

1. Rheumatic diseases or autoimmune diseases or muscoskeletal diseases: all forms of rheumatic diseases including e.g. soft tissue rheumatism, rheumatoid arthritis, polymyalgia rheumatica, reactive arthritis, tenosynovitis, gout or metabolic arthritis, bursitis, tendonitis, juvenile arthritis, spondyloarthropathies like e.g. spondylitis, ankylosing spondylitis, psoriatric arthropathy; sarcoidosis, fibromyalgia, myositis, polymyositis, osteoarthritis, traumatic arthritis, collagenoses of any origin e.g. systemic lupus erythematosus, scleroderma, dermatomyositis, Still's Disease, Sjögren syndrome, Felty syndrome; rheumatic fever and rheumatic heart disease, diseases of blood vessels like vasculitis, polyarthritis nodosa, Behcet's syndrome, giant cell arthritis, Wegener's granulomatosis, Henoch-Schönlein purpura; psoriatic arthritis, fungal arthritis, in particular including pain associated with any of the aforementioned conditions;
2. Headaches such as migraines with and without aura, tension-type headaches, cluster headaches and headaches with different origins;
3. Sympathetically maintained pain like complex regional pain syndrome Type I and II;
4. Neuropathic pain such as low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain;
5. Cancer pain induced by or associated with tumors such as bone tumors, lymphatic leukemia; Hodgkin's disease, malignant lymphoma; lymphogranulomatoses; lymphosarcoma; solid malignant tumors; extensive metastases
6. Visceral disorders such as chronic pelvic pain, pancreatitis, peptic ulcer, interstitial cystitis, cystitis, renal colic, angina, dysmenorrhea, menstruation, gynecological pain, irritable bowel disease (IBS), inflammatory bowel disease, Crohn's disease and ulcerative colitis, nephritis, prostatitis, vulvodynia, non-ulcer dyspepsia, non-cardiac chest pain, myocardial ischemia;
7. Inflammation associated diseases of ear, nose, mouth and throat like influenza and viral/bacterial infections such as the common cold, allergic rhinitis (seasonal and perennial), pharyngitis, tonsillitis, gingivitis, larhyngitis, sinusitis, and vasomotor rhinitis, fever, hay fever, thyroiditis, otitis, dental conditions like toothache, perioperative and post-operative conditions, trigeminal neuralgia, uveitis; iritis, allergic keratitis, conjunctivitis, blepharitis, neuritis nervi optici, choroiditis, glaucoma and sympathetic opthalmia, as well as pain thereof.
8. Neurological diseases such as cerebral oedema and angioedema, cerebral dementia like e.g. Parkinson's and Alzheimers disease, senile dementia; multiple sclerosis, epilepsy, drug resistant epilepsy, stroke, myasthenia gravis, brain and meningeal infections like encephalomyelitis, meningitis, including HIV as well as schizophrenia, delusional disorders, autism, affective disorders and tic disorders;
9. Work-related diseases like pneumoconiosis, including aluminosis, anthracosis, asbestosis, chalicosis, ptilosis, siderosis, silicosis, tabacosis and byssinosis;
10. Lung diseases such as asthma including allergic asthma (atopic or non-atopic) as well as exercise-induced bronchoconstriction, occupational asthma, viral- or bacterial exacerbation of asthma, other non-allergic asthmas and "wheezy-infant syndrome", Chronic obstructive pulmonary disease (COPD) including emphysema, adult respiratory distress syndrome, bronchitis, pneumonia, adult respiratory distress syndrome (ARDS), pigeon fancier's disease, farmers lung;
11. Skin diseases such as psoriasis and eczema, dermatitis, sunburn, burns as well as aprains and strains and tissue trauma;
12. Vascular and heart diseases which are inflammation-related like artheriosclerosis including cardiac transplant atherosclerosis, panarteritis nodosa, periarteritis nodosa, arteritis temporalis, Wegner granulomatosis, giant cell arthritis, reperfusion injury and erythema nodosum, thrombosis (e.g. deep vein thrombosis, renal, hepatic, portal vein thrombosis); coronary artery disease, aneurysm, vascular rejection, myocardial infarction, embolism, stroke, thrombosis including venous thrombosis, angina including unstable angina, coronary plaque inflammation, bacterial-induced inflammation including *Chlamydia*-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries, artery restenosis;
13. Diabetes-associated symptoms such as diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion);
14. Benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers effecting epithelial cells throughout the body; neoplasias like gastrointestinal cancer, Barrett's esophagus, liver cancer, bladder cancer, pancreatic cancer, ovarian cancer, prostate cancer, cervical cancer, lung cancer, breast cancer and skin cancer; adenomatous polyps, including familial adenomatous polyposis (FAP) as well preventing polyps from forming in patients at risk of FAP.
15. Various other disease states and conditions like epilepsy, septic shock e.g. as antihypovolemic and/or antihypotensive agents, sepsis, osteoporosis, benign prostatic hyperplasia and hyperactive bladder, nephritis, pruritis, vitiligo, disturbances of visceral motility at respiratory, genitourinary, gastrointestinal or vascular regions, wounds, allergic skin reactions, mixed-vascular and non-vascular syndromes, septic shock associated with bacterial infections or with trauma, central nervous system injury, tissue damage and postoperative fever, syndromes associated with itching.

Preferred according to the present invention is the use of a compound of formula I for the treatment and/or prevention of pain; in particular pain that is associated with any one of the diseases or conditions listed above.

Another aspect of the present invention is a method for the treatment and/or prevention of above mentioned diseases and conditions, which method comprises the administration of an effective amount of a compound of formula I to a human being.

Dosage

The dose range of the compounds of formula I applicable per day is usually from 0.01 to 5000 mg, preferably from 1 to 2000 mg, more preferably from 5 to 500 mg, most preferably 10 to 250 mg. Each dosage unit may conveniently contain from 2 to 500 mg, preferably 5 to 250 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Formulations

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

A further aspect of the invention is a pharmaceutical formulation including a compound of formula I in admixture with a pharmaceutically acceptable adjuvant, diluent or carrier.

Combination Therapy

The compounds according to the present invention can be combined with other treatment options known to be used in the art in connection with a treatment of any of the indications the treatment of which is in the focus of the present invention.

Among such treatment options that are considered suitable for combination with the treatment according to the present inventions are:

non-steroidal antiinflammatory drugs (NSAIDs) including COX-2 inhibitors;
opiate receptor agonists;
Cannabionoid agonists or inhibitors of the endocannabinoid pathway
Sodium channel blockers;
N-type calcium channel blockers;
serotonergic and noradrenergic modulators;
corticosteroids;
histamine H1 receptor antagonists;
histamine H2 receptor antagonists;
proton pump inhibitors;
leukotriene antagonists and 5-lipoxygenase inhibitors;
local anesthetics;
VR1 agonists and antagonists;
Nicotinic acetylcholine receptor agonists;
P2X3 receptor antagonists;
NGF agonists and antagonists or anti-NGF antibodies;
NK1 and NK2 antagonists;
Bradykinin B1 antagonists
CCR2 antagonists
iNOS or nNOS or eNOS inhibitors
NMDA antagonist;
potassium channel modulators;
GABA modulators;
serotonergic and noradrenergic modulators;
anti-migraine drugs;
neuropathic pain drugs such as pregabaline or duloxetine.

Said list is not considered to have a limiting character.

In the Following Representative Examples of Such Treatment Options Shall be Given.

Non-steroidal antiinflammatory drugs (NSAIDs) including COX-2 inhibitors: propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenylcarboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) and the like;

Antiviral drugs like acyclovir, tenovir, pleconaril, peramivir, pocosanol and the like.

Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol and the like;

Opiate receptor agonists: morphine, propoxyphene (Darvon), tramadol, buprenorphin and the like.

Glucocorticosteroids such as bethamethasone, budesonide, dexamethasone, hydrocortisone, methylprednisolone, prednisolone, prednisone, triamcinolone and deflazacort;

immunosuppressive, immunomodulatory, or cytsostatic drugs including but not limited to hydroxychlorquine, D-penicillamine, sulfasalizine, auranofin, gold mercaptopurine, tacrolimus, sirolimus, mycophenolate mofetil, cyclosporine, leflunomide, methotrexate, azathioprine, cyclophosphamide and glatiramer acetate and novantrone, fingolimod (FTY720), minocycline and thalidomide and the like;

anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab and the like;

IL-1 receptor antagonists such as but not limited to Kineret;

Sodium channel blockers: carbamazepine, mexiletine, lamotrigine, tectin, lacosamide and the like.

N-type calcium channel blockers: Ziconotide and the like.

Serotonergic and noradrenergic modulators: paroxetine, duloxetine, clonidine, amitriptyline, citalopram;

Histamine H1 receptor antagonists: bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, deslo-ratadine, fexofenadine and levocetirizine and the like;

Histamine H2 receptor antagonists: cimetidine, famotidine and ranitidine and the like;

Proton pump inhibitors: omeprazole, pantoprazole and esomeprazole and the like;

Leukotriene antagonists and 5-lipoxygenase inhibitors: zafirlukast, mon-telukast, pranlukast and zileuton and the like;

Local anesthetics such as ambroxol, lidocaine and the like;

Potassium channel modulators: like retigabine;

GABA modulators: lacosamide, pregabalin, gabapentin and the like;

Anti-migraine drugs: sumatriptan, zolmitriptan, naratriptan, eletriptan, telcegepant and the like;

NGF antibodies such as RI-724 and the like.

Combination therapy is also possible with new principles for the treatment of pain e.g. P2X3 antagonists, VR1 antagonists, NK1 and NK2 antagonists, NMDA antagonists, mGluR antagonists and the like.

The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased pharmacological effect, or some other beneficial effect of the combination compared with the individual components.

EXPERIMENTAL SECTION

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

Abbreviations:
AcOH acetic acid
ALOX B aluminium oxide
aq aqueous
BSTFA N,O-bis(trimethylsilyl) trifluoroacetamide
Boc tert-butoxycarbonyl
CE chromatography equipment
CH cyclohexane
conc concentrated
DCM dichloromethane
DIC N,N-diisopropylcarbodiimide
DIPEA N-ethyldiisopropylamine
DMAP N,N-dimethylaminopyridine
DMSO dimethylsulphoxide
DMF N,N-dimethylformamide
EDC 1-(3-dimethylaminopropyl)-3-ethylcarbodiimide hydrochloride
EtOAc ethyl acetate
Et2O diethyl ether
EtOH ethanol
HBTU O-(benzotriazol-1-yl)-N,N,N',N'-tetramethyluronium hexafluorophospate HPLC high performance liquid chromatography
i-PrOH isopropanol
MeCN acetonitrile
MeOH methanol
MS mass spectrometry
MTBE methyl-tert-butyl ether
Pd/C 10% Palladium on carbon
PE petrol ether
PPA 1-propylphosphonic-acid cyclic anhydride
RP reversed phase
rt room temperature
Ra—Ni Raney-Nickel
$R_f$ retention factor
$R_t$ retention time
sat saturated
TBTU O-(benzotriazol-1-yl)-N,N,N',N'-tetramethyluronium tetrafluoroborate
TCDI thiocarbonyl diimidazole
TEA triethylamine
THF tetrahydrofuran
TFA trifluoroacetic acid
TLC thin layer chromatography
Analytical Methods All compounds specified in the examples below give the correct mass spectra matching the theoretical isotope pattern. For practical reasons, only one of the major isotope peaks is given as representative data for the mass spectrum.

The TLC data is obtained by using the following tlc plates
a) Silica gel plates 60 F254 Merck No 1.05714.0001 abbreviated in the experimental part as "silica gel"
b) Reversed phase plates: RP-8 F 254 s Merck No: 1.15684.0001 abbreviated in the experimental part as "RP-8".
c) Aluminiumoxide plates 60 F254 Merck 1.05713.0001 abbreviated in the experimental part as "Alox"

The $R_f$ values given are determined without chamber saturation.

Flash chromatography purifications are performed using silica gel from Millipore (MATREX™, 35 bis 70 μm) or Alox (E. Merck, Darmstadt, Aluminiumoxid 90 standardisiert, 63 bis 200 μm, Artikel-Nr: 1.01097.9050).

The HPLC/MS data, where specified, are obtained under the following conditions:

CE 1:
Agilent 1200 with binary pump, Agilent MS 6140, HiPALS1367C

The diode array detection took place in a wavelength range from 190-400 nm.

Range of mass-spectrometric detection: m/z 100 to m/z 1000.

CE 2:
Agilent HP 1200 with binary pump, Agilent MS 1200

The diode array detection took place in a wavelength of 254 nm and 230 nm.

Range of mass-spectrometric detection: m/z 100 to m/z 800.

CE 3:
Agilent HP 100 with binary pump, WatersZQ2000,

The diode array detection is measured in a wavelength of 210-500 nm.

Range of mass-spectrometric detection: m/z 120 to m/z 820.

CE 4:
Acquity HPLC, Waters SQD MS,

The diode array detection is measured in a wavelength of 210-500 nm.

Range of mass-spectrometric detection: m/z 120 to m/z 820.

The following methods are used:

Method A (CE 1)
Mobile phase: E1: water with 0.15% formic acid, E2: MeCN
Stationary phase: (column temperature: constant at 25° C.): XBridge C18, 2.5 μm, 3.0×30 mm
Eluent Gradient:

| time in min | % E1 | % E2 | flow rate in mL/min |
|---|---|---|---|
| 0.0 | 95 | 5 | 1.6 |
| 2.25 | 10 | 90 | 1.6 |
| 2.50 | 10 | 90 | 1.6 |
| 2.75 | 90 | 10 | 1.6 |

Method B (CE1):
Mobile phase: E1: water with 0.15% formic acid, E2: MeCN
Stationary phase: (column temperature: constant at 25° C.): Zorbax Stable Bond C18, 1.8 μm, 3.0×30 mm
Eluent Gradient:

| time in min | % E1 | % E2 | flow rate in mL/min |
|---|---|---|---|
| 0.00 | 95 | 5 | 1.6 |
| 1.00 | 10 | 90 | 1.6 |
| 2.50 | 10 | 90 | 1.6 |
| 2.75 | 95 | 5 | 1.6 |

Method C(CE1):
Mobile phase and eluent gradient as described in method A.
Stationary phase: (column temperature: constant at 25° C.): Zorbax Stable Bond C18, 1.8 μm, 3.0×30 mm Method D (CE1):
Mobile phase: E1: water with 0.15% formic acid, E2: MeCN
Stationary phase: (column temperature: constant at 25° C.): Zorbax Stable Bond C18, 1.8 μm, 3.0×30 mm
Eluent Gradient:

| time in min | % E1 | % E2 | flow rate in mL/min |
|---|---|---|---|
| 0.00 | 95 | 5 | 1.6 |
| 2.00 | 50 | 50 | 1.6 |
| 2.25 | 10 | 90 | 1.6 |
| 2.50 | 10 | 90 | 1.6 |
| 2.75 | 95 | 5 | 1.6 |

Method E (CE1):
Mobile phase and eluent gradient as described in method B.
Stationary phase: (column temperature: constant at 25° C.): XBridge C18, 2.5 μm, 3.0×30 mm Method F (CE2):
Mobile phase: E1: water with 0.2% formic acid, E2: MeOH with 3% water
Stationary phase: (column temperature: constant at 40° C.): XBridge C18, 2.5 μm, 3.0×30 mm
Eluent Gradient:

| time in min | % E1 | % E2 | flow rate in mL/min |
|---|---|---|---|
| 0.00 | 95 | 5 | 1.3 |
| 0.20 | 95 | 5 | 1.3 |
| 2.20 | 5 | 95 | 1.3 |
| 2.30 | 5 | 95 | 1.3 |
| 2.40 | 0 | 100 | 1.3 |
| 2.60 | 0 | 100 | 1.3 |

Method G (CE2):
Mobile phase: E1: water with 0.2% formic acid, E2: MeOH with 3% water
Stationary phase: (column temperature: constant at 25° C.): XBridge C18, 2.5 μm, 3.0×30 mm. Eluent gradient:

| time in min | % E1 | % E2 | flow rate in mL/min |
|---|---|---|---|
| 0.00 | 95 | 5 | 1.4 |
| 1.60 | 50 | 50 | 1.4 |
| 1.80 | 10 | 90 | 1.4 |
| 2.00 | 10 | 90 | 1.4 |
| 2.20 | 95 | 5 | 1.4 |

Method H (CE 4)

Stationary phase (column temperature: constant at 60° C.): Supelco; Ascentis Express C18, 2.7 µm, 2.1×50 mm Mobile phase: E1: water with 0.1% TFA, E2: MeCN+ 0.08% TFA Eluent Gradient:

| time in min | % E1 | % E2 | flow rate in mL/min |
|---|---|---|---|
| 0.0 | 95 | 5 | 1.5 |
| 0.70 | 0 | 100 | 1.5 |
| 0.80 | 0 | 100 | 1.5 |
| 0.81 | 95 | 5 | 1.5 |
| 1.90 | 95 | 5 | 0.2 |
| 2.00 | 0 | 100 | 0.2 |
| 3.00 | 0 | 5 | 0.2 |

Method I (CE 3):

Stationary phase (column temperature: constant at 60° C.): XBridge C18, 3.5 µm, 4.6×50 mm Mobile phase: E1: water with 0.1% NH$_4$OH, E2: MeOH Eluent Gradient:

| time in min | % E1 | % E2 | flow rate in mL/min |
|---|---|---|---|
| 0.0 | 80 | 20 | 2.0 |
| 1.70 | 0 | 100 | 2.0 |
| 2.50 | 0 | 100 | 2.0 |
| 2.60 | 80 | 20 | 2.0 |

Method J (CE 4):

Stationary phase (column temperature: constant at 60° C.): Waters Sunfire C18, 3.5 µm, 4.6×50 mm Mobile phase: E1: water with 0.1% TFA, E2: MeCN with 0.1% TFA Eluent Gradient:

| time in min | % E1 | % E2 | flow rate in mL/min |
|---|---|---|---|
| 0.0 | 95 | 5 | 1.5 |
| 2.00 | 0 | 100 | 1.5 |
| 2.50 | 0 | 100 | 1.5 |
| 2.60 | 95 | 5 | 1.5 |

Method K (CE 4)

Stationary phase (column temperature: constant at 60° C.): Waters XBridge C18, 1.7 µm, 2.1×50 mm Mobile phase: E1: water with 0.1% NH$_4$OH, E2: MeCN Eluent Gradient:

| time in min | % E1 | % E2 | flow rate in mL/min |
|---|---|---|---|
| 0.0 | 95 | 5 | 1.5 |
| 0.70 | 0 | 100 | 1.5 |
| 0.80 | 0 | 100 | 1.5 |
| 0.81 | 95 | 5 | 1.5 |
| 1.90 | 95 | 5 | 0.2 |
| 2.00 | 0 | 100 | 0.2 |
| 3.00 | 0 | 5 | 0.2 |

Synthesis of building blocks of the 2,3,4-trisubstituted benzylamine-type

Building Block A:

N-(2,4-Dichloro-3-isothiocyanato-benzyl)-2,2-dimethyl-propionamide

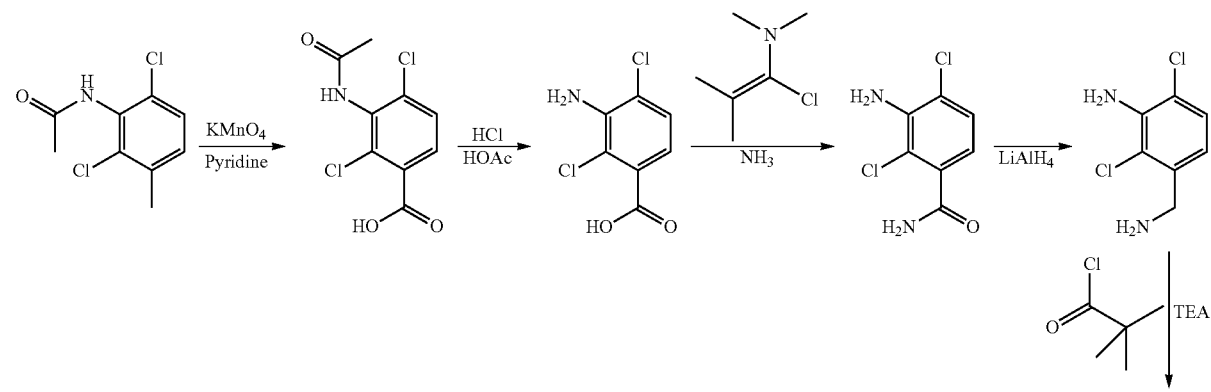

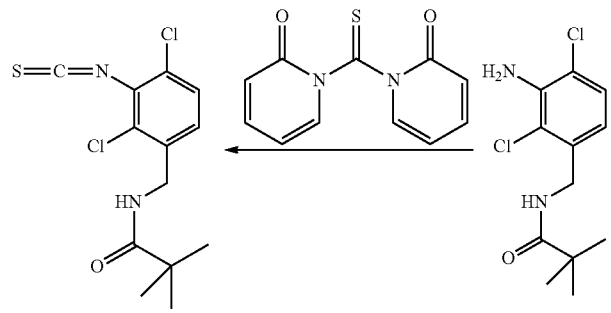

(a) 3-Acetylamino-2,4-dichloro-benzoic acid

Water (110 mL) is added to N-(2,6-dichloro-3-methyl-phenyl)-acetamide (13 g, 59 mmol) in pyridine (30 mL). The mixture is heated to 70° C. and $KMnO_4$ (47 g, 298 mmol) is cautiously added portionwise. After 6 h at reflux the reaction mixture is filtered through a pad of celite and washed with hot water. The filtrate is cooled to rt, concentrated and slowly acidified with 6 M aq. HCl solution. The mixture is cooled in an ice bath, filtered and the filtercake is washed with cold water and dried to give the sub-title compound.

Yield: 11.6 g (78%). $R_f$=0.1 (silica gel, DCM:EtOH 9:1). MS m/z: 248 $[M+H]^+$.

(b) 3-Amino-2,4-dichloro-benzoic acid

3-Acetylamino-2,4-dichloro-benzoic acid (21.0 g, 84.6 mmol) is stirred in 6 M aq. HCl-solution (120 mL) and acetic acid (250 mL) at reflux for 24 h. The reaction mixture is cooled, concentrated, diluted with water and concentrated again. The residue is diluted with water, stirred under cooling and filtered. The filtercake is washed and dried to give the sub-title compound.

Yield: 16.8 g (96%). MS m/z: 204 $[M-H]^-$. HPLC-method C: $R_t$=1.46 min.

(c) 3-Amino-2,4-dichloro-benzamide (1-Chloro-2-methyl-propenyl)-dimethyl-amine (16.1 mL, 116 mmol) is added to 3-amino-2,4-dichloro-benzoic acid (20.0 g, 97.1 mmol) in THF (320 mL). After 4 h at rt the mixture is added dropwise to conc. $NH_3$ (320 mL) and stirred at rt overnight. The reaction mixture is concentrated, cooled and filtered. The filtercake is dried to give the sub-title compound.

Yield: 17.4 g (87%). MS m/z: 205 $[M+H]^+$. HPLC-method C: $R_t$=1.19 min.

(d) 3-Amino-2,4-dichloro-benzylamine

3-Amino-2,4-dichloro-benzamide (2.00 g, 9.8 mmol) in THF (45 mL) is added dropwise to $LiAlH_4$ (1 M in THF, 24.4 mL) in THF (45 mL). The reaction mixture is stirred for 1 h at rt and 10 h at reflux. Excess $LiAlH_4$ is destroyed under cooling as described by L. F. Fieser & M. Fieser Vol 1, p 584 Wiley 1967. After 30 min the mixture is filtered and the filtrate is concentrated to give the sub-title compound.

Yield: 1.85 g (99%). $R_f$=0.12 (silica gel, DCM:EtOH 95:5). MS m/z: 191 $[M+H]^+$.

(e) N-(3-Amino-2,4-dichloro-benzyl)-2,2-dimethyl-propionamide

3-Amino-2,4-dichloro-benzylamine (2.28 g, 11.9 mmol) is added to a mixture of 2,2-dimethyl-propionic acid chloride (1.47 mL, 11.9 mmol) and TEA (4.14 mL, 29.8 mmol) in THF (90 mL) and it is stirred for 3 h. The reaction mixture is concentrated, diluted with EtOAc, washed with 5% aq. $NaHCO_3$ solution and water, dried with $Na_2SO_4$ filtered and concentrated to give the sub-title compound.

Yield: 3.1 g (94%). $R_f$=0.61 (silica gel, DCM:EtOH 95:5).

(f) N-(2,4-Dichloro-3-isothiocyanato-benzyl)-2,2-dimethyl-propionamide 1,1'-Thiocarbonyldi-2-pyridone (4.87 g, 21 mmol) is added to a mixture of N-(3-amino-2,4-dichloro-benzyl)-2,2-dimethyl-propionamide (5.50 g, 20 mmol) and dioxane (200 mL) and stirred at rt for 2 h and at reflux for 8 h. The mixture is concentrated, diluted with DCM and filtered over silica gel. The filtrate is concentrated to give the sub-title compound.

Yield: 6.00 g (95%). HPLC-method B: $R_t$=1.58 min. MS m/z: 318 $[M+H]^+$.

Alternatively, building block A can also be prepared according to the following scheme:

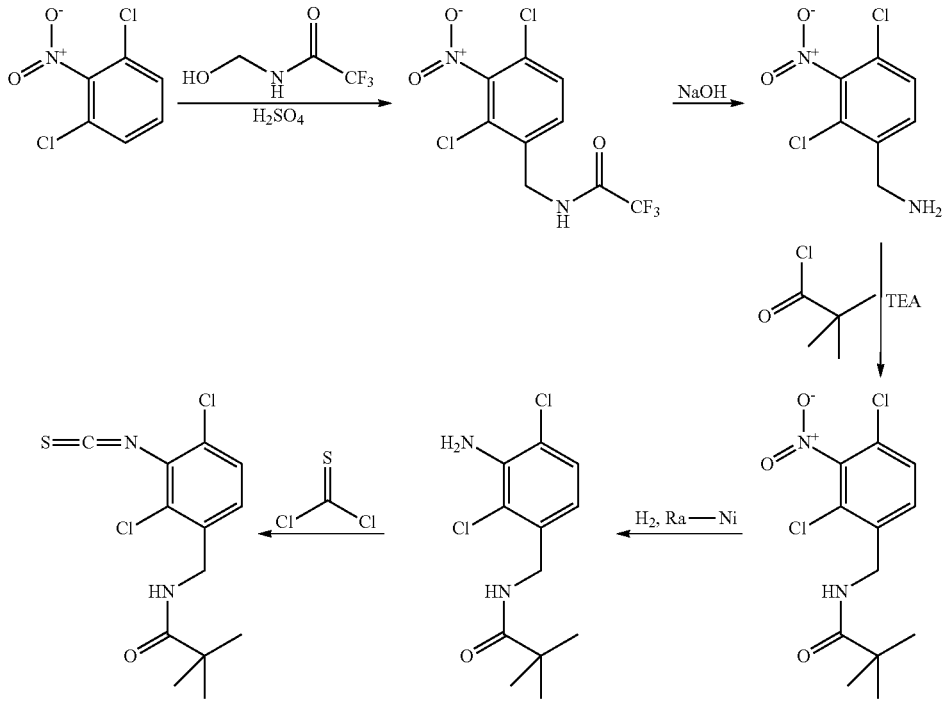

(g) N-(3-Nitro-2,4-dichloro-benzyl)-2,2,2-trifluoro-acetamide

N-(Hydroxymethyl)trifluoroacetamide (6.6 mmol; 0.946 g) is added to a mixture of 2,6-dichloro-nitrobenzene (0.899 mL; 6.6 mmol) and conc. $H_2SO_4$ (15 mL) at 75° C. The mixture is stirred at 75° C. overnight, poured into ice water and stirred for 1 h. The precipitate is collected by filtration and dried. Yield 0.32 g (15%). MS [M−H]$^-$=315, HPLC-method B: $R_t$=1.43 min.

(h) 3-Nitro-2,4-dichloro-benzylamine

A mixture of N-(3-nitro-2,4-dichloro-benzyl)-2,2,2-trifluoroacetamide (0.66 g, impure, content ~50%), 4M NaOH-solution (1.3 mL, 5.2 mmol) and MeOH (15 mL) is refluxed for 4 h. Then the mixture is concentrated, diluted with water, acidified with 4M HCl, filtered, 4M NaOH-solution is added and it is extracted with EtOAc. The organic phase is dried with $Na_2SO_4$, filtered and concentrated. Yield 0.17 g MS m/z: 221 [M+H]$^+$. HPLC-method B: $R_t$=1.02 min.

(i) N-(3-Nitro-2,4-dichloro-benzyl)-2,2-dimethyl-propionamide 2,2-Dimethyl-propionic acid chloride (0.124 mL, 1.01 mmol) is added to a mixture of 3-nitro-2,4-dichloro-benzylamine (0.28 g, 1.01 mmol) and TEA (0.35 mL, 2.52 mmol) in THF (10 mL) and it is stirred overnight. The reaction mixture is concentrated, diluted with EtOAc, washed successively with 5% aq. $NaHCO_3$ solution and brine, dried with $Na_2SO_4$ filtered and concentrated.

Yield: 0.29 g. MS m/z: 306 [M+H]$^+$. HPLC-method B: $R_t$=1.42 min.

(g) N-(3-Amino-2,4-dichloro-benzyl)-2,2-dimethyl-propionamide

A mixture of 3-nitro-2,4-dichloro-benzylamine (290 mg, 0.95 mmol), Ra—Ni (50 mg) and THF (15 mL) is stirred for 7 h under a hydrogen atmosphere (50 psi). The catalyst is removed by filtration and the filtrate is concentrated.

Yield: 0.26 g. MS m/z: 276 [M+H]$^+$. HPLC-method B: $R_t$=1.32 min.

(h) N-(2,4-Dichloro-3-isothiocyanato-benzyl)-2,2-dimethyl-propionamide

A mixture of N-(3-amino-2,4-dichloro-benzyl)-2,2-dimethyl-propionamide (0.95 g, 3.4 mmol) in 4.0 mL dioxane is added to thiophosgene (0.45 mL, 5.8 mmol) in 2.5 mL water. The mixture is stirred overnight, extracted with DCM and the organic phase is washed with 5% aq $NaHCO_3$ solution and water and dried with $Na_2SO_4$. After filtration and concentration, the crude product is diluted with DCM, filtered through a pad of silica gel and concentrated.

Building Block B:

(2,4-Dichloro-3-isothiocyanato-benzyl)-carbamic acid tert-butyl ester

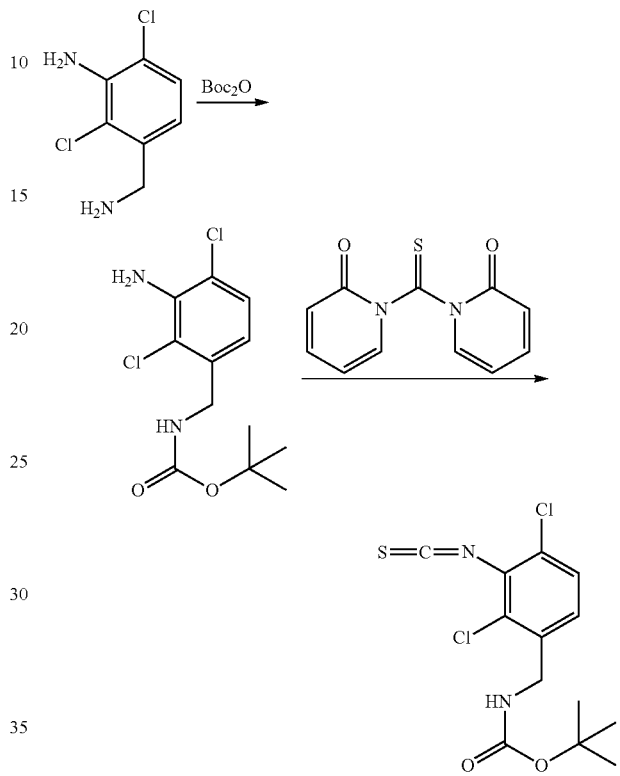

(a) (3-Amino-2,4-dichloro-benzyl)-carbamic acid tert-butyl ester $Boc_2O$ (1.48 g, 6.68 mmol) in 3.3 mL DCM is added at 0° C. to a mixture of 3-amino-2,4-dichloro-benzylamine (1.16 g, 6.07 mmol), 6.7 mL DCM and 12.1 mL 1 N NaOH-solution. The mixture is stirred vigourously for 2d and diluted with 5% aq $NH_3$-solution. The organic phase is separated and the aq. phase is washed 2× with DCM. The combined organic phase is washed with brine, dried with $Na_2SO_4$, filtered and concentrated to give the sub-title compound.

Yield: 1.71 g (97%). $R_f$=0.65 (silica gel, DCM:EtOH 95:5). MS m/z: 291 [M+H]$^+$.

(b) (2,4-Dichloro-3-isothiocyanato-benzyl)-carbamic acid tert-butyl ester 1,1'-Thiocarbonyldi-2-pyridone (0.42 g, 1.8 mmol) is added to a mixture of (3-amino-2,4-dichloro-benzyl)-carbamic acid tert-butyl ester (0.50 g, 1.7 mmol) and dioxane (25 mL) and stirred at rt for 2 h and at reflux for 2 d. The mixture is concentrated, diluted with DCM and filtered over silica gel. The filtrate is concentrated to give the title compound.

Yield: 0.49 g (86%). $R_f$=0.83 (silica gel, DCM:EtOH 95:5).

Building Block C:

N-(2,4-Difluoro-3-isothiocyanato-benzyl)-2,2-dimethyl-propionamide

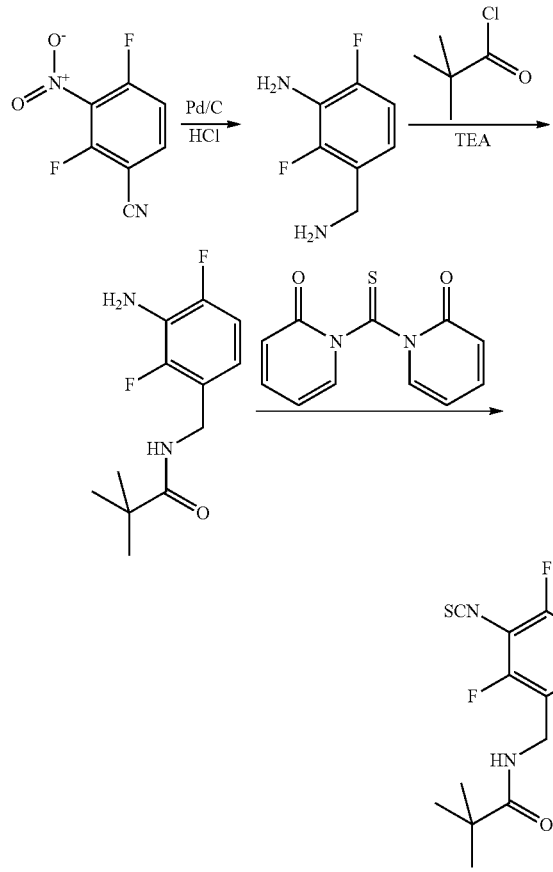

(a) 3-Aminomethyl-2,6-difluoro-aniline

A mixture of 3-nitro-2,4-difluoro-benzonitrile (500 mg, 2.72 mmol), Pd/C (200 mg), conc. HCl (1.50 mL, 18.0 mmol) and MeOH (25 mL) is stirred at rt overnight under a hydrogen atmosphere (3.2 bar). The catalyst is removed by filtration, the filtrate is concentrated and evaporated twice from EtOH to give the sub-title compound as HCl salt.

Yield: 580 mg. MS m/z: 159 [M+H]$^+$.

(b) N-(3-Amino-2,4-difluoro-benzyl)-2,2-dimethyl-propionamide

TEA (400 µL, 2.86 mmol) followed by pivaloyl chloride (60 µL, 0.52 mmol) are added to 3-aminomethyl-2,6-difluoro-aniline (120 mg as HCl salt) in THF (10 mL) and stirred at rt overnight. The reaction mixture is diluted with EtOAc and sat. NaHCO$_3$-solution, the organic layer is washed with water and brine, dried and concentrated to give the sub-title compound.

Yield: 110 mg. HPLC-method B: R$_t$=1.19 min. MS m/z: 243 [M+H]$^+$. R$_f$=0.45 (silica gel, DCM:EtOH 95:5).

(c) N-(2,4-Difluoro-3-isothiocyanato-benzyl)-2,2-dimethyl-propionamide

A mixture of N-(3-amino-2,4-difluoro-benzyl)-2,2-dimethyl-propionamide (570 mg, 2.35 mmol), 1,1'-thiocarbonyldi-2(1H)-pyridone (550 mg, 2.35 mmol) and dioxane (20 mL) is stirred at reflux overnight. The reaction mixture is concentrated, diluted with DCM, filtered through a pad of silica gel and the filtrate is concentrated to give the title compound.

Yield: 440 mg (65%). R$_f$=0.80 (silica gel, DCM:EtOH 95:5).

Building Block D:

N-(4-Chloro-fluoro-3-isothiocyanato-benzyl)-2,2-dimethyl-propionamide

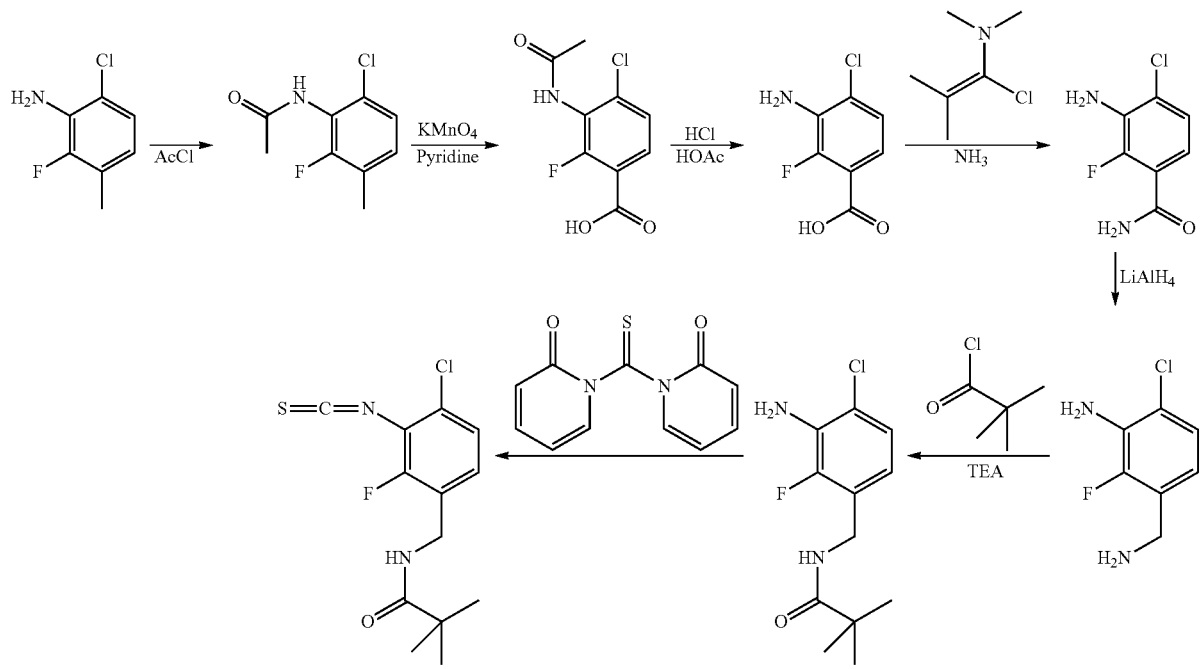

(a) N-(6-Chloro-2-fluoro-3-methyl-phenyl)-acetamide

Acetylchloride (2.56 mL, 36.0 mmol) is added to a mixture of 6-chloro-2-fluoro-3-methyl-aniline (5.00 g, 31.3 mmol) and toluene (200 mL), additional toluene (50 mL) is added and the mixture is heated to reflux for 3 h. Then it is cooled with an ice bath and the formed precipitate is filtered off, washed with cold toluene and dried.

Yield: 4.75 g (75%). HPLC-method B: $R_t$=1.12 min. MS m/z: 202 [M+H]$^+$.

(b) 3-Acetylamino-4-chloro-2-fluoro-benzoic acid

The sub-title compound is prepared from N-(6-chloro-2-fluoro-3-methyl-phenyl)-acetamide and KMnO$_4$ in pyridine in analogy to step Aa.

Yield: 49%. $R_f$=0.2 (silica gel, DCM/EtOH 4:1). HPLC $R_t$=0.93 min (method B). MS m/z: 232 [M+H]$^+$.

(c) 3-Amino-4-chloro-2-fluoro-benzoic acid

The sub-title compound is prepared from 3-acetylamino-4-chloro-2-fluoro-benzoic acid and 6 M HCl-solution in analogy to step Ab.

Yield: 96%. HPLC $R_t$=1.10 min (method B). MS m/z: 190 [M+H]$^+$.

(d) 3-Amino-4-chloro-2-fluoro-benzamide

The sub-title compound is prepared from 3-amino-4-chloro-2-fluoro-benzoic acid, (1-chloro-2-methyl-propenyl)-dimethyl-amine and conc. NH$_3$ in analogy to step Ac.

Yield: 69%. $R_f$=0.3 (silica gel, PE:EtOAc 4:6). HPLC-method B: $R_t$=0.97 min. MS m/z: 189 [M+H]$^+$.

(e) 3-Amino-4-chloro-2-fluoro-benzylamine

The crude sub-title compound is prepared from 3-amino-4-chloro-2-fluoro-benzamide and LiAlH$_4$ in analogy to step Ad.

HPLC-method B: $R_t$=0.37 min. MS m/z: 175 [M+H]$^+$.

(f) N-(3-Amino-4-chloro-2-fluoro-benzyl)-2,2-dimethyl-propionamide

The sub-title compound is prepared from crude 3-amino-4-chloro-2-fluoro-benzylamine, 2,2-dimethyl-propionic acid chloride and TEA in analogy to step Ae.

Yield: 36% (side product in 29%: N-(3-Amino-4-chloro-benzyl)-2,2-dimethyl-propionamide). $R_f$=0.6 (silica gel, PE:EtOAc 6:4). HPLC-method B: $R_t$=1.27 min. MS m/z: 259 [M+H]$^+$.

(g) N-(4-Chloro-2-fluoro-3-isothiocyanato-benzyl)-2,2-dimethyl-propionamide

The title compound is prepared from N-(3-amino-4-chloro-2-fluoro-benzyl)-2,2-dimethyl-propionamide, 1,1'-thiocarbonyldi-2-pyridone in analogy to step Af.

Yield: 65%. $R_f$=0.9 (silica gel, DCM:EtOH 95:5).

Building Block E:

N-(2,4-Dimethyl-3-isothiocyanato-benzyl)-2,2-dimethyl-propionamide

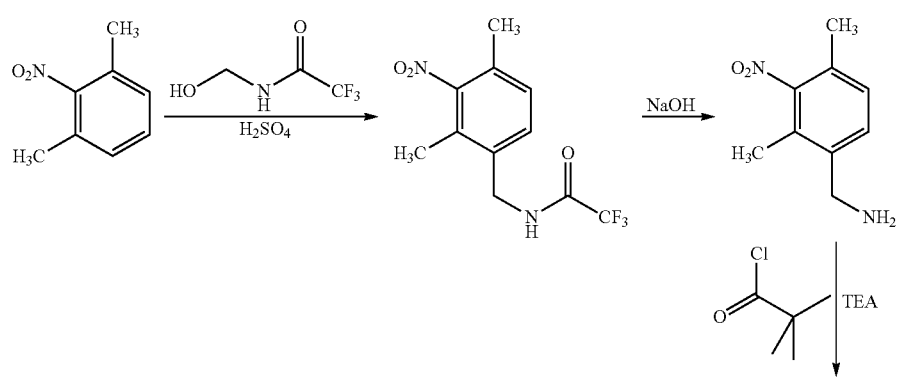

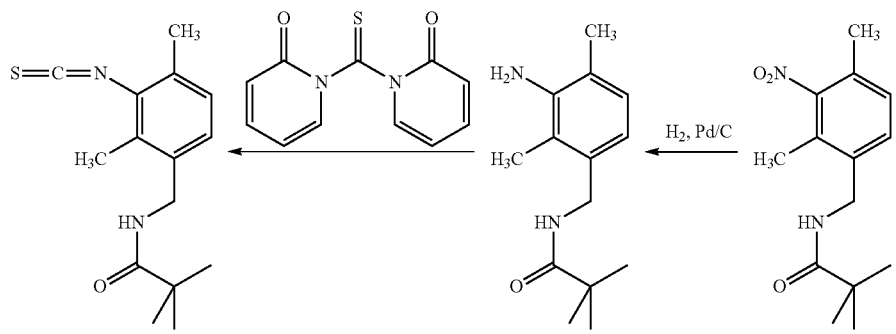

(a) N-(3-Nitro-2,4-dimethyl-benzyl)-2,2,2-trifluoro-acetamide

N-(Hydroxymethyl)trifluoroacetamide (6.6 mmol; 0.946 g) is added to a mixture of 2,6-dimethyl-nitrobenzene (0.899 mL; 6.6 mmol) and conc. $H_2SO_4$ (15 mL). The mixture is stirred at rt overnight, poured into ice water and stirred for 2 h. The precipitate is collected by filtration and dried. Yield 1.5 g (84%). MS [M−H]⁻=275, TLC: $R_f$=0.67 (silica gel, DCM:EtOH 95:5)).

(b) 3-Nitro-2,4-dimethyl-benzylamine

A mixture of N-(3-nitro-2,4-dimethyl-benzyl)-2,2,2-trifluoroacetamide (1.53 g, 5.54 mmol), 4M NaOH-solution (6.9 mL, 28 mmol) and MeOH (30 mL) is refluxed for 2 h. Then the mixture is concentrated, diluted with water and extracted with EtOAc. The organic phase is dried with $Na_2SO_4$, filtered and concentrated.

MS m/z: 181 [M+H]⁺. HPLC-method C: $R_t$=1.13 min.

(c) N-(3-Nitro-2,4-dimethyl-benzyl)-2,2-dimethyl-propionamide

3-Nitro-2,4-dimethyl-benzylamine (1.40 g, crude) is added to a mixture of 2,2-dimethyl-propionic acid chloride (0.682 mL, 5.5 mmol) and TEA (1.92 mL, 13.8 mmol) in THF (30 mL) and it is stirred overnight. The reaction mixture is concentrated, diluted with EtOAc, washed successively with 2 M HCl-solution, 5% aq. $NaHCO_3$ solution and water, dried with $Na_2SO_4$ filtered and concentrated.

Yield: 1.41 g. MS m/z: 265 [M+H]⁺. HPLC-method B: $R_t$=1.37 min.

(d) N-(3-Amino-2,4-dimethyl-benzyl)-2,2-dimethyl-propionamide

A mixture of N-(3-nitro-2,4-dimethyl-benzyl)-2,2-dimethyl-propionamide (500 mg, 1.89 mmol), Pd/C (50 mg) and MeOH (20 mL) is stirred for 9 h under a hydrogen atmosphere (50 psi). The catalyst is removed by filtration and the filtrate is concentrated.

Yield: 0.42 g. MS m/z: 235 [M+H]⁺. HPLC-method B: $R_t$=1.32 min.

(e) N-(2,4-Dimethyl-3-isothiocyanato-benzyl)-2,2-dimethyl-propionamide

The title compound is prepared from N-(3-amino-2,4-dimethyl-benzyl)-2,2-dimethyl-propionamide, 1,1'-thiocarbonyldi-2-pyridone in analogy to example Af.

Yield: 65%. $R_f$=0.81 (silica gel, DCM:EtOH 95:5).

Building Block F:

N-(2,4-Dichloro-3-isothiocyanato-benzyl)-1-trifluoromethyl-cyclopropane carboxamide

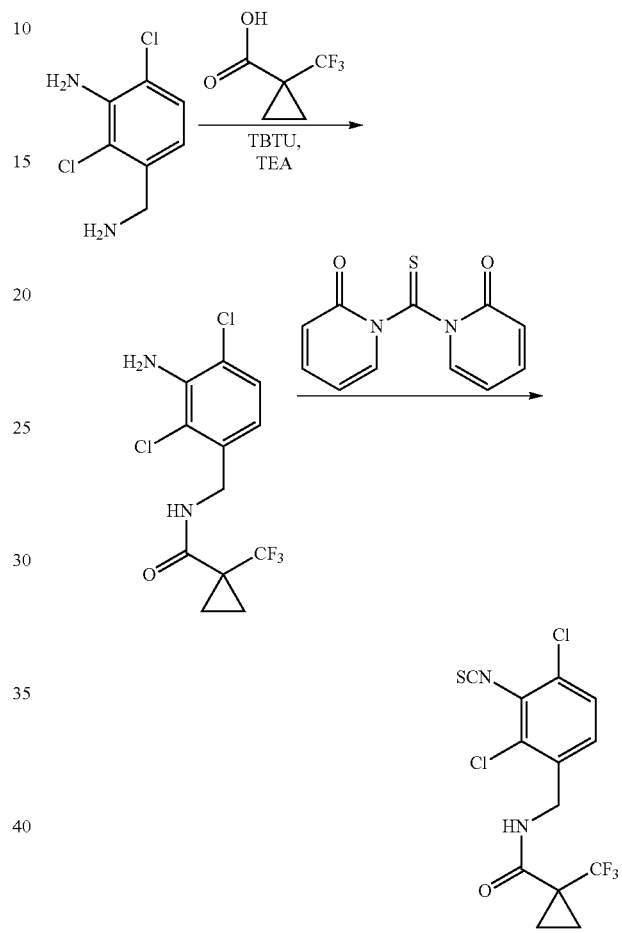

(a) N-(2,4-Dichloro-3-amino-benzyl)-1-trifluoromethyl-cyclopropane carboxamide The sub-title compound is prepared from 3-amino-2,4-dichloro-benzylamine (0.310 g, 1.01 mmol), 1-trifluoromethyl-cyclopropane carboxylic acid (0.17 g, 1.1 mmol), TBTU (0.39 g, 1.2 mmol) and TEA (0.71 mL) in DMF in analogy to example 3e.

Yield: 289 mg (83%). MS m/z: 327 [M+H]⁺.

(b) N-(2,4-Dichloro-3-isothiocyanato-benzyl)-1-trifluoromethyl-cyclopropane carboxamide The title compound is prepared from N-(2,4-dichloro-3-amino-benzyl)-1-trifluoromethyl-cyclopropane carboxamide (150 mg, 0.45 mmol) and 1,1'-thiocarbonyldi-2-pyridone (89 mg, 0.38 mmol) in analogy to example Af.

Yield: 92 mg (crude).

Example 1
N-{4-Chloro-3-[6-(4-bromo-phenylcarbamoyl)-5-(2,2-difluoro-ethoxy)-3-methyl-3H-imidazo[4,5-b]pyridin-2-ylamino]benzyl}-2,2-dimethyl-propionamide
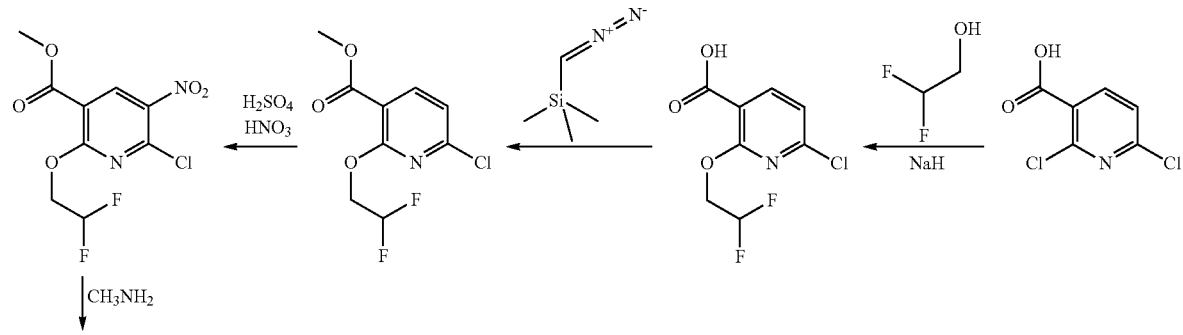
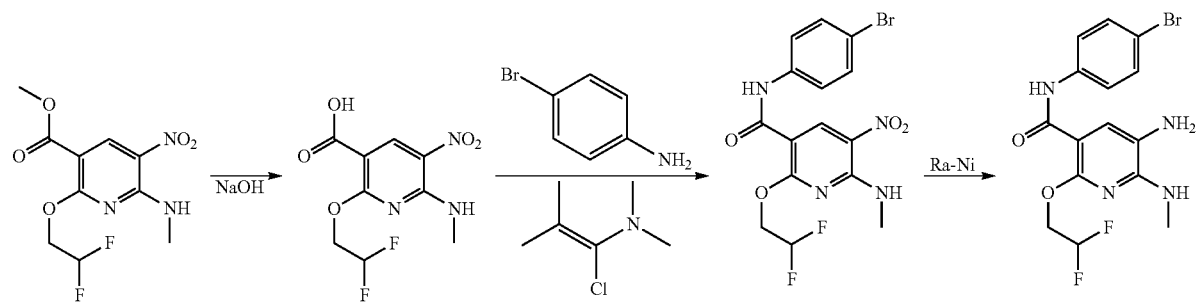
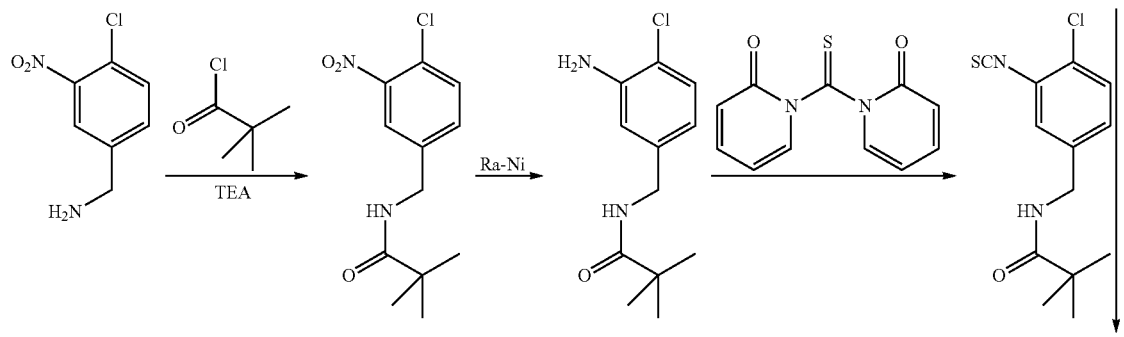
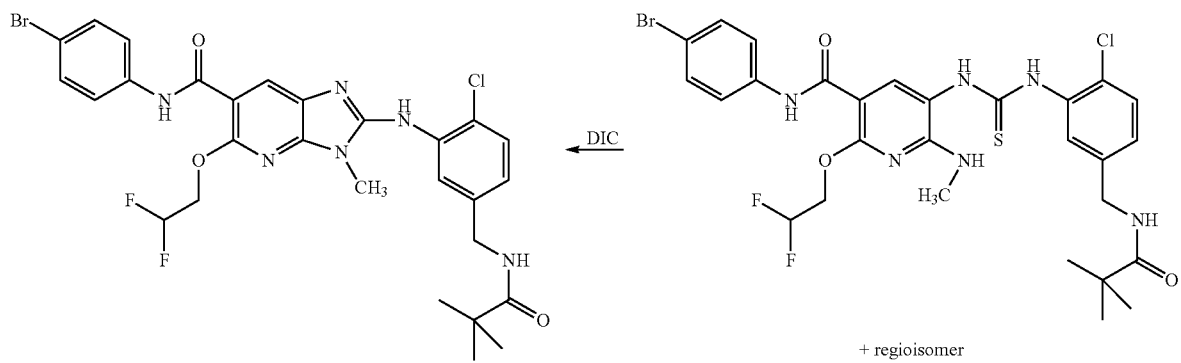
+ regioisomer

(a) 6-Chloro-2-(2,2-difluoro-ethoxy)-nicotinic acid

NaH (55% dispersion in oil; 5.0 g, 114.6 mmol) is added portionwise at 10° C. to 2,2-difluoroethanol (6.25 mL, 99.0 mmol), DCM (200 mL) and THF (75 mL). After 10 min 2,6-dichloro-nicotinic acid (5.0 g, 24.7 mmol) is added to the reaction mixture and it is stirred at rt overnight. Then water is added and it is concentrated. The residue is diluted with water and extracted with $Et_2O$. Formic acid is added to the aqueous layers the precipitate is filtered off, washed with water and dried to give the sub-title compound.

Yield: 5.6 g (95%). HPLC-method A: $R_f$=1.72 min. MS m/z: 238 $[M+H]^+$.

(b) 6-Chloro-2-(2,2-difluoro-ethoxy)-nicotinic acid methyl ester

Trimethylsilyl diazomethane (2 M in hexane; 15.0 mL, 30.0 mmol) is added to a mixture of 6-chloro-2-(2,2-difluoro-ethoxy)-nicotinic acid (6.0 g, 25.3 mmol) in MeOH (50 mL) and DCM (100 mL). The reaction mixture is stirred at rt for 10 min, quenched with AcOH and concentrated. The residue is diluted with water and filtered. The filtercake is washed with water and dried at 40° C.

Yield: 5.0 g (78%). HPLC-method A: $R_f$=1.99 min. MS m/z: 252 $[M+H]^+$.

(c) 6-Chloro-2-(2,2-difluoro-ethoxy)-5-nitro-nicotinic acid methyl ester

Fuming $HNO_3$ (25 mL) is added at rt to 6-chloro-2-(2,2-difluoro-ethoxy)-nicotinic acid methyl ester (10.7 g, 42.5 mmol) in concentrated $H_2SO_4$ (50 mL) and stirred for 10 min. The reaction mixture is added dropwise to ice water, stirred and filtered. The filtercake is washed with water and dried at 50° C.

Yield: 12.4 g (98%). HPLC-method A: $R_f$=2.01 min. MS m/z: 297 $[M+H]^+$.

(d) 2-(2,2-Difluoro-ethoxy)-6-methylamino-5-nitro-nicotinic acid methyl ester Methylamine (2 M in THF; 32.0 mL, 64.0 mmol) is added at 10° C. to 6-chloro-2-(2,2-difluoro-ethoxy)-5-nitro-nicotinic acid methyl ester (9.1 g, 30.7 mmol) in THF (50 mL). After 1 h at rt the reaction mixture is concentrated, treated with water and filtered. The filtercake is washed with water and dried to give the sub-title compound.

Yield: 8.4 g (94%). $R_f$(TLC): 0.21 (silica gel, CH:EtOAc 8:2). MS m/z: 292 $[M+H]^+$.

(e) 2-(2,2-Difluoro-ethoxy)-6-methylamino-5-nitro-nicotinic acid 2-(2,2-Difluoro-ethoxy)-6-methylamino-5-nitro-nicotinic acid methyl ester (1.5 g, 5.15 mmol) is stirred at rt for 5 h in a mixture of 1 M aq. NaOH solution (10 mL), water (10 mL) and THF (20 mL). The reaction mixture is diluted with water, neutralized with 1 M aq.HCl-solution, concentrated and filtered. The filtercake is washed with water and dried.

Yield: 0.9 g (62%). $R_f$(TLC): 0.22 (silica gel, PE:EtOAc 1:1). MS m/z: 278 $[M+H]^+$.

(f) N-(4-Bromo-phenyl)-2-(2,2-difluoro-ethoxy)-6-methylamino-5-nitro-nicotinamide (1-Chloro-2-methyl-propenyl)-dimethylamine (1.54 mL, 5.63 mmol) is added to 2-(2,2-difluoro-ethoxy)-6-methylamino-5-nitro-nicotinic acid (880 mg, 5.12 mmol) in DCM (15 mL) and THF (15 mL) and stirred at rt for 15 min. Pyridine (607 µL, 7.67 mmol) followed by 4-bromoaniline are added to the reaction mixture and it is stirred for 1 h at rt. The mixture is concentrated, diluted with water and filtered. The filtercake is washed with water and dried to give the sub-title compound.

Yield: 1.27 g (57%). HPLC-method B: $R_f$=1.58 min.

(g) 5-Amino-N-(4-bromo-phenyl)-2-(2,2-difluoro-ethoxy)-6-methylamino-nicotinamide A mixture of N-(4-bromo-phenyl)-2-(2,2-difluoro-ethoxy)-6-methylamino-5-nitro-nicotinamide (150 mg, 0.35 mmol), THF (10 mL) and Ra—Ni (15 mg) is stirred for 6 h at rt under a hydrogen atmosphere (3.0 bar). The catalyst is removed by filtration and the filtrate is concentrated to give the sub-title compound.

Yield: 136 mg (97%). $R_f$(TLC): 0.25 (silica gel, PE:EtOAc 1:1)

(h) N-(4-Chloro-3-nitrobenzyl)-2,2-dimethyl-propionamide

TEA (8.00 mL, 57.5 mmol) followed by pivaloyl chloride (2.80 mL, 22.8 mmol) in THF (25 mL) are added to 4-chloro-3-nitrobenzylamine (5.00 g) in THF (100 mL). The reaction mixture is diluted with THF and stirred at rt for 1.5 h. The mixture is filtered and washed and the filtrate is concentrated.

Yield: 5.92 g. HPLC-method A: $R_t$=1.911 min. MS m/z: 271 $[M+H]^+$.

(i) N-(3-Amino-4-chlorobenzyl)-2,2-dimethyl-propionamide

A mixture of N-(4-chloro-3-nitrobenzyl)-2,2-dimethyl-propionamide (5.92 g, 21.9 mmol), THF (150 mL) and Ra—Ni (1.50 g) is stirred for 2 days at RT under a hydrogen atmosphere (3.0 bar). The catalyst is removed by filtration and the mixture is concentrated and purified by chromatography.

Yield: 4.31 g (82%). $R_f$(TLC): 0.68 (silica gel, DCM:EtOH 9:1). MS m/z: 241 $[M+H]^+$.

(j) N-(4-Chloro-3-isothiocyanatobenzyl)-2,2-dimethyl-propionamide 1,1'-Thiocarbonyldi-2-pyridone (2.12 g, 9.1 mmol) is added to a mixture of N-(3-amino-4-chlorobenzyl)-2,2-dimethyl-propionamide (2.00 g, 8.3 mmol) and DCM (60 mL) and it is stirred at rt for 1.5 h. The mixture is filtered over a pad of silica gel and the organic layer is concentrated.

Yield: 1.48 g (63%). $R_f$(TLC): 0.73 (silica gel, DCM:EtOH 9:1).

(k) N-(4-Chloro-3-{[3-(4-bromo-phenylcarbamoyl)-2-(2,2-difluoro-ethoxy)-6-methylamino-pyridin-2-yl]-thioureido}-benzyl)-2,2-dimethyl-propionamide N-(4-Chloro-3-isothiocyanatobenzyl)-2,2-dimethyl-propionamide (66 mg, 0.23 mmol) is added to 5-amino-N-(4-bromo-phenyl)-2-(2,2-difluoro-ethoxy)-6-methylamino-nicotinamide (93 mg, 0.23 mmol) in MeCN (3.5 mL) and stirred at rt overnight. The reaction mixture is filtered and the filtercake is dried.

Yield: 160 mg (100%). HPLC-method A: $R_f$=2.36 min. MS m/z: 685 $[M+H]^+$.

(l) N-{4-Chloro-3-[6-(4-bromo-phenylcarbamoyl)-5-(2,2-difluoro-ethoxy)-3-methyl-3H-imidazo[4,5-b]pyridin-2-ylamino]benzyl}-2,2-dimethyl-propionamide DIC (40 µL, 0.28 mmol) is added to a mixture of N-(4-Chloro-3-{[3-(4-bromo-phenylcarbamoyl)-2-(2,2-difluoro-ethoxy)-6-methylamino-pyridin-2-yl]-thioureido}-benzyl)-2,2-dimethyl-propionamide (160 mg, 0.23 mmol) and MeCN (4 mL). The reaction mixture is stirred at 60° C. overnight, allowed to cool and filtered. The filtercake is dried to give the title compound.

Yield: 119 mg (78%). $R_f$(TLC): 0.65 (silica gel, DCM:EtOH 9:1). MS m/z: 649 [M+H]$^+$.

Example 2

N-{4-Chloro-3-[6-(trans-4-trifluoromethyl-cyclohexylcarbamoyl)-5-(2,2-difluoro-ethoxy)-3-methyl-3H-imidazo[4,5-b]pyridin-2-ylamino]benzyl}-2,2-dimethyl-propionamide

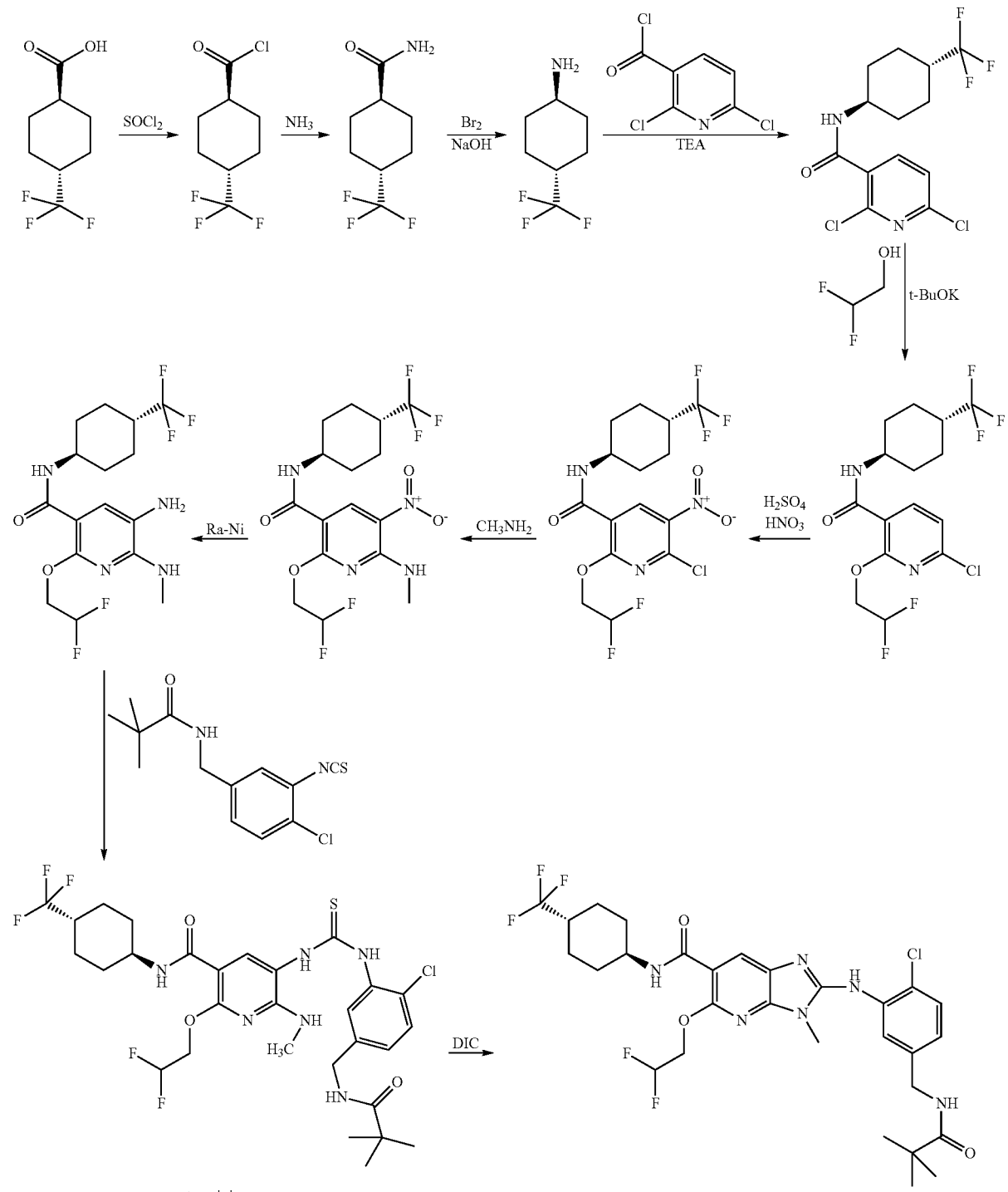

(a) trans-4-Trifluoromethyl-cyclohexanecarbonyl chloride trans-4-Trifluoromethyl-cyclohexanecarboxylic acid (2.0 g, 10.2 mmol) is stirred in thionyl chloride (30 mL) for 1 h at reflux. The reaction mixture is concentrated and used directly in the next step without further purification.

Yield: 2.2 g (100%).

(b) trans-4-Trifluoromethyl-cyclohexanecarboxamide

A mixture of trans-4-trifluoromethyl-cyclohexanecarbonyl chloride (17.3 g, 80.6 mmol) and THF (150 mL) is added dropwise at 15° C. to conc. $NH_3$ (400 mL). The reaction mixture is stirred for 15 min, concentrated and the precipitate is filtered off, washed with water and dried to give the sub-title compound.

Yield: 14.9 g (95%). MS m/z: 196 $[M+H]^+$.

(c) trans-4-Trifluoromethyl-cyclohexylamine

Bromine (4.5 mL, 87.6 mmol) is added at 10° C. to 1 M aq. NaOH solution (300 mL) and stirred at 15° C. for 15 min. After the portionwise addition of trans-4-trifluoro-methyl-cyclohexanecarboxamide (14.9 g, 76.2 mmol) the reaction mixture is stirred at rt for 1 h and at reflux for 3 h. The mixture is allowed to cool, acidified with conc. HCl and filtered. The filtrate is basified by 10 M aq.NaOH solution and extracted with diethyl ether. The combined extracts are dried over $MgSO_4$, diluted with 2 M HCl in diethyl ether, concentrated and evaporated twice from toluene.

Yield: 11.7 g. MS m/z: 168 $[M+H]^+$.

(d) 2,6-Dichloro-N-(trans-4-trifluoromethyl-cyclohexyl)-nicotinamide

A mixture of trans-4-trifluoromethyl-cyclohexylamine (4.8 g) and TEA (8.3 mL, 59.4 mmol) in THF (150 mL) is stirred for 20 min at rt. 2,6-Dichloro-nicotinoyl chloride (5.0 g, 23.8 mmol) in THF (50 mL) is added dropwise under cooling and the mixture is stirred at rt for 2 h. The reaction mixture is filtered and the filtrate is concentrated. The residue is treated with water, filtered off, washed with water and dried to give the sub-title compound.

Yield: 7.5 g (92%). $R_f$(TLC): 0.47 (silica gel, DCM). MS m/z: 341 $[M+H]^+$.

(e) 6-Chloro-2-(2,2-difluoro-ethoxy)-N-(trans-4-trifluoromethyl-cyclohexyl)-nicotinamide 2,2-Difluoroethanol (710 μL, 10.3 mmol) is added at rt to KOtBu (1.3 g, 11.3 mmol) in THF (50 mL) and stirred for 15 min. 2,6-Dichloro-N-(trans-4-trifluoromethyl-cyclohexyl)-nicotinamide (3.5 g, 10.3 mmol) in THF (50 mL) is added dropwise to the reaction mixture and it is stirred for 5 h at rt. Additional KOtBu (0.3 g) in THF (3 mL) and 2,2-difluoroethanol (140 μL) are added and stirring is continued for 2 h. The reaction mixture is diluted with water and NaCl is added. The precipitate is filtered off, dried and purified by chromatography.

Yield: 3.7 g (93%). $R_f$(TLC): 0.43 (silica gel, CH:EtOAc 8:2). MS m/z: 387 $[M+H]^+$.

(f) 6-Chloro-2-(2,2-difluoro-ethoxy)-5-nitro-N-(trans-4-trifluoromethyl-cyclohexyl)-nicotinamide The sub-title compound is prepared from 6-chloro-2-(2,2-difluoro-ethoxy)-N-(trans-4-trifluoromethyl-cyclohexyl)-nicotinamide (7.2 g, 18.6 mmol) and fuming $HNO_3$ (20 mL) in conc. $H_2SO_4$ (40 mL) in analogy with example 1c.

Yield: 7.2 g (96%). HPLC-method A: $R_t$=2.28 min. MS m/z: 432 $[M+H]^+$.

(g) 2-(2,2-Difluoro-ethoxy)-6-methylamino-5-nitro-N-(trans-4-trifluoromethyl-cyclohexyl)-nicotinamide The subtitle compound is prepared from 6-chloro-2-(2,2-difluoro-ethoxy)-5-nitro-N-(trans-4-trifluoromethyl-cyclohexyl)-nicotinamide (2.5 g, 5.8 mmol) and $CH_3NH_2$ (2 M in THF; 6.0 mL, 12.0 mmol) in THF (25 mL) in analogy with example 1d.

Yield: 2.4 g (98%). $R_f$(TLC): 0.58 (silica gel, PE:EtOAc 1:1). MS m/z: 472 $[M+H]^+$.

(h) 5-Amino-2-(2,2-difluoro-ethoxy)-6-methylamino-N-(trans-4-trifluoromethyl-cyclohexyl)-nicotinamide A mixture of 2-(2,2-difluoro-ethoxy)-6-methylamino-5-nitro-N-(trans-4-trifluoromethyl-cyclohexyl)-nicotinamide (500 mg, 1.17 mmol), THF (10 mL), MeOH (10 mL) and Ra—Ni (100 mg) is stirred for 6 h at rt under a hydrogen atmosphere (3.0 bar). The catalyst is removed by filtration and the mixture is concentrated.

Yield: 510 mg (quantitative). $R_f$(TLC): 0.45 (silica gel, DCM:MeOH 9:1).

(i) N-{4-Chloro-3-[3-(trans-4-trifluoromethyl-cyclohexylcarbamoyl)-2-(2,2-difluoro-ethoxy)-6-methylamino-pyridin-5-ylthioureido]benzyl}-2,2-dimethyl-propionamide N-(4-Chloro-3-isothiocyanatobenzyl)-2,2-dimethyl-propionamide (68 mg, 0.24 mmol) is added to 5-amino-2-(2,2-difluoro-ethoxy)-6-methylamino-N-(trans-4-trifluoromethyl-cyclohexyl)-nicotinamide (95 mg, 0.24 mmol) in MeCN (3.5 mL) and stirred at rt overnight. The reaction mixture is concentrated and used directly in the next step without further purification.

Yield: 135 mg (83%). HPLC-method A: $R_t$=2.27 min. MS m/z: 679 $[M+H]^+$.

(j) N-{4-Chloro-3-[6-(trans-4-trifluoromethyl-cyclohexylcarbamoyl)-5-(2,2-difluoro-ethoxy)-3-methyl-3H-imidazo[4,5-b]pyridin-2-ylamino]benzyl}-2,2-dimethyl-propionamide DIC (40 μL, 0.24 mmol) is added to a mixture of N-{4-chloro-3-[3-(trans-4-trifluoromethyl-cyclohexylcarbamoyl)-2-(2,2-difluoro-ethoxy)-6-methylamino-pyridin-5-ylthioureido]benzyl}-2,2-dimethyl-propionamide (135 mg, 0.20 mmol) and MeCN (3.5 mL). The reaction mixture is stirred at 60° C. overnight, allowed to cool and concentrated. The residue is treated with MeCN, filtered off and dried.

Yield: 99 mg (77%). HPLC-method A: $R_t$=2.23 min. MS m/z: 645 $[M+H]^+$.

Example 3
N-{4-Chloro-3-[6-(trans-4-trifluoromethyl-cyclohexylcarbamoyl)-5-(2-methoxy-ethoxy))-1H-imidazo[4,5-b]pyridin-2-ylamino]-benzyl}-1-trifluoromethyl-cyclopropionamide
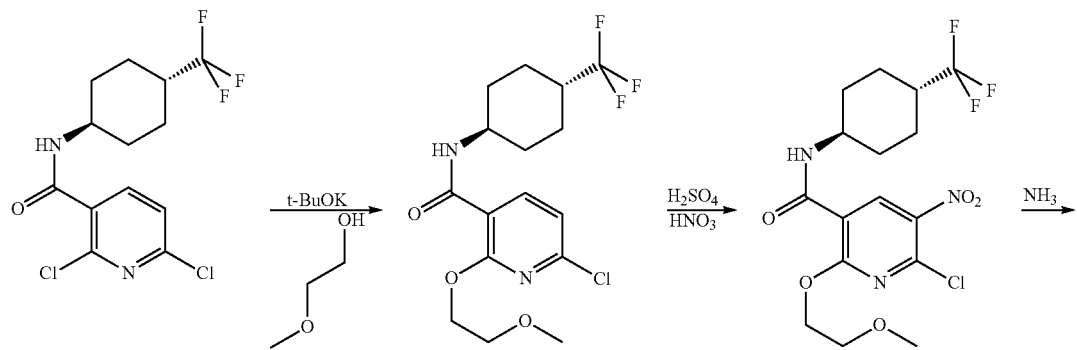
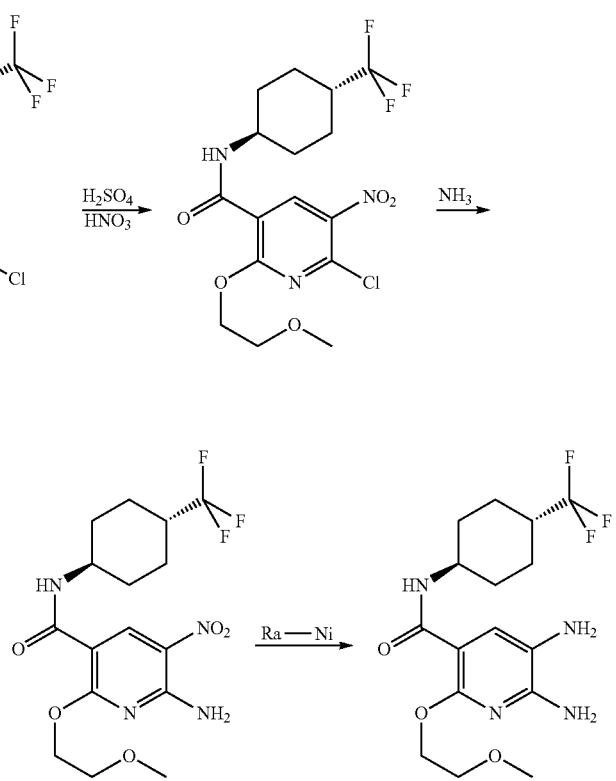
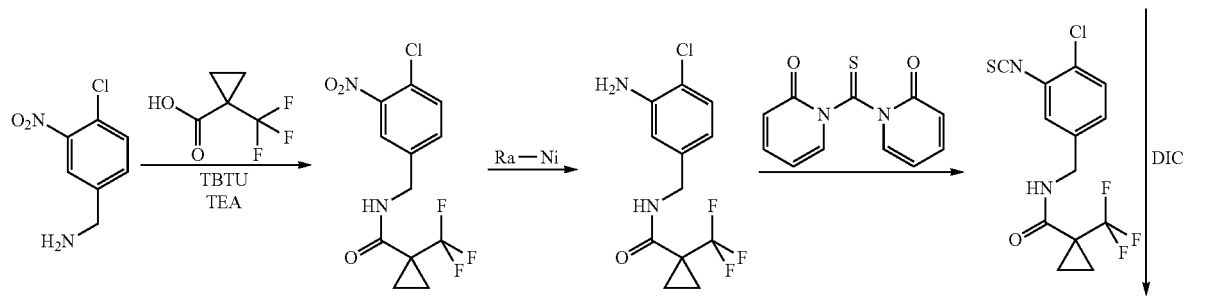
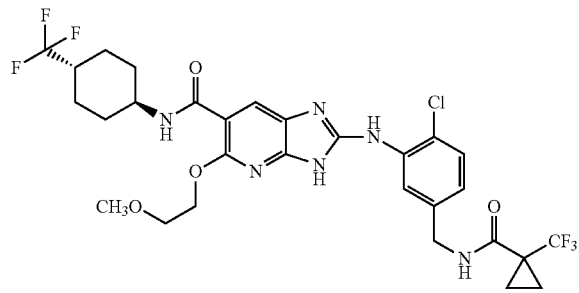

(a) 6-Chloro-2-(2-methoxy-ethoxy)-N-(trans-4-trifluoromethyl-cyclohexyl)-nicotinamide 2-Methoxyethanol (550 µL, 6.94 mmol) is added at rt to KOtBu (750 mg, 6.35 mmol) in THF (30 mL) and it is stirred for 5 min. 2,6-Dichloro-N-(trans-4-trifluoromethyl-cyclohexyl)-nicotinamide (2.00 g, 5.86 mmol) is added to the reaction mixture and it is stirred for 10 min at rt. The reaction mixture is diluted with water, filtered and the filtrate is concentrated. The residue is treated with water, filtered off, washed with water and dried.

Yield: 2.20 g (99%). HPLC-method A: $R_f$=2.24 min. MS m/z: 381 [M+H]$^+$.

(b) 6-Chloro-2-(2-methoxy-ethoxy)-5-nitro-N-(trans-4-trifluoromethyl-cyclohexyl)-nicotinamide The sub-title compound is prepared from 6-chloro-2-(2-methoxy-ethoxy)-N-(trans-4-trifluoromethyl-cyclohexyl)-nicotinamide (2.20 g, 5.78 mmol), fuming HNO$_3$ (5 mL) and conc. H$_2$SO$_4$ (10 mL) in analogy to example 1c.

Yield: 2.20 g (89%). HPLC-method A: $R_f$=2.27 min. MS m/z: 426 [M+H]$^+$.

(c) 6-Amino-2-(2-methoxy-ethoxy)-5-nitro-N-(trans-4-trifluoromethyl-cyclohexyl)-nicotinamide Conc. ammonia (200 µL, 3.31 mmol) is added to 6-chloro-2-(2-methoxy-ethoxy)-5-nitro-N-(trans-4-trifluoromethyl-cyclohexyl)-nicotinamide (150 mg, 0.35 mmol) in THF (10 mL) and it is stirred at rt for 3 h. The reaction mixture is diluted with water and concentrated. The precipitate is filtered off, washed with water and dried.

Yield: 140 mg (98%). $R_f$(TLC): 0.35 (silica gel, PE:EtOAc 1:1). MS m/z: 407 [M+H]$^+$.

(d) 5,6-Diamino-2-(2-methoxy-ethoxy)-N-(trans-4-trifluoromethyl-cyclohexyl)-nicotinamide 6-Amino-2-(2-methoxy-ethoxy)-5-nitro-N-(trans-4-trifluoromethyl-cyclohexyl)-nicotinamide (140 mg, 0.34 mmol), THF (20 mL) and Ra—Ni (40 mg) is stirred for 2 h at rt under a hydrogen atmosphere (3.0 bar). The catalyst is removed by filtration and the mixture is concentrated to give the sub-title compound.

Yield: 110 mg (85%). $R_f$(TLC): 0.20 (silica gel, PE:EtOAc 1:1). HPLC-method C: $R_f$=1.68 min. MS m/z: 377 [M+H]$^+$.

(e) N-(4-Chloro-3-nitro-benzyl)-1-trifluoromethyl-cyclopropane carboxamide

TBTU (0.44 g, 1.4 mmol) and TEA (0.43 mL, 3.1 mmol) are added to 1-trifluoromethyl-cyclopropanecarboxylic acid (0.19 g, 1.2 mmol) in THF (5 mL). After 10 min at rt 4-chloro-3-nitro-benzylamine (0.23 g, 1.2 mmol) is added to the reaction mixture and stirring is continued overnight. The mixture is concentrated, the crude is diluted with EtOAc and washed with sat.aq. NaHCO$_3$-solution, water and brine. The organic layer is dried with Na$_2$SO$_4$ and concentrated.

Yield: 340 mg (86%). MS m/z: 321 [M+H]$^+$. HPLC-method I: $R_f$=2.76 min.

(f) N-(4-Chloro-3-amino-benzyl)-1-trifluoromethyl-cyclopropane carboxamide

A mixture of N-(4-chloro-3-nitro-benzyl)-1-trifluoromethyl-cyclopropane carboxamide (340 mg, 1.1 mmol), EtOAc (10 mL) and Ra—Ni (30 mg) is stirred at rt under a hydrogen atmosphere (3.0 bar). The catalyst is removed by filtration and the filtrate is concentrated.

Yield: 250 mg (81%). $R_f$(TLC): 0.50 (silica gel, DCM:EtOH 95:5). HPLC-method B: $R_f$=1.30 min. MS m/z: 293 [M+H]$^+$.

(g) N-(4-Chloro-3-isothiocyanato-benzyl)-1-trifluoromethyl-cyclopropane carboxamide A mixture of N-(4-chloro-3-amino-benzyl)-1-trifluoromethyl-cyclopropane carboxamide (100 mg, 0.3 mmol), 1,1'-thiocarbonyldi-2-pyridone (0.32 mmol), DIC (87 mg, 0.4 mmol) and DCM (5 mL) is stirred at rt overnight. The reaction mixture is filtered through a pad of silica gel and the filtrate is concentrated.

Yield: 95 mg (83%). $R_f$(TLC): 0.75 (silica gel, CH:EtOAc 1:1). MS m/z: 335 [M+H]$^+$.

(h) N-{4-Chloro-3-[6-(trans-4-trifluoromethyl-cyclohexylcarbamoyl)-5-(2-methoxy-ethoxy))-1H-imidazo[4,5-b]pyridin-2-ylamino]benzyl}-1-trifluoromethyl-cyclopropionamide A mixture of 5,6-diamino-2-(2-methoxy-ethoxy)-N-(trans-4-trifluoromethyl-cyclohexyl)-nicotinamide (110 mg, 0.29 mmol) and N-(4-chloro-3-isothiocyanato-benzyl)-1-trifluoromethyl-cyclopropane carboxamide (100 mg, 0.30 mmol) in MeCN (5 mL) is stirred at rt for 3 h. DIC (60 µL, 0.38 mmol) is added to the reaction mixture and it is stirred at 70° C. for 1 h and at rt overnight. The precipitate is filtered off, washed with MeCN and dried to give the title compound.

Yield: 85 mg (43%). HPLC-method C: $R_f$=2.24 min. MS m/z: 677 [M+H]$^+$.

Example 4

N-{4-Chloro-3-[6-(trans-4-trifluoromethyl-cyclohexylcarbamoyl)-5-(2-methoxy-ethoxy))-3-methyl-3H-imidazo[4,5-b]pyridin-2-ylamino]-benzyl}-1-trifluoromethyl-cyclopropionamide

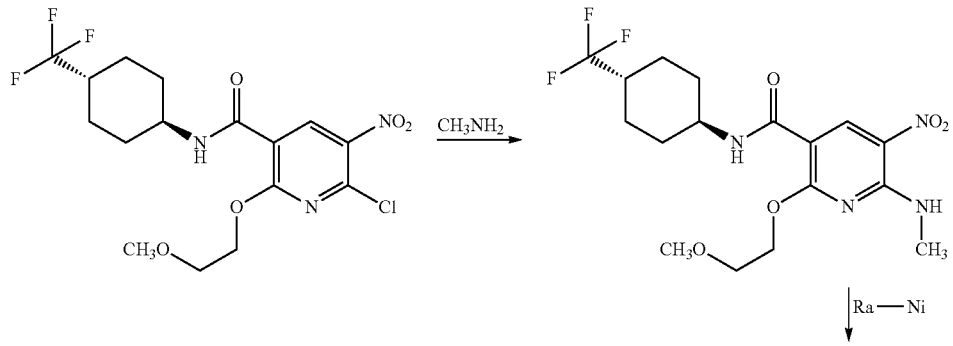

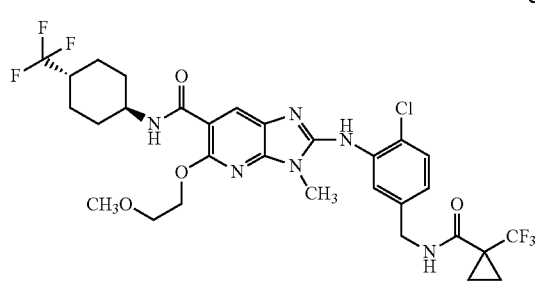
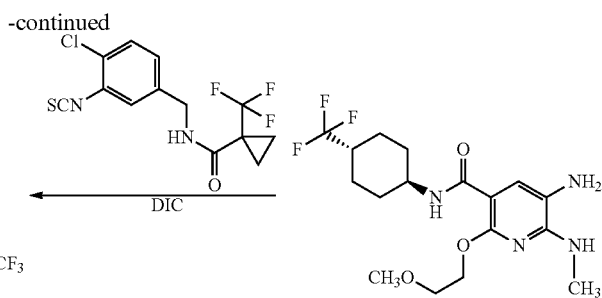

(a) 2-(2-Methoxy-ethoxy)-6-methylamino-5-nitro-N-(trans-4-trifluoromethyl-cyclohexyl)-nicotinamide Methylamine (2 M in THF; 400 μL, 0.80 mmol) is added to 6-chloro-2-(2-methoxy-ethoxy)-5-nitro-N-(trans-4-trifluoromethyl-cyclohexyl)-nicotinamide (150 mg, 0.35 mmol) in THF (10 mL). After 45 min at rt the reaction mixture is diluted with water, concentrated and filtered. The filtercake is washed with water and dried.

Yield: 110 mg (74%). HPLC-method C: $R_t$=2.26 min. MS m/z: 421 [M+H]⁺.

(b) 5-Amino-2-(2-methoxy-ethoxy)-6-methylamino-N-(trans-4-trifluoromethyl-cyclohexyl)-nicotinamide A mixture of 2-(2-methoxy-ethoxy)-6-methylamino-5-nitro-N-(trans-4-trifluoromethyl-cyclohexyl)-nicotinamide (170 mg, 0.40 mmol), Ra—Ni (50 mg), MeOH (5 mL) and THF (15 mL) is stirred at rt for 2 h under a hydrogen atmosphere (3.0 bar). The catalyst is removed by filtration and the filtrate is concentrated.

Yield: 150 mg (95%). HPLC-method A: $R_t$=1.76 min. MS m/z: 391 [M+H]⁺.

(c) N-{4-Chloro-3-[6-(trans-4-trifluoromethyl-cyclohexylcarbamoyl)-5-(2-methoxy-ethoxy))-3-methyl-3H-imidazo[4,5-b]pyridin-2-ylamino]benzyl}-1-trifluoromethyl-cyclopropionamide The title compound is prepared from 5-amino-2-(2-methoxy-ethoxy)-6-methylamino-N-(trans-4-trifluoromethyl-cyclohexyl)-nicotinamide (100 mg, 0.26 mmol), N-(4-chloro-3-isothiocyanato-benzyl)-1-trifluoromethyl-cyclopropane carboxamide (90 mg, 0.27 mmol) and DIC (50 μL, 0.32 mmol) in MeCN (5 mL) in analogy with example 3 h.

Yield: 60 mg (34%). HPLC-method C: $R_t$=2.29 min. MS m/z: 691 [M+H]⁺.

Example 5

N-{4-Chloro-3-[6-(trans-4-trifluoromethyl-cyclohexylcarbamoyl)-5-(2,2-difluoro-ethoxy))-1H-imidazo[4,5-b]pyridin-2-ylamino]-benzyl}-1-trifluoromethyl-cyclopropionamide

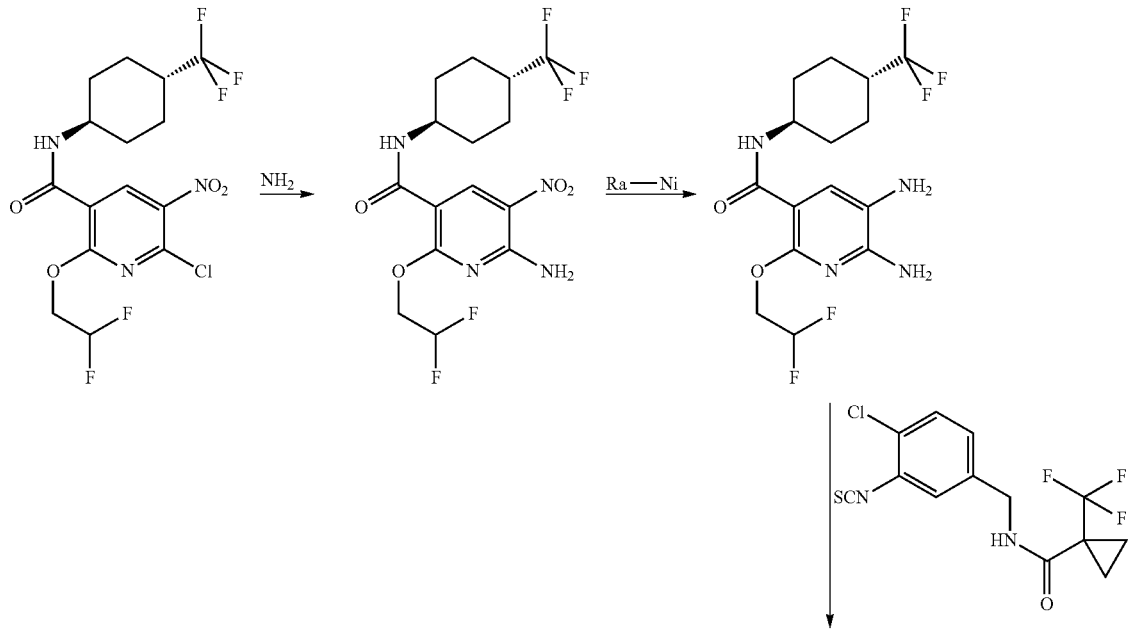

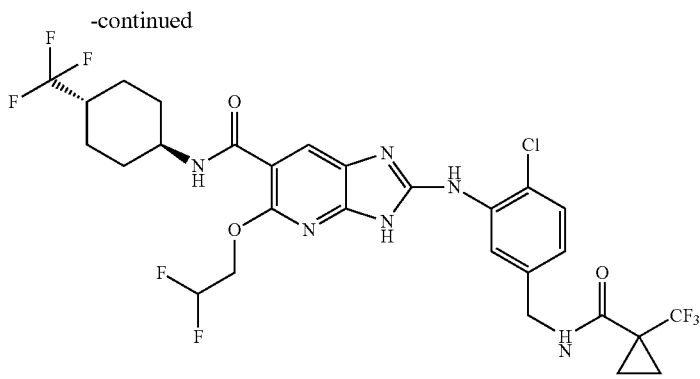

(a) 6-Amino-2-(2,2-difluoro-ethoxy)-5-nitro-N-(trans-4-trifluoromethyl-cyclohexyl)-nicotinamide A mixture of conc. NH₃ (3 mL, 49.6 mmol) and water (3 mL) is added dropwise at 0° C. to 6-chloro-2-(2,2-difluoro-ethoxy)-5-nitro-N-(trans-4-trifluoromethyl-cyclohexyl)-nicotinamide (1.9 g, 4.4 mmol) in THF (10 mL) and it is stirred for 90 min at rt. Additional conc. NH₃ (1 mL) is added and the reaction mixture is stirred for further 60 min at rt, diluted with water and concentrated. The precipitate is filtered off, washed with water and dried.
Yield: 1.7 g (85%). $R_f$(TLC): 0.49 (silica gel, PE:EtOAc 1:1). MS m/z: 413 [M+H]⁺.

(b) 5,6-Diamino-2-(2,2-difluoro-ethoxy)-N-(trans-4-trifluoromethyl-cyclohexyl)-nicotinamide A mixture of 6-amino-2-(2,2-difluoro-ethoxy)-5-nitro-N-(trans-4-trifluoromethyl-cyclohexyl)-nicotinamide (250 mg, 0.61 mmol), Ra—Ni (30 mg) and THF (10 mL) is stirred at rt for 2 h under a hydrogen atmosphere (3.0 bar). The catalyst is removed by filtration and the filtrate is concentrated.
Yield: 240 mg (quantitative). HPLC-method B: $R_t$=1.27 min. MS m/z: 383 [M+H]⁺.

(c) N-{4-Chloro-3-[6-(trans-4-trifluoromethyl-cyclohexylcarbamoyl)-5-(2,2-difluoro-ethoxy))-1H-imidazo[4,5-b]pyridin-2-ylamino]benzyl}-1-trifluoromethyl-cyclopropionamide A mixture of 5,6-diamino-2-(2,2-difluoro-ethoxy)-N-(trans-4-trifluoromethyl-cyclohexyl)-nicotinamide (190 mg, 0.40 mmol) and N-(4-chloro-3-isothiocyanato-benzyl)-1-trifluoromethyl-cyclopropane carboxamide (150 mg, 0.44 mmol) in MeCN (5 mL) is stirred at rt overnight. DIC (70 μL, 0.44 mmol) is added to the mixture and it is stirred at 70° C. for 2.5 h. Additional DIC (35 μL) is added and stirring is continued at 70° C. for 2 h and at rt over the weekend. The precipitate is filtered off, washed with MeCN and dried.
Yield: 110 mg (33%). HPLC-method C: $R_t$=2.30 min. MS m/z: 683 [M+H]⁺.

Example 6

N-{4-Chloro-3-[6-(trans-4-trifluoromethyl-cyclohexylcarbamoyl)-5-(2-fluoro-ethoxy))-3-methyl-3H-imidazo[4,5-b]pyridin-2-ylamino]-benzyl}-1-trifluoromethyl-cyclopropionamide

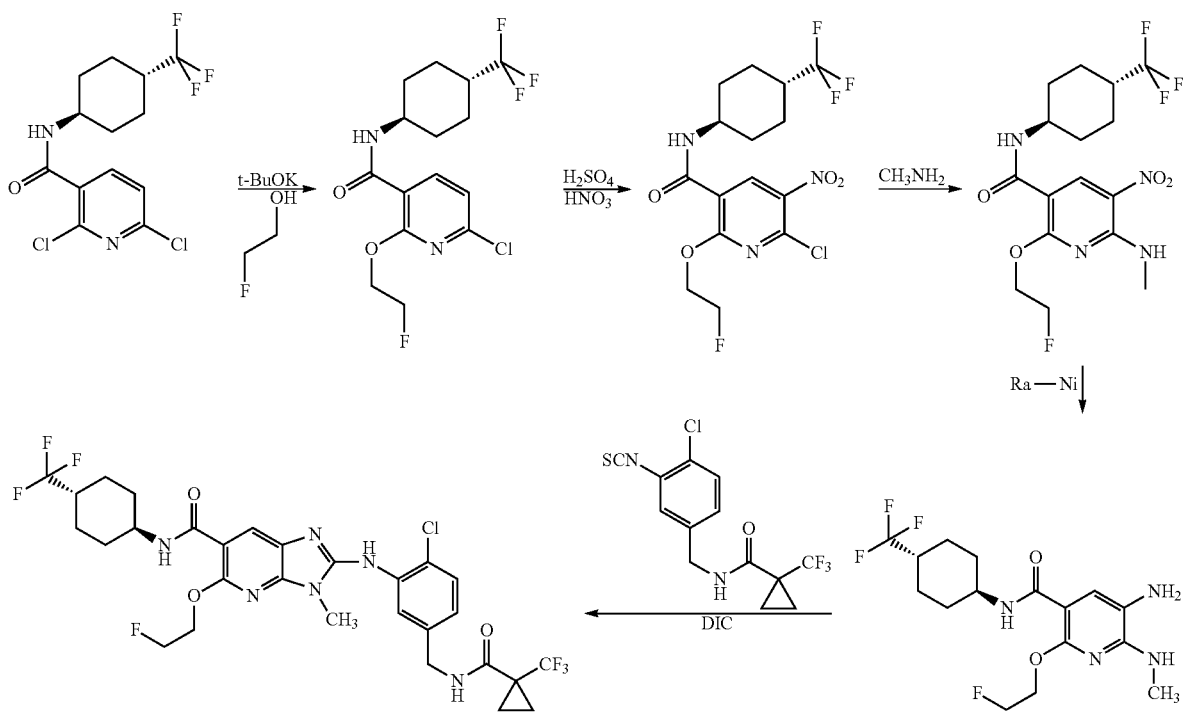

(a) 6-Chloro-2-(2-fluoro-ethoxy)-N-(trans-4-trifluoromethyl-cyclohexyl)-nicotinamide 2-Fluoroethanol (380 µL, 6.45 mmol) is added to potassium tert-butoxide (730 mg, 6.16 mmol) in THF (60 mL) and stirred for 5 min at rt. After the addition of 2,6-dichloro-N-(4-trifluoromethyl-cyclohexyl)-nicotinamide (2.00 g, 5.86 mmol) the reaction mixture is stirred for 1 h hour at rt, then diluted with water and concentrated. The residue is stirred in ice water, the precipitate is filtered off and dried.

Yield: 2.09 g (97%). HPLC-method A: $R_t$=2.22 min. MS m/z: 369 [M+H]$^+$.

(b) 6-Chloro-2-(2-fluoro-ethoxy)-5-nitro-N-(trans-4-trifluoromethyl-cyclohexyl)-nicotinamide The sub-title compound is prepared from 6-chloro-2-(2-fluoro-ethoxy)-N-(trans-4-trifluoromethyl-cyclohexyl)-nicotinamide (2.08 g, 5.64 mmol), HNO$_3$ (5.5 mL) and conc. H$_2$SO$_4$ (16 mL) in analogy with method described in example 1c.

Yield: 2.30 g (99%). HPLC-method A: $R_t$=2.25 min. MS m/z: 414 [M+H]$^+$.

(c) 2-(2-Fluoro-ethoxy)-6-methylamino-5-nitro-N-(trans-4-trifluoromethyl-cyclohexyl)-nicotinamide The sub-title compound is prepared from 6-chloro-2-(2-fluoro-ethoxy)-5-nitro-N-(trans-4-trifluoromethyl-cyclohexyl)-nicotinamide (1.00 g, 2.30 mmol) and methylamine (2 M in THF; 2.75 mL, 5.50 mmol) in THF (15 mL) in analogy with method described in example 1d.

Yield: 0.86 g (92%). HPLC-method C: $R_t$=2.23 min. MS m/z: 409 [M+H]$^+$.

(d) 5-Amino-2-(2-fluoro-ethoxy)-6-methylamino-N-(trans-4-trifluoromethyl-cyclohexyl)-nicotinamide A mixture of 2-(2-fluoro-ethoxy)-6-methylamino-5-nitro-N-(trans-4-trifluoromethyl-cyclohexyl)-nicotinamide (105 mg, 0.26 mmol), Ra—Ni (25 mg), MeOH (5 mL) and THF (10 mL) is stirred at rt for 2.5 h under a hydrogen atmosphere (3.0 bar). The catalyst is removed by filtration and the filtrate is concentrated.

Yield: 95 mg (98%). HPLC-method A: $R_t$=1.81 min. MS m/z: 379 [M+H]$^+$.

(e) N-{4-Chloro-3-[6-(trans-4-trifluoromethyl-cyclohexylcarbamoyl)-5-(2-fluoro-ethoxy))-3-methyl-3H-imidazo[4,5-b]pyridin-2-ylamino]benzyl}-1-trifluoromethyl-cyclopropionamide The title compound is prepared from 5-amino-2-(2-fluoro-ethoxy)-6-methylamino-N-(trans-4-trifluoromethyl-cyclohexyl)-nicotinamide (200 mg, 0.53 mmol), N-(4-chloro-3-isothiocyanato-benzyl)-1-trifluoromethyl-cyclopropane carboxamide (190 mg, 0.56 mmol) and DIC (90 µL, 0.58 mmol) in MeCN (10 mL) in analogy with the method described in example 5c.

Yield: 270 mg (75%). HPLC-method C: $R_t$=2.25 min. MS m/z: 679 [M+H]$^+$.

Example 7

N-{4-Chloro-3-[6-(trans-4-trifluoromethyl-cyclohexylcarbamoyl)-5-(2-fluoro-ethoxy))-1H-imidazo[4,5-b]pyridin-2-ylamino]-benzyl}-1-trifluoromethyl-cyclopropionamide

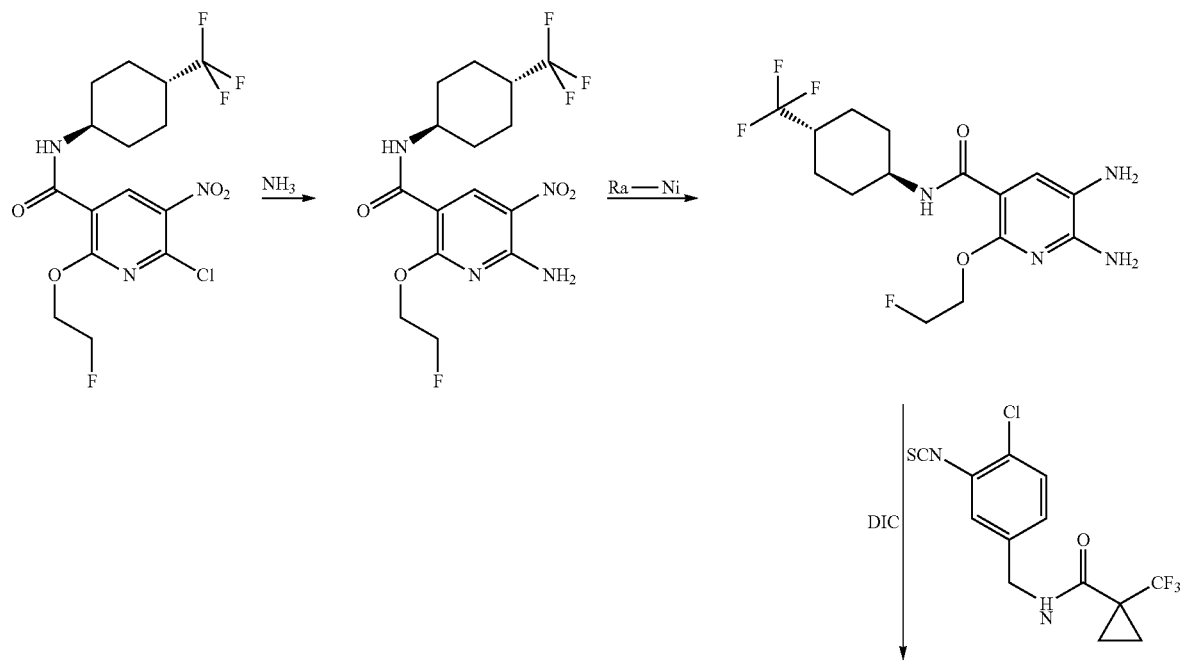

-continued

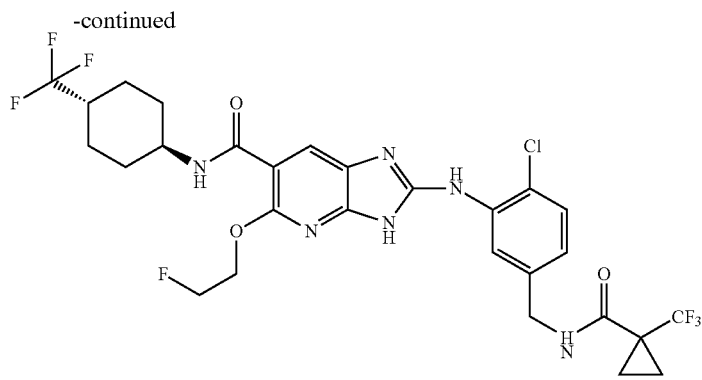

(a) (2-(2-Fluoro-ethoxy)-6-amino-5-nitro-N-(trans-4-trifluoromethyl-cyclohexyl)-nicotinamide The sub-title compound is prepared from 6-chloro-2-(2-fluoro-ethoxy)-5-nitro-N-(trans-4-trifluoromethyl-cyclohexyl)-nicotinamide (1.30 g, 2.98 mmol) and conc. ammonia (0.90 mL, 14.92 mmol) in THF (30 mL) in analogy with method described in example 3c.

Yield: 1.15 g (98%). HPLC-method C: $R_t$=2.07 min. MS m/z: 395 [M+H]$^+$.

(b) 5,6-Diamino-2-(2-fluoro-ethoxy)-N-(trans-4-trifluoromethyl-cyclohexyl)-nicotinamide A mixture of 2-(2-fluoro-ethoxy)-6-amino-5-nitro-N-(trans-4-trifluoromethyl-cyclohexyl)-nicotinamide (220 mg, 0.56 mmol), Ra—Ni (50 mg), MeOH (5 mL) and THF (15 mL) is stirred at rt for 2 h under a hydrogen atmosphere (3.0 bar). The catalyst is removed by filtration and the filtrate is concentrated.

Yield: 200 mg (98%). HPLC-method A: $R_t$=1.66 min. MS m/z: 365 [M+H]$^+$.

(c) N-{4-Chloro-3-[6-(trans-4-trifluoromethyl-cyclohexylcarbamoyl)-5-(2-fluoro-ethoxy))-1H-imidazo[4,5-b]pyridin-2-ylamino]benzyl}-1-trifluoromethyl-cyclopropionamide The title compound is prepared from 5,6-diamino-2-(2-fluoro-ethoxy)-N-(trans-4-trifluoromethyl-cyclohexyl)-nicotinamide (150 mg, 0.41 mmol), N-(4-chloro-3-isothiocyanato-benzyl)-1-trifluoromethyl-cyclopropane carboxamide (140 mg, 0.43 mmol) and DIC (70 µL, 0.58 mmol) in MeCN (10 mL) in analogy to the method described in example 5c.

Yield: 100 mg (38%). MS m/z: 665 [M+H]$^+$.

Example 8

N-{2,4-Dichloro-3-[6-(trans-4-trifluoromethyl-cyclohexylcarbamoyl)-5-(2,2-difluoro-ethoxy)-1H-imidazo[4,5-b]pyridin-2-ylamino]benzyl}-2,2-dimethyl-propionamide

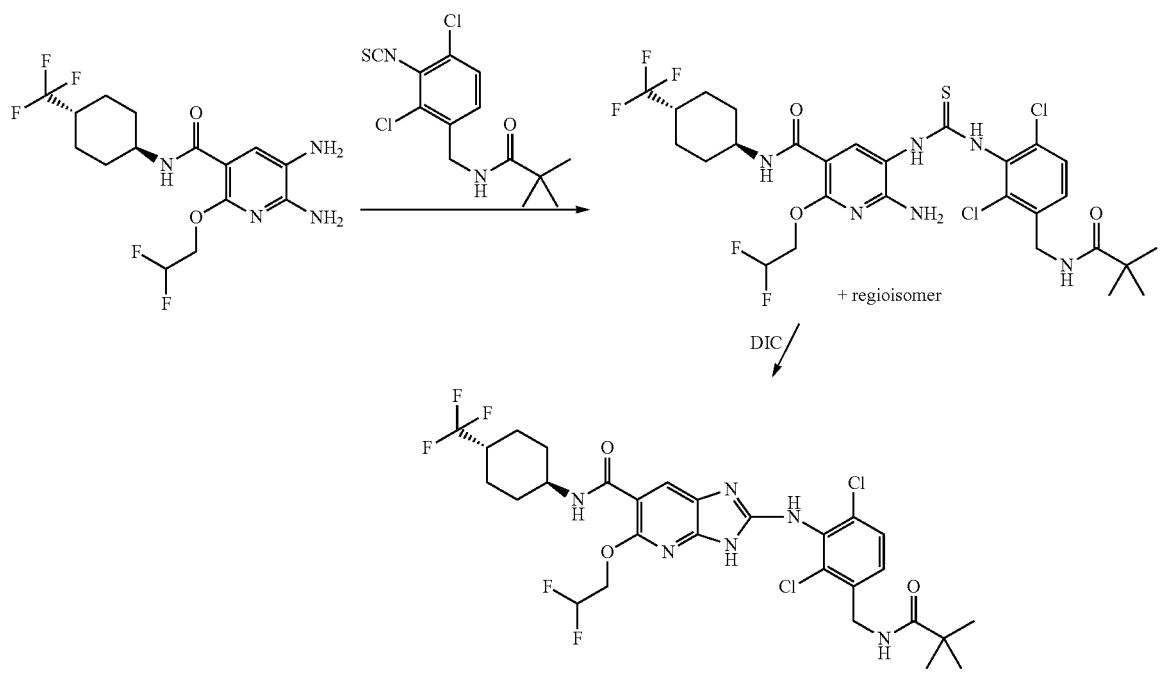

(a) N-{2,4-Dichloro-3-[6-amino-3-(trans-4-trifluoromethyl-cyclohexylcarbamoyl)-2-(2,2-difluoro-ethoxy)-pyridin-5-ylthioureido]benzyl}-2,2-dimethyl-propionamide N-(2,4-Dichloro-3-isothiocyanato-benzyl)-2,2-dimethyl-propionamide (100 mg, 0.30 mmol) is added to 5,6-diamino-2-(2,2-difluoro-ethoxy)-N-(trans-4-trifluoromethyl-cyclohexyl)-nicotinamide (120 mg, 0.30 mmol) in DMF (5 mL) and it is stirred at rt overnight. The reaction mixture is diluted with water, extracted with EtOAc, the organic layer is washed with water, dried and concentrated to give the sub-title compound.

Yield: 210 mg (99%). HPLC-method B: $R_f$=1.45 min. MS m/z: 700 [M+H]$^+$.

(b) N-{2,4-Dichloro-3-[6-(trans-4-trifluoromethyl-cyclohexylcarbamoyl)-5-(2,2-difluoro-ethoxy)-1H-imidazo[4,5-b]pyridin-2-ylamino]benzyl}-2,2-dimethyl-propionamide DIC (60 μL, 0.39 mmol) is added to a mixture of N-{2,4-dichloro-3-[6-amino-3-(trans-4-trifluoromethyl-cyclohexylcarbamoyl)-2-(2,2-difluoro-ethoxy)-pyridin-5-ylthioureido]benzyl}-2,2-dimethyl-propionamide (210 mg, 0.30 mmol) and DMF (5 mL). The reaction mixture is stirred at 80° C. overnight, allowed to cool and concentrated. The residue is diluted with EtOAc, washed with water, dried and concentrated. The crude mixture is purified by chromatography.

Yield: 120 mg (60%). $R_f$(TLC): 0.29 (silica gel, DCM:EtOH 95:5). MS m/z: 665 [M+H]$^+$.

Example 9

N-{2,4-Dichloro-3-[6-(trans-4-trifluoromethyl-cyclohexylcarbamoyl)-5-(2,2-difluoro-ethoxy)-3-methyl-3H-imidazo[4,5-b]pyridin-2-ylamino]benzyl}-2,2-dimethyl-propionamide

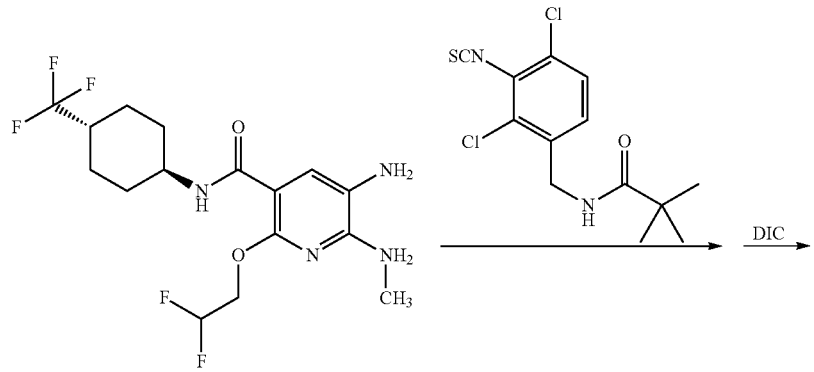

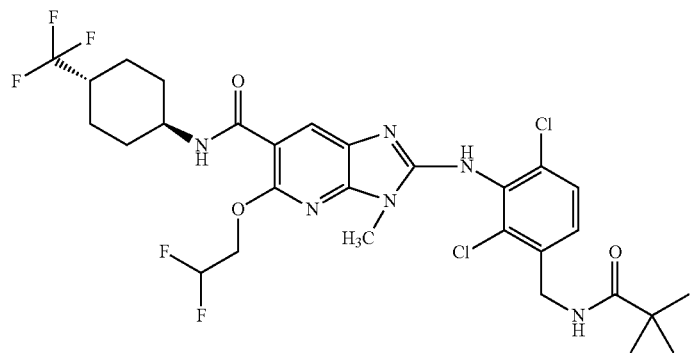

The title compound is prepared from N-(2,4-dichloro-3-isothiocyanato-benzyl)-2,2-dimethyl-propionamide (120 mg, 0.38 mmol) and 5-amino-2-(2,2-difluoro-ethoxy)-N-(trans-4-trifluoromethyl-cyclohexyl)-6-methylamino-nicotinamide (150 mg, 0.38 mmol) with DIC in analogy to examples 8a/8b.

Yield: 200 mg. $R_f$(TLC): 0.22 (silica gel, DCM:EtOH 95:5). MS m/z: 679 [M+H]$^+$.

Example 10

N-{2,4-Difluoro-3-[6-(trans-4-trifluoromethyl-cylohexylcarbamoyl)-5-(2,2-difluoro-ethoxy)-3-methyl-3H-imidazo[4,5-b]pyridin-2-ylamino]benzyl}-2,2-dimethyl-propionamide

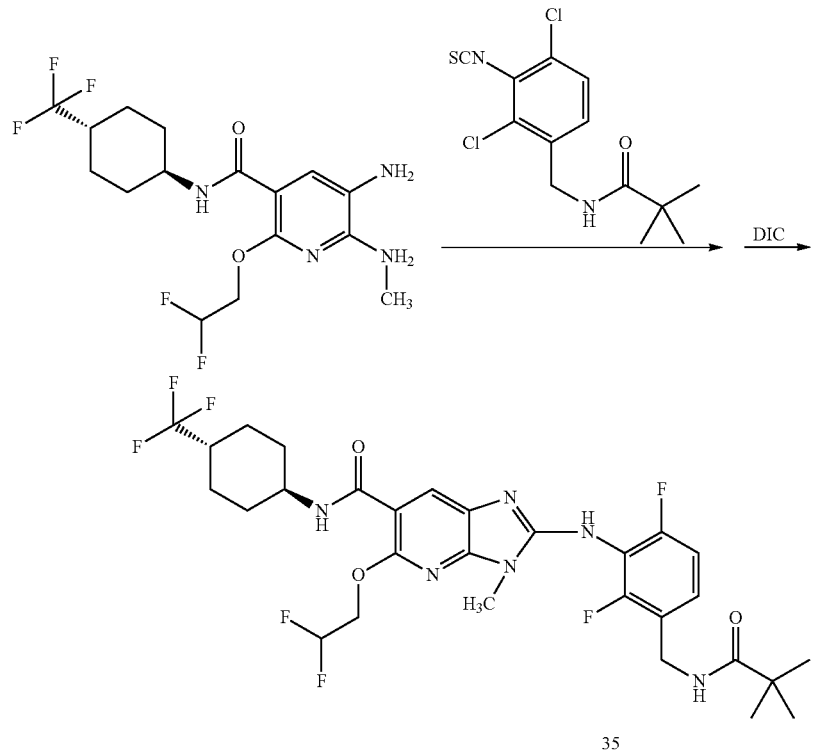

The title compound is prepared from N-(2,4-difluoro-3-isothiocyanato-benzyl)-2,2-dimethyl-propionamide (150 mg, 0.38 mmol) and 5-amino-2-(2,2-difluoro-ethoxy)-N-(trans-4-trifluoromethyl-cyclohexyl)-6-methylamino-nicotinamide (150 mg, 0.38 mmol) with DIC in analogy to examples 8a/8b.

Yield: 140 mg. MS m/z: 647 [M+H]$^+$.

Example 12

N-{2,4-Dichloro-3-[6-(trans-4-trifluoromethyl-cylohexylcarbamoyl)-5-(2-difluoromethoxy-ethoxy))-1H-imidazo[4,5-b]pyridin-2-ylamino]-benzyl}-1-trifluoromethyl-cyclopropionamide

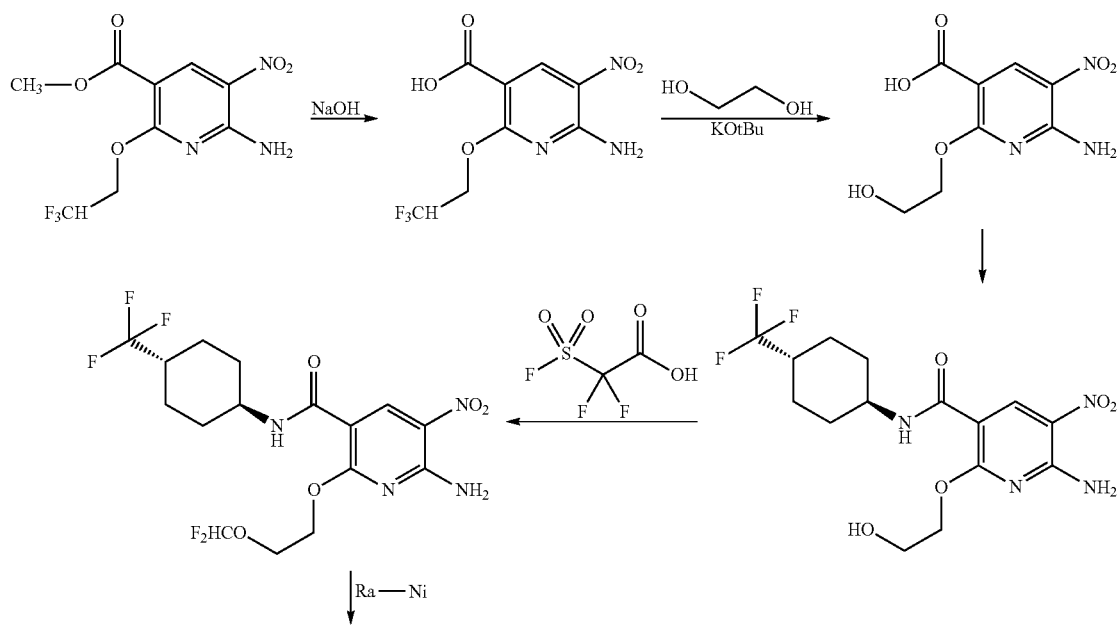

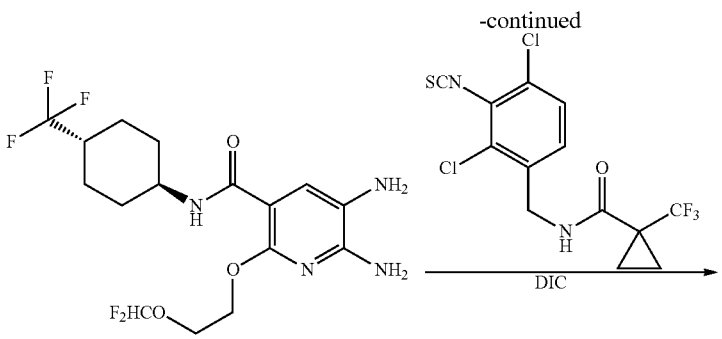
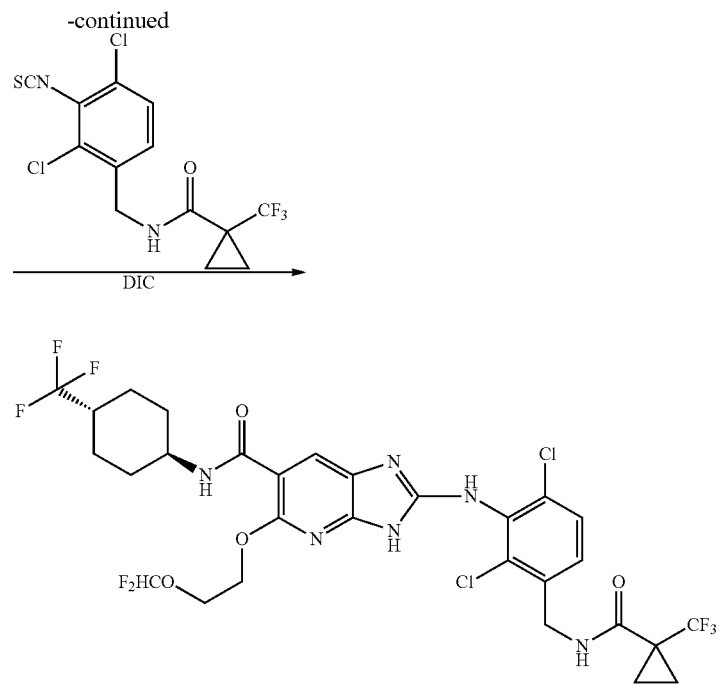

(a) 2-(2,2-Difluoro-ethoxy)-6-amino-5-nitro-nicotinic acid

The sub-title compound is prepared from 2-(2,2-difluoro-ethoxy)-6-amino-5-nitro-nicotinic acid methyl ester (1.3 g, 4.8 mmol) and 1 M NaOH in analogy to example 1e. Yield: 0.88 g (70%).

(b) 2-(2-Hydroxy-ethoxy)-6-amino-5-nitro-nicotinic acid

A mixture of ethylene glycol (3.53 ml, 63 mmol) and KOtBu (398 mg, 3.5 mmol) in THF (6.5 ml) is stirred for 15 min, then 2-(2,2-difluoro-ethoxy)-6-amino-5-nitro-nicotinic acid (415 mg, 81 mmol) is added and it is stirred for 3 h. The mixture is diluted with ice-water, acidified with $KHSO_4$ solution (~pH6) and concentrated. The water phase is saturated with NaCl and extracted with EtOAc. The organic phase is washed with brine, dried with $MgSO_4$, concentrated and dried.

Yield: 370 mg (crude). $R_f$(TLC): 0.33 (silica gel, DCM: EtOH 9:1 and a drop HOAc).

(c) N-(trans-4-Trifluoromethyl-cyclohexyl)-2-(2-hydroxy-ethoxy)-6-amino-5-nitro-nicotinamide trans-4-Trifluoromethyl-cyclohexylamine (285 mg, 1.40 mmol) and TEA (410 μl) are added successively to a mixture of 2-(2-hydroxy-ethoxy)-6-amino-5-nitro-nicotinic acid (360 mg, 1.33 mmol), TBTU (285 mg, 1.33 mmol) and TEA (195 μl) and it is stirred for 1.5 h. The mixture is concentrated filtered and purified via chromatography.

Yield: 410 mg. HPLC-method C: $R_t$=1.83 min. MS m/z: 393 [M+H]$^+$.

(d) N-(trans-4-Trifluoromethyl-cyclohexyl)-2-(2-difluoromethoxy-ethoxy)-6-amino-5-nitro-nicotinamide 2,2-Difluoro-2-fluorosulfonylacetic acid (205 μl, 1.98 mmol) in MeCN (20 ml) is added via a syringe pump to a mixture of N-(trans-4-trifluoromethyl-cyclohexyl)-2-(2-hydroxy-ethoxy)-6-amino-5-nitro-nicotinamide (390 mg, 0.994 mmol) and CuI (94 mg, 0.49 mmol) in MeCN (40 ml) over 2.5 h at 55° C. It is stirred for additional 20 min, then the mixture is concentrated and purified via extensive chromatography.

Yield: 152 mg (crude). HPLC-method C: $R_t$=2.17 min. MS m/z: 443 [M+H]$^+$.

(e) N-(trans-4-Trifluoromethyl-cyclohexyl)-2-(2-difluoromethoxy-ethoxy)-5,6-diamino-nicotinamide The sub-title compound is prepared from N-(trans-4-trifluoromethyl-cyclohexyl)-2-(2-difluoromethoxy-ethoxy)-6-amino-5-nitro-nicotinamide (150 mg, 0.339 mmol), Ra—Ni/$H_2$ (3 bar) in analogy to example 7b.

Yield: 160 mg. HPLC-method C: $R_t$=1.80 min.

(f) N-{2,4-Dichloro-3-[6-(trans-4-trifluoromethyl-cyclohexylcarbamoyl)-5-(2-difluoromethoxy-ethoxy))-1H-imidazo[4,5-b]pyridin-2-ylamino]benzyl}-1-trifluoromethyl-cyclopropionamide The title compound is prepared from N-(trans-4-trifluoromethyl-cyclohexyl)-2-(2-difluoromethoxy-ethoxy)-5,6-diamino-nicotinamide (80 mg, 0.165 mmol), N-(2,4-dichloro-3-isothiocyanato-benzyl)-1-trifluoromethyl-cyclopropane carboxamide (67 mg, 0.181) and DIC (29 μl) in MeCN in analogy to example 5c.

Yield: 42 mg. HPLC-method A: $R_t$=1.43 min. MS m/z: 747 [M+H]$^+$.

Example 14

N-{2,4-Dichloro-3-[6-(2,2-difluoro-ethylcarbamoyl)-5-(2-difluoro-ethoxy))-3-(2,2-difluoro-ethyl)-3H-imidazo[4,5-b]pyridin-2-ylamino]-benzyl}-2,2-dimethyl-propionamide

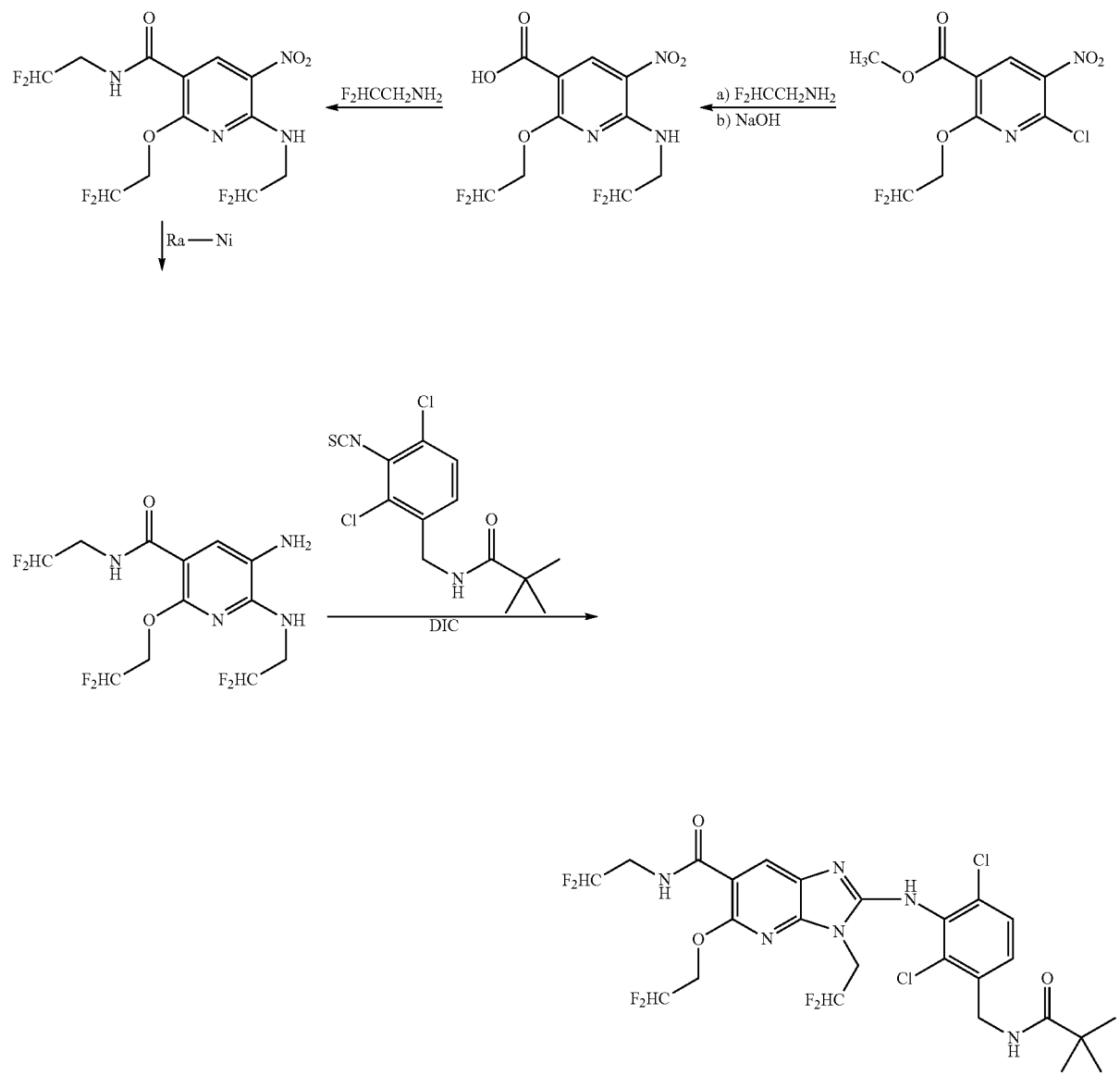

The title compound is prepared in analogy to the following reaction sequence: a) from 6-chloro-2-(2,2-difluoro-ethoxy)-5-nitro-nicotinic acid methyl ester and 2,2-difluoroethylamine (according to example 1d); b) NaOH; (in analogy to example 1e); c) 2,2-difluoroethylamine (according to example 1f); d) Ra—Ni/H$_2$ (according to example 1g) and e) with N-(2,4-dichloro-3-isothiocyanato-benzyl)-2,2-dimethyl-propionamide (in analogy to example 5c).

Yield: 90 mg. HPLC-method A: R$_t$=2.12 min. MS m/z: 643 [M+H]$^+$.

Example 16

N-{2,4-Dichloro-3-[6-(trans-4-trifluoromethyl-cyclohexylcarbamoyl)-5-(2,2-difluoro-ethoxy)-3H-imidazo[4,5-b]pyridin-2-ylamino]benzyl}-carbamic acid tert-butyl ester

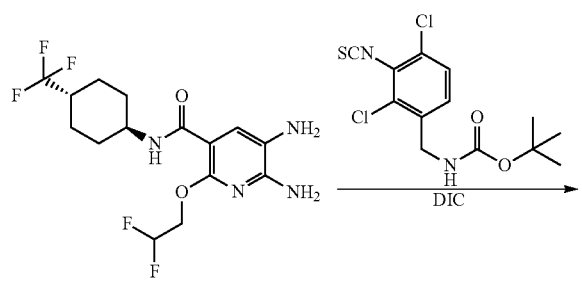

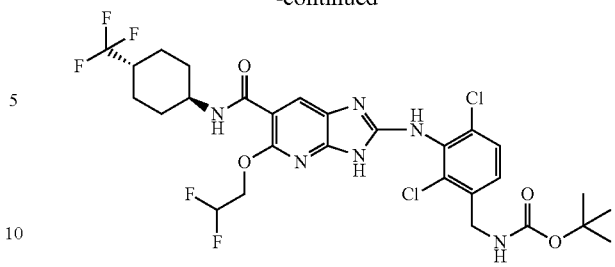

The title compound is prepared from (2,4-dichloro-3-isothiocyanato-benzyl)-carbamic acid tert-butyl ester (3.15 g, 9.45 mmol), 5,6-diamino-2-(2,2-difluoro-ethoxy)-N-(trans-4-trifluoromethyl-cyclohexyl)-nicotinamide (3.60 g, 9.42 mmol), EDC (2.0 g, 10.4 mmol) in MeCN (40 ml) in analogy to example 5c.

Yield: 6.3 g (98%). HPLC-method A: $R_t$=2.23 min. MS m/z: 681 [M+H]$^+$.

Example 17

N-{2,4-Dichloro-3-[6-(trans-4-trifluoromethyl-cyclohexylcarbamoyl)-5-(2,2-difluoro-ethoxy)-3H-imidazo[4,5-b]pyridin-2-ylamino]benzyl}-2-methyl-2-fluoro-propionamide

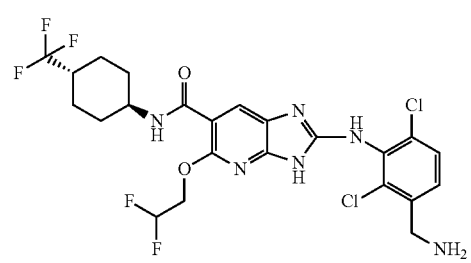

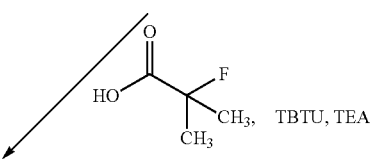

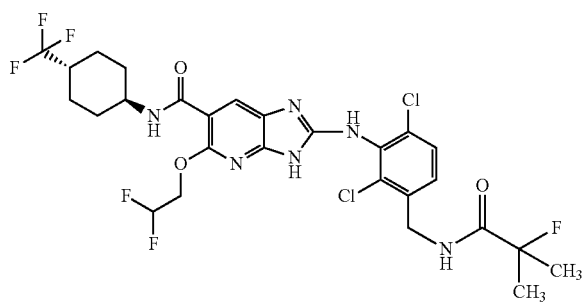

(a) 2,4-Dichloro-3-[6-(trans-4-trifluoromethyl-cyclohexylcarbamoyl)-5-(2,2-difluoro-ethoxy)-3H-imidazo[4,5-b]pyridin-2-ylamino]benzylamine A mixture of N-{2,4-dichloro-3-[6-(trans-4-trifluoromethyl-cyclohexylcarbamoyl)-5-(2,2-difluoro-ethoxy)-3H-imidazo[4,5-b]pyridin-2-ylamino]benzyl}-carbamic acid tert-butyl ester (6.3 g, 9.3 mmol), 4 M HCl in dioxane (60 ml) and MeOH (5 ml) is stirred for 15 min. The mixture is concentrated, diluted with water and basified with conc. $NH_3$. The precipitate is collected by filtration, washed with water, dried and purified via prep HPLC. The product fractions are concentrated, basified with conc. $NH_3$, extracted with EtOAc. The organic phases are dried with $Na_2SO_4$ and concentrated to give the crude sub-title compound (4.8 g).

(b) N-{2,4-Dichloro-3-[6-(trans-4-trifluoromethyl-cyclohexylcarbamoyl)-5-(2,2-difluoro-ethoxy)-3H-imidazo[4,5-b]pyridin-2-ylamino]benzyl}-2-methyl-2-fluoro-propionamide TBTU (1.0 ml of a 0.11 M solution in DMF) is added to a mixture of 2,4-dichloro-3-[6-(trans-4-trifluoromethyl-cyclohexylcarbamoyl)-5-(2,2-difluoro-ethoxy)-3H-imidazo[4,5-b]pyridin-2-ylamino]benzylamine (1.0 ml of a 0.10 M solution in DMF), DIPEA (52 µl, 0.3 mmol) and 2-fluoro-2-methylpropionic acid (1.0 ml of a 0.13 M solution in DMF) and it is stirred for 3 d and the mixture is purified by prep. HPLC.

Yield: 18%. HPLC $R_t$=1.99 min (method I). MS m/z: 670 $[M+H]^+$.

Example 154

N-{2,4-Dichloro-3-[6-(cyclopropylmethylcarbamoyl)-5-(2,2-difluoro-ethoxy)-1H-imidazo[4,5-b]pyridin-2-ylamino]-benzyl}-2,2-dimethyl-propionamide

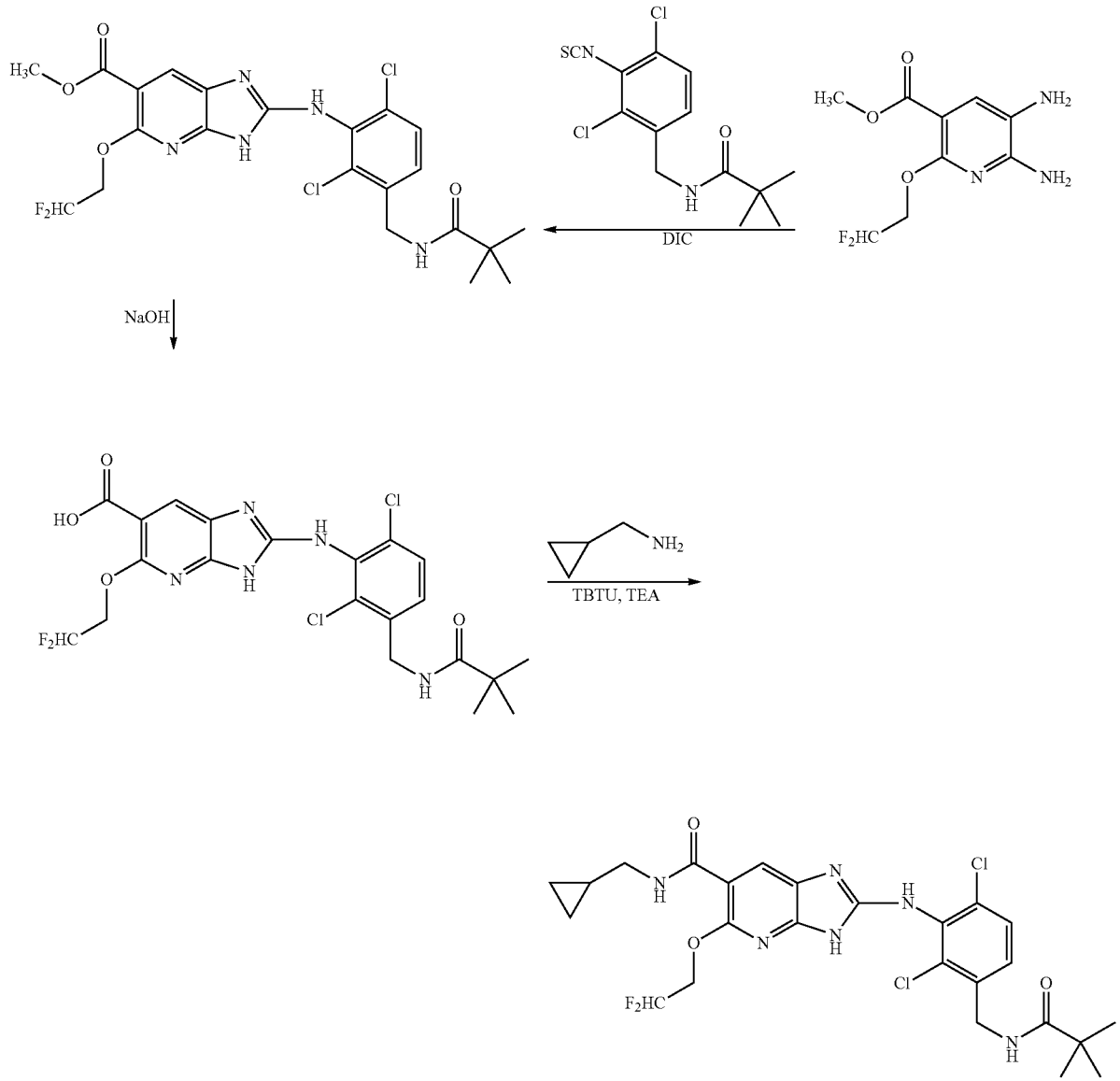

(a) N-{2,4-Dichloro-3-[6-methoxycarbonyl-5-(2,2-difluoro-ethoxy)-1H-imidazo[4,5-b]pyridin-2-ylamino]benzyl)-2,2-dimethyl-propionamide A mixture of N-(2,4-dichloro-3-isothiocyanato-benzyl)-2,2-dimethyl-propionamide (4.00 g, 12.6 mmol) and 5,6-diamino-2-(2,2-difluoro-ethoxy)-nicotinic acid methyl ester (3.10 g, 12.5 mmol, prepared according to WO2010/034799) in MeCN (30 ml) is stirred for 2.5 h, then EDC (2.75 g, 14.3 mmol) is added and it is stirred at reflux for 15 min. The mixture is diluted with water, concentrated and extracted with DCM. The organic phase is dried with $MgSO_4$, filtered and concentrated.

Yield: 9.8 g (crude). HPLC-method A: $R_t$=1.79 min. MS m/z: 530 $[M+H]^+$.

(b) N-{2,4-Dichloro-3-[6-hydroxycarbonyl-5-(2,2-difluoro-ethoxy)-1H-imidazo[4,5-b]pyridin-2-ylamino]benzyl)-2,2-dimethyl-propionamide A mixture of N-{2,4-dichloro-3-[6-methoxycarbonyl-5-(2,2-difluoro-ethoxy)-1H-imidazo[4,5-b]pyridin-2-ylamino]-benzyl)-2,2-dimethyl-propionamide (9.80 g, 12.0 mmol) and 1 N NaOH (40 ml) in MeOH (40 ml) is stirred overnight at rt and 45 min at reflux. Then the mixture is concentrated, acidified with 1 N aq. HCl-solution and the precipitate is filtered, dried and purified by HPLC.

Yield: 4.0 g (crude). HPLC-method A: $R_t$=1.63 min. MS m/z: 516 $[M+H]^+$.

(c) N-{2,4-Dichloro-3-[6-(cyclopropylmethylcarbamoyl)-5-(2,2-difluoro-ethoxy)-1H-imidazo[4,5-b]pyridin-2-ylamino]benzyl}-2,2-dimethyl-propionamide The title compound is prepared from N-{2,4-dichloro-3-[6-hydroxycarbonyl-5-(2,2-difluoro-ethoxy)-1H-imidazo[4,5-b]pyridin-2-ylamino]-benzyl)-2,2-dimethyl-propionamide (125 mg, 0.242 mmol), cyclopropylmethyl-amine (25 µl, 0.29 mmol), TBTU (80 mg, 0.25 mmol), TEA (150 µl) in DMF in analogy to example 12c.

Yield: 90 mg (65%). HPLC-method A: $R_t$=1.88 min. MS m/z: 569 $[M+H]^+$.

Example 155

N-{2,4-Dimethyl-3-[6-(trans-4-trifluoromethyl-cyclohexylcarbamoyl)-5-(2,2-difluoro-ethoxy)-1H-imidazo[4,5-b]pyridin-2-ylamino]benzyl}-2,2-dimethyl-propionamide

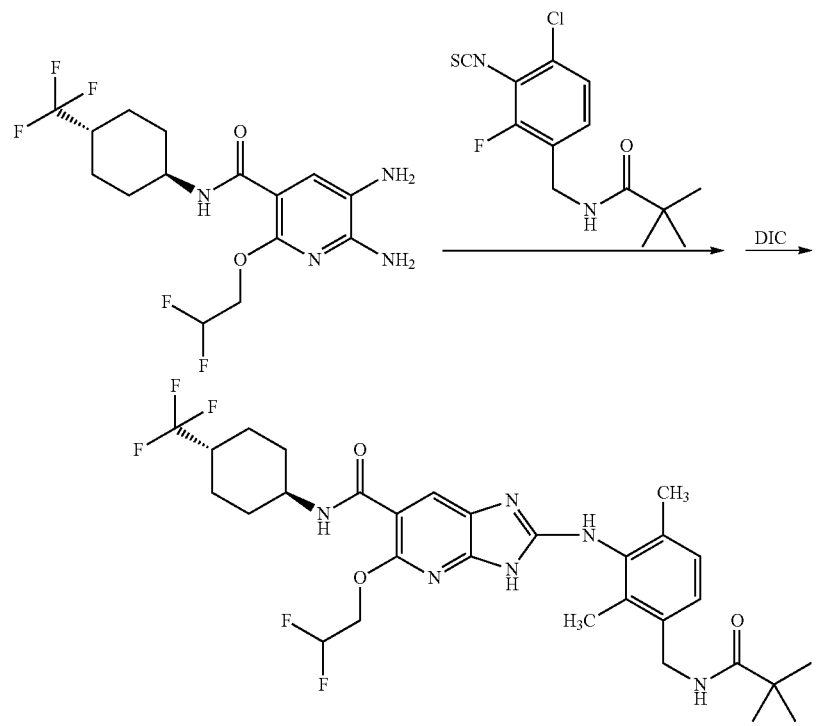

The title compound is prepared from N-(2,4-dimethyl-3-isothiocyanato-benzyl)-2,2-dimethyl-propionamide (65 mg, 0.24 mmol) and 5,6 diamino-2-(2,2-difluoro-ethoxy)-N-(trans-4-trifluoromethyl-cyclohexyl)-nicotinamide (90 mg, 0.24 mmol) with DIC in analogy to examples 8a/8b.

Yield: 65 mg (49%). $R_f$(TLC): 0.16 (silica gel, DCM:EtOH 95:5). MS m/z: 625 $[M+H]^+$.

Example 156

N-{2-Fluoro-4-chloro-3-[6-(trans-4-trifluoromethyl-cyclohexylcarbamoyl)-5-(2,2-difluoro-ethoxy)-1H-imidazo[4,5-b]pyridin-2-ylamino]benzyl}-2,2-dimethyl-propionamide

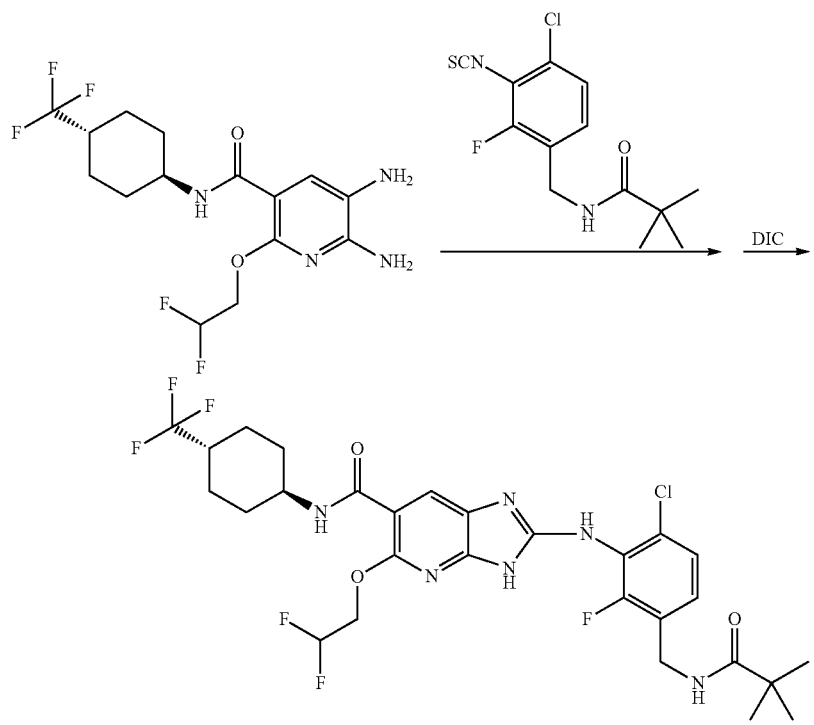

The title compound is prepared from N-(2-fluoro-4-chloro-3-isothiocyanato-benzyl)-2,2-dimethyl-propionamide (55 mg, 0.18 mmol) and 5,6 diamino-2-(2,2-difluoro-ethoxy)-N-(trans-4-trifluoromethyl-cyclohexyl)-nicotinamide (70 mg, 0.18 mmol) with DIC in analogy to examples 8a/8b.

Yield: 80 mg (67%). $R_f$(TLC): 0.25 (silica gel, DCM:EtOH 95:5). HPLC-method B: $R_t$=1.45 min. MS m/z: 649 [M+H]$^+$.

The following examples in Table 1 are prepared in analogy to the methods described above.

TABLE 1

| Ex. | Structure | Formula/ Mw. | MS m/z [M + H]$^+$ | $R_f$(TLC, silica gel) or $R_t$ [min] (HPLC-method) | Prepared in analogy to example |
|---|---|---|---|---|---|
| 11 | F$_3$C,,,, [structure] | C$_{28}$H$_{31}$F$_7$N$_6$O$_3$ 632.573 | 633 | $R_F$ = 0.19 (DCM/EtOH 95:5) | 10 |

TABLE 1-continued

| Ex. | Structure | Formula/ Mw. | MS m/z [M + H]+ | R$_f$ (TLC, silica gel) or R$_t$ [min] (HPLC-method) | Prepared in analogy to example |
|---|---|---|---|---|---|
| 15 | 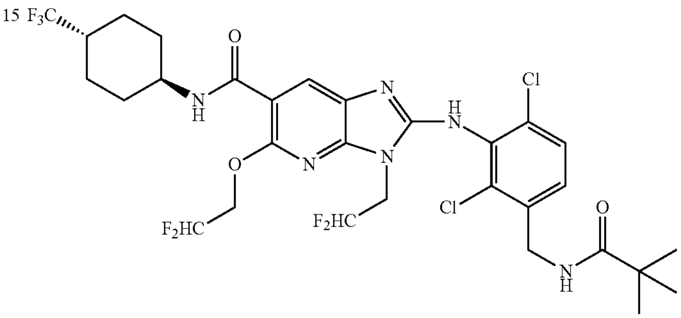 | C$_{30}$H$_{33}$Cl$_2$F$_7$N$_6$O$_3$S 729.516 | 729 | R$_t$ = 2.40 (method A) | 14 |
| 157 | 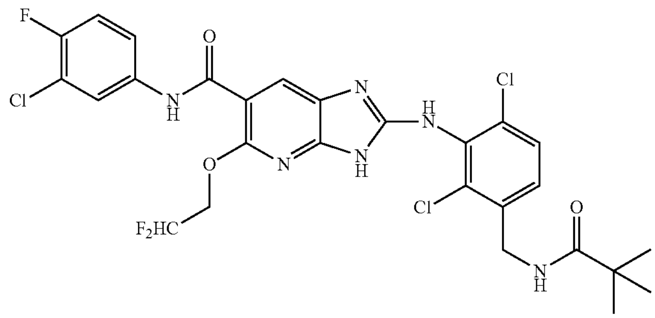 [SMILES: CC(C)(C)C(=O)NCc1ccc(Cl)c(Nc2nc3cc(C(=O)Nc4ccc(F)c(Cl)c4)c(OCC(F)F)nc3[nH]2)c1Cl] | C$_{27}$H$_{24}$Cl$_3$F$_3$N$_6$O$_3$ 643.871 | 643 | R$_t$ = 2.22 (method A) | 154 |

The following examples in Table 2 are prepared in analogy to example 17

TABLE 2

| Ex. | Structure | Formula/Mw. | MS m/z [M + H]+ | Rt [min] (HPLC-method) |
|---|---|---|---|---|
| 18 | 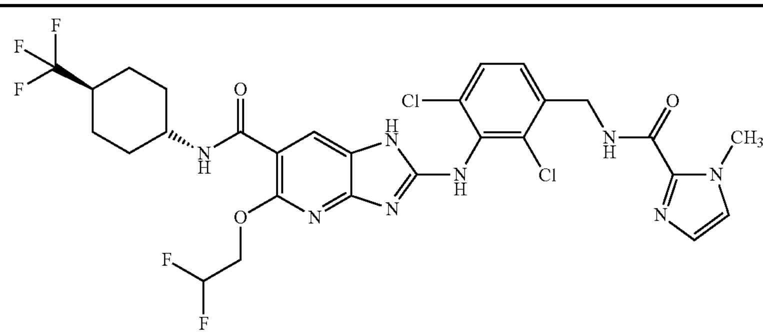 | C$_{28}$H$_{27}$Cl$_2$F$_5$N$_8$O$_3$ 689.47 | 689 | Rf = 0.47 Method H |
| 19 | 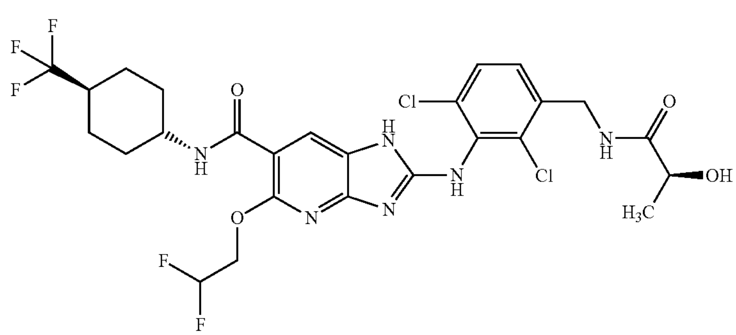 | C$_{26}$H$_{27}$Cl$_2$F$_5$N$_6$O$_4$ 653.433 | 653 | Rf = 0.47 Method H |

TABLE 2-continued

| Ex. | Structure | Formula/Mw. | MS m/z [M + H]+ | Rt [min] (HPLC-method) |
|---|---|---|---|---|
| 20 | 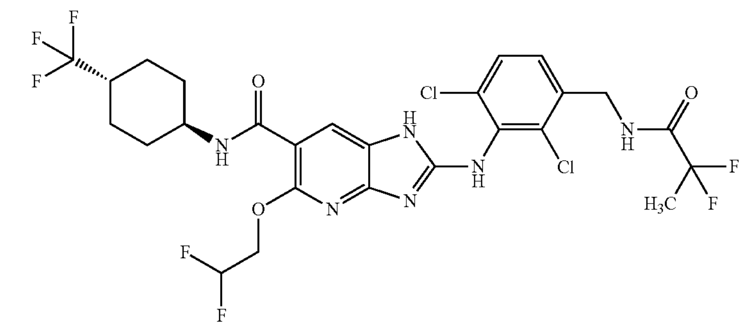 [SMILES: CC(F)(F)C(=O)NCc1ccc(Cl)c(Nc2nc3nc(OCC(F)F)c(C(=O)N[C@H]4CC[C@H](C(F)(F)F)CC4)cc3[nH]2)c1Cl] | $C_{26}H_{25}Cl_2F_7N_6O_3$ 673.415 | 673 | Rf = 1.96 Method I |
| 21 | 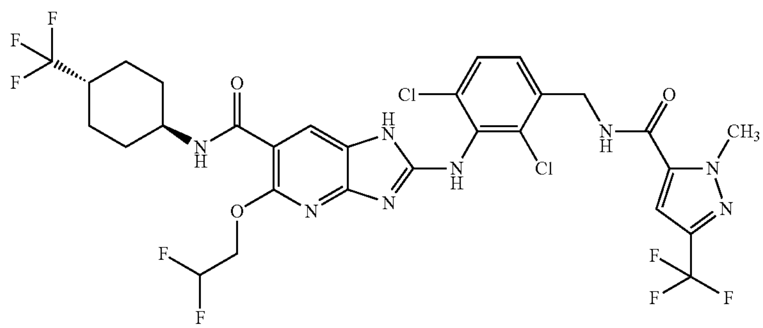 [SMILES: Cn1nc(C(F)(F)F)cc1C(=O)NCc1ccc(Cl)c(Nc2nc3nc(OCC(F)F)c(C(=O)N[C@H]4CC[C@H](C(F)(F)F)CC4)cc3[nH]2)c1Cl] | $C_{29}H_{26}Cl_2F_8N_8O_3$ 757.467 | 757 | Rf = 0.56 Method H |
| 22 | 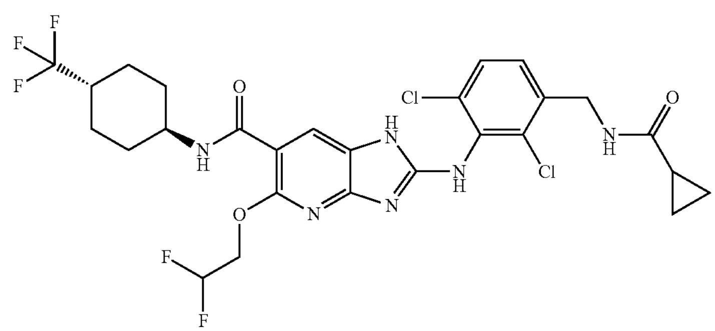 [SMILES: O=C(N[C@H]1CC[C@H](C(F)(F)F)CC1)c1cc2[nH]c(Nc3c(Cl)ccc(CNC(=O)C4CC4)c3Cl)nc2nc1OCC(F)F] | $C_{27}H_{27}Cl_2F_5N_6O_3$ 649.445 | 649 | Rf = 0.50 Method H |
| 23 | 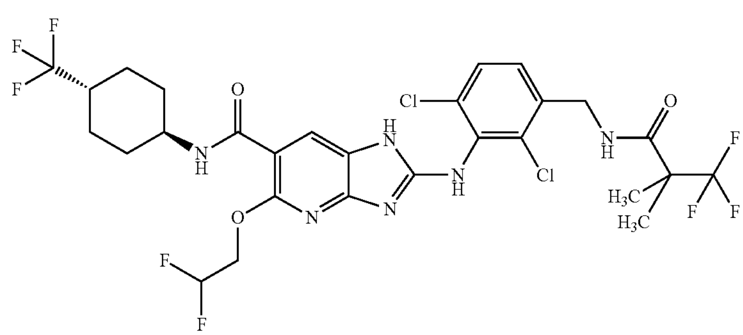 [SMILES: CC(C)(C(=O)NCc1ccc(Cl)c(Nc2nc3nc(OCC(F)F)c(C(=O)N[C@H]4CC[C@H](C(F)(F)F)CC4)cc3[nH]2)c1Cl)C(F)(F)F] | $C_{28}H_{28}Cl_2F_8N_6O_3$ 719.458 | 719 | Rf = 2.05 Method I |

TABLE 2-continued

| Ex. | Structure | Formula/Mw. | MS m/z [M + H]+ | Rt [min] (HPLC-method) |
|---|---|---|---|---|
| 24 | 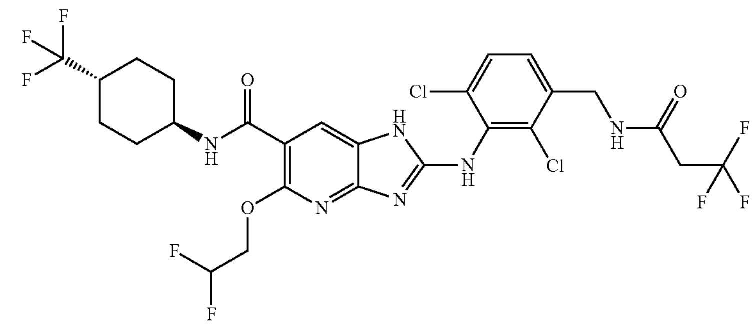 [SMILES: O=C(CC(F)(F)F)NCc1ccc(Cl)c(Nc2nc3nc(OCC(F)F)c(C(=O)N[C@H]4CC[C@H](C(F)(F)F)CC4)cc3[nH]2)c1Cl] | C26H24Cl2F8N6O3 691.405 | 691 | Rf = 0.51 Method H |
| 25 | 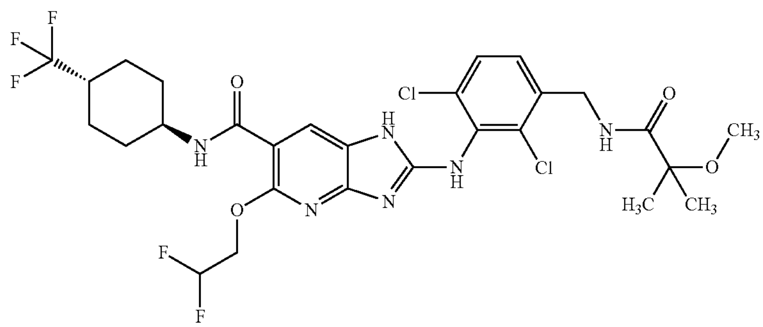 [SMILES: COC(C)(C)C(=O)NCc1ccc(Cl)c(Nc2nc3nc(OCC(F)F)c(C(=O)N[C@H]4CC[C@H](C(F)(F)F)CC4)cc3[nH]2)c1Cl] | C28H31Cl2F5N6O4 681.487 | 681 | Rf = 1.99 Method I |
| 26 | 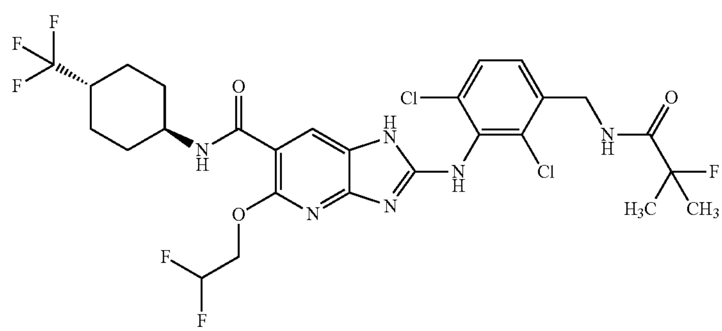 [SMILES: CC(C)(F)C(=O)NCc1ccc(Cl)c(Nc2nc3nc(OCC(F)F)c(C(=O)N[C@H]4CC[C@H](C(F)(F)F)CC4)cc3[nH]2)c1Cl] | C27H28Cl2F6N6O3 689.47 | 689 | Rf = 1.99 Method I |
| 27 | 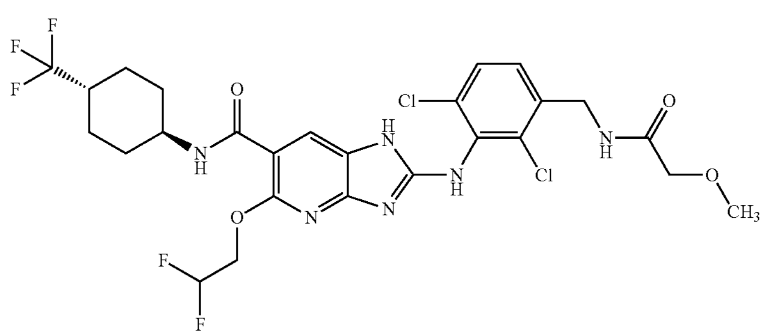 [SMILES: COCC(=O)NCc1ccc(Cl)c(Nc2nc3nc(OCC(F)F)c(C(=O)N[C@H]4CC[C@H](C(F)(F)F)CC4)cc3[nH]2)c1Cl] | C26H27Cl2F5N6O4 653.433 | 653 | Rf = 0.48 Method H |

TABLE 2-continued

| Ex. | Structure | Formula/Mw. | MS m/z [M + H]+ | Rt [min] (HPLC-method) |
|---|---|---|---|---|
| 28 | 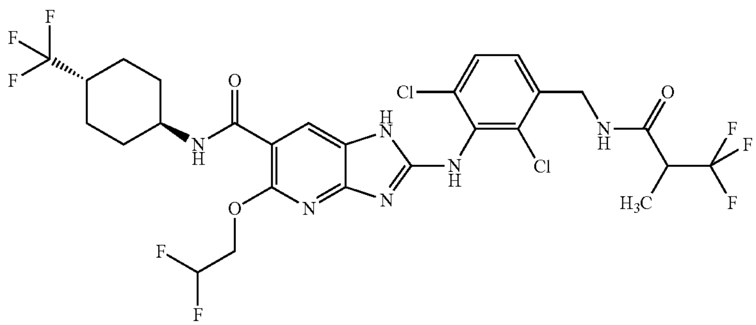 | C27H26Cl2F8N6O3 705.431 | 705 | Rf = 0.53 Method H |
| 29 | 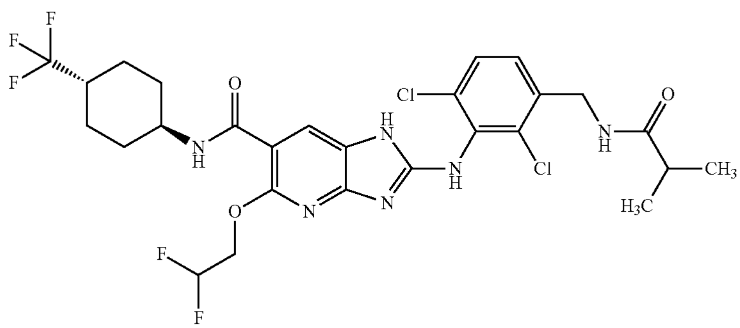 [SMILES: CC(C)C(=O)NCc1ccc(Cl)c(Nc2nc3nc(OCC(F)F)c(C(=O)N[C@H]4CC[C@H](C(F)(F)F)CC4)cc3[nH]2)c1Cl] | C27H29Cl2F5N6O3 651.461 | 651 | Rf = 0.51 Method H |
| 30 | 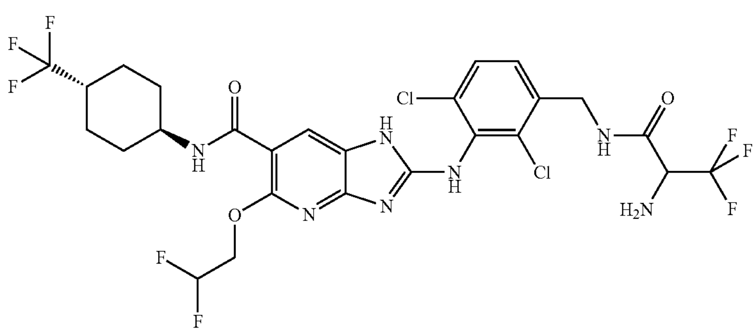 [SMILES: NC(C(=O)NCc1ccc(Cl)c(Nc2nc3nc(OCC(F)F)c(C(=O)N[C@H]4CC[C@H](C(F)(F)F)CC4)cc3[nH]2)c1Cl)C(F)(F)F] | C26H25Cl2F8N7O3 706.419 | 706 | Rf = 1.93 Method I |
| 31 | 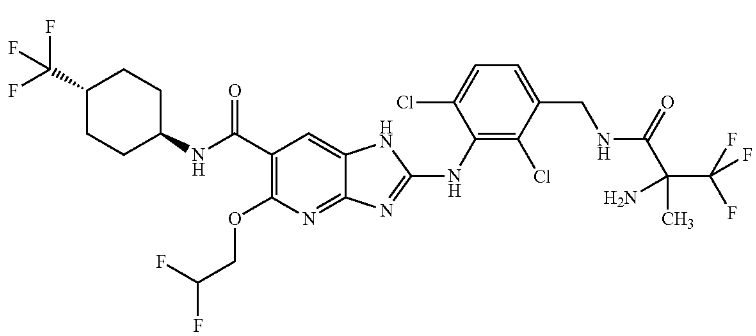 [SMILES: CC(N)(C(=O)NCc1ccc(Cl)c(Nc2nc3nc(OCC(F)F)c(C(=O)N[C@H]4CC[C@H](C(F)(F)F)CC4)cc3[nH]2)c1Cl)C(F)(F)F] | C27H27Cl2F8N7O3 720.446 | 720 | Rf = 0.47 Method H |

TABLE 2-continued

| Ex. | Structure | Formula/Mw. | MS m/z [M + H]+ | Rt [min] (HPLC-method) |
|---|---|---|---|---|
| 32 | 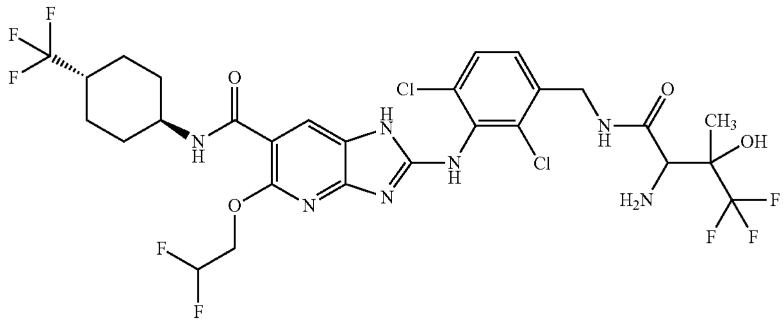 [SMILES: CC(O)(C(N)C(=O)NCc1ccc(Cl)c(Nc2nc3nc(OCC(F)F)c(C(=O)N[C@H]4CC[C@H](C(F)(F)F)CC4)cc3[nH]2)c1Cl)C(F)(F)F] | C28H29Cl2F8N7O4 750.472 | 750 | Rf = 0.44 Method H |
| 33 | 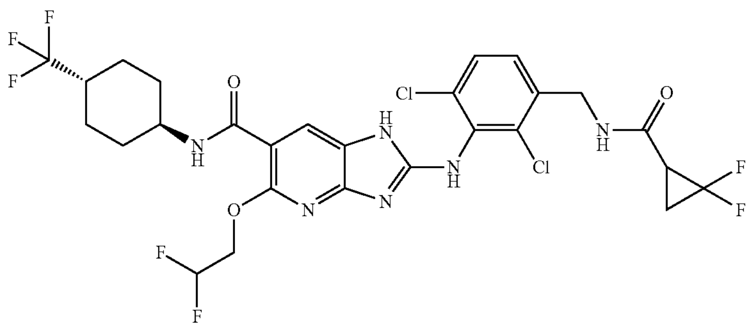 [SMILES: O=C(N[C@H]1CC[C@H](C(F)(F)F)CC1)c1cc2[nH]c(Nc3c(Cl)ccc(CNC(=O)C4CC4(F)F)c3Cl)nc2nc1OCC(F)F] | C27H25Cl2F7N6O3 685.426 | 685 | Rf = 0.51 Method H |
| 34 | 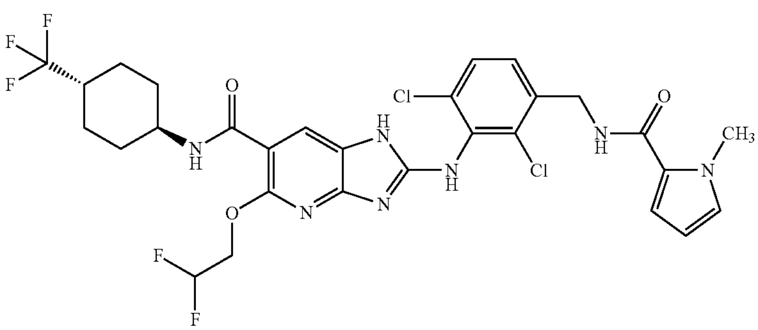 [SMILES: Cn1cccc1C(=O)NCc1ccc(Cl)c(Nc2nc3nc(OCC(F)F)c(C(=O)N[C@H]4CC[C@H](C(F)(F)F)CC4)cc3[nH]2)c1Cl] | C29H28Cl2F5N7O3 688.482 | 688 | Rf = 0.53 Method H |
| 35 | 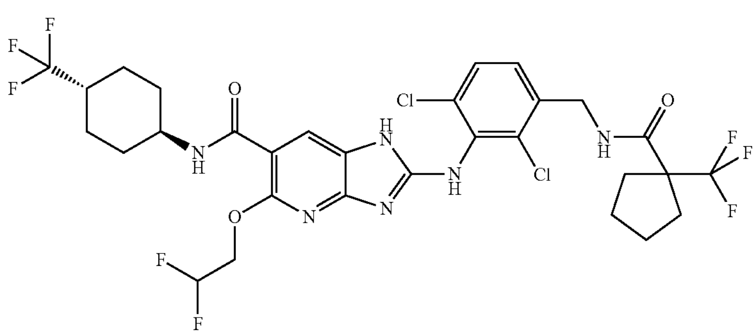 [SMILES: O=C(N[C@H]1CC[C@H](C(F)(F)F)CC1)c1cc2[nH]c(Nc3c(Cl)ccc(CNC(=O)C4(C(F)(F)F)CCCC4)c3Cl)nc2nc1OCC(F)F] | C30H30Cl2F8N6O3 745.496 | 745 | Rf = 2.11 Method I |

TABLE 2-continued
| Ex. | Structure | Formula/Mw. | MS m/z [M + H]+ | Rt [min] (HPLC-method) |
|---|---|---|---|---|
| 36 | 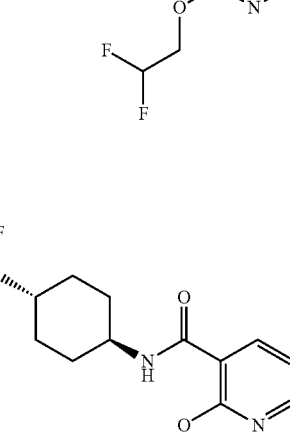 | C26H24Cl2F8N6O4 707.404 | 707 | Rf = 0.50 Method H |
| 37 | 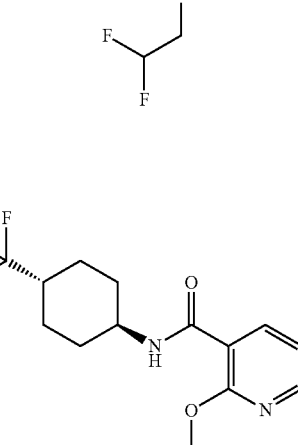 | C27H27Cl2F5N6O4 665.444 | 665 | Rf = 0.48 Method H |
| 38 | 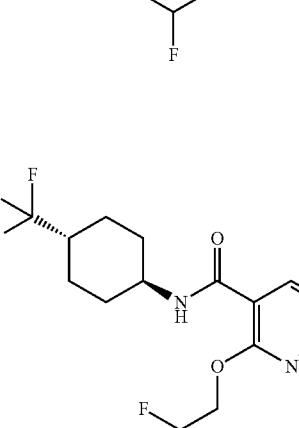 | C28H29Cl2F5N6O3 663.472 | 663 | Rf = 0.51 Method H |
| 39 | 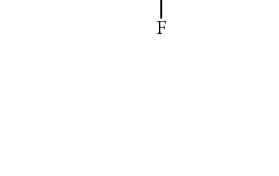 | C25H25Cl2F5N6O3 623.408 | 623 | Rf = 0.47 Method H |

TABLE 2-continued

| Ex. | Structure | Formula/Mw. | MS m/z [M + H]+ | Rt [min] (HPLC-method) |
|---|---|---|---|---|
| 40 | 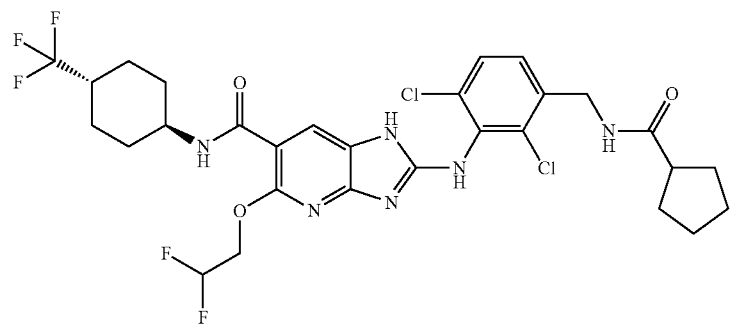 | $C_{29}H_{31}Cl_2F_5N_6O_3$ 677.499 | 677 | Rf = 0.53 Method H |
| 41 | 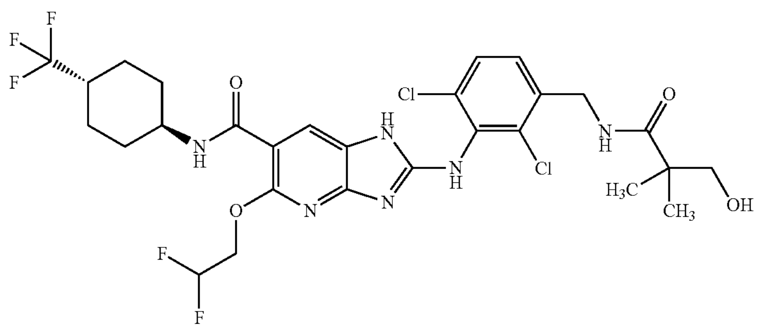 [SMILES: CC(C)(CO)C(=O)NCc1ccc(Cl)c(Nc2nc3nc(OCC(F)F)c(C(=O)N[C@H]4CC[C@H](C(F)(F)F)CC4)cc3[nH]2)c1Cl] | $C_{28}H_{31}Cl_2F_5N_6O_4$ 681.487 | 681 | Rf = 0.48 Method H |
| 42 | 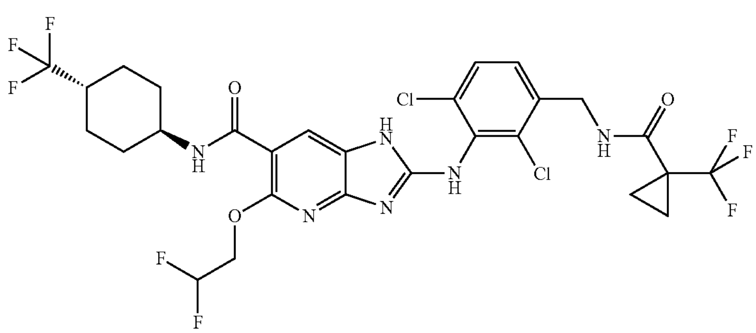 [SMILES: O=C(N[C@H]1CC[C@H](C(F)(F)F)CC1)c1cc2[nH]c(Nc3c(Cl)ccc(CNC(=O)C4(C(F)(F)F)CC4)c3Cl)nc2nc1OCC(F)F] | $C_{28}H_{26}Cl_2F_8N_6O_3$ 717.442 | 717 | Rf = 2.03 Method I |
| 43 | 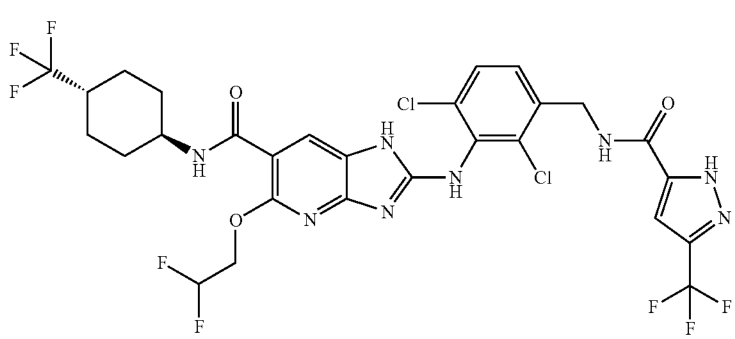 [SMILES: O=C(NCc1ccc(Cl)c(Nc2nc3nc(OCC(F)F)c(C(=O)N[C@H]4CC[C@H](C(F)(F)F)CC4)cc3[nH]2)c1Cl)c1cc(C(F)(F)F)n[nH]1] | $C_{28}H_{24}Cl_2F_8N_8O_3$ 743.441 | 743 | Rf = 0.53 Method H |

TABLE 2-continued

| Ex. | Structure | Formula/Mw. | MS m/z [M + H]+ | Rt [min] (HPLC-method) |
|---|---|---|---|---|
| 44 | 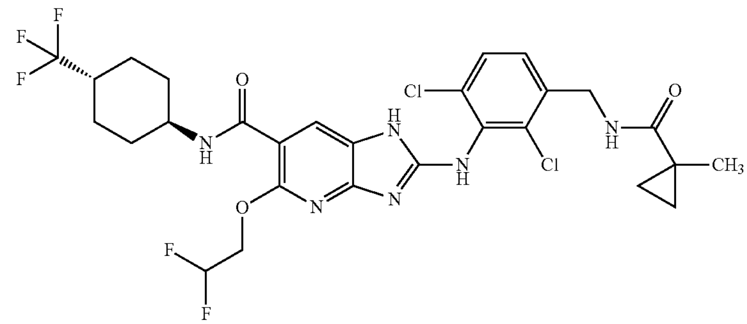 [SMILES: CC1(C(=O)NCc2ccc(Cl)c(Nc3nc4nc(OCC(F)F)c(C(=O)N[C@H]5CC[C@H](C(F)(F)F)CC5)cc4[nH]3)c2Cl)CC1] | C28H29Cl2F5N6O3  663.472 | 663 | Rf = 0.52  Method H |
| 45 | 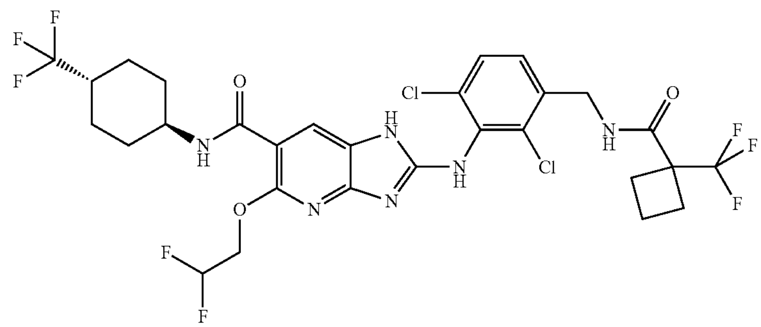 [SMILES: O=C(N[C@H]1CC[C@H](C(F)(F)F)CC1)c1cc2[nH]c(Nc3c(Cl)ccc(CNC(=O)C4(C(F)(F)F)CCC4)c3Cl)nc2nc1OCC(F)F] | C29H28Cl2F8N6O3  731.469 | 731 | Rf = 0.55  Method H |
| 46 | 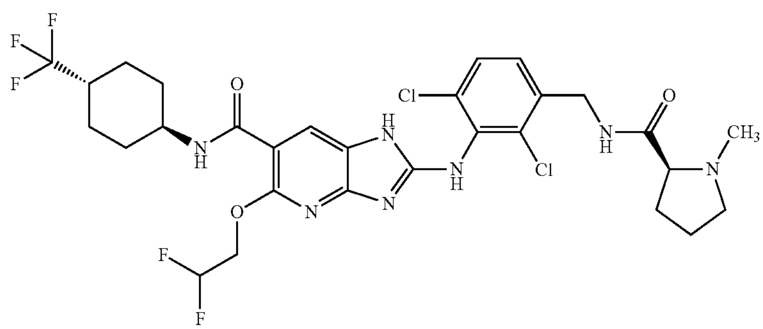 [SMILES: CN1CCC[C@H]1C(=O)NCc1ccc(Cl)c(Nc2nc3nc(OCC(F)F)c(C(=O)N[C@H]4CC[C@H](C(F)(F)F)CC4)cc3[nH]2)c1Cl] | C29H32Cl2F5N7O3  692.514 | 692 | Rf = 2.02  Method I |
| 47 | 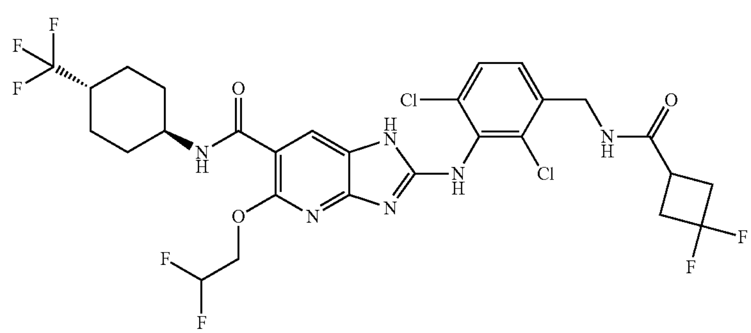 [SMILES: O=C(N[C@H]1CC[C@H](C(F)(F)F)CC1)c1cc2[nH]c(Nc3c(Cl)ccc(CNC(=O)C4CC(F)(F)C4)c3Cl)nc2nc1OCC(F)F] | C28H27Cl2F7N6O3  699.452 | 699 | Rf = 0.52  Method H |

TABLE 2-continued

| Ex. | Structure | Formula/Mw. | MS m/z [M + H]+ | Rt [min] (HPLC-method) |
|---|---|---|---|---|
| 48 | 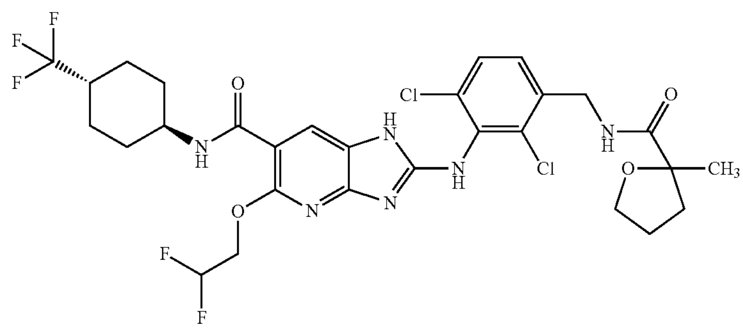 [SMILES: CC1(C(=O)NCc2ccc(Cl)c(Nc3nc4nc(OCC(F)F)c(C(=O)N[C@H]5CC[C@H](C(F)(F)F)CC5)cc4[nH]3)c2Cl)CCCO1] | C29H31Cl2F5N6O4 693.498 | 693 | Rf = 0.51 Method H |
| 49 | 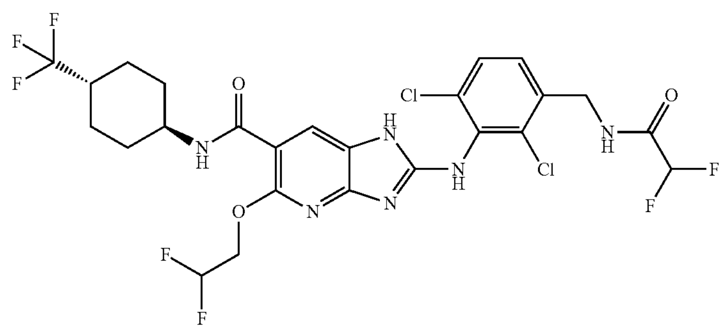 [SMILES: O=C(N[C@H]1CC[C@H](C(F)(F)F)CC1)c1cc2[nH]c(Nc3c(Cl)ccc(CNC(=O)C(F)F)c3Cl)nc2nc1OCC(F)F] | C25H23Cl2F7N6O3 659.388 | 659 | Rf = 0.50 Method H |
| 50 | 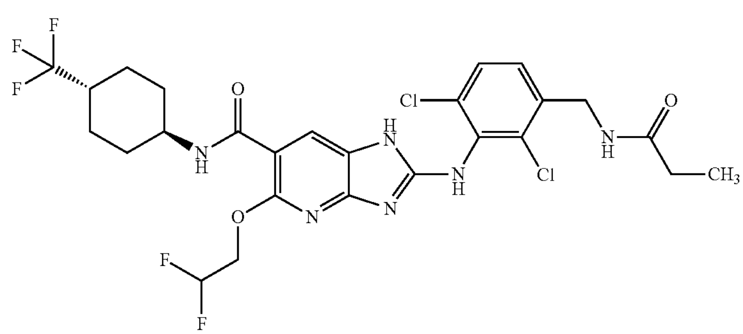 [SMILES: CCC(=O)NCc1ccc(Cl)c(Nc2nc3nc(OCC(F)F)c(C(=O)N[C@H]4CC[C@H](C(F)(F)F)CC4)cc3[nH]2)c1Cl] | C26H27Cl2F5N6O3 637.434 | 637 | Rf = 0.49 Method H |
| 51 | 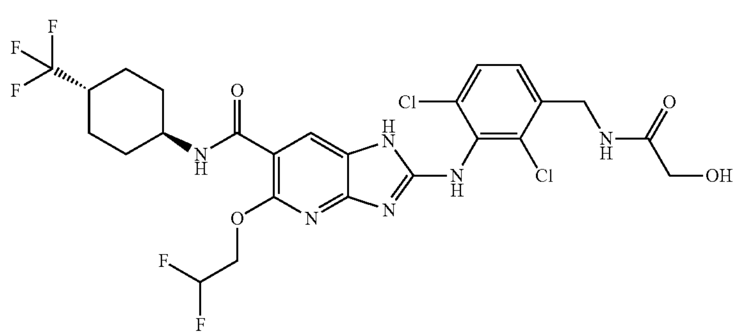 [SMILES: O=C(CO)NCc1ccc(Cl)c(Nc2nc3nc(OCC(F)F)c(C(=O)N[C@H]4CC[C@H](C(F)(F)F)CC4)cc3[nH]2)c1Cl] | C25H25Cl2F5N6O4 639.407 | 639 | Rf = 0.46 Method H |

TABLE 2-continued

| Ex. | Structure | Formula/Mw. | MS m/z [M + H]+ | Rt [min] (HPLC-method) |
|---|---|---|---|---|
| 52 | 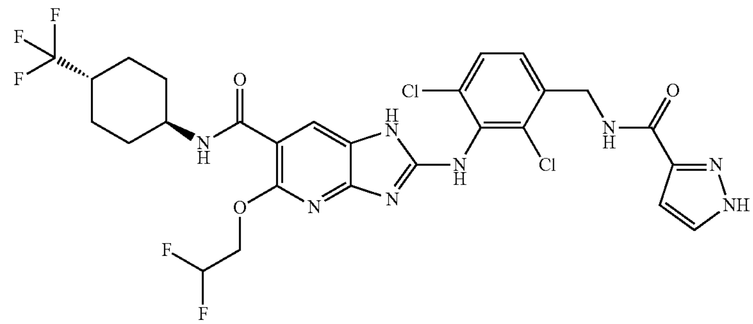 [SMILES: O=C(NCc1ccc(Cl)c(Nc2nc3nc(OCC(F)F)c(C(=O)N[C@H]4CC[C@H](C(F)(F)F)CC4)cc3[nH]2)c1Cl)c1cc[nH]n1] | C27H25Cl2F5N8O3 675.444 | 675 | Rf = 0.48 Method H |
| 53 | 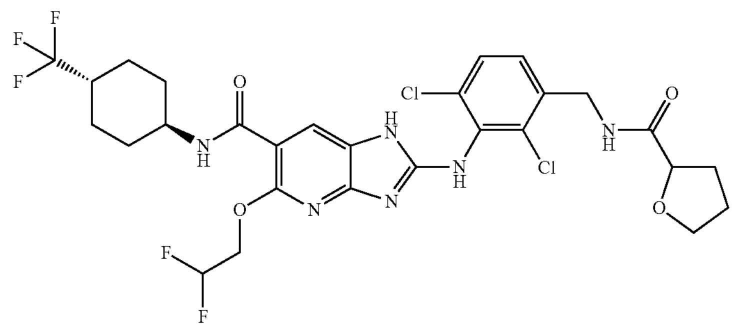 [SMILES: O=C(N[C@H]1CC[C@H](C(F)(F)F)CC1)c1cc2[nH]c(Nc3c(Cl)ccc(CNC(=O)C4CCCO4)c3Cl)nc2nc1OCC(F)F] | C28H29Cl2F5N6O4 679.471 | 679 | Rf = 0.49 Method H |
| 54 | 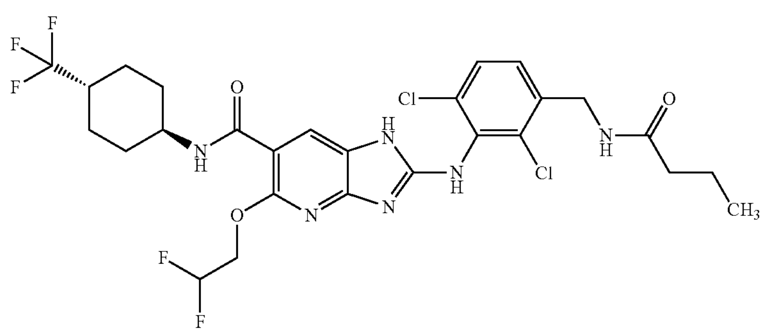 | C27H29Cl2F5N6O3 651.461 | 651 | Rf = 0.51 Method H |
| 55 | 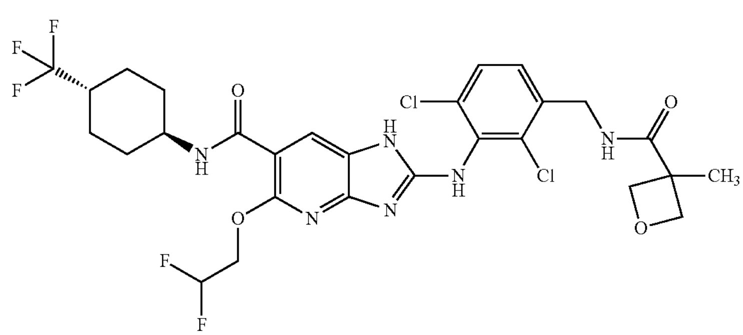 [SMILES: CC1(C(=O)NCc2ccc(Cl)c(Nc3nc4nc(OCC(F)F)c(C(=O)N[C@H]5CC[C@H](C(F)(F)F)CC5)cc4[nH]3)c2Cl)COC1] | C28H29Cl2F5N6O4 679.471 | 679 | Rf = 0.48 Method H |

| Ex. | Structure | Formula/Mw. | MS m/z [M + H]+ | Rt [min] (HPLC-method) |
|---|---|---|---|---|
| 56 | 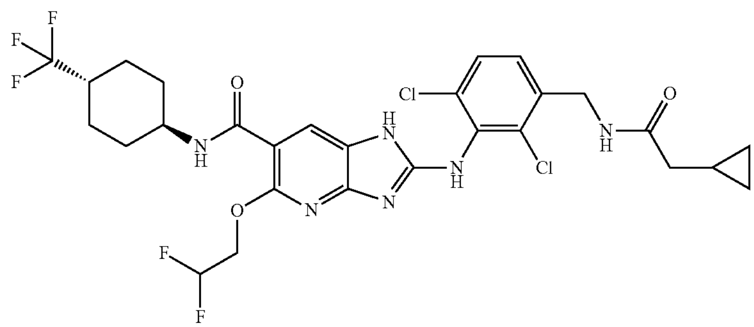 [SMILES: O=C(CC1CC1)NCc1ccc(Cl)c(Nc2nc3nc(OCC(F)F)c(C(=O)N[C@H]4CC[C@H](C(F)(F)F)CC4)cc3[nH]2)c1Cl] | C₂₈H₂₉Cl₂F₅N₆O₃ 663.472 | 663 | Rf = 1.99 Method I |
| 57 | 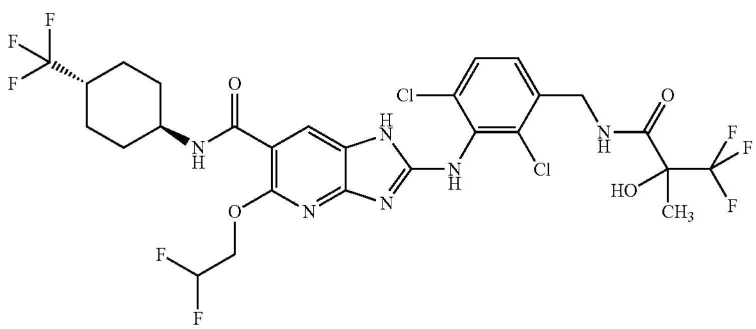 | C₂₇H₂₆Cl₂F₈N₆O₄ 721.43 | 721 | Rf = 0.51 Method H |
| 58 | 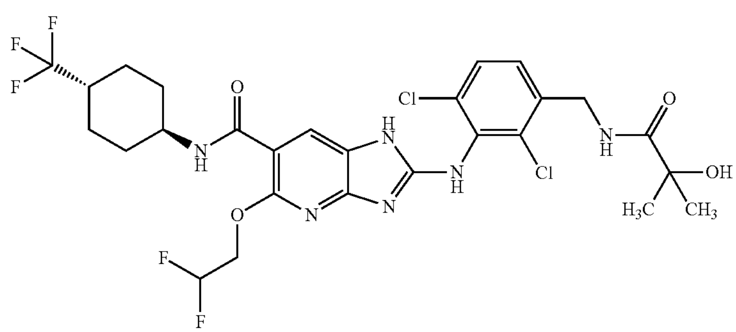 [SMILES: CC(C)(O)C(=O)NCc1ccc(Cl)c(Nc2nc3nc(OCC(F)F)c(C(=O)N[C@H]4CC[C@H](C(F)(F)F)CC4)cc3[nH]2)c1Cl] | C₂₇H₂₉Cl₂F₅N₆O₄ 667.46 | 667 | Rf = 0.48 Method H |
| 59 | 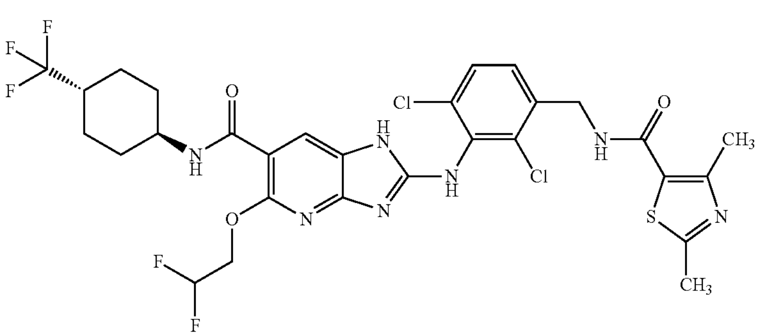 [SMILES: Cc1nc(C)c(C(=O)NCc2ccc(Cl)c(Nc3nc4nc(OCC(F)F)c(C(=O)N[C@H]5CC[C@H](C(F)(F)F)CC5)cc4[nH]3)c2Cl)s1] | C₂₉H₂₈Cl₂F₅N₇O₃S 720.548 | 720 | Rf = 0.50 Method H |

TABLE 2-continued

| Ex. | Structure | Formula/Mw. | MS m/z [M + H]+ | Rt [min] (HPLC-method) |
|---|---|---|---|---|
| 60 | 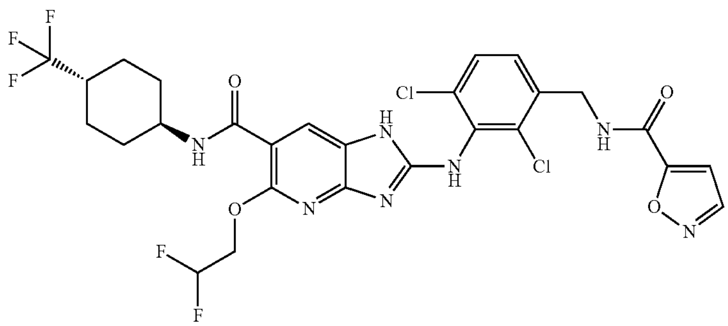 [SMILES: O=C(NCc1ccc(Cl)c(Nc2nc3nc(OCC(F)F)c(C(=O)N[C@H]4CC[C@H](C(F)(F)F)CC4)cc3[nH]2)c1Cl)c1ccno1] | $C_{27}H_{24}Cl_2F_5N_7O_4$ 676.428 | 676 | Rf = 0.50 Method H |
| 61 | 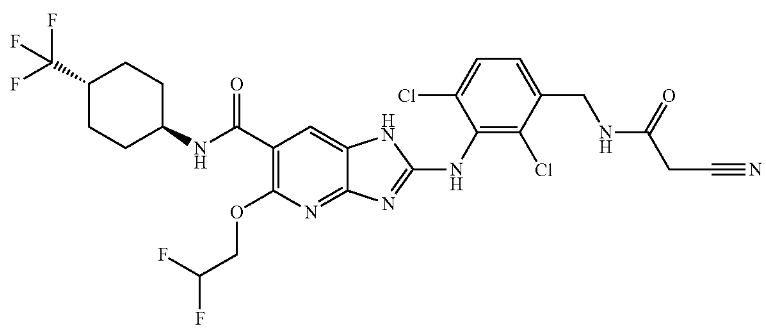 [SMILES: N#CCC(=O)NCc1ccc(Cl)c(Nc2nc3nc(OCC(F)F)c(C(=O)N[C@H]4CC[C@H](C(F)(F)F)CC4)cc3[nH]2)c1Cl] | $C_{26}H_{24}Cl_2F_5N_7O_3$ 648.418 | 648 | Rf = 0.48 Method H |
| 62 | 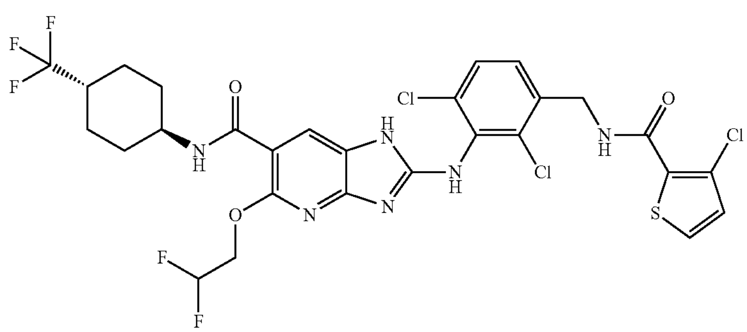 [SMILES: O=C(N[C@H]1CC[C@H](C(F)(F)F)CC1)c1cc2[nH]c(Nc3c(Cl)ccc(CNC(=O)c4sccc4Cl)c3Cl)nc2nc1OCC(F)F] | $C_{28}H_{24}Cl_3F_5N_6O_3S$ 725.952 | 725 | Rf = 0.55 Method H |
| 63 | 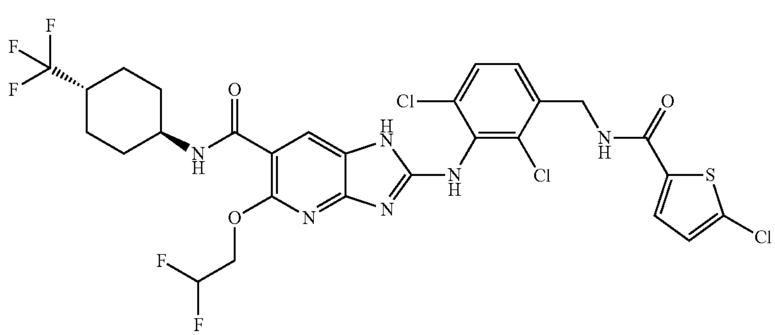 [SMILES: O=C(NCc1ccc(Cl)c(Nc2nc3nc(OCC(F)F)c(C(=O)N[C@H]4CC[C@H](C(F)(F)F)CC4)cc3[nH]2)c1Cl)c1ccc(Cl)s1] | $C_{28}H_{24}Cl_3F_5N_6O_3S$ 725.95 | 767 | Rf = 2.1 Method I |

The following examples in Table 3 are prepared in analogy to example 17.

TABLE 3

| Ex. | R⁶ = *—CH₃ | Ex. | R⁶ = *—H | W = |
|---|---|---|---|---|
| 64 | C₂₉H₃₂F₈N₆O₃<br>MW: 664.595<br>MS m/z [M + H]⁺ = 665<br>$R_t$ = 0.52 (method H) | 65 | C₂₈H₃₀F₈N₆O₃<br>MW: 650.568<br>MS m/z [M + H]⁺ = 651<br>$R_t$ = 0.44 (method K) | *—CH₂CH₂CH₃ |
| 66 | C₂₈H₃₀F₈N₆O₃<br>MW: 650.568<br>MS m/z [M + H]⁺ = 651<br>$R_t$ = 0.50 (method H) | 67 | C₂₇H₂₈F₈N₆O₃<br>MW: 636.541<br>MS m/z [M + H]⁺ = 637<br>$R_t$ = 0.42 (method K) | *—CH₂CH₃ |
| 68 | C₂₇H₂₈F₈N₆O₄<br>MW: 652.54<br>MS m/z [M + H]⁺ = 653<br>$R_t$ = 0.48 (method H) | 69 | C₂₆H₂₆F₈N₆O₄<br>MW: 638.513<br>MS m/z [M + H]⁺ = 639<br>$R_t$ = 0.46 (method H) | *—CH₂OH |
| 70 | C₂₈H₃₀F₈N₆O₄<br>MW: 666.567<br>MS m/z [M + H]⁺ = 666<br>$R_t$ = 2.04 (method I) | 71 | C₂₇H₂₈F₈N₆O₄<br>MW: 652.540<br>MS m/z [M + H]⁺ = 652<br>$R_t$ = 1.70 (method J) | *—CH₂OCH₃ |
| 72 | C₂₈H₂₇F₁₁N₆O₃<br>MW: 704.538<br>MS m/z [M + H]⁺ = 705<br>$R_t$ = 0.53 (method H) | 73 | C₂₇H₂₅F₁₁N₆O₃<br>MW: 690.512<br>MS m/z [M + H]⁺ = 691<br>$R_t$ = 0.45 (method K) | *—CH₂CF₃ |
| 74 | C₂₇H₂₈F₈N₆O₃<br>MW: 636.541<br>MS m/z [M + H]⁺ = 637<br>$R_t$ = 0.49 (method H) | 75 | C₂₆H₂₆F₈N₆O₃<br>MW: 622.514<br>MS m/z [M + H]⁺ = 622<br>$R_t$ = 1.67 (method J) | *—CH₃ |
| 76 | C₂₇H₂₆F₁₀N₆O₃<br>MW: 672.521<br>MS m/z [M + H]⁺ = 673<br>$R_t$ = 0.52 (method H) | 77 | C₂₆H₂₄F₁₀N₆O₃<br>MW: 658.495<br>MS m/z [M + H]⁺ = 659<br>$R_t$ = 0.43 (method K) | *—CHF₂ |
| 78 | C₂₉H₃₂F₈N₆O₃<br>MW: 664.595<br>MS m/z [M + H]⁺ = 665<br>$R_t$ = 0.52 (method H) | 79 | C₂₈H₃₀F₈N₆O₃<br>MW: 650.568<br>MS m/z [M + H]⁺ = 651<br>$R_t$ = 1.77 (method J) | *—CH(CH₃)₂ |
| 80 | C₂₈H₂₇F₈N₇O₃<br>MW: 661.551<br>MS m/z [M + H]⁺ = 661<br>$R_t$ = 2.01 (method I) | 81 | C₂₇H₂₅F₈N₇O₃<br>MW: 647.525<br>MS m/z [M + H]⁺ = 647<br>$R_t$ = 1.70 (method J) | *—CH₂CN |
| 82 | C₂₈H₃₀F₈N₆O₄<br>MW: 666.567<br>MS m/z [M + H]⁺ = 667<br>$R_t$ = 0.48 (method H) | 83 | C₂₇H₂₈F₈N₆O₄<br>MW: 652.54<br>MS m/z [M + H]⁺ = 653<br>$R_t$ = 0.40 (method K) | *—CH(OH)CH₃ |
| 84 | C₃₀H₃₄F₈N₆O₄<br>MW: 694.621<br>MS m/z [M + H]⁺ = 695<br>$R_t$ = 0.52 (method H) | | | *—C(CH₃)₂OCH₃ |

TABLE 3-continued

[Structure: core scaffold with trans-4-(trifluoromethyl)cyclohexyl amide, imidazopyridine with 2,2-difluoroethoxy group, and 2-[(3-(aminomethyl)-6-(trifluoromethyl)phenyl)amino] linker to NH-C(=O)-W, with R6 on the imidazole nitrogen]

| Ex. | R6 = *–CH3 | Ex. | R6 = *–H | W = |
|---|---|---|---|---|
| 85 | C30H34F8N6O4<br>MW: 694.621<br>MS m/z [M + H]+ = 694<br>Rt = 2.04 (method I) | 86 | C29H32F8N6O4<br>MW: 680.567<br>MS m/z [M + H]+ = 681<br>Rt = 0.42 (method K) | *–C(CH3)2–CH2OH |
| 87 | C29H32F8N6O4<br>MW: 680.594<br>MS m/z [M + H]+ = 681<br>Rt = 0.50 (method H) | 88 | C28H30F8N6O4<br>MW: 666.567<br>MS m/z [M + H]+ = 666<br>Rt = 1.68 (method J) | *–C(CH3)2–OH |
| 89 | C29H31F9N6O3<br>MW: 682.585<br>MS m/z [M + H]+ = 682<br>Rt = 2.07 (method I) | 90 | C28H29F9N6O3<br>MW: 668.558<br>MS m/z [M + H]+ = 669<br>Rt = 0.52 (method H) | *–C(CH3)2–F |
| 91 | C28H28F10N6O3<br>MW: 686.548<br>MS m/z [M + H]+ = 687<br>Rt = 0.53 (method H) | 92 | C27H26F10N6O3<br>MW: 672.521<br>MS m/z [M + H]+ = 672<br>Rt = 1.84 (method I) | *–CF2–CH3 |
| 93 | C29H29F11N6O3<br>MW: 718.565<br>MS m/z [M + H]+ = 719<br>Rt = 0.54 (method H) | 94 | C28H27F11N6O3<br>MW: 704.538<br>MS m/z [M + H]+ = 705<br>Rt = 0.53 (method H) | *–CF2–CF2–CH3 |
| 95 | C28H27F11N6O4<br>MW: 720.537<br>MS m/z [M + H]+ = 721<br>Rt = 0.51 (method H) | 96 | C27H25F11N6O4<br>MW: 706.511<br>MS m/z [M + H]+ = 707<br>Rt = 0.50 (method H) | *–CF2–CF2–CH2OH |
| 97 | C28H28F11N7O3<br>MW: 719.553<br>MS m/z [M + H]+ = 720<br>Rt = 0.47 (method H) | | | *–CF2–CF2–CH2NH2 |
| 98 | C29H30F11N7O3<br>MW: 733.58<br>MS m/z [M + H]+ = 734<br>Rt = 0.49 (method H) | 99 | C28H28F11N7O3<br>MW: 719.553<br>MS m/z [M + H]+ = 720<br>Rt = 0.48 (method H) | *–CF2–C(CH3)(NH2)F |
| 100 | C29H29F11N6O4<br>MW: 734.564<br>MS m/z [M + H]+ = 735<br>Rt = 0.52 (method H) | 101 | C28H27F11N6O4<br>MW: 720.537<br>MS m/z [M + H]+ = 720<br>Rt = 1.84 (method I) | *–CF2–C(CH3)(OH)F |
| 102 | C30H31F11N6O3<br>MW: 732.592<br>MS m/z [M + H]+ = 733<br>Rt = 0.55 (method H) | | | *–CF2–C(CH3)2F |

TABLE 3-continued

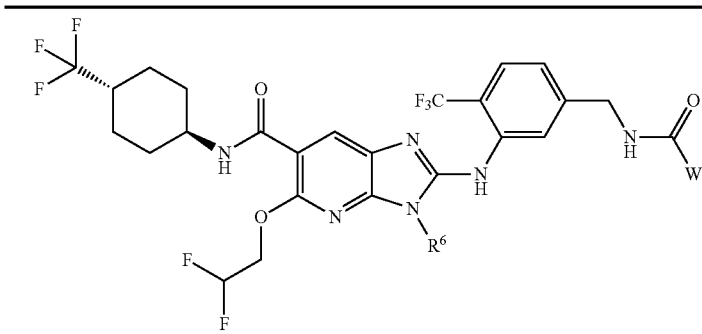

| Ex. | R⁶ = *−CH₃ | Ex. | R⁶ = *−H | W = |
|---|---|---|---|---|
| 103 | $C_{29}H_{30}F_8N_6O_3$<br>MW: 662.579<br>MS m/z [M + H]⁺ = 662<br>$R_t$ = 2.06 (method I) | 104 | $C_{28}H_{28}F_8N_6O_3$<br>MW: 648.552<br>MS m/z [M + H]⁺ = 648<br>$R_t$ = 1.75 (method J) | *−cyclopropyl |
| 105 | $C_{30}H_{32}F_8N_6O_3$<br>MW: 676.06<br>MS m/z [M + H]⁺ = 676<br>$R_t$ = 2.09 (method I) | 106 | $C_{29}H_{30}F_8N_6O_3$<br>MW: 662.579<br>MS m/z [M + H]⁺ = 662<br>$R_t$ = 1.78 (method K) | *−cyclobutyl |
| 107 | $C_{31}H_{34}F_8N_6O_3$<br>MW: 690.633<br>MS m/z [M + H]⁺ = 691<br>$R_t$ = 0.54 (method H) | 108 | $C_{30}H_{32}F_8N_6O_3$<br>MW: 676.606<br>MS m/z [M + H]⁺ = 677<br>$R_t$ = 0.47 (method K) | *−cyclopentyl |
| 109 | $C_{30}H_{32}F_8N_6O_4$<br>MW: 692.605<br>MS m/z [M + H]⁺ = 692<br>$R_t$ = 2.06 (method I) | 110 | $C_{29}H_{30}F_8N_6O_4$<br>MW: 678.578<br>MS m/z [M + H]⁺ = 679<br>$R_t$ = 0.43 (method K) | *−tetrahydrofuran-2-yl |
| 111 | $C_{31}H_{34}F_8N_6O_4$<br>MW: 706.632<br>MS m/z [M + H]⁺ = 707<br>$R_t$ = 0.52 (method H) | 112 | $C_{30}H_{32}F_8N_6O_4$<br>MW: 692.605<br>MS m/z [M + H]⁺ = 693<br>$R_t$ = 0.52 (method H) | *−2-methyltetrahydrofuran-2-yl |
| 113 | $C_{31}H_{35}F_8N_7O_3$<br>MW: 705.648<br>MS m/z [M + H]⁺ = 706<br>$R_t$ = 0.45 (method H) | 114 | $C_{30}H_{33}F_8N_7O_3$<br>MW: 691.621<br>MS m/z [M + H]⁺ = 692<br>$R_t$ = 0.44 (method H) | *−(1-methylpyrrolidin-2-yl) |
| 115 | $C_{30}H_{32}F_8N_6O_4$<br>MW: 692.605<br>MS m/z [M + H]⁺ = 692<br>$R_t$ = 2.04 (method I) | 116 | $C_{29}H_{30}F_8N_6O_4$<br>MW: 678.578<br>MS m/z [M + H]⁺ = 679<br>$R_t$ = 0.49 (method H) | *−(3-methyloxetan-3-yl) |
| 117 | $C_{29}H_{30}F_8N_6O_4$<br>MW: 678.58<br>MS m/z [M + H]⁺ = 679<br>$R_t$ = 0.49 (method H) | 118 | $C_{28}H_{28}F_8N_6O_4$<br>MW: 664.551<br>MS m/z [M + H]⁺ = 665<br>$R_t$ = 0.41 (method K) | *−(1-hydroxycyclopropyl) |
| 119 | $C_{30}H_{32}F_8N_6O_3$<br>MW: 676.606<br>MS m/z [M + H]⁺ = 676<br>$R_t$ = 2.09 (method I) | 120 | $C_{29}H_{30}F_8N_6O_3$<br>MW: 662.579<br>MS m/z [M + H]⁺ = 663<br>$R_t$ = 0.46 (method K) | *−(1-methylcyclopropyl) |
| 121 | $C_{30}H_{30}F_{10}N_6O_3$<br>MW: 712.586<br>MS m/z [M + H]⁺ = 713<br>$R_t$ = 0.53 (method H) | 122 | $C_{29}H_{28}F_{10}N_6O_3$<br>MW: 698.559<br>MS m/z [M + H]⁺ = 699<br>$R_t$ = 0.53 (method H) | *−(3,3-difluorocyclobutyl) |
| 123 | $C_{31}H_{31}F_{11}N_6O_3$<br>MW: 744.603<br>MS m/z [M + H]⁺ = 745<br>$R_t$ = 0.56 (method H) | 124 | $C_{30}H_{29}F_{11}N_6O_3$<br>MW: 730.576<br>MS m/z [M + H]⁺ = 731<br>$R_t$ = 0.55 (method H) | *−(3-(trifluoromethyl)cyclobutyl) |

TABLE 3-continued

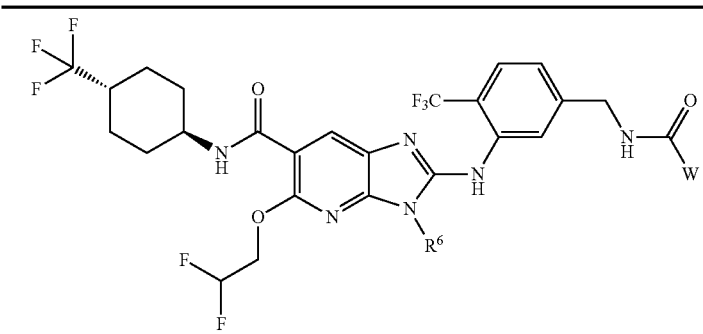

| Ex. | R⁶ = *-CH₃ | Ex. | R⁶ = *-H | W = |
|---|---|---|---|---|
| 125 | $C_{29}H_{28}F_{10}N_6O_3$<br>MW: 698.559<br>MS m/z [M + H]⁺ = 699<br>$R_t$ = 0.52 (method H) | 126 | $C_{28}H_{26}F_{10}N_6O_3$<br>MW: 684.532<br>MS m/z [M + H]⁺ = 685<br>$R_t$ = 0.52 (method H) | cyclopropyl-CF₂ (gem-difluoro cyclopropyl) |
| 127 | $C_{30}H_{29}F_8N_7O_3$<br>MW: 687.589<br>MS m/z [M + H]⁺ = 688<br>$R_t$ = 0.52 (method H) | 128 | $C_{29}H_{27}F_8N_7O_3$<br>MW: 673.562<br>MS m/z [M + H]⁺ = 674<br>$R_t$ = 0.51 (method H) | 1-cyanocyclopropyl |
| 129 | $C_{30}H_{29}F_{11}N_6O_3$<br>MW: 730.576<br>MS m/z [M + H]⁺ = 731<br>$R_t$ = 0.55 (method H) | 130 | $C_{29}H_{27}F_{11}N_6O_3$<br>MW: 716.549<br>MS m/z [M + H]⁺ = 717<br>$R_t$ = 0.54 (method H) | 1-(trifluoromethyl)cyclopropyl |
| 131 | $C_{32}H_{33}F_{11}N_6O_3$<br>MW: 758.63<br>MS m/z [M + H]⁺ = 759<br>$R_t$ = 0.57 (method H) | 132 | $C_{31}H_{31}F_{11}N_6O_3$<br>MW: 744.603<br>MS m/z [M + H]⁺ = 745<br>$R_t$ = 0.57 (method H) | 1-(trifluoromethyl)cyclopentyl |
| 133 | $C_{30}H_{32}F_8N_6O_3$<br>MW: 676.606<br>MS m/z [M + H]⁺ = 677<br>$R_t$ = 0.52 (method H) | 134 | $C_{29}H_{30}F_8N_6O_3$<br>MW: 662.579<br>MS m/z [M + H]⁺ = 663<br>$R_t$ = 0.45 (method K) | cyclopropylmethyl |
| 135 | $C_{29}H_{27}F_8N_7O_4$<br>MW: 689.561<br>MS m/z [M + H]⁺ = 690<br>$R_t$ = 0.51 (method H) | 136 | $C_{28}H_{25}F_8N_7O_4$<br>MW: 675.535<br>MS m/z [M + H]⁺ = 676<br>$R_t$ = 0.43 (method K) | isoxazol-5-yl |
| 137 | $C_{29}H_{28}F_8N_8O_3$<br>MW: 688.577<br>MS m/z [M + H]⁺ = 688<br>$R_t$ = 0.49 (method H) | | | 1H-pyrazol-3-yl |
| 138 | $C_{31}H_{31}F_8N_7O_3$<br>MW: 701.616<br>MS m/z [M + H]⁺ = 702<br>$R_t$ = 0.54 (method H) | 139 | $C_{30}H_{29}F_8N_7O_3$<br>MW: 687.589<br>MS m/z [M + H]⁺ = 687<br>$R_t$ = 1.92 (method I) | 1-methyl-1H-pyrrol-2-yl |
| 140 | $C_{30}H_{30}F_8N_8O_3$<br>MW: 702.604<br>MS m/z [M + H]⁺ = 703<br>$R_t$ = 0.49 (method H) | 141 | $C_{29}H_{28}F_8N_8O_3$<br>MW: 688.577<br>MS m/z [M + H]⁺ = 689<br>$R_t$ = 0.44 (method K) | 1-methyl-1H-imidazol-2-yl |
| 142 | $C_{30}H_{27}ClF_8N_6O_3S$<br>MW: 739.085<br>MS m/z [M + H]⁺ = 739<br>$R_t$ = 2.10 (method H) | 143 | $C_{29}H_{25}ClF_8N_6O_3S$<br>MW: 725.059<br>MS m/z [M + H]⁺ = 725<br>$R_t$ = 0.54 (method H) | 3-chlorothiophen-2-yl |

TABLE 3-continued

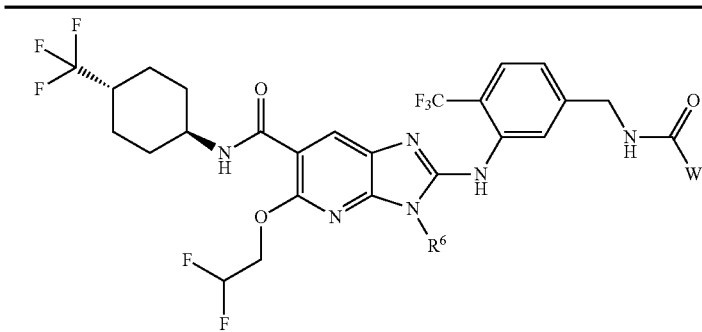

| Ex. | R⁶ = *—CH₃ | Ex. | R⁶ = *—H | W = |
|---|---|---|---|---|
| 144 | C₃₀H₂₇ClF₈N₆O₃S<br>MW: 739.085<br>MS m/z [M + H]⁺ = 739<br>R_t = 0.56 (method H) | 145 | C₂₉H₂₅ClF₈N₆O₃S<br>MW: 725.059<br>MS m/z [M + H]⁺ = 725<br>R_t = 1.92 (method J) | 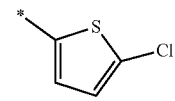 |
| 146 | C₃₁H₃₁F₈N₇O₃S<br>MW: 733.682<br>MS m/z [M + H]⁺ = 733<br>R_t = 2.07 (method I) | 147 | C₃₀H₂₉F₈N₇O₃S<br>MW: 719.655<br>MS m/z [M + H]⁺ = 719<br>R_t = 1.88 (method I) | 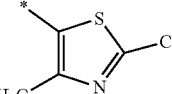 |
| 148 | C₃₀H₂₇F₁₁N₈O₃<br>MW: 756.574<br>MS m/z [M + H]⁺ = 757<br>Rt = 0.54 (method H) | 149 | C₂₉H₂₅F₁₁N₈O₃<br>MW: 742.548<br>MS m/z [M + H]⁺ = 743<br>Rt = 0.53 (method H) | 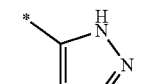 |
| 150 | C₃₁H₂₉F₁₁N₈O₃<br>MW: 770.601<br>MS m/z [M + H]⁺ = 771<br>R_t = 0.57 (method H) | 151 | C₃₀H₂₇F₁₁N₈O₃<br>MW: 756.574<br>MS m/z [M + H]⁺ = 757<br>R_t = 0.49 (method K) | 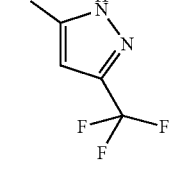 |
| 152 | C₃₂H₂₈ClF₉N₆O₃<br>MW: 751.047<br>MS m/z [M + H]⁺ = 751<br>Rt = 2.08 (method I) | 153 | C₃₁H₂₆ClF₉N₆O₃<br>MW: 737.02<br>MS m/z [M + H]⁺ = 737<br>Rt = 0.54 (method H) | 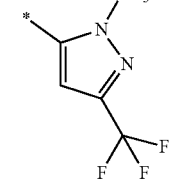 |

The invention claimed is:

1. A compound of formula I

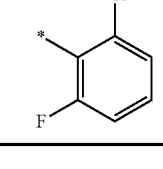

in which $R^1$ represents halo, —$C_{1-3}$alkyl, which latter alkyl group is optionally substituted by one or more fluorine atoms;

$R^2$ represent hydrogen, halo, —$C_{1-3}$alkyl, which latter alkyl group is optionally substituted by one or more fluorine atoms;

W represents —C(O)—, —C(O)O—, which groups are bound to the nitrogen of the —NH— moiety via the carbon atom;

M represents

—$C_{1-6}$alkyl, —$C_{3-7}$cycloalkyl, both of which groups are optionally substituted by one or more groups selected from —F, —OH, —CN, —NH₂, —NH($C_{1-2}$alkyl), —N($C_{1-2}$alkyl)₂, —O$C_{1-3}$alkyl, —$C_{1-5}$alkyl, —$C_{3-4}$ cycloalkyl, in which latter three groups the alkyl or cycloalkyl groups are optionally substituted by one or more fluorine atoms;

or
oxetanyl-, tetrahydrofuranyl-, tetrahydropyranyl-, azetidinyl-, pyrrolidinyl-, piperidinyl-, all of which groups are optionally substituted by one or more substituents selected from fluoro, —CN, —$C_{1-3}$ alkyl, which latter alkyl group is optionally substituted by one or more fluorine atoms;
or
phenyl-, pyridyl-, thienyl-, pyrrolyl-, pyrazolyl-, imidazolyl-, thiazolyl-, oxazolyl-, or isoxazolyl-, all of which groups are optionally substituted by one or more substituents selected from halo, —CN or —$C_{1-3}$alkyl, which latter alkyl group is optionally further substituted by one or more fluorine atoms;

$R^6$ represents —H, —$C_{1-5}$alkyl, —$C_{0-2}$alkyl-$C_{3-5}$cycloalkyl, in which latter two groups the alkyl or cycloalkyl fragments are optionally substituted by one or more fluorine atoms;

$R^7$ represents $C_{1-5}$alkyl-O—, $C_{3-7}$cycloalkyl-$C_{0-2}$alkyl-O—, 4-7-membered heterocycloalkyl-$C_{0-2}$alkyl-O—, in which latter three groups the alkyl, cycloalkyl or heterocycloalkyl fragments are optionally substituted by one or more substituents selected from —F and —O$C_{1-3}$ alkyl which latter alkyl group is optionally further substituted by one or more fluorine atoms;

A represents $C_{1-8}$ alkyl-, phenyl-, pyridyl-, thienyl-, pyrrolyl-, pyrazolyl-, thiazolyl-, oxazolyl-, isoxazolyl-, phenyl-$C_{1-3}$alkyl-, thienyl-$C_{1-3}$alkyl-, pyridyl-$C_{1-3}$alkyl-, $C_{3-7}$cycloalkyl-$C_{0-3}$alkyl-, oxetanyl-$C_{0-3}$alkyl-, tetrahydrofuranyl-$C_{0-3}$alkyl, tetrahydropyranyl-$C_{0-3}$alkyl, in which groups the alkyl-, cycloalkyl- and heterocycloalkyl fragments are optionally substituted by one or more substituents selected from $R^{9a}$ and the aryl and heteroaryl fragments are optionally substituted by one or more substituents selected from $R^{9b}$;

each $R^{9a}$ independently represents —F, —Cl, $C_{1-3}$alkyl which is optionally substituted by one or more substituents selected from —F, —O$C_{1-3}$ alkyl;

each $R^{9b}$ represents independently -halo, —CN; —$C_{1-3}$ alkyl which is optionally substituted by one or more fluorine atoms;

or a salt thereof.

2. A compound according to claim 1, wherein
$R^6$ represents —H, —$CH_3$, or —$CH_2CHF_2$;
or a pharmaceutically acceptable salt thereof.

3. A compound according to claim 1, wherein
$R^1$ represents chloro, fluoro or —$CH_3$, —$CH_2F$, —$CHF_2$, —$CF_3$;
or a pharmaceutically acceptable salt thereof.

4. A compound according to claim 1, wherein
$R^2$ represents —H, chloro, -fluoro, —$CH_3$, —$CH_2F$, —$CHF_2$, —$CF_3$;
or a pharmaceutically acceptable salt thereof.

5. A compound according to claim 1, wherein
$R^7$ represents fluoro, —$OCHF_2$, —$OCF_3$, —$OCH_2CHF_2$, —$OCH_2CF_3$, —$OCH_2CH_2OCH_3$, —$OCH_2CH_2OCHF_2$;
or a pharmaceutically acceptable salt thereof.

6. A compound according to claim 1, wherein
A represents $C_{1-4}$ alkyl-, $C_{3-6}$cycloalkyl-$C_{0-2}$alkyl-, phenyl-, in which groups the alkyl- and cycloalkyl-fragments are optionally substituted by one or more substituents selected from —F, —$CH_3$, —$CH_2F$, —$CHF_2$, —$CF_3$, and the phenyl fragment is optionally substituted by —F, —Cl, —Br;
or a pharmaceutically acceptable salt thereof.

7. A compound according to claim 1, wherein
M represents
—$C_{1-4}$ alkyl, —$C_{3-5}$ cycloalkyl, both of which groups are optionally substituted by one or more groups selected from —F, —OH, —CN, —$NH_2$, —$OCH_3$, —$CH_3$, —$CH_2F$, —$CHF_2$, —$CF_3$, cyclopropyl;
or
oxetanyl-, tetrahydrofuranyl- or pyrrolidinyl-, all of which groups are optionally substituted by one or more substituents selected from —F, —$CH_3$, —$CH_2F$, —$CHF_2$, —$CF_3$;
or
phenyl-, thienyl-, pyrrolyl-, pyrazolyl-, imidazolyl-, thiazolyl-, or isoxazolyl-, all of which groups are optionally substituted by one or more substituents selected from —F, —Cl, —$CH_3$, —$CH_2F$, —$CHF_2$, —$CF_3$;
or a pharmaceutically acceptable salt thereof.

8. A compound according to claim 1, which is a compound of formula Ia

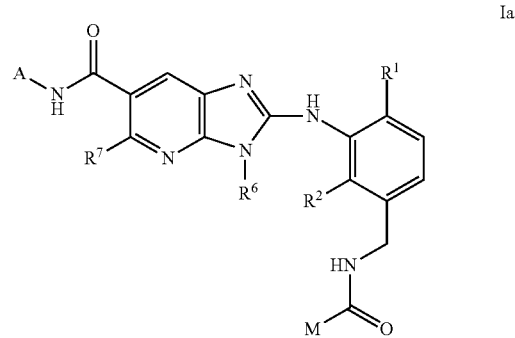

Ia in which
M represents
methyl, ethyl, propyl, i-propyl, n-butyl, s-butyl, t-butyl, cyclopropyl, —$CH_2$-cyclopropyl, cyclobutyl, cyclopentyl, all of which groups are optionally substituted by one or more groups selected from —F, —OH, —CN, —$NH_2$, —$OCH_3$, —$CH_3$, —$CF_3$;
or is selected from the following groups

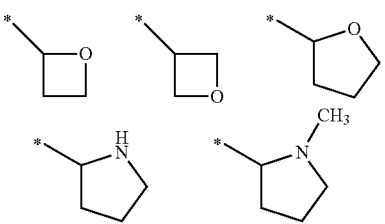

which latter five groups are optionally substituted by one or more substituents selected from —F, —$CH_3$, —$CF_3$;
or is selected from the following groups

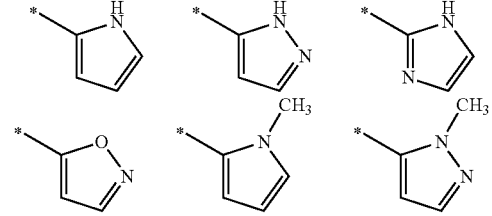

-continued

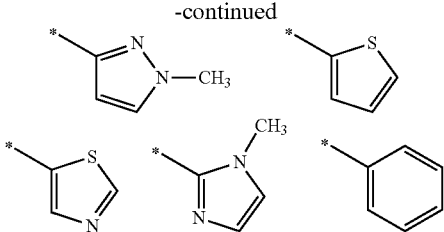

which latter eleven groups are optionally substituted by one or more substituents selected from —F, —Cl, —CH$_3$, —CF$_3$; and A, R$^1$, R$^2$, R$^6$, R$^7$ have the same meaning as defined in claim 1;

or a pharmaceutically acceptable salt thereof.

9. A compound according to claim 8, wherein

A represents methyl, ethyl, propyl, butyl, which latter four groups are optionally substituted by one or more fluorine atoms, or cyclopropyl, cyclobutyl, cyclopentyl, cyclohexyl, which latter four groups are optionally substituted by one or more substituents selected from —F, —CH$_3$, —CHF$_2$, —CF$_3$;

or the group

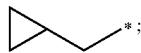

or phenyl which is optionally substituted by one or more substituents selected from —F, —Cl, —Br;

or a pharmaceutically acceptable salt thereof.

10. A compound according to claim 1, which is a compound of formula Ia or Ib

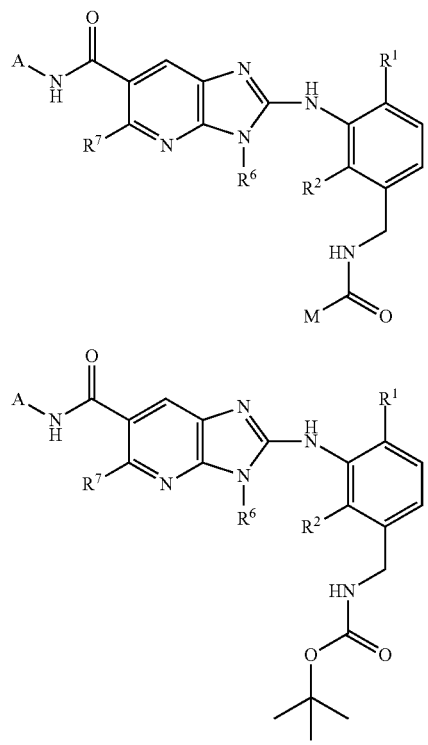

in which

R$^1$ represents chloro, fluoro or —CH$_3$, —CH$_2$F, —CHF$_2$, —CF$_3$;

R$^2$ represents —H, chloro, fluoro, —CH$_3$, —CH$_2$F, —CHF$_2$, —CF$_3$;

R$^6$ represents —H; —CH$_3$, —CH$_2$CHF$_2$;

R$^7$ represents fluoro, —OCHF$_2$, —OCF$_3$, —OCH$_2$CHF$_2$, —OCH$_2$CF$_3$, —OCH$_2$CH$_2$OCH$_3$, —OCH$_2$CH$_2$OCHF$_2$;

A represents methyl, ethyl, propyl, butyl, which latter four groups are optionally substituted by one or more fluorine atoms, or cyclopropyl, cyclobutyl, cyclopentyl, cyclohexyl, which latter four groups are optionally substituted by one or more substituents selected from —F, —CH$_3$, —CHF$_2$, —CF$_3$;

or the group

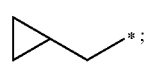

or phenyl which is optionally substituted by one or more substituents selected from —F, —Cl, —Br;

M represents methyl, ethyl, propyl, i-propyl, n-butyl, s-butyl, t-butyl, cyclopropyl, —CH$_2$— cyclopropyl, cyclobutyl, cyclopentyl, all of which groups are optionally substituted by one or more groups selected from —F, —OH, —CN, —NH$_2$, —OCH$_3$, —CH$_3$, —CF$_3$;

or is selected from the following groups

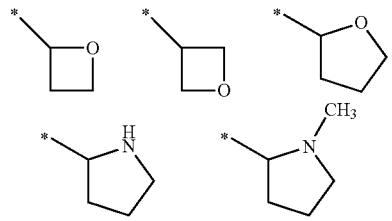

which latter five groups are optionally substituted by one or more substituents selected from —F, —CH$_3$, —CF$_3$;

or is selected from the following groups

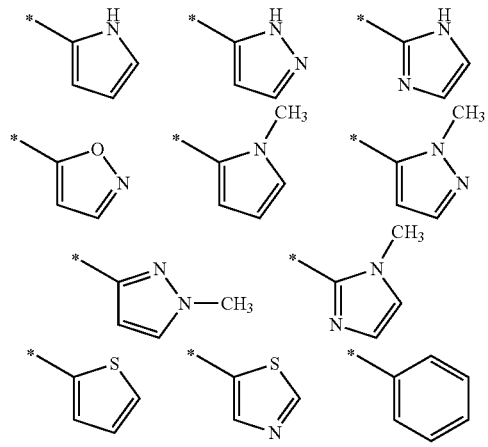

which latter eleven groups are optionally substituted by one or more substituents selected from —F, —Cl, —CH$_3$, —CF$_3$;

or a salt thereof.

11. A compound according to claim 1, wherein

R$^1$ and R$^2$ independently represent chloro, fluoro, —CH$_3$, —CH$_2$F, —CHF$_2$, —CF$_3$;

or a pharmaceutically acceptable salt thereof.

12. A compound according to claim 1 selected from the compounds in the following table, or the pharmaceutically acceptable salts thereof:
| | Structure |
|---|---|
| 1 | 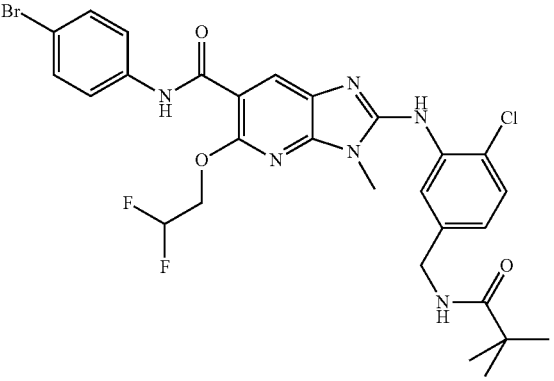 [SMILES: Cn1c(Nc2cc(CNC(=O)C(C)(C)C)ccc2Cl)nc2cc(C(=O)Nc3ccc(Br)cc3)c(OCC(F)F)nc21] |
| 2 | 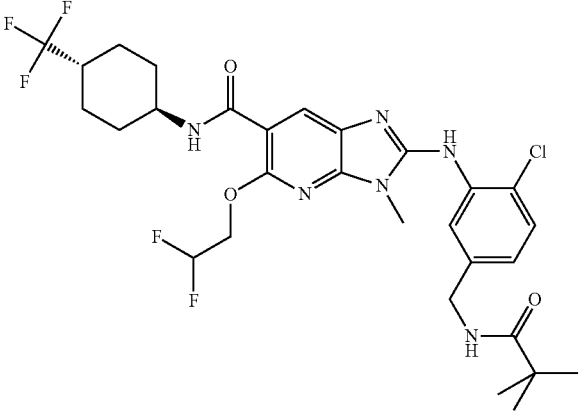 [SMILES: Cn1c(Nc2cc(CNC(=O)C(C)(C)C)ccc2Cl)nc2cc(C(=O)N[C@H]3CC[C@H](C(F)(F)F)CC3)c(OCC(F)F)nc21] |
| 3 | 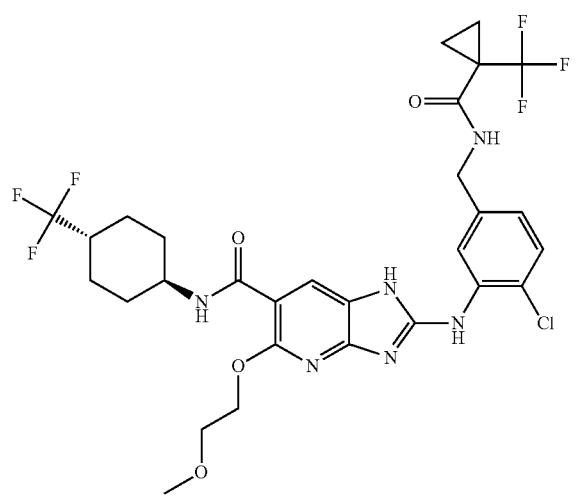 [SMILES: COCCOc1nc2nc(Nc3cc(CNC(=O)C4(C(F)(F)F)CC4)ccc3Cl)[nH]c2cc1C(=O)N[C@H]1CC[C@H](C(F)(F)F)CC1] |

| | Structure |
|---|---|
| 6 | 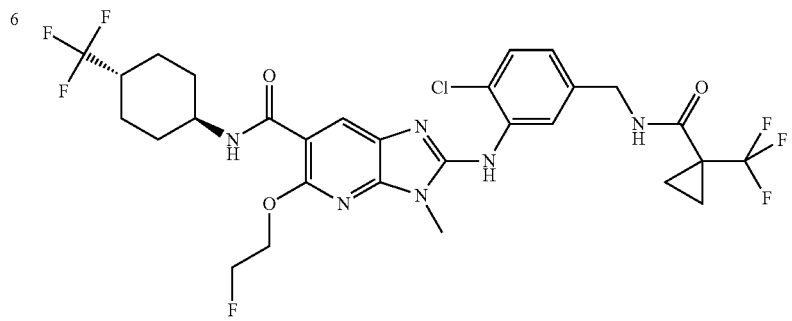 |
| 7 | 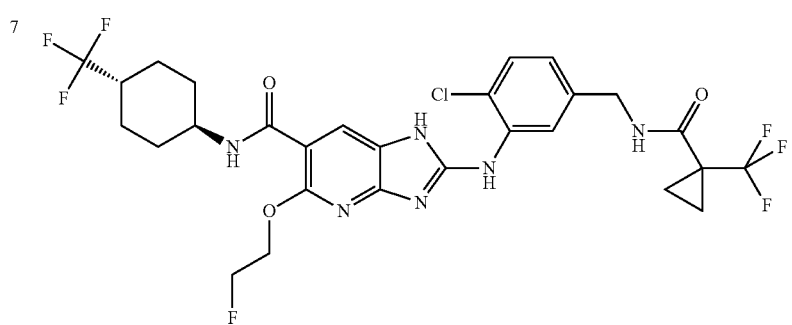 |
| 8 | 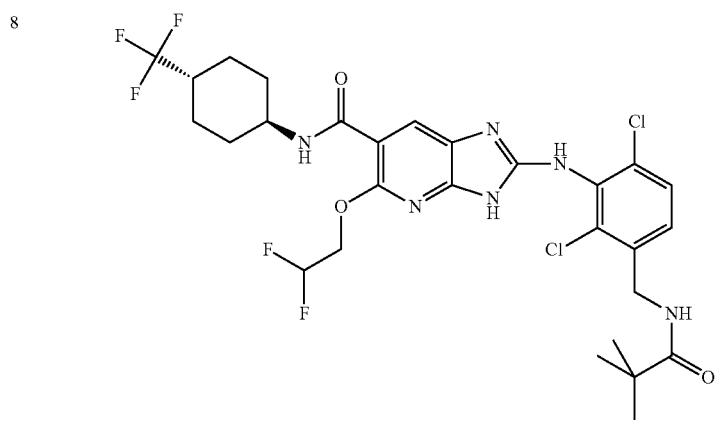 |
| 4 | 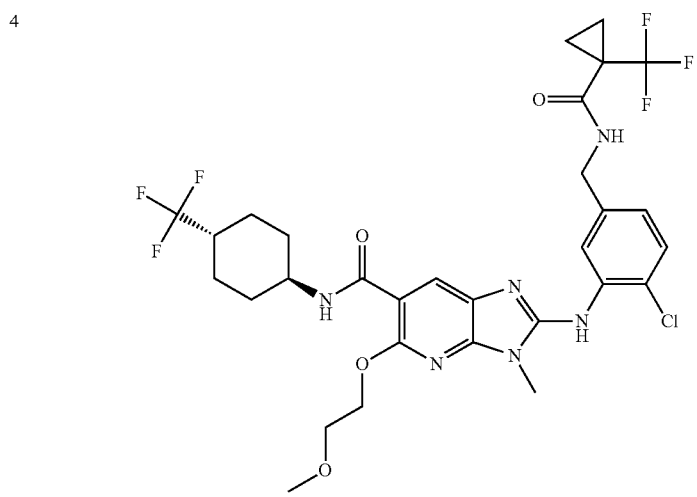 |

-continued
| | Structure |
|---|---|
| 5 | 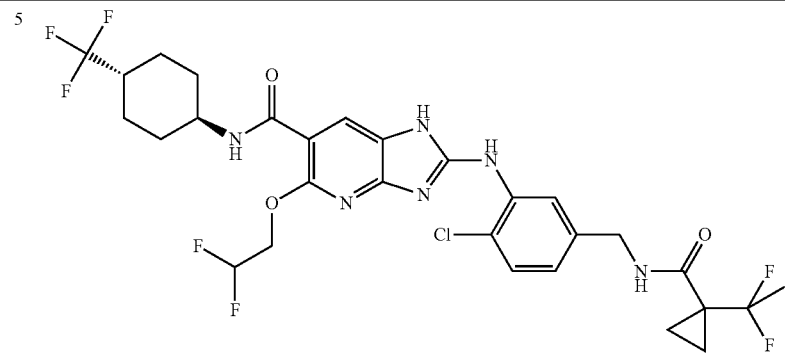 |
| 11 | 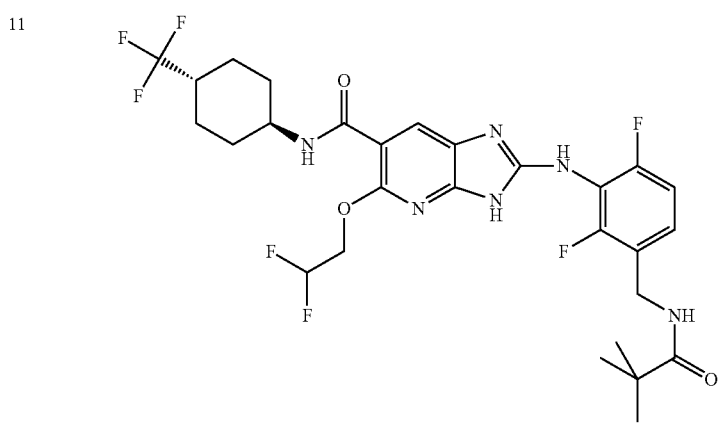 |
| 12 | 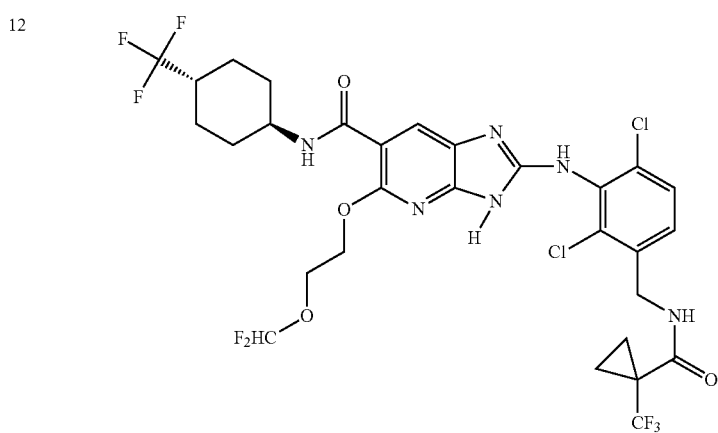 |
| 9 | 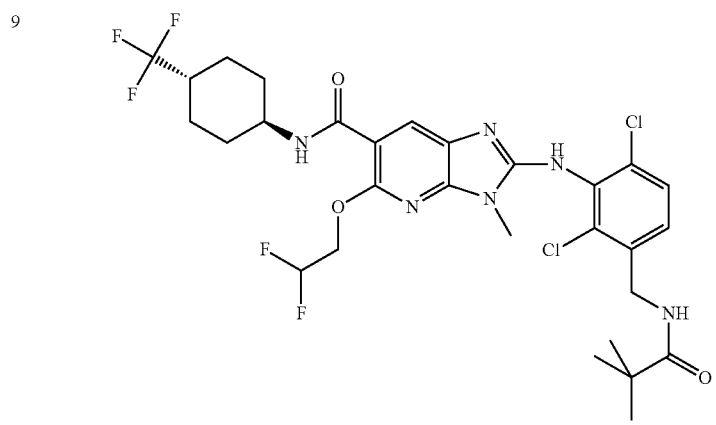 |

-continued
| | Structure |
|---|---|
| 10 | 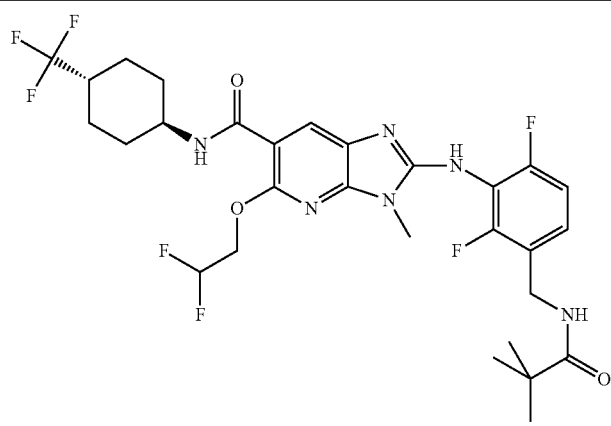 |
| 16 | 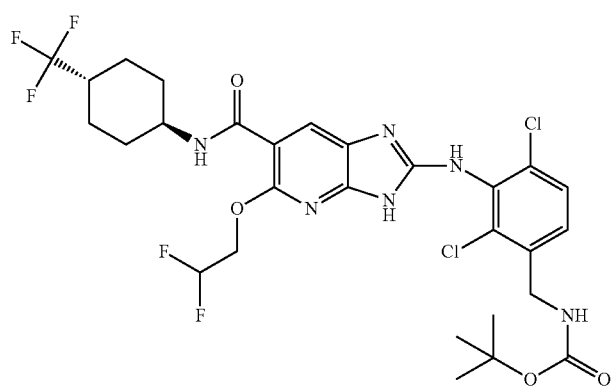 [SMILES: CC(C)(C)OC(=O)NCc1ccc(Cl)c(Nc2nc3cc(C(=O)N[C@H]4CC[C@H](C(F)(F)F)CC4)c(OCC(F)F)nc3[nH]2)c1Cl] |
| 17 | 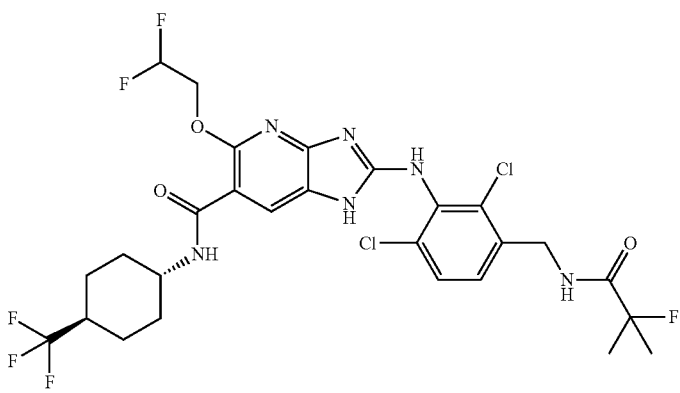 [SMILES: CC(C)(F)C(=O)NCc1ccc(Cl)c(Nc2nc3nc(OCC(F)F)c(C(=O)N[C@H]4CC[C@H](C(F)(F)F)CC4)cc3[nH]2)c1Cl] |
| 14 | 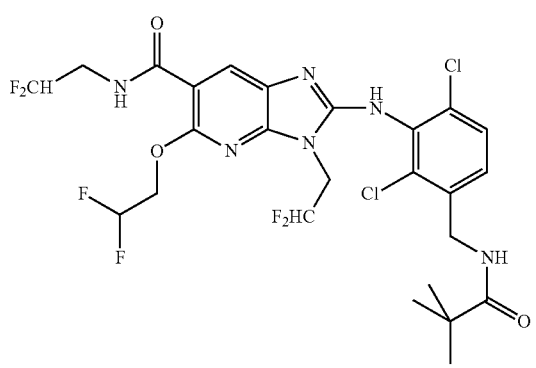 |

| Structure |
|---|
| 15 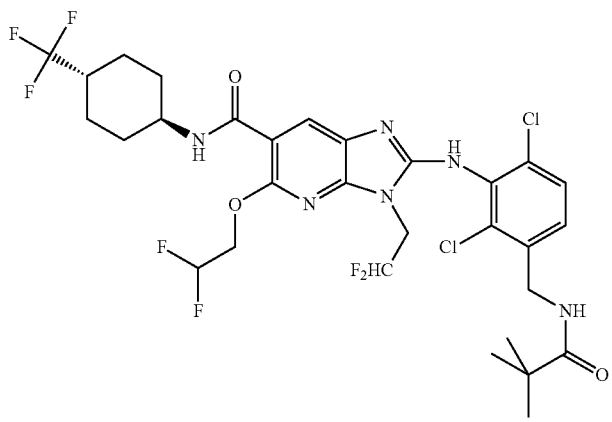 [SMILES: CC(C)(C)C(=O)NCc1ccc(Cl)c(Nc2nc3cc(C(=O)N[C@H]4CC[C@H](C(F)(F)F)CC4)c(OCC(F)F)nc3n2CC(F)F)c1Cl] |
| 21 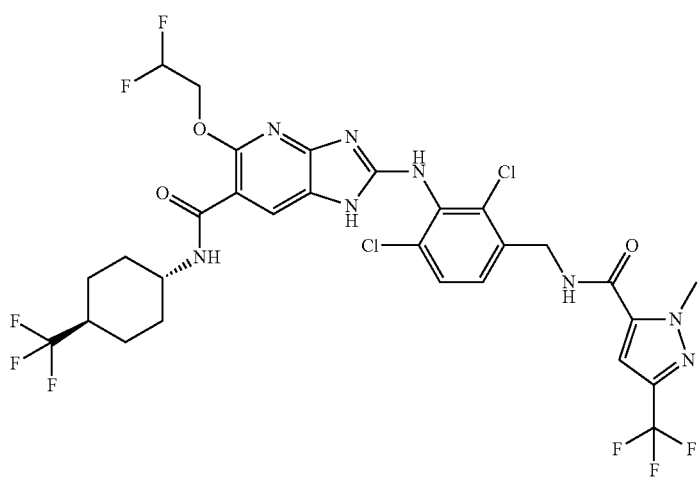 [SMILES: Cn1nc(C(F)(F)F)cc1C(=O)NCc1ccc(Cl)c(Nc2nc3nc(OCC(F)F)c(C(=O)N[C@H]4CC[C@H](C(F)(F)F)CC4)cc3[nH]2)c1Cl] |
| 22 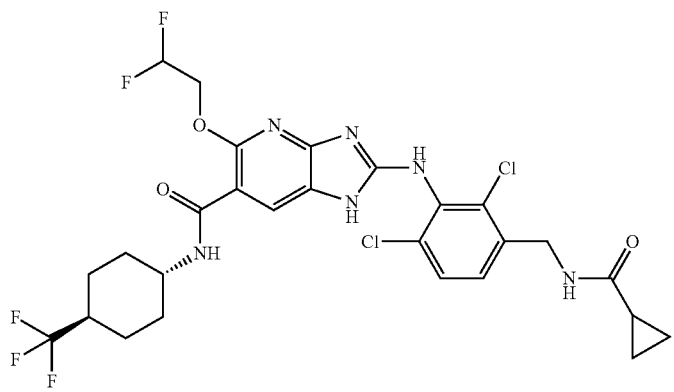 [SMILES: O=C(N[C@H]1CC[C@H](C(F)(F)F)CC1)c1cc2[nH]c(Nc3c(Cl)ccc(CNC(=O)C4CC4)c3Cl)nc2nc1OCC(F)F] |

| Structure |
|---|
| 18 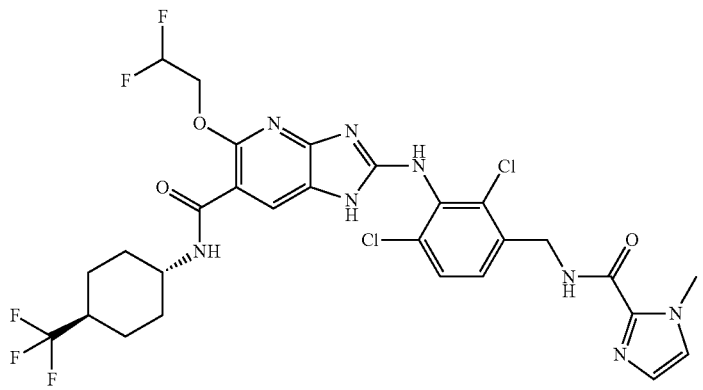 |
| 19 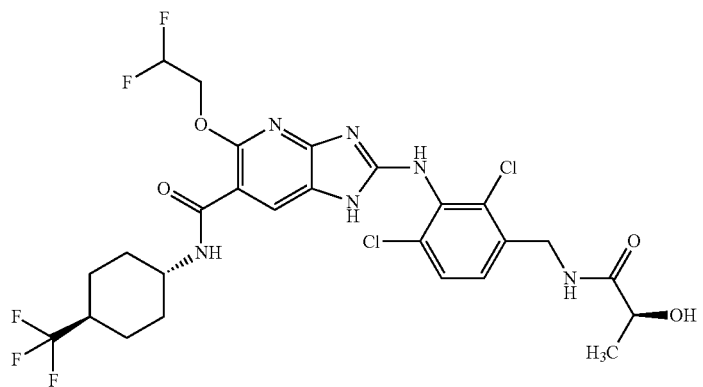 [SMILES: C[C@H](O)C(=O)NCc1ccc(Cl)c(Nc2nc3nc(OCC(F)F)c(C(=O)N[C@H]4CC[C@H](C(F)(F)F)CC4)cc3[nH]2)c1Cl] |
| 20 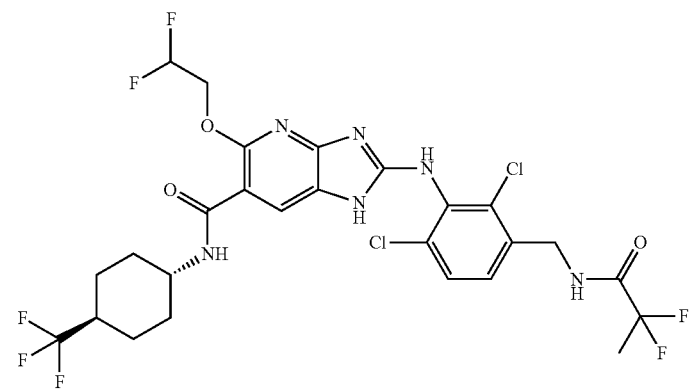 [SMILES: CC(F)(F)C(=O)NCc1ccc(Cl)c(Nc2nc3nc(OCC(F)F)c(C(=O)N[C@H]4CC[C@H](C(F)(F)F)CC4)cc3[nH]2)c1Cl] |
| 26 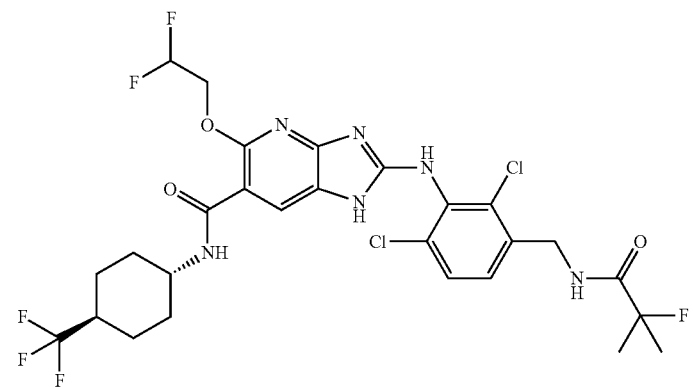 [SMILES: CC(C)(F)C(=O)NCc1ccc(Cl)c(Nc2nc3nc(OCC(F)F)c(C(=O)N[C@H]4CC[C@H](C(F)(F)F)CC4)cc3[nH]2)c1Cl] |

-continued
| Structure |
|---|
| 27 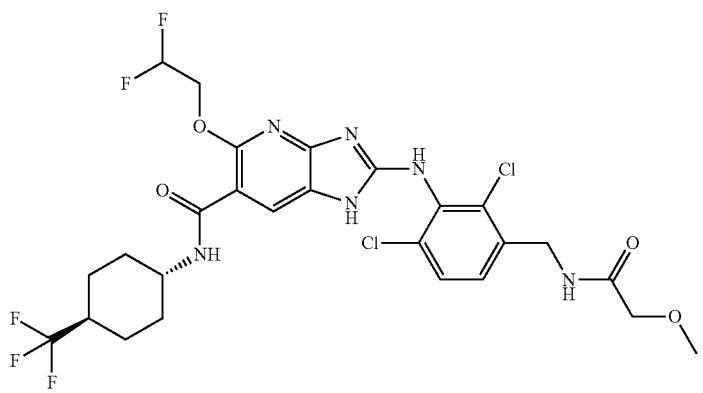 |
| 23 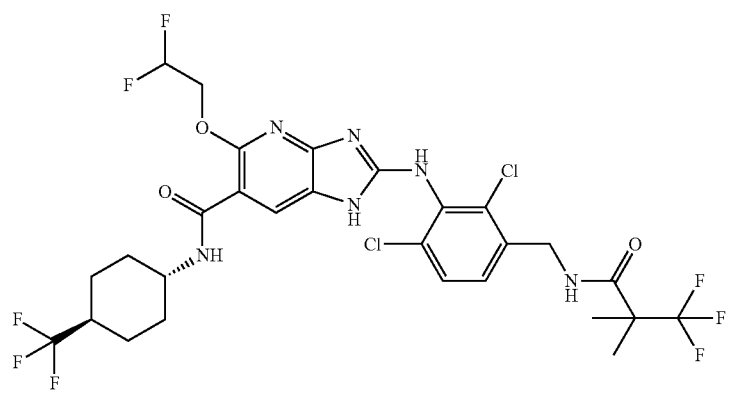 [SMILES: CC(C)(C(=O)NCc1ccc(Cl)c(Nc2nc3nc(OCC(F)F)c(C(=O)N[C@H]4CC[C@H](C(F)(F)F)CC4)cc3[nH]2)c1Cl)C(F)(F)F] |
| 24 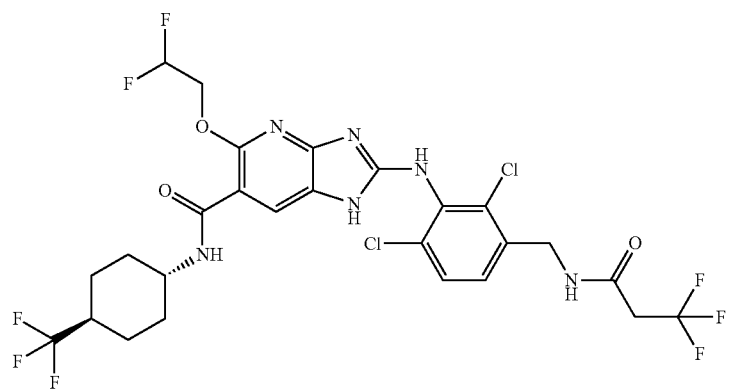 [SMILES: O=C(CC(F)(F)F)NCc1ccc(Cl)c(Nc2nc3nc(OCC(F)F)c(C(=O)N[C@H]4CC[C@H](C(F)(F)F)CC4)cc3[nH]2)c1Cl] |
| 25 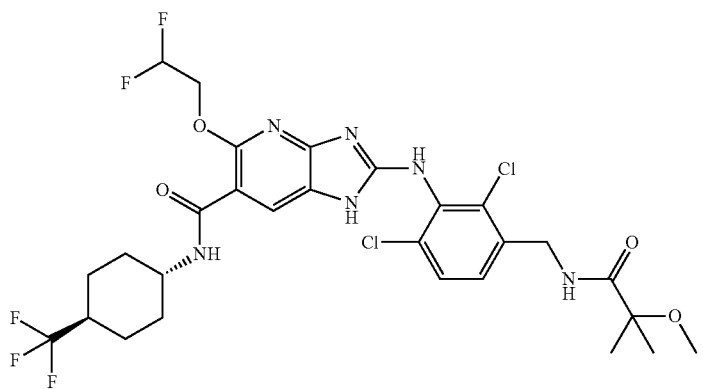 [SMILES: COC(C)(C)C(=O)NCc1ccc(Cl)c(Nc2nc3nc(OCC(F)F)c(C(=O)N[C@H]4CC[C@H](C(F)(F)F)CC4)cc3[nH]2)c1Cl] |

-continued
| Structure |
|---|
| 31 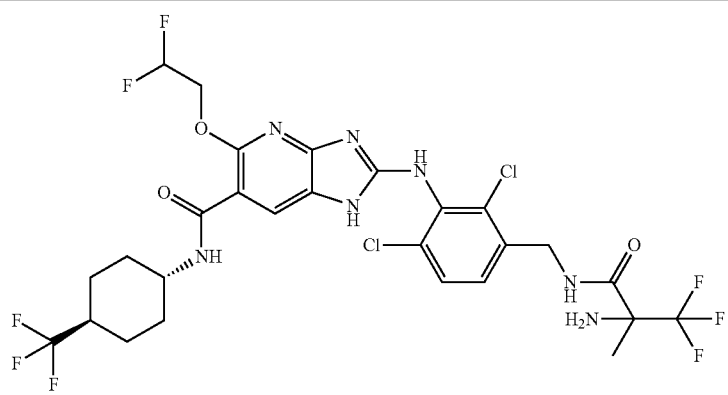 [SMILES: CC(N)(C(=O)NCc1ccc(Cl)c(Nc2nc3nc(OCC(F)F)c(C(=O)N[C@H]4CC[C@H](C(F)(F)F)CC4)cc3[nH]2)c1Cl)C(F)(F)F] |
| 32 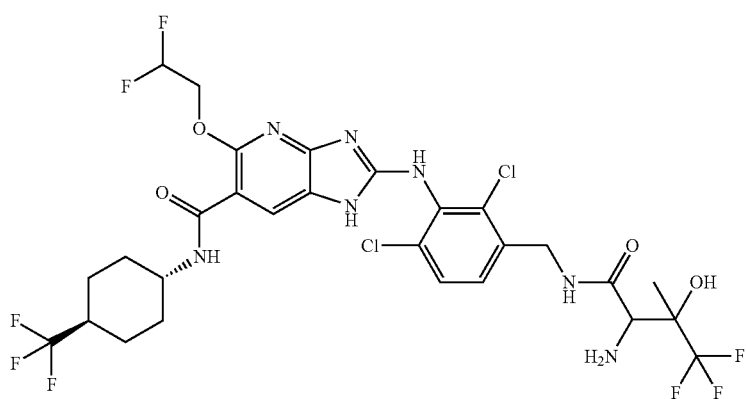 [SMILES: CC(O)(C(N)C(=O)NCc1ccc(Cl)c(Nc2nc3nc(OCC(F)F)c(C(=O)N[C@H]4CC[C@H](C(F)(F)F)CC4)cc3[nH]2)c1Cl)C(F)(F)F] |
| 28 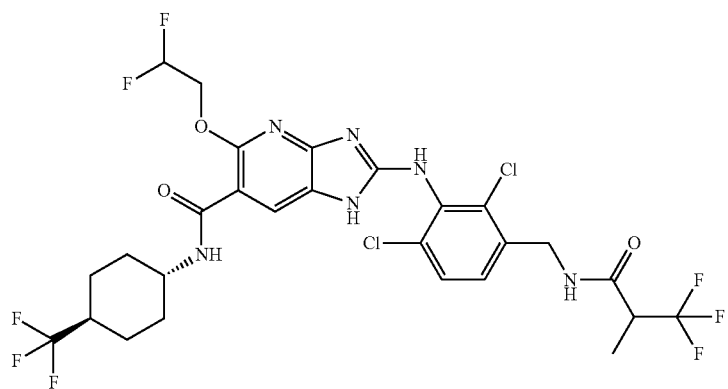 [SMILES: CC(C(=O)NCc1ccc(Cl)c(Nc2nc3nc(OCC(F)F)c(C(=O)N[C@H]4CC[C@H](C(F)(F)F)CC4)cc3[nH]2)c1Cl)C(F)(F)F] |
| 29 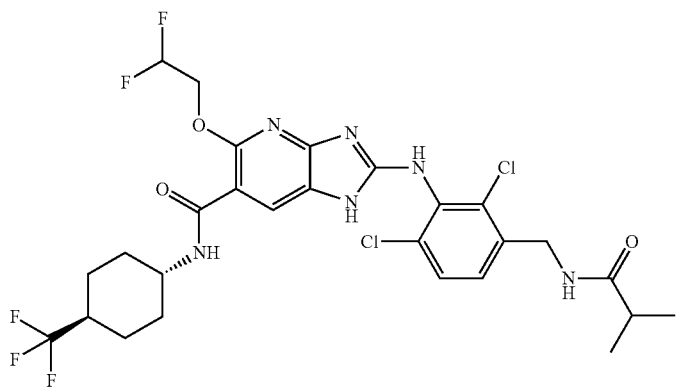 [SMILES: CC(C)C(=O)NCc1ccc(Cl)c(Nc2nc3nc(OCC(F)F)c(C(=O)N[C@H]4CC[C@H](C(F)(F)F)CC4)cc3[nH]2)c1Cl] |

-continued
| Structure |
|---|
| 30 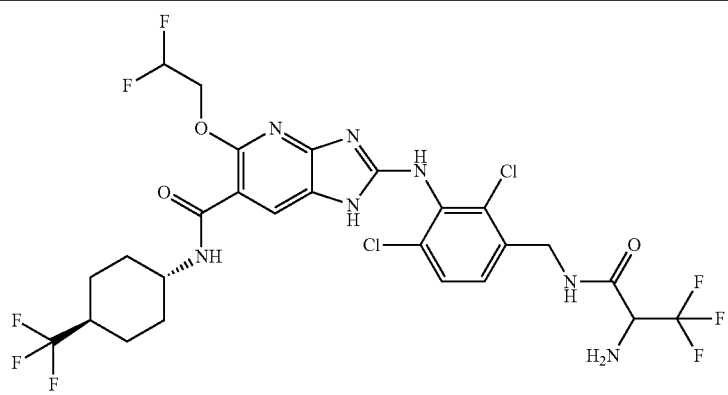 |
| 37 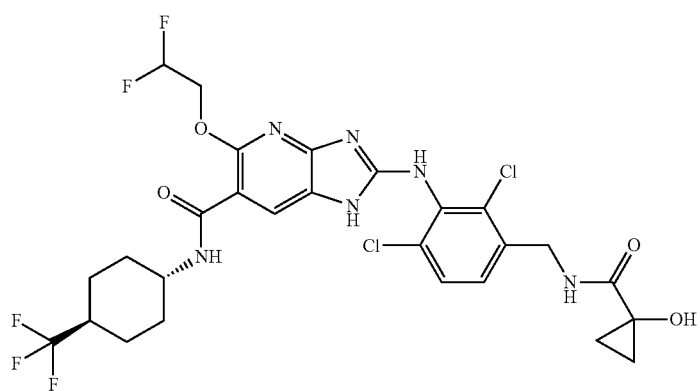 [SMILES: O=C(N[C@H]1CC[C@H](C(F)(F)F)CC1)c1cc2[nH]c(Nc3c(Cl)ccc(CNC(=O)C4(O)CC4)c3Cl)nc2nc1OCC(F)F] |
| 38 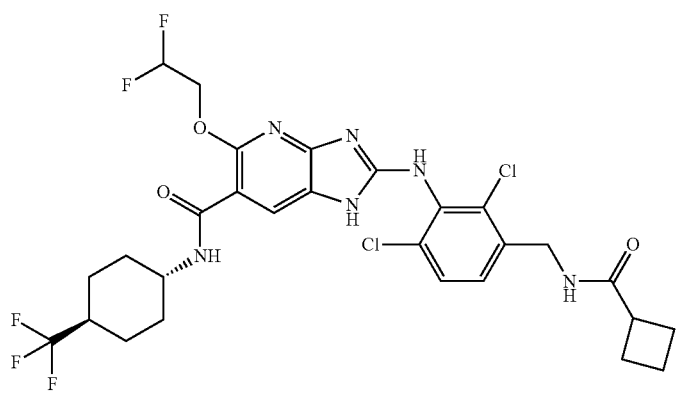 [SMILES: O=C(N[C@H]1CC[C@H](C(F)(F)F)CC1)c1cc2[nH]c(Nc3c(Cl)ccc(CNC(=O)C4CCC4)c3Cl)nc2nc1OCC(F)F] |
| 33 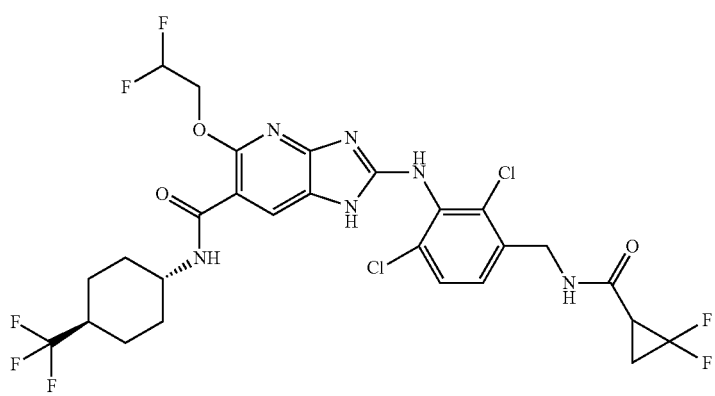 [SMILES: O=C(N[C@H]1CC[C@H](C(F)(F)F)CC1)c1cc2[nH]c(Nc3c(Cl)ccc(CNC(=O)C4CC4(F)F)c3Cl)nc2nc1OCC(F)F] |

-continued
| | Structure |
|---|---|
| 34 | 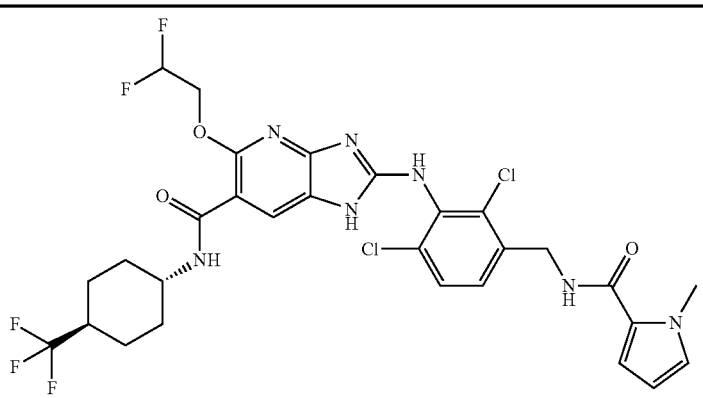 |
| 35 | 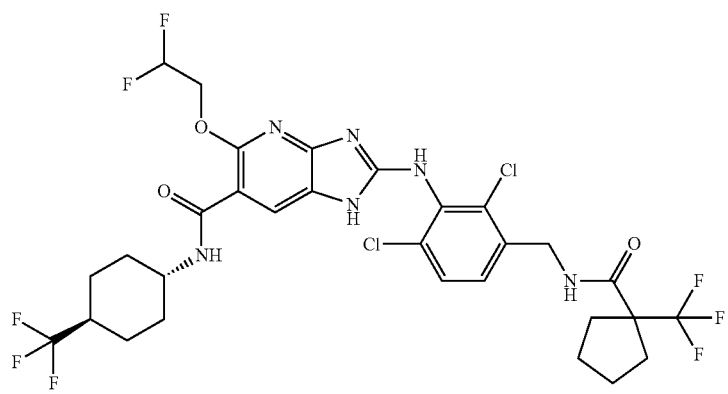 [SMILES: O=C(N[C@H]1CC[C@H](C(F)(F)F)CC1)c1cc2[nH]c(Nc3c(Cl)ccc(CNC(=O)C4(C(F)(F)F)CCCC4)c3Cl)nc2nc1OCC(F)F] |
| 36 | 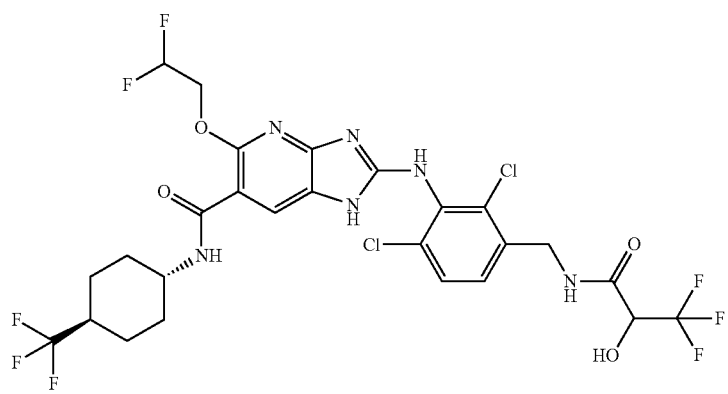 [SMILES: O=C(N[C@H]1CC[C@H](C(F)(F)F)CC1)c1cc2[nH]c(Nc3c(Cl)ccc(CNC(=O)C(O)C(F)(F)F)c3Cl)nc2nc1OCC(F)F] |
| 43 | 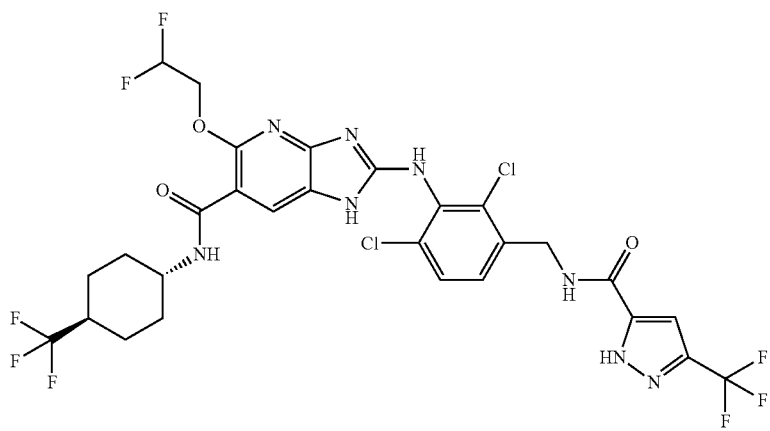 [SMILES: O=C(NCc1ccc(Cl)c(Nc2nc3nc(OCC(F)F)c(C(=O)N[C@H]4CC[C@H](C(F)(F)F)CC4)cc3[nH]2)c1Cl)c1cc(C(F)(F)F)n[nH]1] |

| | -continued |
|---|---|
| | Structure |
| 39 | 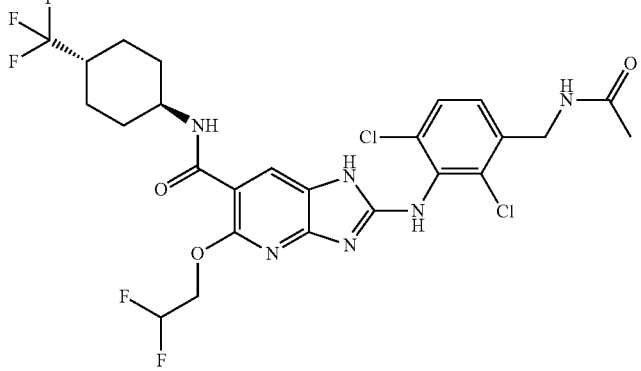 |
| 40 | 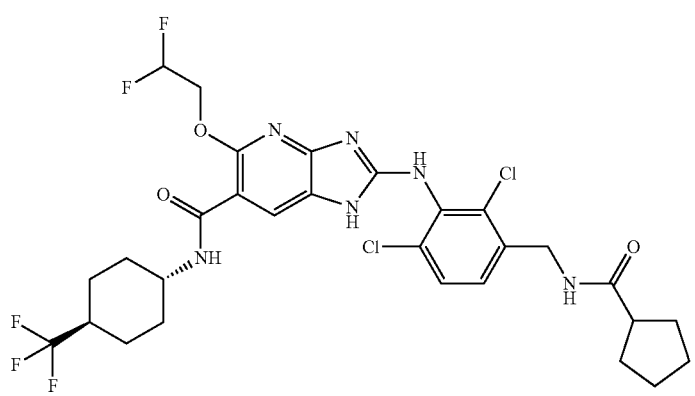 |
| 41 | 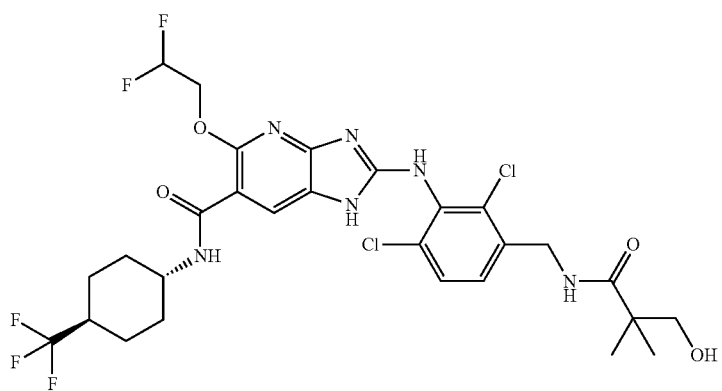 [SMILES: CC(C)(CO)C(=O)NCc1ccc(Cl)c(Nc2nc3nc(OCC(F)F)c(C(=O)N[C@H]4CC[C@H](C(F)(F)F)CC4)cc3[nH]2)c1Cl] |
| 42 | 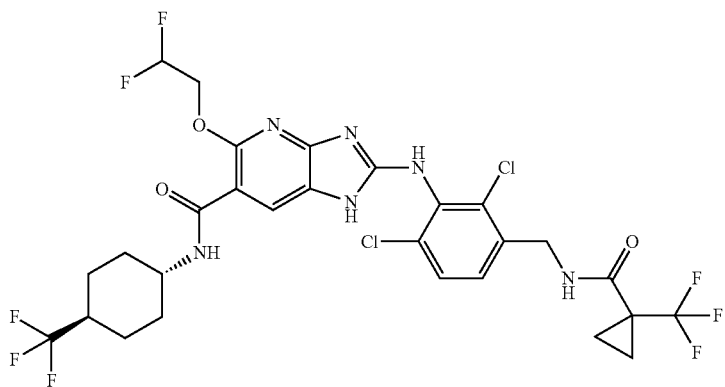 [SMILES: O=C(N[C@H]1CC[C@H](C(F)(F)F)CC1)c1cc2[nH]c(Nc3c(Cl)ccc(CNC(=O)C4(C(F)(F)F)CC4)c3Cl)nc2nc1OCC(F)F] |

-continued
| Structure |
|---|
| 48 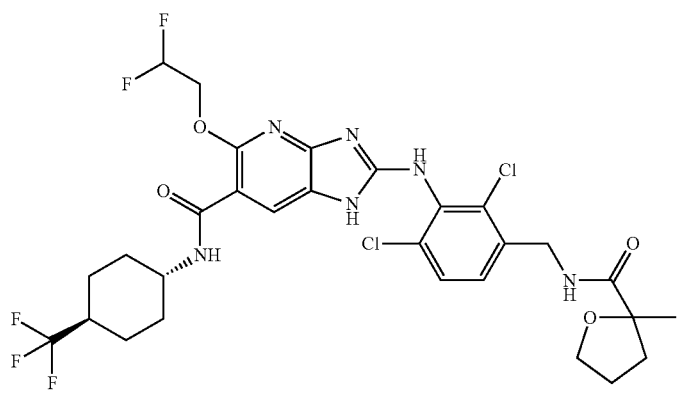 [SMILES: CC1(C(=O)NCc2ccc(Cl)c(Nc3nc4nc(OCC(F)F)c(C(=O)N[C@H]5CC[C@H](C(F)(F)F)CC5)cc4[nH]3)c2Cl)CCCO1] |
| 44 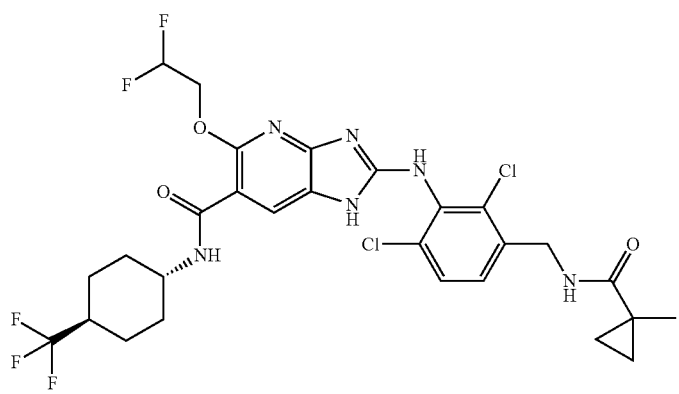 [SMILES: CC1(C(=O)NCc2ccc(Cl)c(Nc3nc4nc(OCC(F)F)c(C(=O)N[C@H]5CC[C@H](C(F)(F)F)CC5)cc4[nH]3)c2Cl)CC1] |
| 45 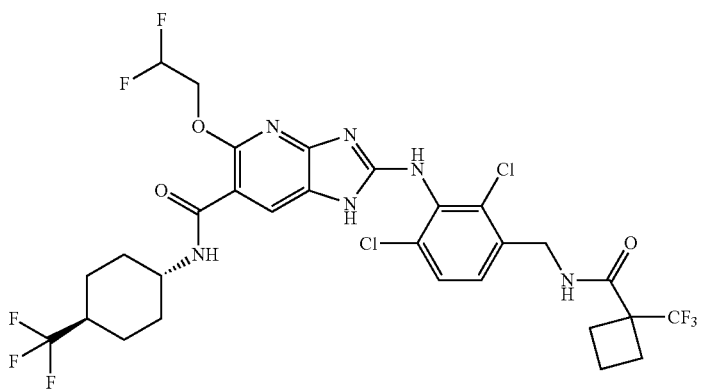 [SMILES: O=C(N[C@H]1CC[C@H](C(F)(F)F)CC1)c1cc2[nH]c(Nc3c(Cl)ccc(CNC(=O)C4(C(F)(F)F)CCC4)c3Cl)nc2nc1OCC(F)F] |
| 46 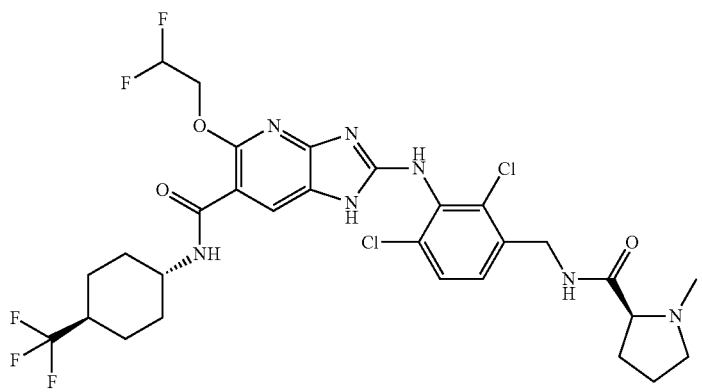 [SMILES: CN1CCC[C@H]1C(=O)NCc1ccc(Cl)c(Nc2nc3nc(OCC(F)F)c(C(=O)N[C@H]4CC[C@H](C(F)(F)F)CC4)cc3[nH]2)c1Cl] |

| | Structure |
|---|---|
| 47 | 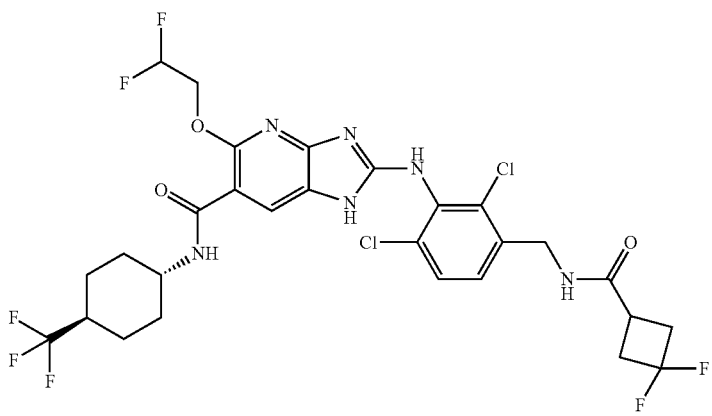 [SMILES: O=C(N[C@H]1CC[C@H](C(F)(F)F)CC1)c1cc2[nH]c(Nc3c(Cl)ccc(CNC(=O)C4CC(F)(F)C4)c3Cl)nc2nc1OCC(F)F] |
| 53 | 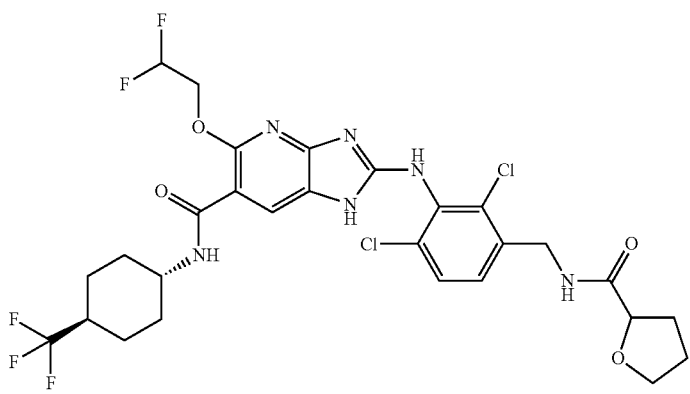 |
| 49 | 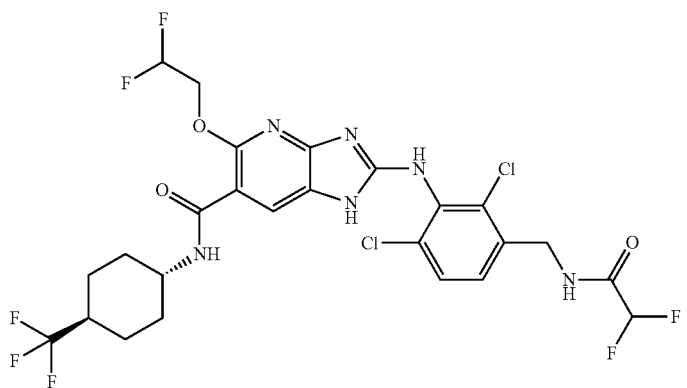 [SMILES: O=C(N[C@H]1CC[C@H](C(F)(F)F)CC1)c1cc2[nH]c(Nc3c(Cl)ccc(CNC(=O)C(F)F)c3Cl)nc2nc1OCC(F)F] |
| 50 | 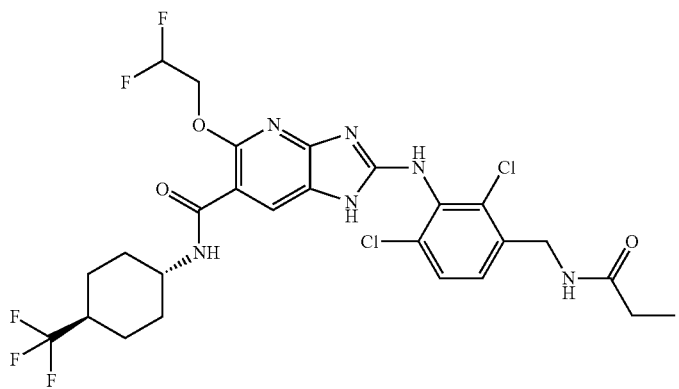 [SMILES: CCC(=O)NCc1ccc(Cl)c(Nc2nc3nc(OCC(F)F)c(C(=O)N[C@H]4CC[C@H](C(F)(F)F)CC4)cc3[nH]2)c1Cl] |

-continued
| | Structure |
|---|---|
| 51 | 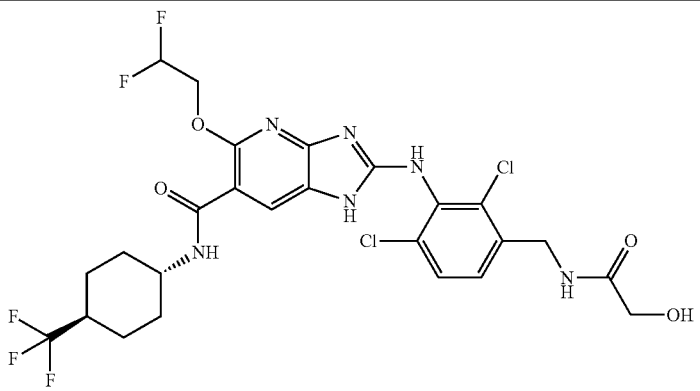 |
| 52 | 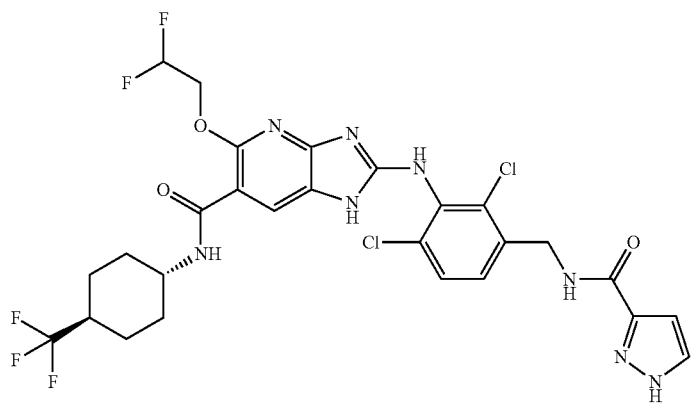 [SMILES: O=C(NCc1ccc(Cl)c(Nc2nc3nc(OCC(F)F)c(C(=O)N[C@H]4CC[C@H](C(F)(F)F)CC4)cc3[nH]2)c1Cl)c1cc[nH]n1] |
| 59 | 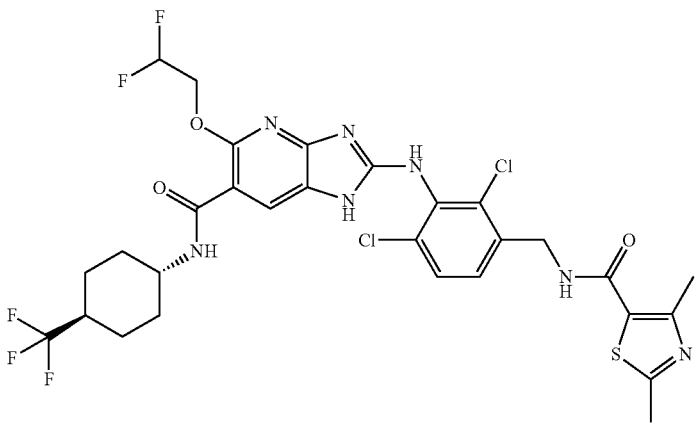 [SMILES: Cc1nc(C)c(C(=O)NCc2ccc(Cl)c(Nc3nc4nc(OCC(F)F)c(C(=O)N[C@H]5CC[C@H](C(F)(F)F)CC5)cc4[nH]3)c2Cl)s1] |
| 54 | 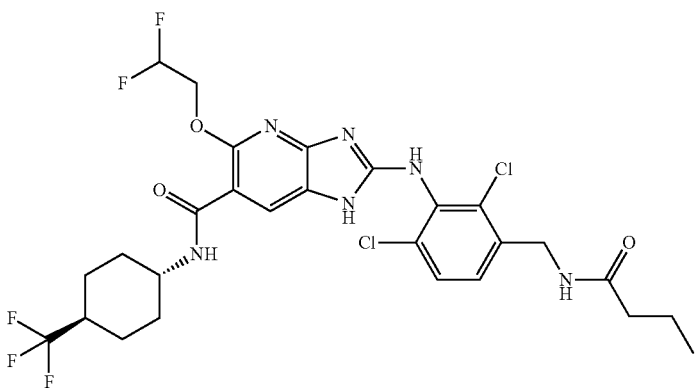 |

-continued
| | Structure |
|---|---|
| 55 | 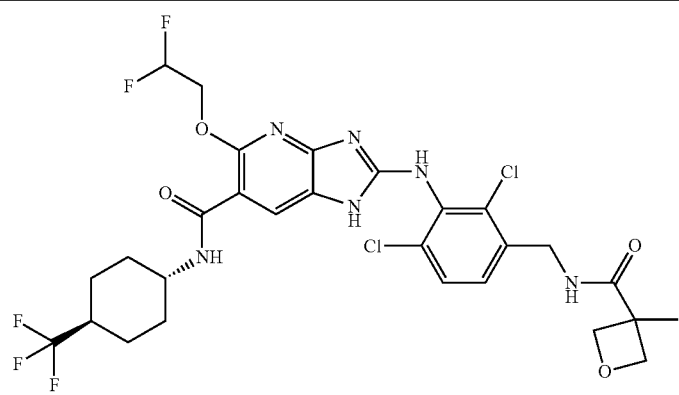 |
| 56 | 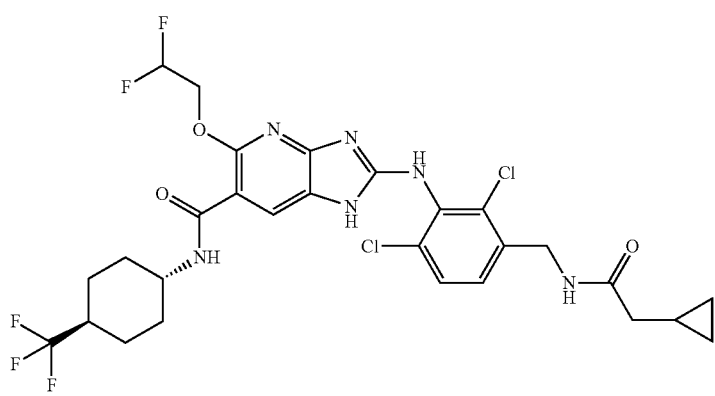 [SMILES: O=C(CC1CC1)NCc1ccc(Cl)c(Nc2nc3nc(OCC(F)F)c(C(=O)N[C@H]4CC[C@H](C(F)(F)F)CC4)cc3[nH]2)c1Cl] |
| 57 | 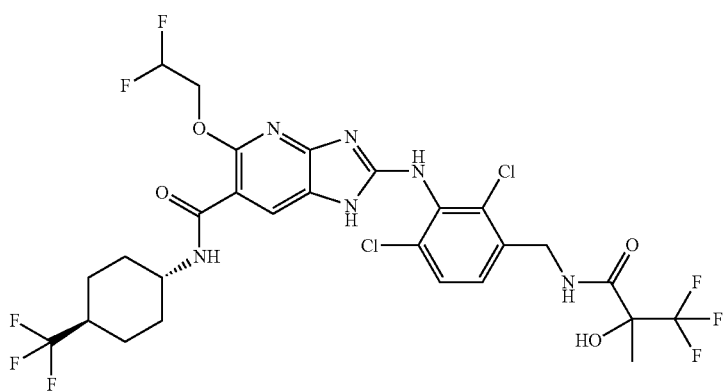 [SMILES: CC(O)(C(=O)NCc1ccc(Cl)c(Nc2nc3nc(OCC(F)F)c(C(=O)N[C@H]4CC[C@H](C(F)(F)F)CC4)cc3[nH]2)c1Cl)C(F)(F)F] |
| 58 | 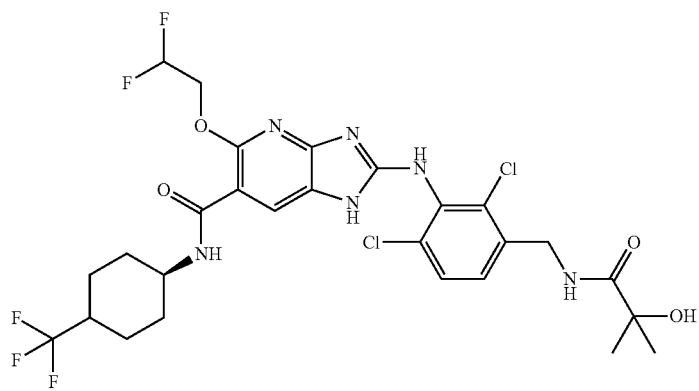 |

-continued
| | Structure |
|---|---|
| 60 | 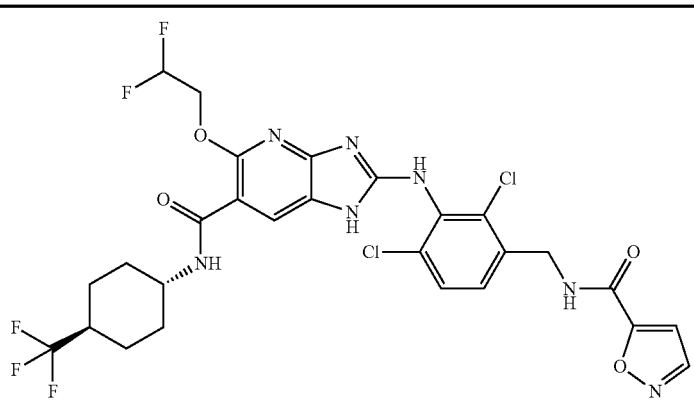 |
| 61 | 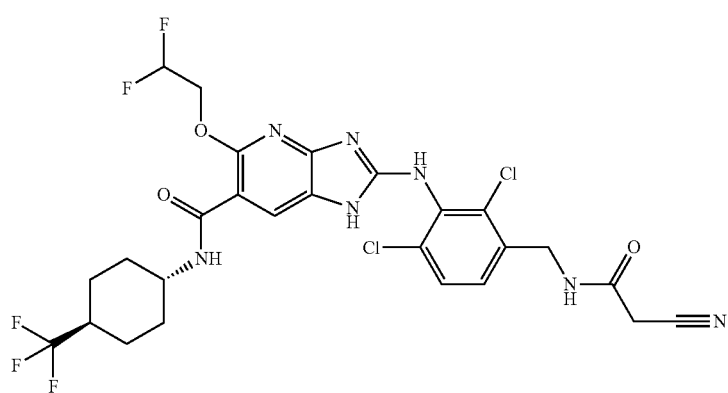 [SMILES: N#CCC(=O)NCc1ccc(Cl)c(Nc2nc3nc(OCC(F)F)c(C(=O)N[C@H]4CC[C@H](C(F)(F)F)CC4)cc3[nH]2)c1Cl] |
| 62 | 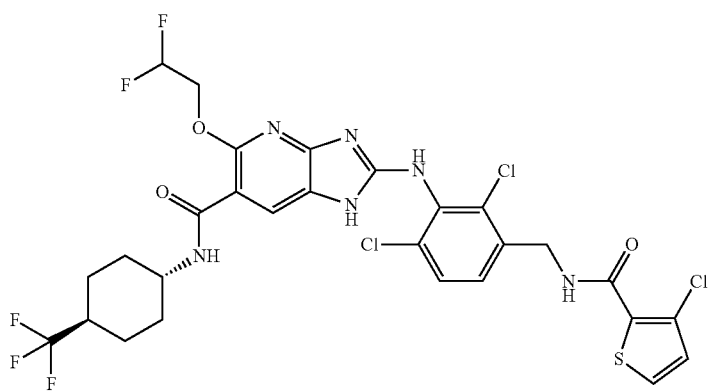 [SMILES: O=C(N[C@H]1CC[C@H](C(F)(F)F)CC1)c1cc2[nH]c(Nc3c(Cl)ccc(CNC(=O)c4sccc4Cl)c3Cl)nc2nc1OCC(F)F] |
| 63 | 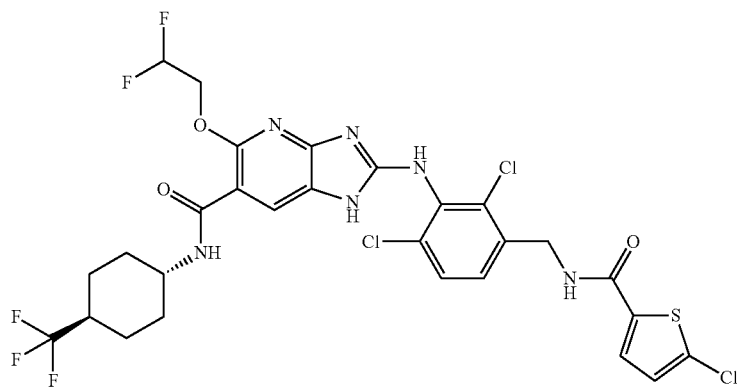 [SMILES: O=C(NCc1ccc(Cl)c(Nc2nc3nc(OCC(F)F)c(C(=O)N[C@H]4CC[C@H](C(F)(F)F)CC4)cc3[nH]2)c1Cl)c1ccc(Cl)s1] |

-continued
| | Structure |
|---|---|
| 64 | 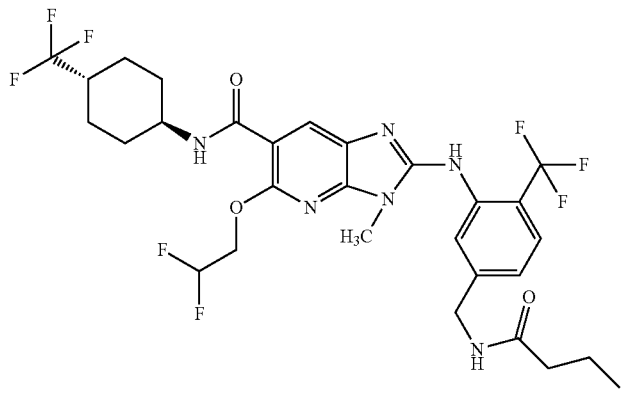 [SMILES: CCCC(=O)NCc1ccc(C(F)(F)F)c(Nc2nc3cc(C(=O)N[C@H]4CC[C@H](C(F)(F)F)CC4)c(OCC(F)F)nc3n2C)c1] |
| 65 | 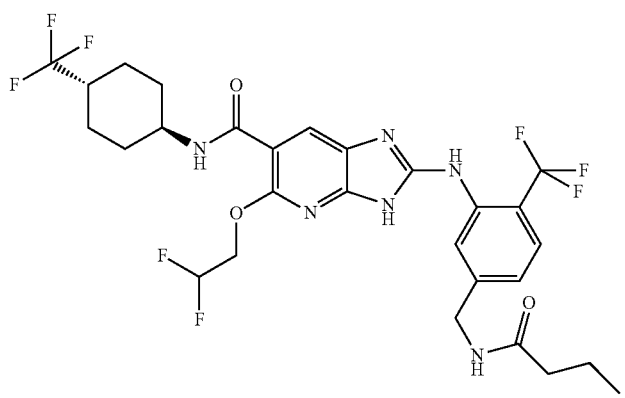 [SMILES: CCCC(=O)NCc1ccc(C(F)(F)F)c(Nc2nc3cc(C(=O)N[C@H]4CC[C@H](C(F)(F)F)CC4)c(OCC(F)F)nc3[nH]2)c1] |
| 66 | 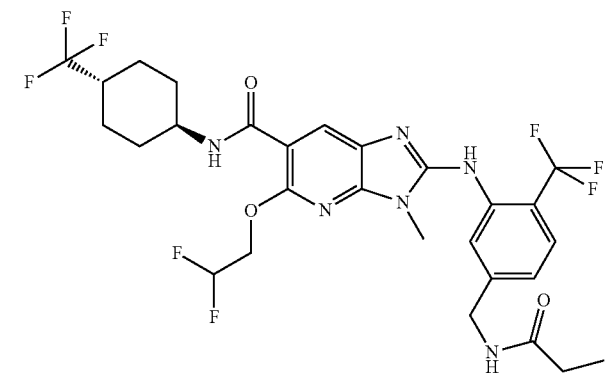 [SMILES: CCC(=O)NCc1ccc(C(F)(F)F)c(Nc2nc3cc(C(=O)N[C@H]4CC[C@H](C(F)(F)F)CC4)c(OCC(F)F)nc3n2C)c1] |
| 67 | 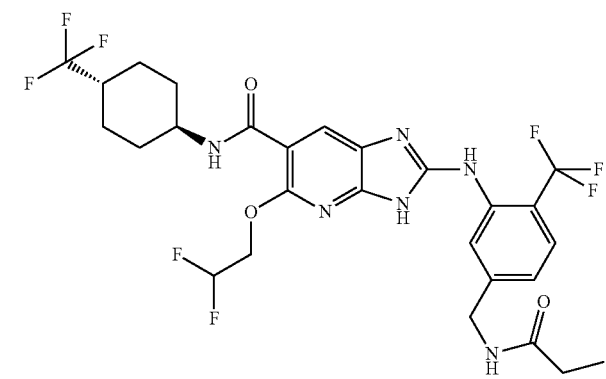 [SMILES: CCC(=O)NCc1ccc(C(F)(F)F)c(Nc2nc3cc(C(=O)N[C@H]4CC[C@H](C(F)(F)F)CC4)c(OCC(F)F)nc3[nH]2)c1] |

-continued
| | Structure |
|---|---|
| 68 | 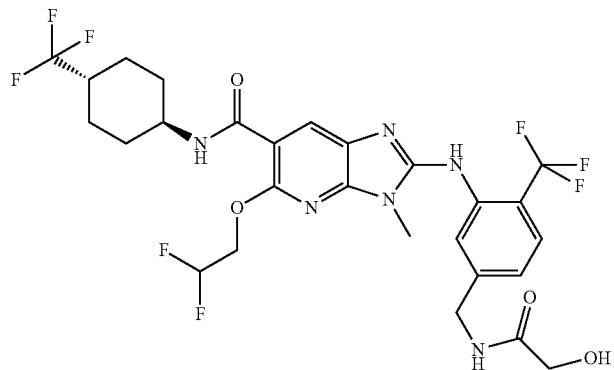 [SMILES: Cn1c(Nc2cc(CNC(=O)CO)ccc2C(F)(F)F)nc2cc(C(=O)N[C@H]3CC[C@H](C(F)(F)F)CC3)c(OCC(F)F)nc21] |
| 69 | 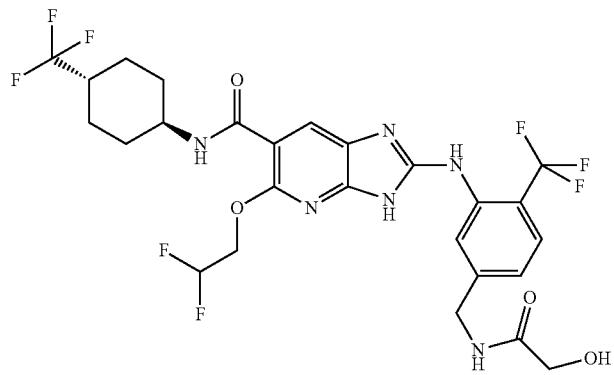 [SMILES: O=C(CO)NCc1ccc(C(F)(F)F)c(Nc2nc3cc(C(=O)N[C@H]4CC[C@H](C(F)(F)F)CC4)c(OCC(F)F)nc3[nH]2)c1] |
| 71 | 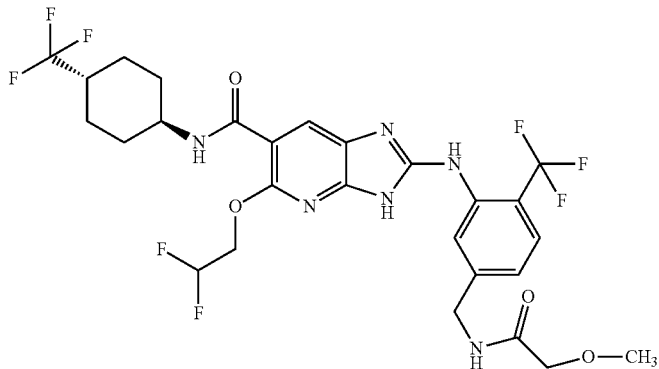 [SMILES: COCC(=O)NCc1ccc(C(F)(F)F)c(Nc2nc3cc(C(=O)N[C@H]4CC[C@H](C(F)(F)F)CC4)c(OCC(F)F)nc3[nH]2)c1] |
| 72 | 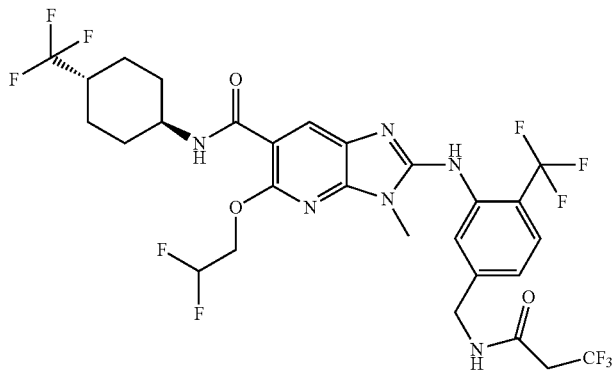 [SMILES: Cn1c(Nc2cc(CNC(=O)CC(F)(F)F)ccc2C(F)(F)F)nc2cc(C(=O)N[C@H]3CC[C@H](C(F)(F)F)CC3)c(OCC(F)F)nc21] |

| | -continued |
|---|---|
| | Structure |
| 73 | 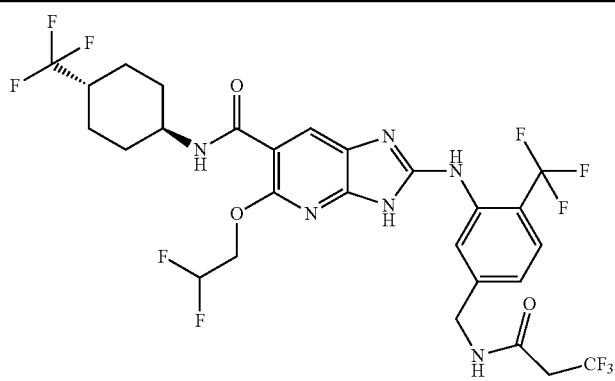 |
| 74 | 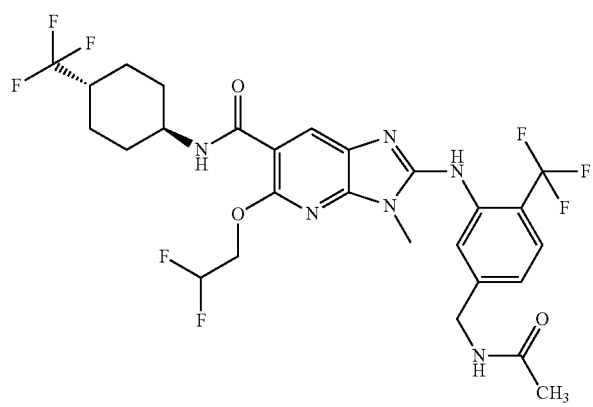 [SMILES: CC(=O)NCc1ccc(C(F)(F)F)c(Nc2nc3cc(C(=O)N[C@H]4CC[C@H](C(F)(F)F)CC4)c(OCC(F)F)nc3n2C)c1] |
| 75 | 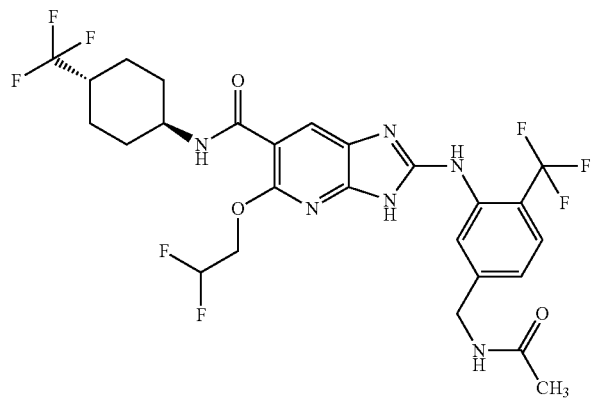 [SMILES: CC(=O)NCc1ccc(C(F)(F)F)c(Nc2nc3cc(C(=O)N[C@H]4CC[C@H](C(F)(F)F)CC4)c(OCC(F)F)nc3[nH]2)c1] |
| 70 | 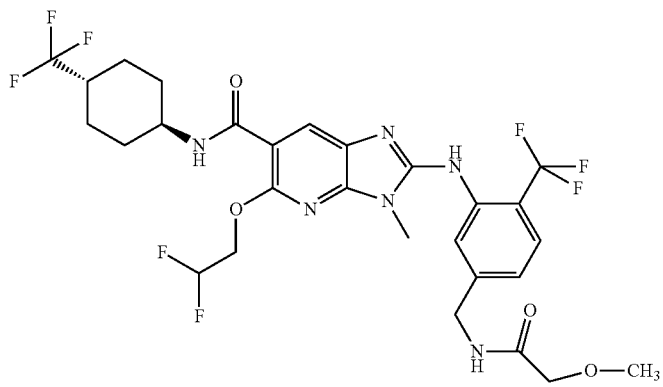 [SMILES: COCC(=O)NCc1ccc(C(F)(F)F)c(Nc2nc3cc(C(=O)N[C@H]4CC[C@H](C(F)(F)F)CC4)c(OCC(F)F)nc3n2C)c1] |

-continued
| | Structure |
|---|---|
| 77 | 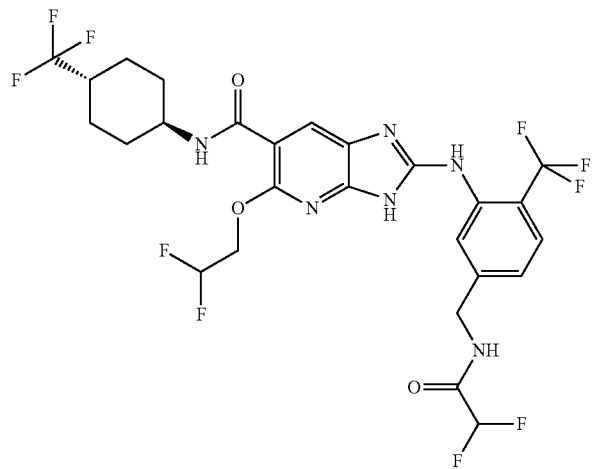 [SMILES: O=C(N[C@H]1CC[C@H](C(F)(F)F)CC1)c1cc2nc(Nc3cc(CNC(=O)C(F)F)ccc3C(F)(F)F)[nH]c2nc1OCC(F)F] |
| 78 | 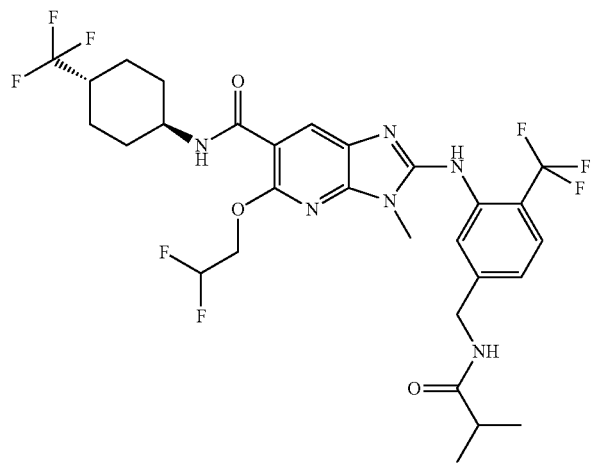 [SMILES: CC(C)C(=O)NCc1ccc(C(F)(F)F)c(Nc2nc3cc(C(=O)N[C@H]4CC[C@H](C(F)(F)F)CC4)c(OCC(F)F)nc3n2C)c1] |
| 79 | 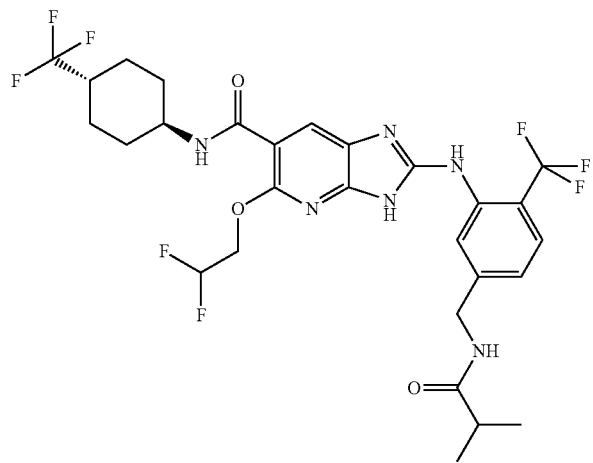 [SMILES: CC(C)C(=O)NCc1ccc(C(F)(F)F)c(Nc2nc3cc(C(=O)N[C@H]4CC[C@H](C(F)(F)F)CC4)c(OCC(F)F)nc3[nH]2)c1] |

| | Structure |
|---|---|
| 76 | 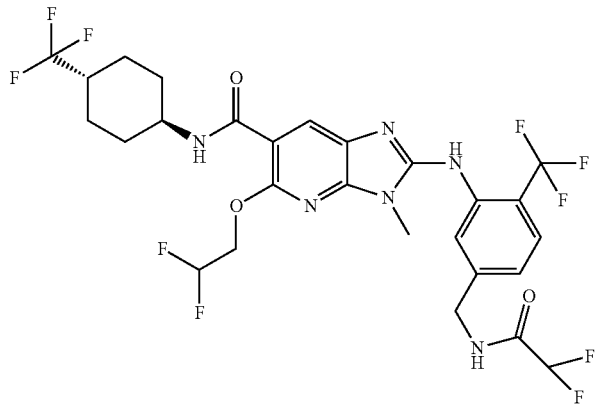 [SMILES: Cn1c(Nc2cc(CNC(=O)C(F)F)ccc2C(F)(F)F)nc2cc(C(=O)N[C@H]3CC[C@H](C(F)(F)F)CC3)c(OCC(F)F)nc21] |
| 82 | 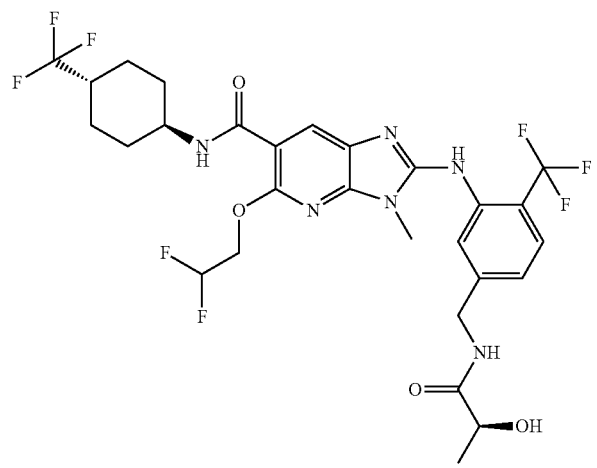 [SMILES: C[C@H](O)C(=O)NCc1ccc(C(F)(F)F)c(Nc2nc3cc(C(=O)N[C@H]4CC[C@H](C(F)(F)F)CC4)c(OCC(F)F)nc3n2C)c1] |
| 83 | 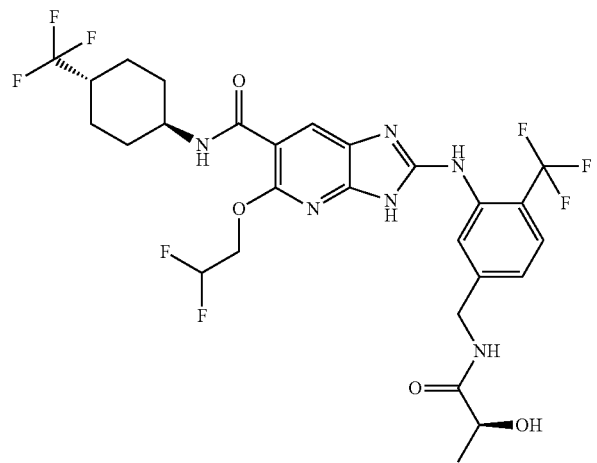 [SMILES: C[C@H](O)C(=O)NCc1ccc(C(F)(F)F)c(Nc2nc3cc(C(=O)N[C@H]4CC[C@H](C(F)(F)F)CC4)c(OCC(F)F)nc3[nH]2)c1] |

| Structure |
|---|
| 84 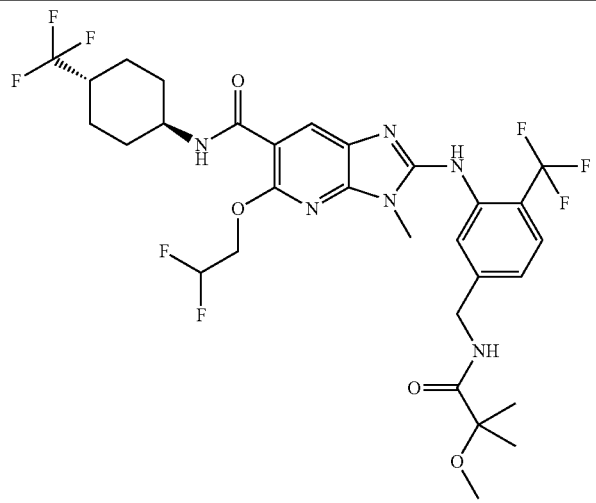 |
| 80 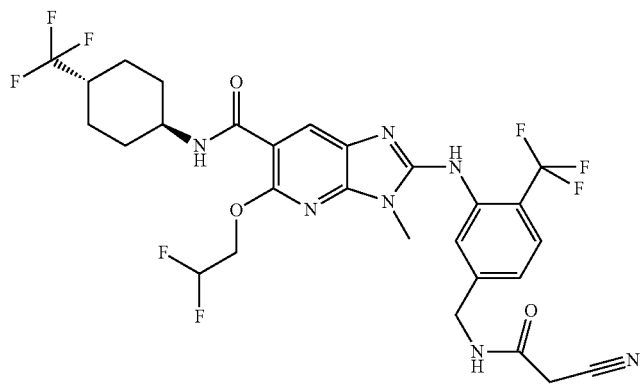 [SMILES: Cn1c(Nc2cc(CNC(=O)CC#N)ccc2C(F)(F)F)nc2cc(C(=O)N[C@H]3CC[C@H](C(F)(F)F)CC3)c(OCC(F)F)nc21] |
| 81 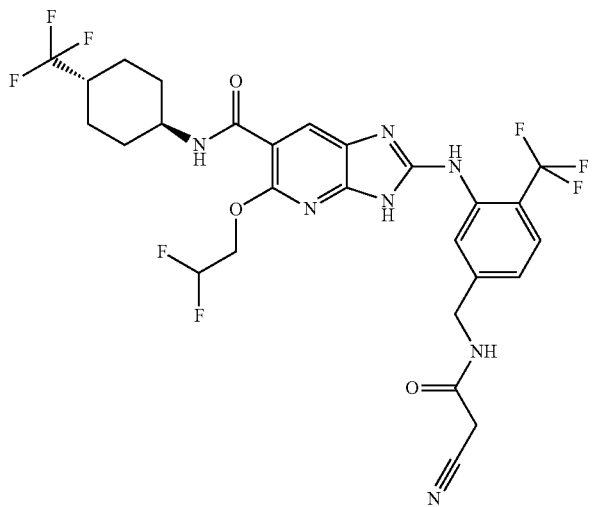 [SMILES: N#CCC(=O)NCc1ccc(C(F)(F)F)c(Nc2nc3cc(C(=O)N[C@H]4CC[C@H](C(F)(F)F)CC4)c(OCC(F)F)nc3[nH]2)c1] |

|   | Structure |
|---|---|
| 87 | 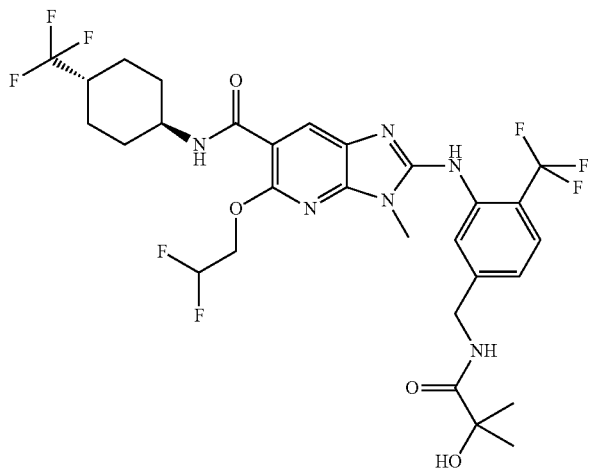 [SMILES: Cn1c(Nc2cc(CNC(=O)C(C)(C)O)ccc2C(F)(F)F)nc2cc(C(=O)N[C@H]3CC[C@H](C(F)(F)F)CC3)c(OCC(F)F)nc21] |
| 88 | 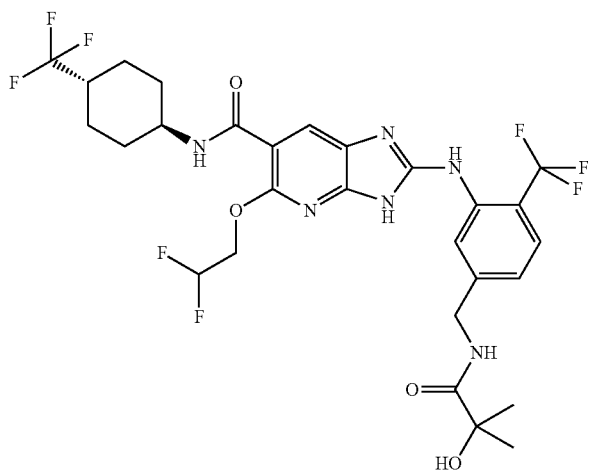 [SMILES: CC(C)(O)C(=O)NCc1ccc(C(F)(F)F)c(Nc2nc3cc(C(=O)N[C@H]4CC[C@H](C(F)(F)F)CC4)c(OCC(F)F)nc3[nH]2)c1] |
| 85 | 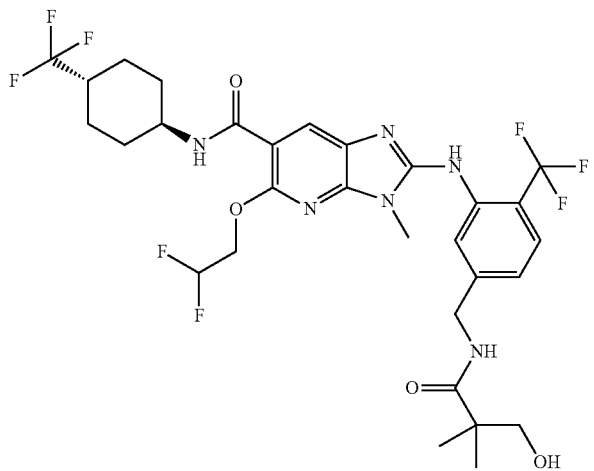 [SMILES: Cn1c(Nc2cc(CNC(=O)C(C)(C)CO)ccc2C(F)(F)F)nc2cc(C(=O)N[C@H]3CC[C@H](C(F)(F)F)CC3)c(OCC(F)F)nc21] |

| | Structure |
|---|---|
| 86 | 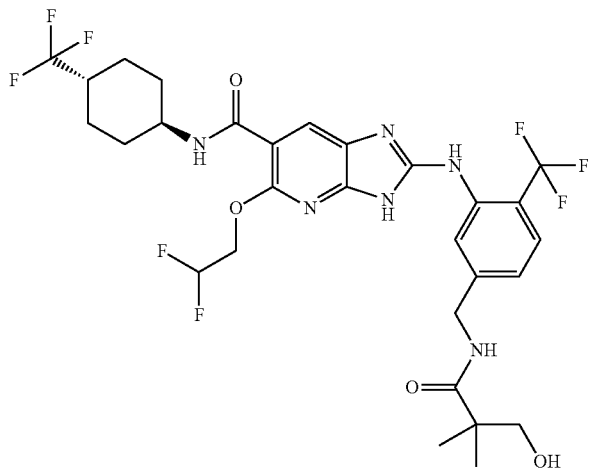 [SMILES: CC(C)(CO)C(=O)NCc1ccc(C(F)(F)F)c(Nc2nc3cc(C(=O)N[C@H]4CC[C@H](C(F)(F)F)CC4)c(OCC(F)F)nc3[nH]2)c1] |
| 92 | 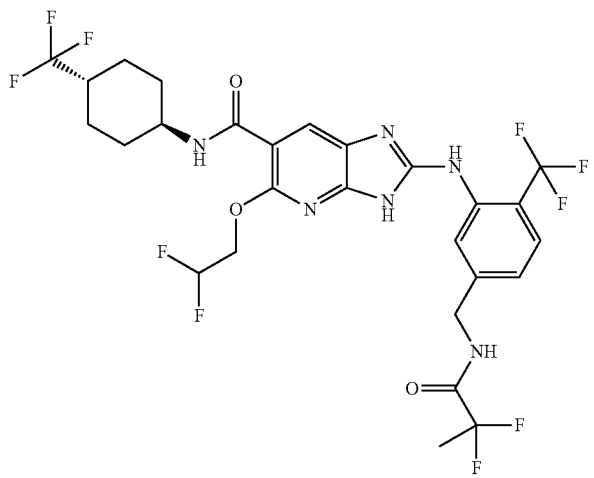 [SMILES: CC(F)(F)C(=O)NCc1ccc(C(F)(F)F)c(Nc2nc3cc(C(=O)N[C@H]4CC[C@H](C(F)(F)F)CC4)c(OCC(F)F)nc3[nH]2)c1] |
| 93 | 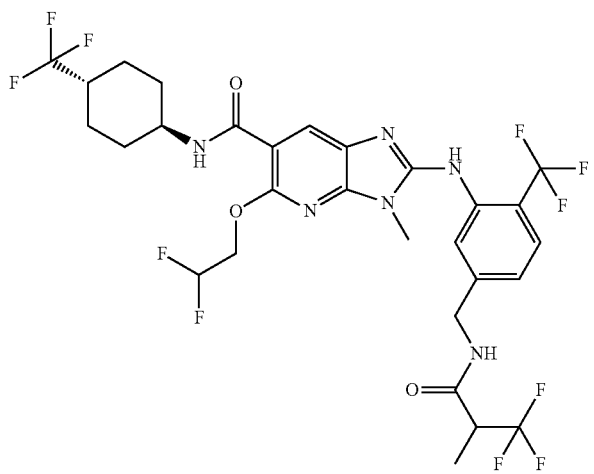 [SMILES: CC(C(=O)NCc1ccc(C(F)(F)F)c(Nc2nc3cc(C(=O)N[C@H]4CC[C@H](C(F)(F)F)CC4)c(OCC(F)F)nc3n2C)c1)C(F)(F)F] |

-continued
| | Structure |
|---|---|
| 89 | 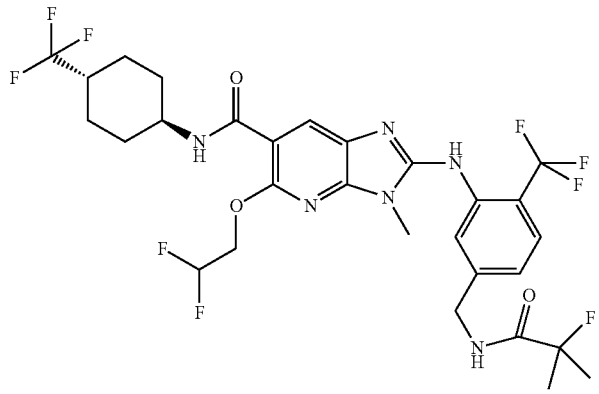 [SMILES: Cn1c(Nc2cc(CNC(=O)C(C)(C)F)ccc2C(F)(F)F)nc2cc(C(=O)N[C@H]3CC[C@H](C(F)(F)F)CC3)c(OCC(F)F)nc21] |
| 90 | 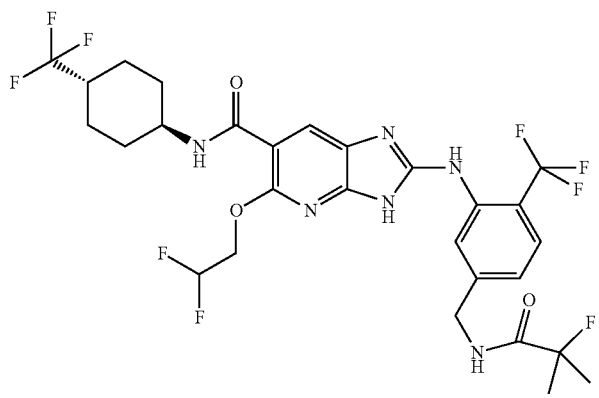 [SMILES: CC(C)(F)C(=O)NCc1ccc(C(F)(F)F)c(Nc2nc3cc(C(=O)N[C@H]4CC[C@H](C(F)(F)F)CC4)c(OCC(F)F)nc3[nH]2)c1] |
| 91 | 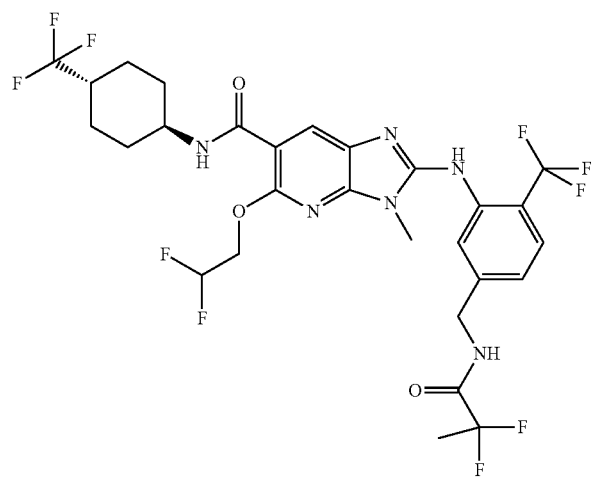 [SMILES: Cn1c(Nc2cc(CNC(=O)C(C)(F)F)ccc2C(F)(F)F)nc2cc(C(=O)N[C@H]3CC[C@H](C(F)(F)F)CC3)c(OCC(F)F)nc21] |

| | Structure |
|---|---|
| 97 | 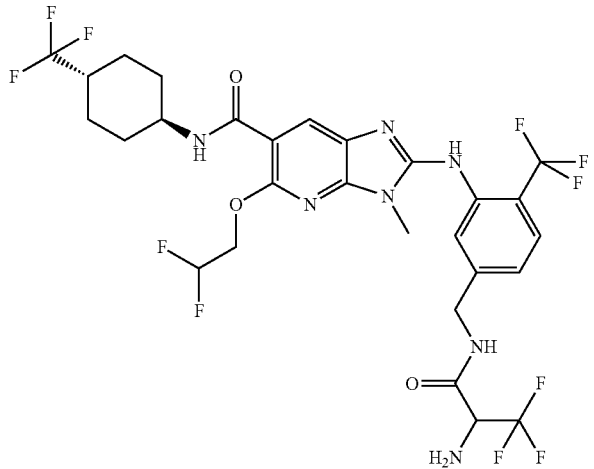 [SMILES: Cn1c(Nc2cc(CNC(=O)C(N)C(F)(F)F)ccc2C(F)(F)F)nc2cc(C(=O)N[C@H]3CC[C@H](C(F)(F)F)CC3)c(OCC(F)F)nc21] |
| 94 | 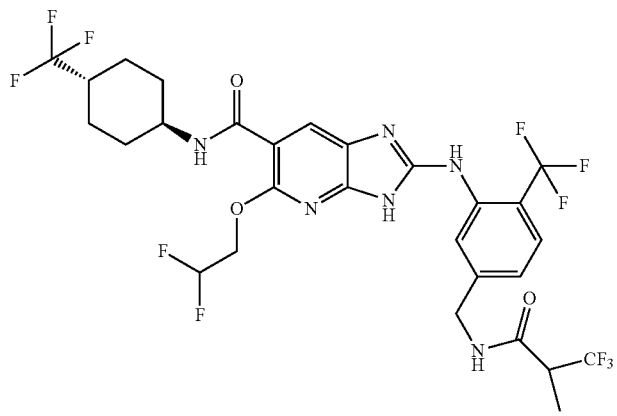 [SMILES: CC(C(=O)NCc1ccc(C(F)(F)F)c(Nc2nc3cc(C(=O)N[C@H]4CC[C@H](C(F)(F)F)CC4)c(OCC(F)F)nc3[nH]2)c1)C(F)(F)F] |
| 95 | 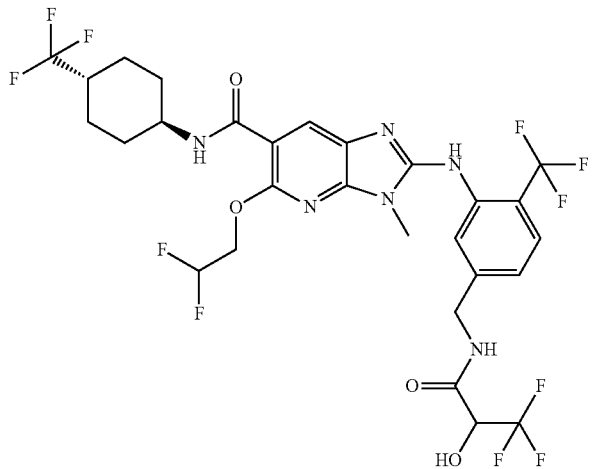 [SMILES: Cn1c(Nc2cc(CNC(=O)C(O)C(F)(F)F)ccc2C(F)(F)F)nc2cc(C(=O)N[C@H]3CC[C@H](C(F)(F)F)CC3)c(OCC(F)F)nc21] |

-continued
| | Structure |
|---|---|
| 96 | 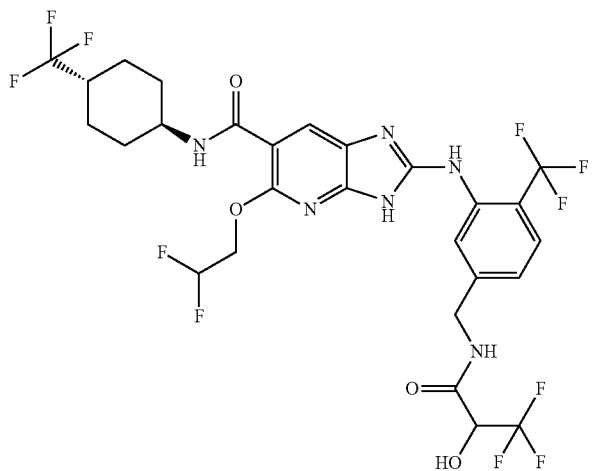 [SMILES: O=C(N[C@H]1CC[C@H](C(F)(F)F)CC1)c1cc2nc(Nc3cc(CNC(=O)C(O)C(F)(F)F)ccc3C(F)(F)F)[nH]c2nc1OCC(F)F] |
| 101 | 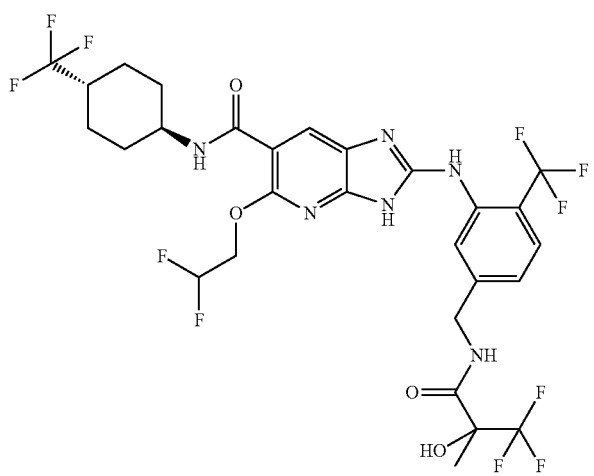 [SMILES: CC(O)(C(=O)NCc1ccc(C(F)(F)F)c(Nc2nc3cc(C(=O)N[C@H]4CC[C@H](C(F)(F)F)CC4)c(OCC(F)F)nc3[nH]2)c1)C(F)(F)F] |
| 98 | 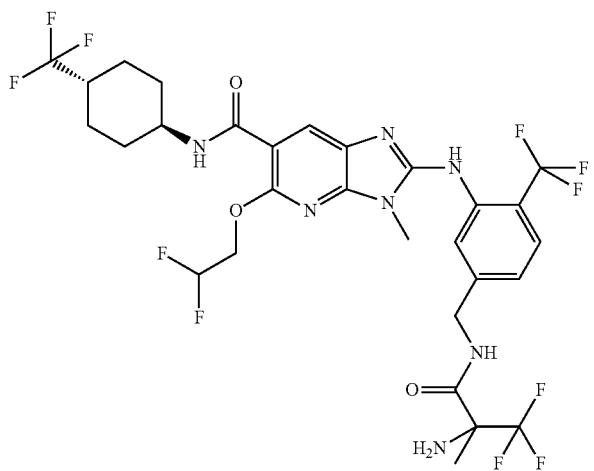 [SMILES: Cn1c(Nc2cc(CNC(=O)C(C)(N)C(F)(F)F)ccc2C(F)(F)F)nc2cc(C(=O)N[C@H]3CC[C@H](C(F)(F)F)CC3)c(OCC(F)F)nc21] |

|   | Structure |
|---|---|
| 99 | 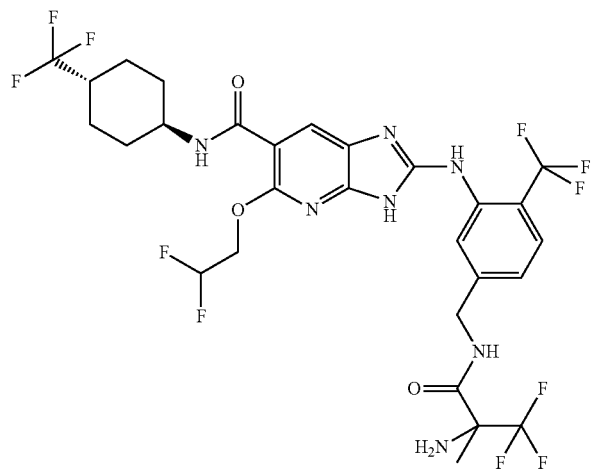 [SMILES: CC(N)(C(=O)NCc1ccc(C(F)(F)F)c(Nc2nc3cc(C(=O)N[C@H]4CC[C@H](C(F)(F)F)CC4)c(OCC(F)F)nc3[nH]2)c1)C(F)(F)F] |
| 100 | 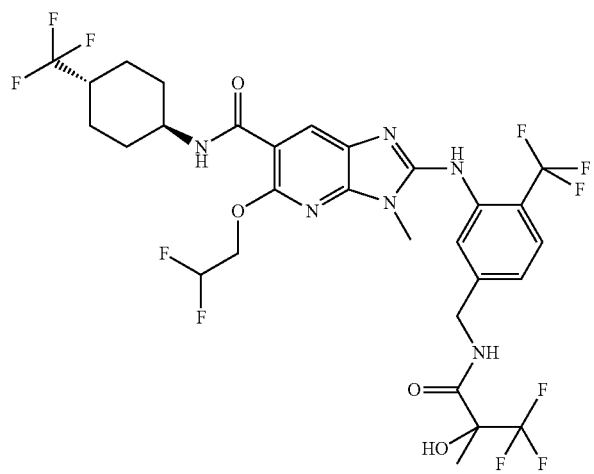 [SMILES: Cn1c(Nc2cc(CNC(=O)C(C)(O)C(F)(F)F)ccc2C(F)(F)F)nc2cc(C(=O)N[C@H]3CC[C@H](C(F)(F)F)CC3)c(OCC(F)F)nc21] |
| 105 | 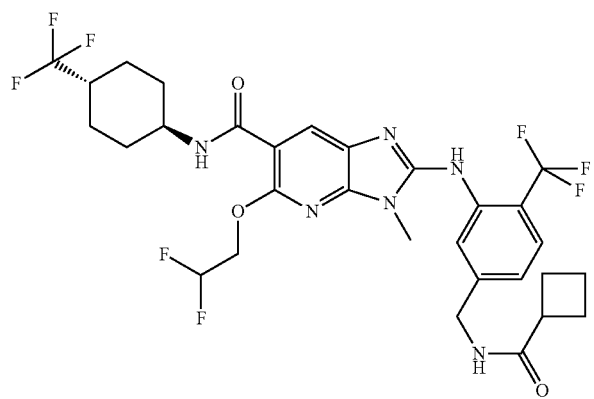 [SMILES: Cn1c(Nc2cc(CNC(=O)C3CCC3)ccc2C(F)(F)F)nc2cc(C(=O)N[C@H]3CC[C@H](C(F)(F)F)CC3)c(OCC(F)F)nc21] |

US 8,586,604 B2
-continued
| | Structure |
|---|---|
| 102 | 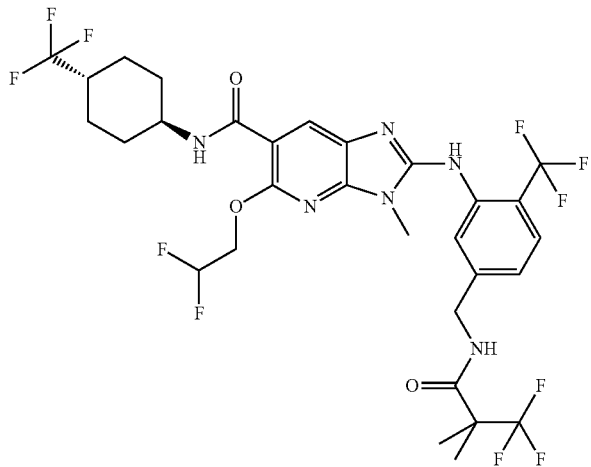 [SMILES: Cn1c(Nc2cc(CNC(=O)C(C)(C)C(F)(F)F)ccc2C(F)(F)F)nc2cc(C(=O)N[C@H]3CC[C@H](C(F)(F)F)CC3)c(OCC(F)F)nc21] |
| 103 | 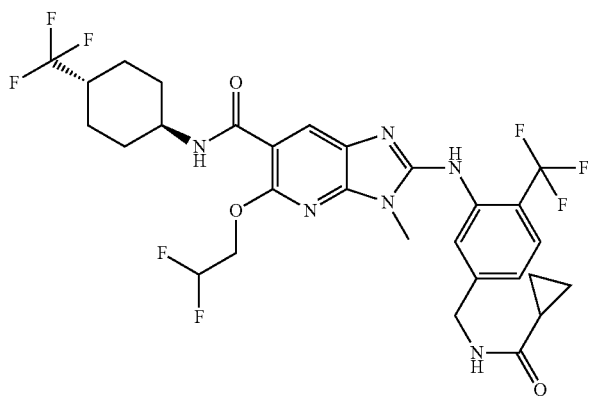 [SMILES: Cn1c(Nc2cc(CNC(=O)C3CC3)ccc2C(F)(F)F)nc2cc(C(=O)N[C@H]3CC[C@H](C(F)(F)F)CC3)c(OCC(F)F)nc21] |
| 104 | 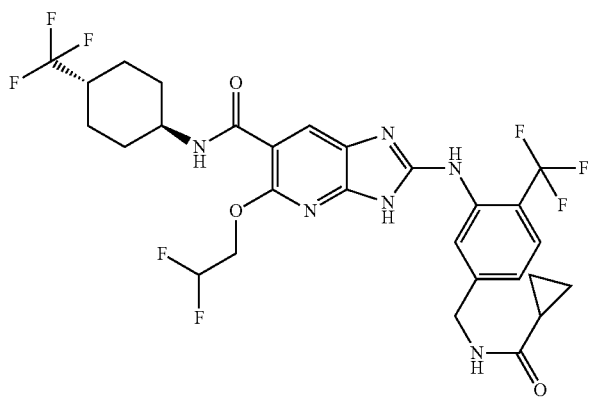 [SMILES: O=C(N[C@H]1CC[C@H](C(F)(F)F)CC1)c1cc2nc(Nc3cc(CNC(=O)C4CC4)ccc3C(F)(F)F)[nH]c2nc1OCC(F)F] |

US 8,586,604 B2
175                                                                         176
-continued
| | Structure |
|---|---|
| 110 | 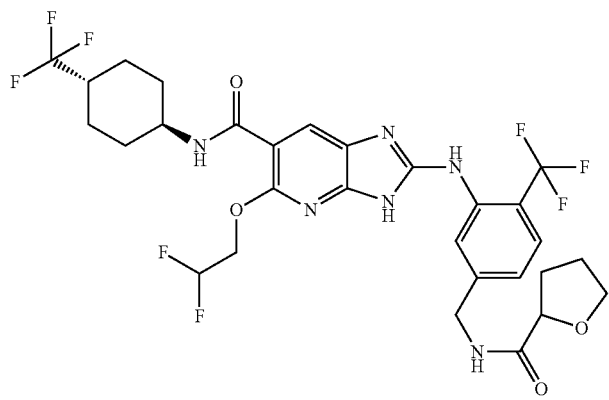 [SMILES: O=C(N[C@H]1CC[C@H](C(F)(F)F)CC1)c1cc2nc(Nc3cc(CNC(=O)C4CCCO4)ccc3C(F)(F)F)[nH]c2nc1OCC(F)F] |
| 106 | 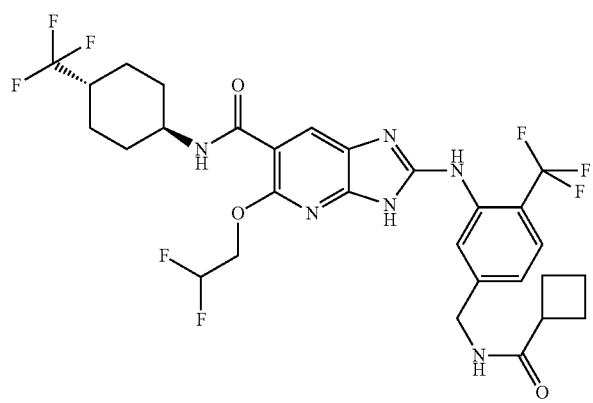 |
| 107 | 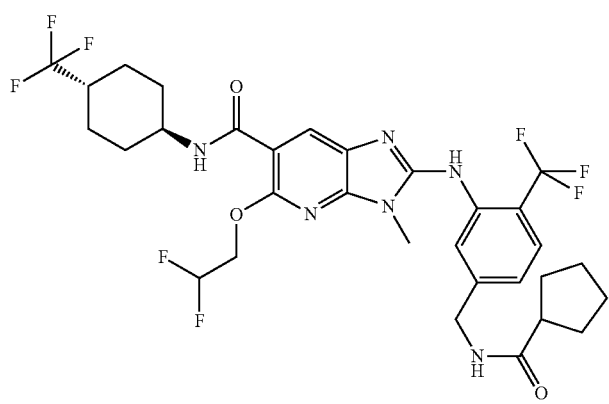 |
| 108 | 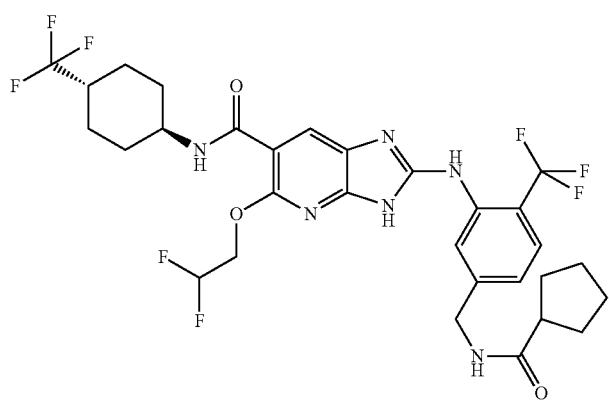 [SMILES: O=C(N[C@H]1CC[C@H](C(F)(F)F)CC1)c1cc2nc(Nc3cc(CNC(=O)C4CCCC4)ccc3C(F)(F)F)[nH]c2nc1OCC(F)F] |

| | Structure |
|---|---|
| 109 | 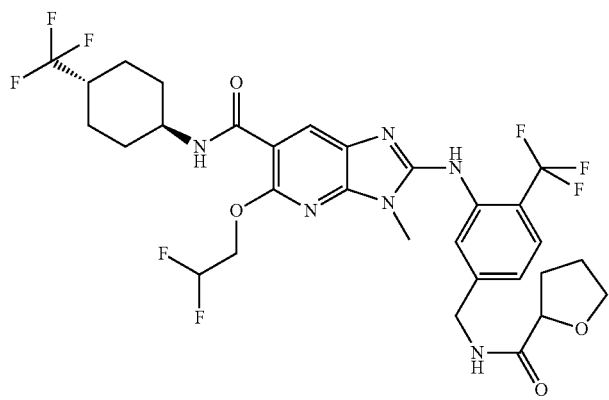 [SMILES: Cn1c(Nc2cc(CNC(=O)C3CCCO3)ccc2C(F)(F)F)nc2cc(C(=O)N[C@H]3CC[C@H](C(F)(F)F)CC3)c(OCC(F)F)nc21] |
| 111 | 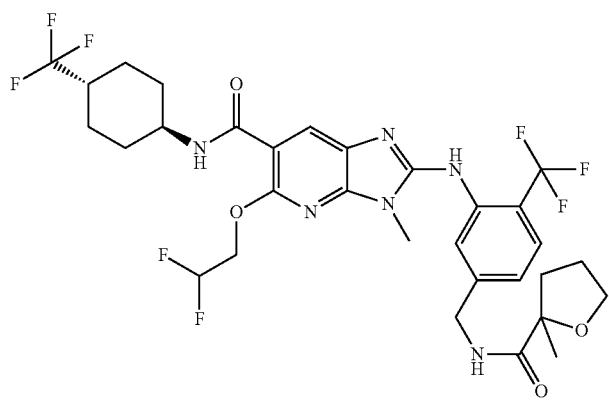 [SMILES: Cn1c(Nc2cc(CNC(=O)C3(C)CCCO3)ccc2C(F)(F)F)nc2cc(C(=O)N[C@H]3CC[C@H](C(F)(F)F)CC3)c(OCC(F)F)nc21] |
| 112 | 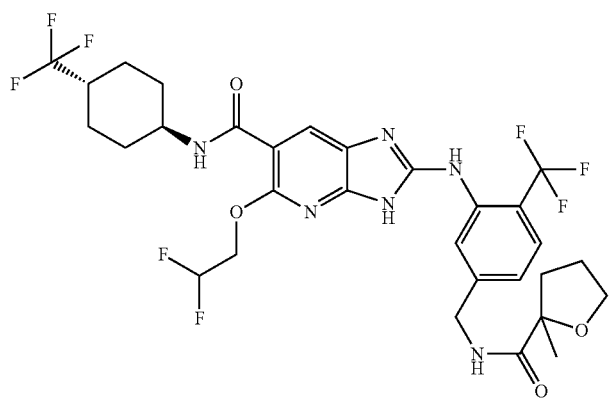 |
| 113 | 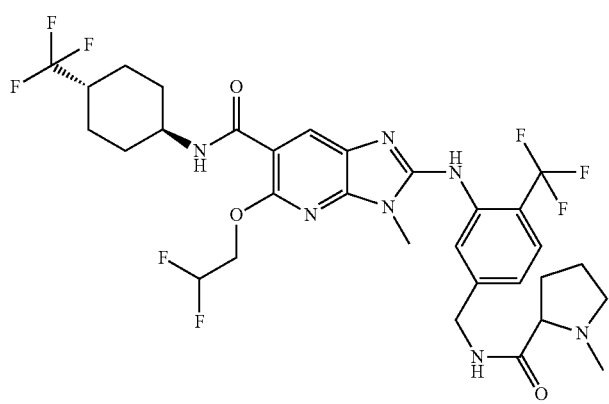 [SMILES: CN1CCCC1C(=O)NCc1ccc(C(F)(F)F)c(Nc2nc3cc(C(=O)N[C@H]4CC[C@H](C(F)(F)F)CC4)c(OCC(F)F)nc3n2C)c1] |

| | -continued |
|---|---|
| | Structure |
| 114 | 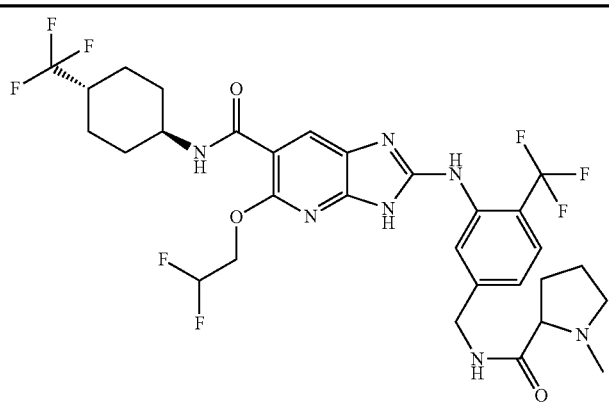 |
| 115 | 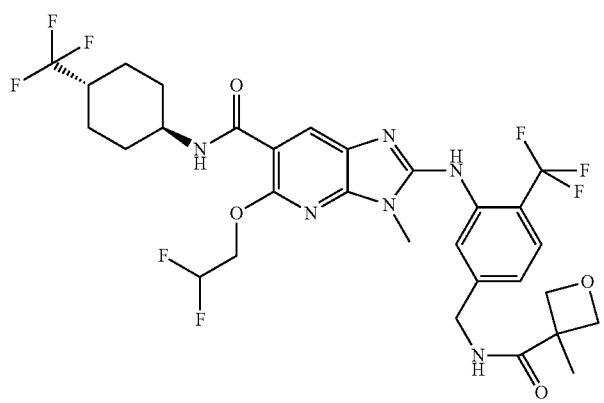 [SMILES: Cn1c(Nc2cc(CNC(=O)C3(C)COC3)ccc2C(F)(F)F)nc2cc(C(=O)N[C@H]3CC[C@H](C(F)(F)F)CC3)c(OCC(F)F)nc21] |
| 116 | 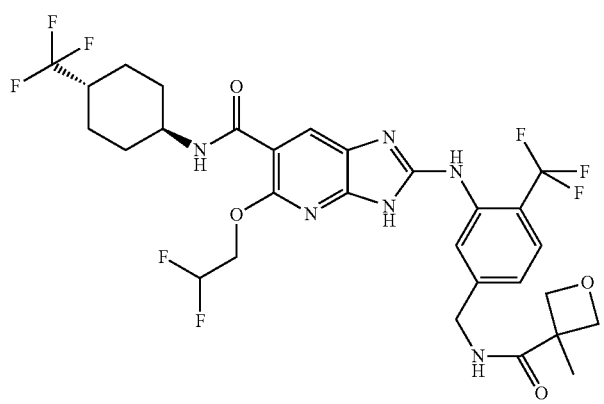 [SMILES: CC1(C(=O)NCc2ccc(C(F)(F)F)c(Nc3nc4cc(C(=O)N[C@H]5CC[C@H](C(F)(F)F)CC5)c(OCC(F)F)nc4[nH]3)c2)COC1] |
| 117 | 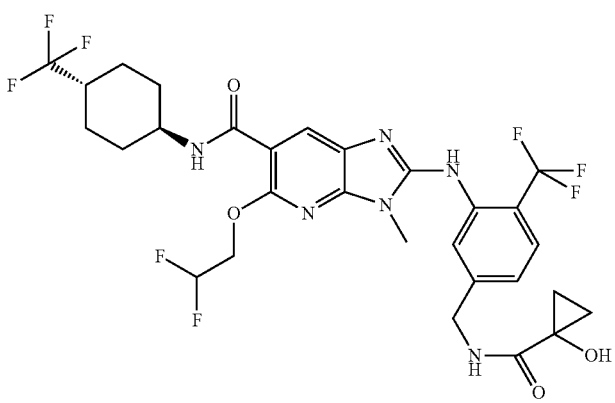 [SMILES: Cn1c(Nc2cc(CNC(=O)C3(O)CC3)ccc2C(F)(F)F)nc2cc(C(=O)N[C@H]3CC[C@H](C(F)(F)F)CC3)c(OCC(F)F)nc21] |

-continued
| | Structure |
|---|---|
| 118 | 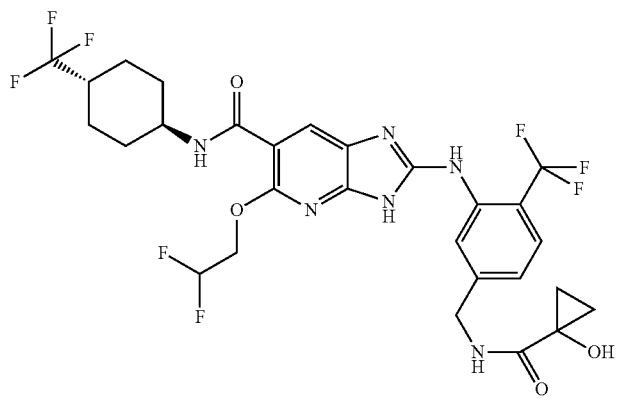 [SMILES: O=C(N[C@H]1CC[C@H](C(F)(F)F)CC1)c1cc2nc(Nc3cc(CNC(=O)C4(O)CC4)ccc3C(F)(F)F)[nH]c2nc1OCC(F)F] |
| 119 | 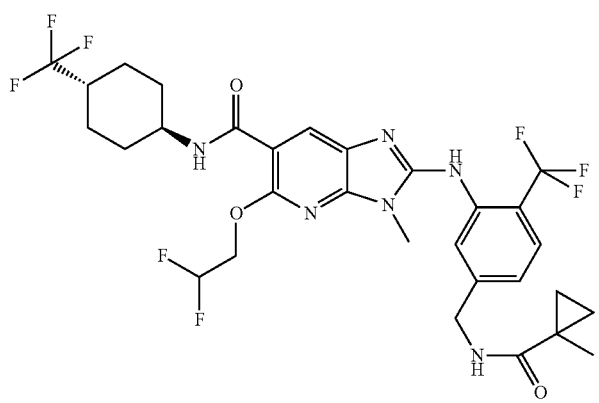 [SMILES: Cn1c(Nc2cc(CNC(=O)C3(C)CC3)ccc2C(F)(F)F)nc2cc(C(=O)N[C@H]3CC[C@H](C(F)(F)F)CC3)c(OCC(F)F)nc21] |
| 120 | 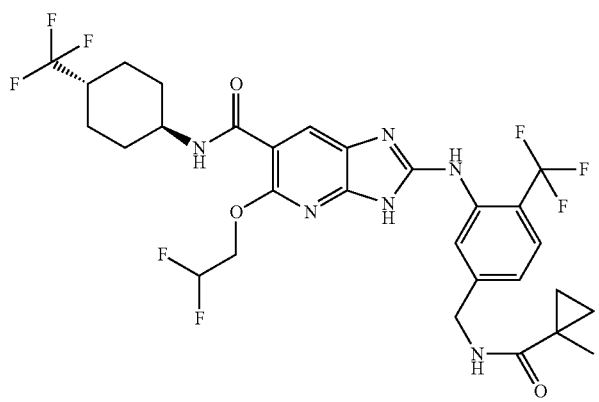 [SMILES: CC1(C(=O)NCc2ccc(C(F)(F)F)c(Nc3nc4cc(C(=O)N[C@H]5CC[C@H](C(F)(F)F)CC5)c(OCC(F)F)nc4[nH]3)c2)CC1] |
| 121 | 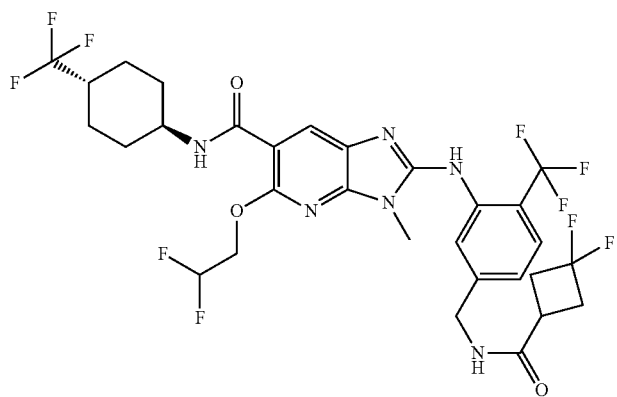 [SMILES: Cn1c(Nc2cc(CNC(=O)C3CC(F)(F)C3)ccc2C(F)(F)F)nc2cc(C(=O)N[C@H]3CC[C@H](C(F)(F)F)CC3)c(OCC(F)F)nc21] |

-continued
| | Structure |
|---|---|
| 122 | 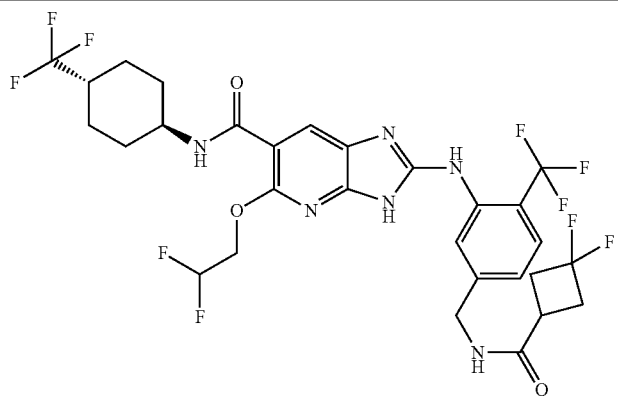 |
| 123 | 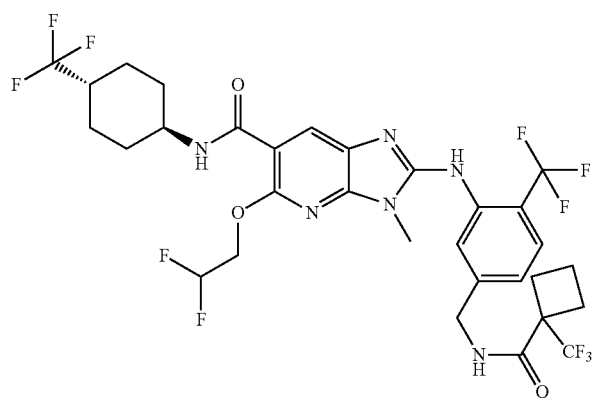 [SMILES: Cn1c(Nc2cc(CNC(=O)C3(C(F)(F)F)CCC3)ccc2C(F)(F)F)nc2cc(C(=O)N[C@H]3CC[C@H](C(F)(F)F)CC3)c(OCC(F)F)nc21] |
| 124 | 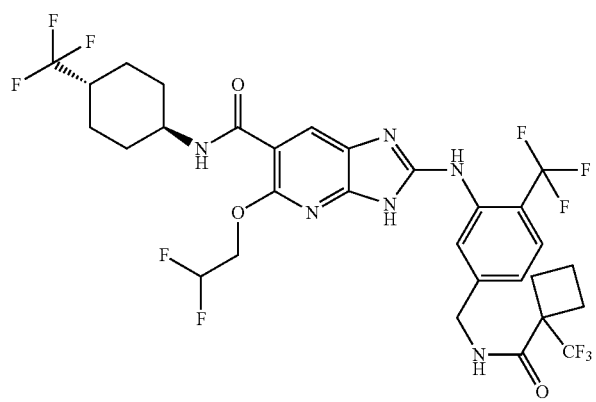 [SMILES: O=C(N[C@H]1CC[C@H](C(F)(F)F)CC1)c1cc2nc(Nc3cc(CNC(=O)C4(C(F)(F)F)CCC4)ccc3C(F)(F)F)[nH]c2nc1OCC(F)F] |
| 125 | 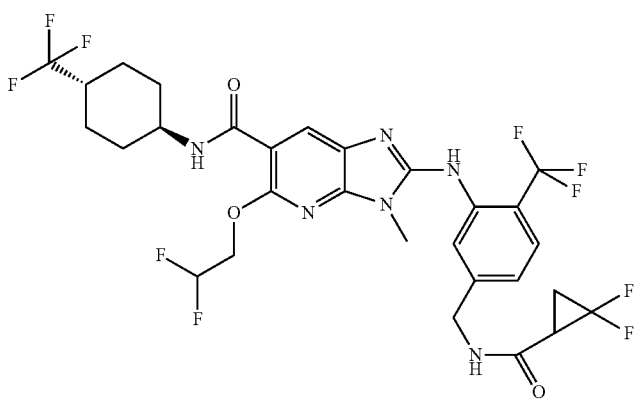 [SMILES: Cn1c(Nc2cc(CNC(=O)C3CC3(F)F)ccc2C(F)(F)F)nc2cc(C(=O)N[C@H]3CC[C@H](C(F)(F)F)CC3)c(OCC(F)F)nc21] |

| | Structure |
|---|---|
| 126 | 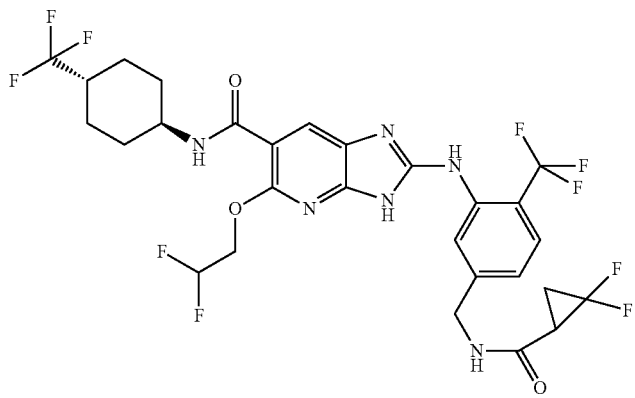 [SMILES: O=C(N[C@H]1CC[C@H](C(F)(F)F)CC1)c1cc2nc(Nc3cc(CNC(=O)C4CC4(F)F)ccc3C(F)(F)F)[nH]c2nc1OCC(F)F] |
| 127 | 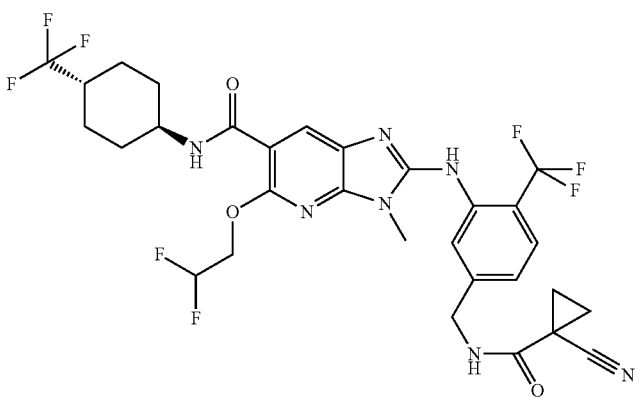 [SMILES: Cn1c(Nc2cc(CNC(=O)C3(C#N)CC3)ccc2C(F)(F)F)nc2cc(C(=O)N[C@H]3CC[C@H](C(F)(F)F)CC3)c(OCC(F)F)nc21] |
| 128 | 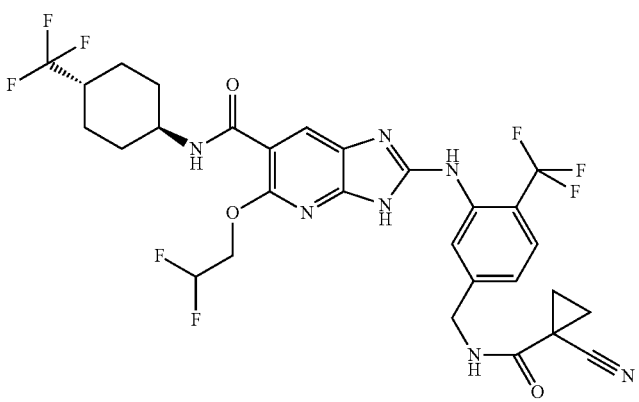 [SMILES: N#CC1(C(=O)NCc2ccc(C(F)(F)F)c(Nc3nc4cc(C(=O)N[C@H]5CC[C@H](C(F)(F)F)CC5)c(OCC(F)F)nc4[nH]3)c2)CC1] |
| 130 | 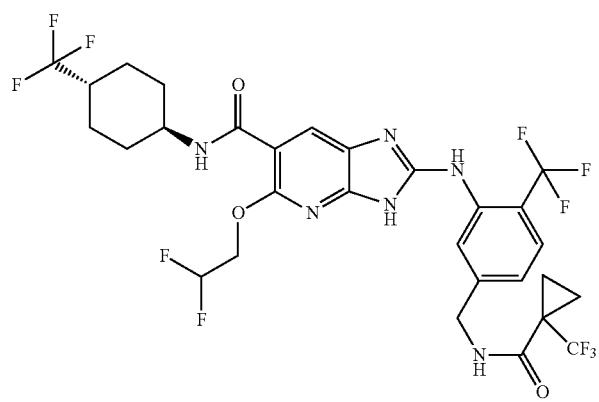 [SMILES: O=C(N[C@H]1CC[C@H](C(F)(F)F)CC1)c1cc2nc(Nc3cc(CNC(=O)C4(C(F)(F)F)CC4)ccc3C(F)(F)F)[nH]c2nc1OCC(F)F] |

-continued
| | Structure |
|---|---|
| 131 | 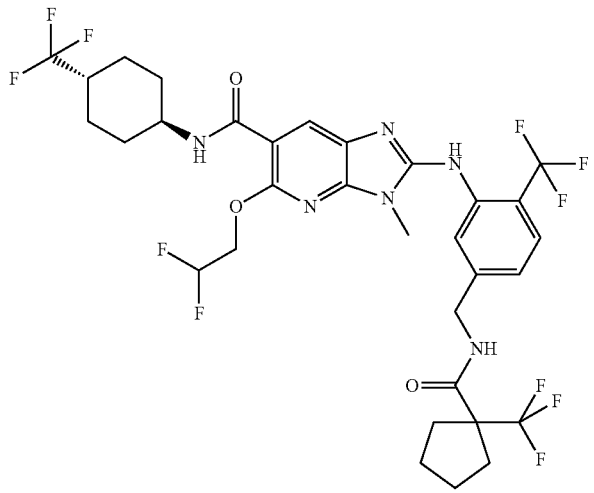 [SMILES: Cn1c(Nc2cc(CNC(=O)C3(C(F)(F)F)CCCC3)ccc2C(F)(F)F)nc2cc(C(=O)N[C@H]3CC[C@H](C(F)(F)F)CC3)c(OCC(F)F)nc21] |
| 132 | 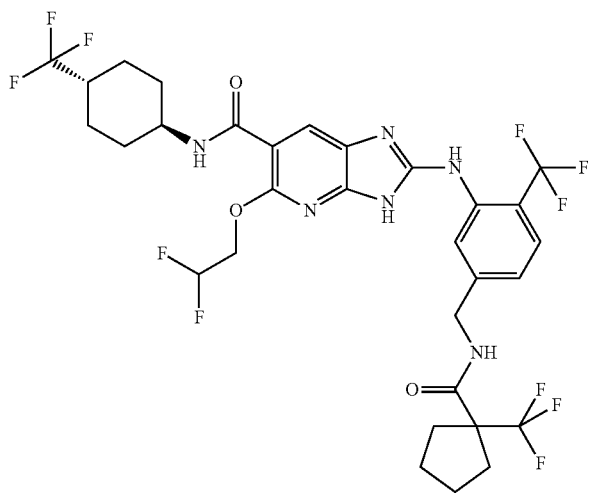 [SMILES: O=C(N[C@H]1CC[C@H](C(F)(F)F)CC1)c1cc2nc(Nc3cc(CNC(=O)C4(C(F)(F)F)CCCC4)ccc3C(F)(F)F)[nH]c2nc1OCC(F)F] |
| 133 | 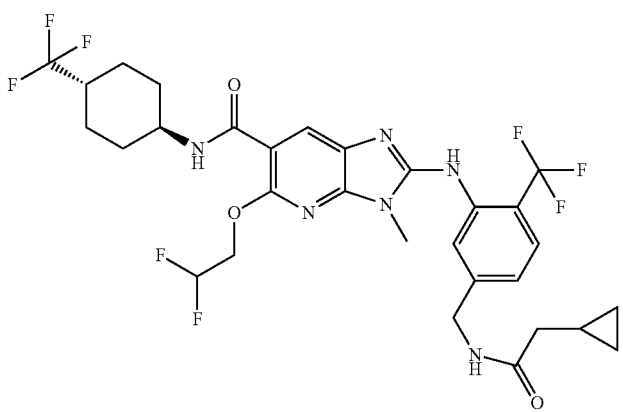 [SMILES: Cn1c(Nc2cc(CNC(=O)CC3CC3)ccc2C(F)(F)F)nc2cc(C(=O)N[C@H]3CC[C@H](C(F)(F)F)CC3)c(OCC(F)F)nc21] |

| | Structure |
|---|---|
| 129 | 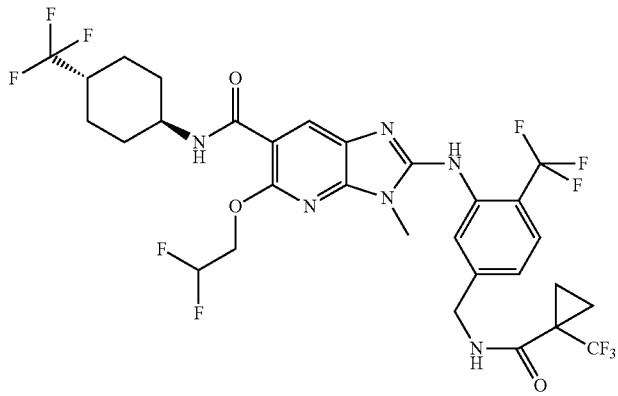 [SMILES: Cn1c(Nc2cc(CNC(=O)C3(C(F)(F)F)CC3)ccc2C(F)(F)F)nc2cc(C(=O)N[C@H]3CC[C@H](C(F)(F)F)CC3)c(OCC(F)F)nc21] |
| 135 | 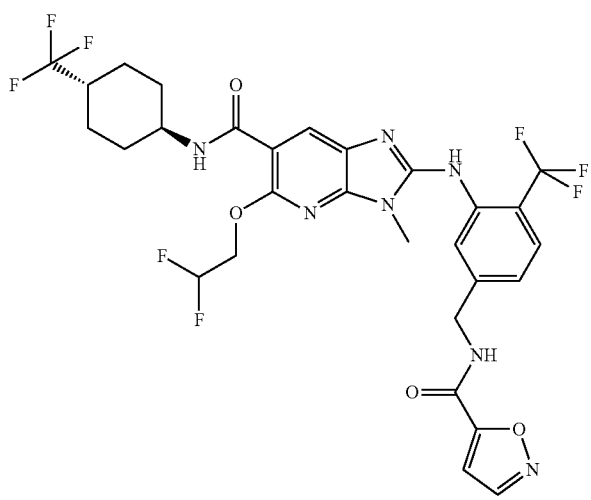 [SMILES: Cn1c(Nc2cc(CNC(=O)c3ccno3)ccc2C(F)(F)F)nc2cc(C(=O)N[C@H]3CC[C@H](C(F)(F)F)CC3)c(OCC(F)F)nc21] |
| 136 | 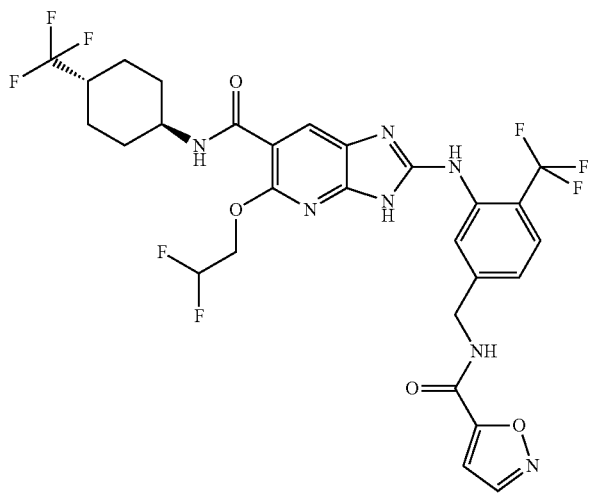 |

-continued
| | Structure |
|---|---|
| 137 | 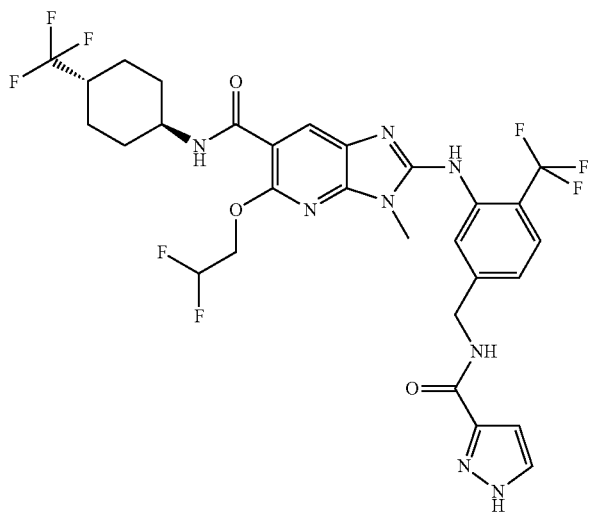 [SMILES: Cn1c(Nc2cc(CNC(=O)c3cc[nH]n3)ccc2C(F)(F)F)nc2cc(C(=O)N[C@H]3CC[C@H](C(F)(F)F)CC3)c(OCC(F)F)nc21] |
| 134 | 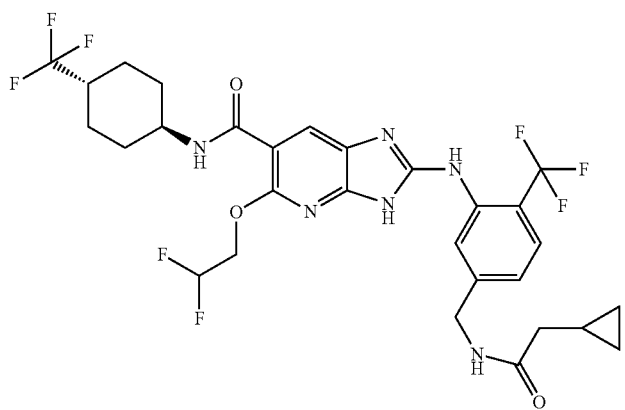 [SMILES: O=C(CC1CC1)NCc1ccc(C(F)(F)F)c(Nc2nc3cc(C(=O)N[C@H]4CC[C@H](C(F)(F)F)CC4)c(OCC(F)F)nc3[nH]2)c1] |
| 139 | 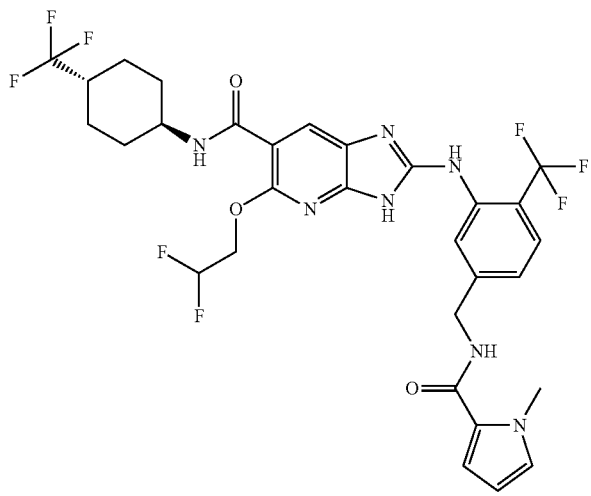 [SMILES: Cn1cccc1C(=O)NCc1ccc(C(F)(F)F)c(Nc2nc3cc(C(=O)N[C@H]4CC[C@H](C(F)(F)F)CC4)c(OCC(F)F)nc3[nH]2)c1] |

| Structure |
|---|
| 140 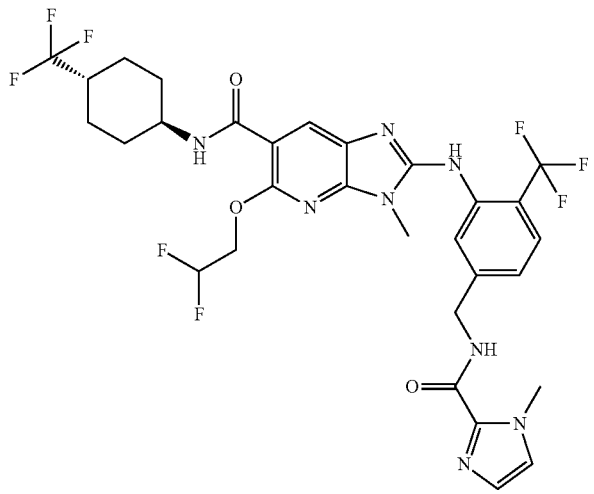 [SMILES: Cn1ccnc1C(=O)NCc1ccc(C(F)(F)F)c(Nc2nc3cc(C(=O)N[C@H]4CC[C@H](C(F)(F)F)CC4)c(OCC(F)F)nc3n2C)c1] |
| 141 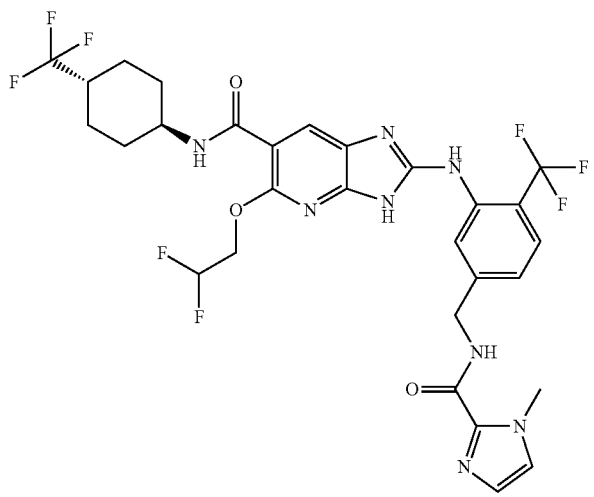 [SMILES: Cn1ccnc1C(=O)NCc1ccc(C(F)(F)F)c(Nc2nc3cc(C(=O)N[C@H]4CC[C@H](C(F)(F)F)CC4)c(OCC(F)F)nc3[nH]2)c1] |
| 138 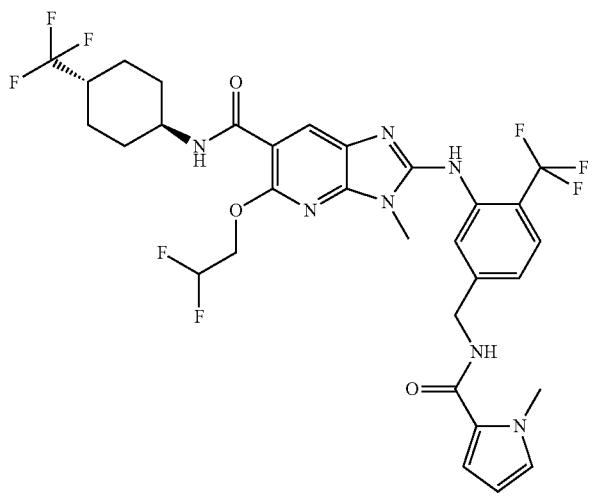 [SMILES: Cn1cccc1C(=O)NCc1ccc(C(F)(F)F)c(Nc2nc3cc(C(=O)N[C@H]4CC[C@H](C(F)(F)F)CC4)c(OCC(F)F)nc3n2C)c1] |

-continued
| | Structure |
|---|---|
| 143 | 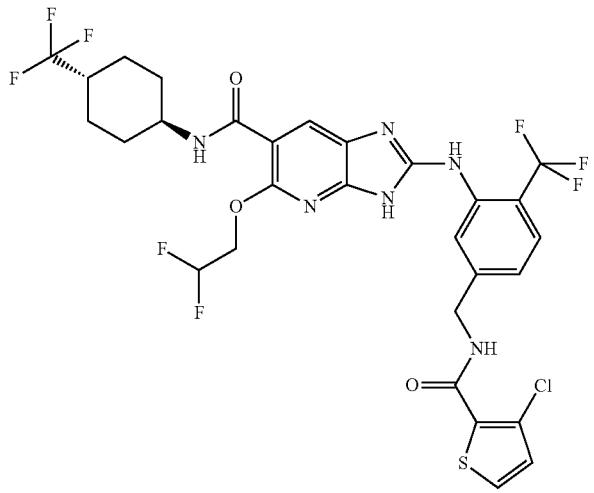 [SMILES: O=C(N[C@H]1CC[C@H](C(F)(F)F)CC1)c1cc2nc(Nc3cc(CNC(=O)c4sccc4Cl)ccc3C(F)(F)F)[nH]c2nc1OCC(F)F] |
| 144 | 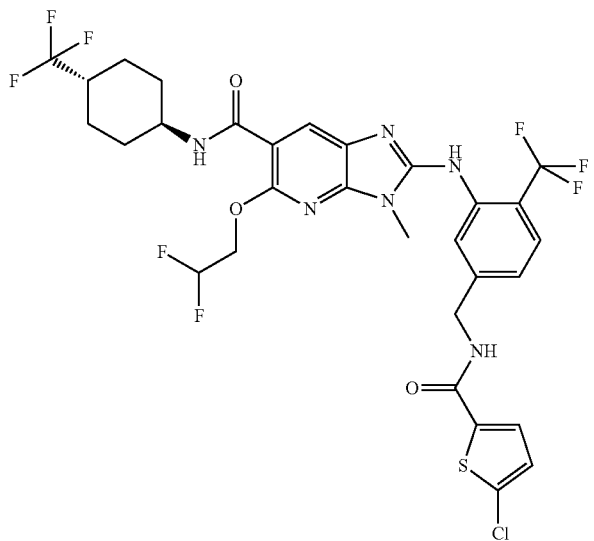 [SMILES: Cn1c(Nc2cc(CNC(=O)c3ccc(Cl)s3)ccc2C(F)(F)F)nc2cc(C(=O)N[C@H]3CC[C@H](C(F)(F)F)CC3)c(OCC(F)F)nc21] |
| 142 | 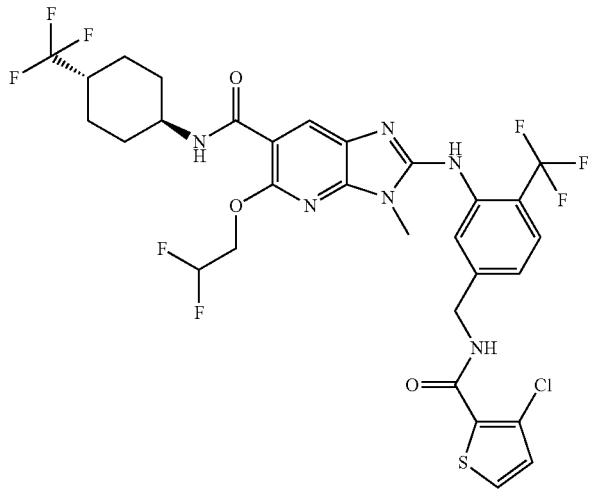 [SMILES: Cn1c(Nc2cc(CNC(=O)c3sccc3Cl)ccc2C(F)(F)F)nc2cc(C(=O)N[C@H]3CC[C@H](C(F)(F)F)CC3)c(OCC(F)F)nc21] |

-continued
| | Structure |
|---|---|
| 147 | 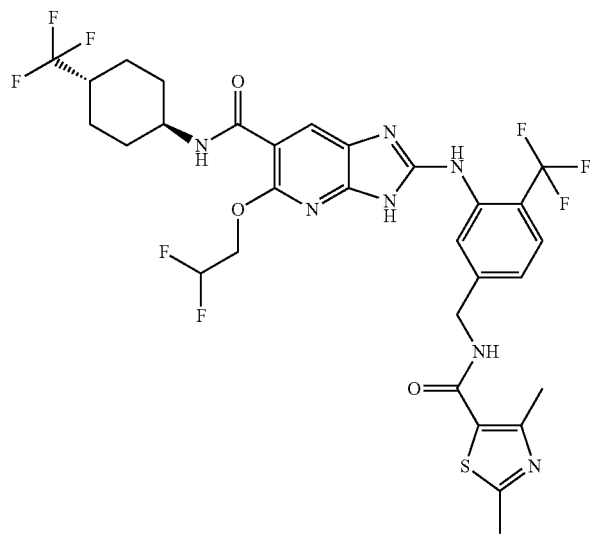 [SMILES: Cc1nc(C)c(C(=O)NCc2ccc(C(F)(F)F)c(Nc3nc4cc(C(=O)N[C@H]5CC[C@H](C(F)(F)F)CC5)c(OCC(F)F)nc4[nH]3)c2)s1] |
| 148 | 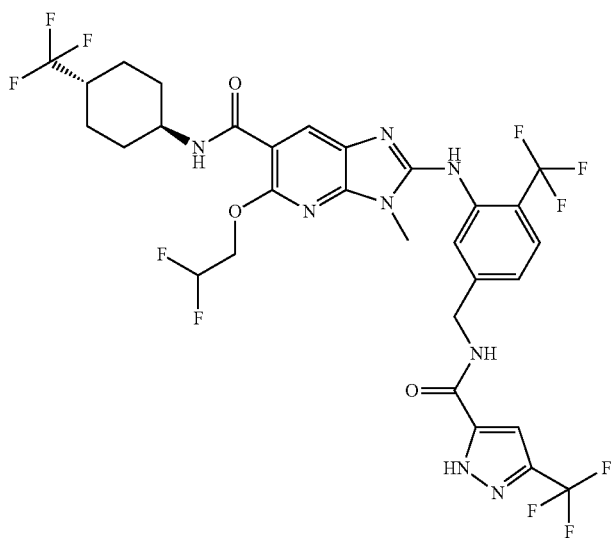 [SMILES: Cn1c(Nc2cc(CNC(=O)c3cc(C(F)(F)F)n[nH]3)ccc2C(F)(F)F)nc2cc(C(=O)N[C@H]3CC[C@H](C(F)(F)F)CC3)c(OCC(F)F)nc21] |
| 145 | 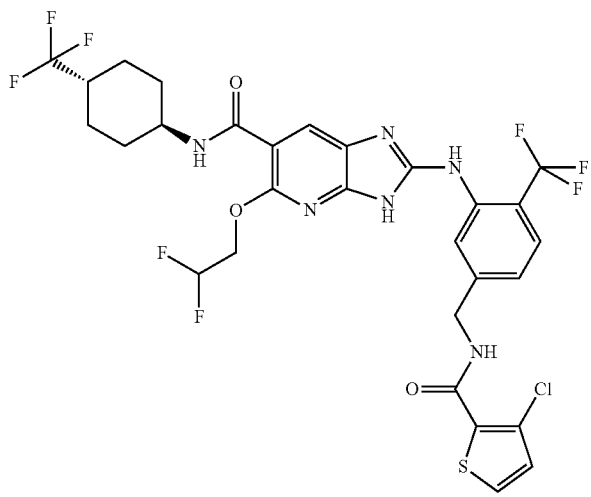 [SMILES: O=C(N[C@H]1CC[C@H](C(F)(F)F)CC1)c1cc2nc(Nc3cc(CNC(=O)c4sccc4Cl)ccc3C(F)(F)F)[nH]c2nc1OCC(F)F] |

-continued
| | Structure |
|---|---|
| 146 | 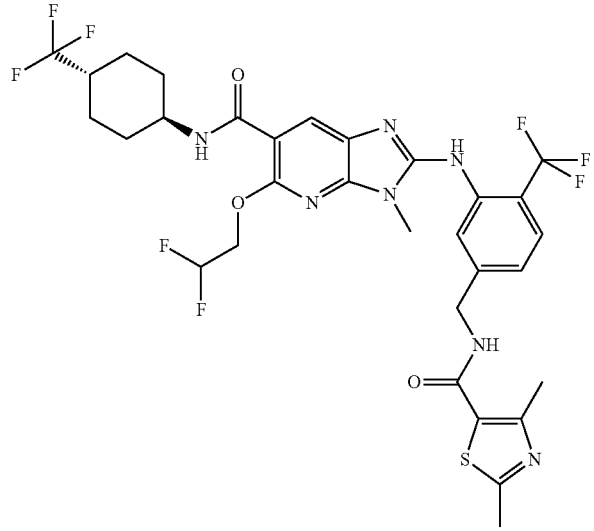 [SMILES: Cc1nc(C)c(C(=O)NCc2ccc(C(F)(F)F)c(Nc3nc4cc(C(=O)N[C@H]5CC[C@H](C(F)(F)F)CC5)c(OCC(F)F)nc4n3C)c2)s1] |
| 151 | 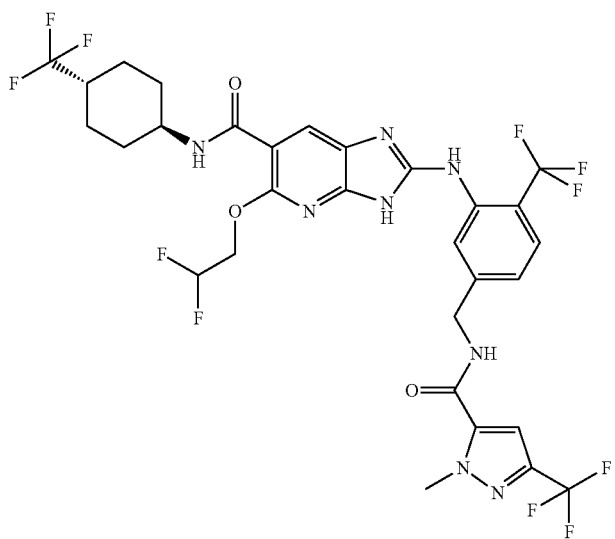 [SMILES: Cn1nc(C(F)(F)F)cc1C(=O)NCc1ccc(C(F)(F)F)c(Nc2nc3cc(C(=O)N[C@H]4CC[C@H](C(F)(F)F)CC4)c(OCC(F)F)nc3[nH]2)c1] |
| 149 | 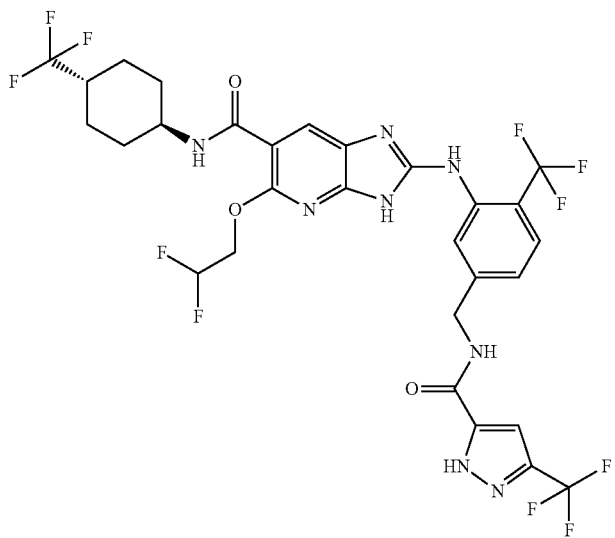 [SMILES: O=C(NCc1ccc(C(F)(F)F)c(Nc2nc3cc(C(=O)N[C@H]4CC[C@H](C(F)(F)F)CC4)c(OCC(F)F)nc3[nH]2)c1)c1cc(C(F)(F)F)n[nH]1] |

-continued
| | Structure |
|---|---|
| 150 | 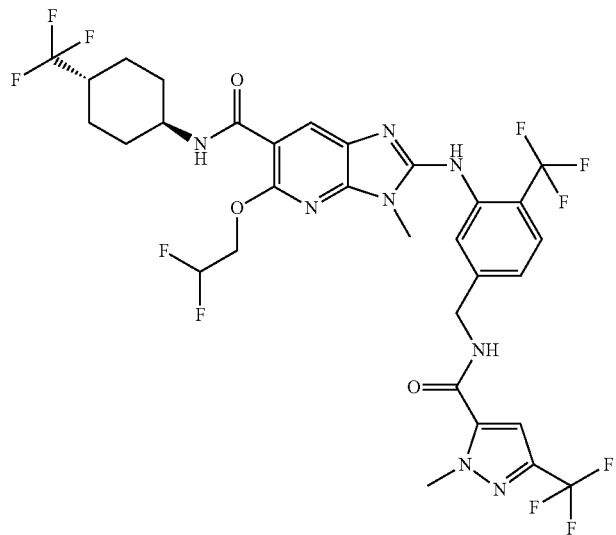 [SMILES: Cn1nc(C(F)(F)F)cc1C(=O)NCc1ccc(C(F)(F)F)c(Nc2nc3cc(C(=O)N[C@H]4CC[C@H](C(F)(F)F)CC4)c(OCC(F)F)nc3n2C)c1] |
| 155 | 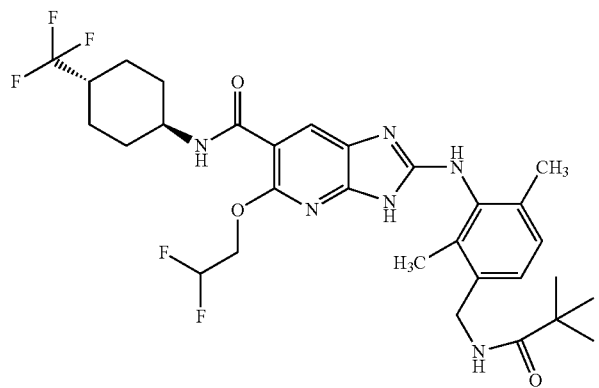 [SMILES: Cc1ccc(CNC(=O)C(C)(C)C)c(C)c1Nc1nc2cc(C(=O)N[C@H]3CC[C@H](C(F)(F)F)CC3)c(OCC(F)F)nc2[nH]1] |
| 152 | 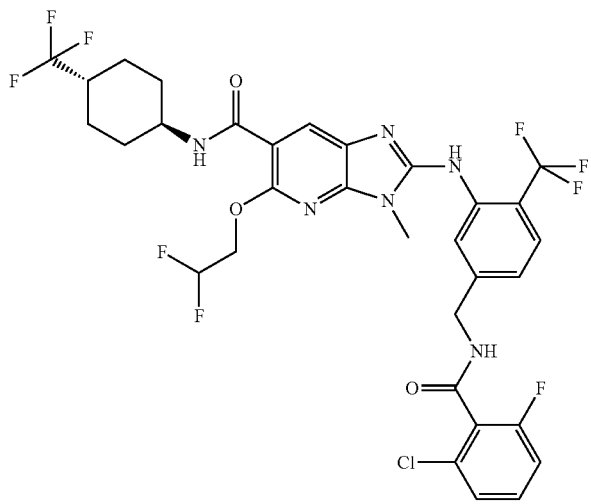 [SMILES: Cn1c(Nc2cc(CNC(=O)c3c(F)cccc3Cl)ccc2C(F)(F)F)nc2cc(C(=O)N[C@H]3CC[C@H](C(F)(F)F)CC3)c(OCC(F)F)nc21] |

-continued
| | Structure |
|---|---|
| 153 | 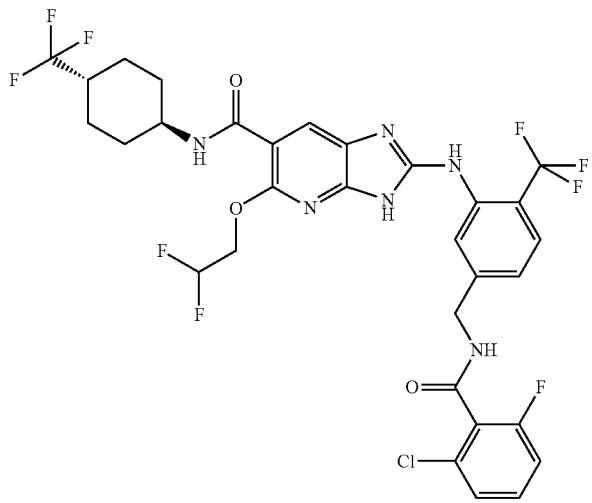 [SMILES: O=C(N[C@H]1CC[C@H](C(F)(F)F)CC1)c1cc2nc(Nc3cc(CNC(=O)c4c(F)cccc4Cl)ccc3C(F)(F)F)[nH]c2nc1OCC(F)F] |
| 154 | 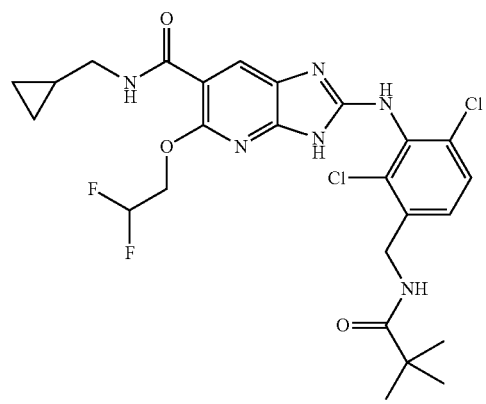 [SMILES: CC(C)(C)C(=O)NCc1ccc(Cl)c(Nc2nc3cc(C(=O)NCC4CC4)c(OCC(F)F)nc3[nH]2)c1Cl] |
| 156 | 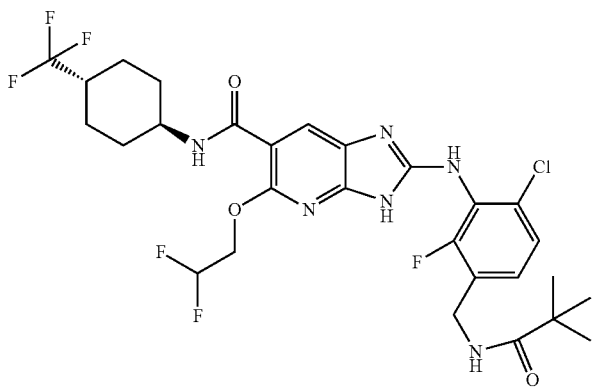 [SMILES: CC(C)(C)C(=O)NCc1ccc(Cl)c(Nc2nc3cc(C(=O)N[C@H]4CC[C@H](C(F)(F)F)CC4)c(OCC(F)F)nc3[nH]2)c1F] |

| | -continued |
|---|---|
| | Structure |
| 157 | 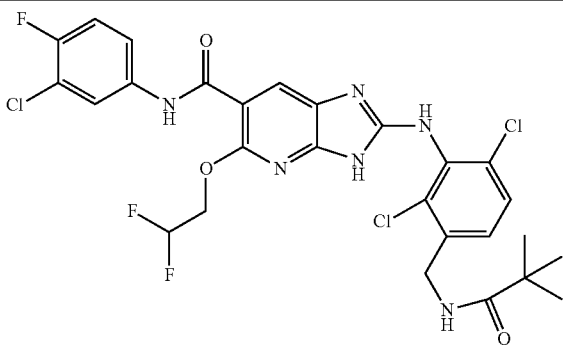 |

13. A pharmaceutical composition comprising at least one compound according to claim 1, or a pharmaceutically acceptable salt thereof, in admixture with a pharmaceutically acceptable adjuvant, diluent and/or carrier.

14. A method of treating an inflammatory disease in a patient comprising administering to said patient a therapeutically effective amount of a compound according to claim 1, or a pharmaceutically acceptable salt thereof.

15. A method of treating pain in a patient comprising administering to said patient a therapeutically effective amount of a compound according to claim 1, or a pharmaceutically acceptable salt thereof.

* * * * *